US011832966B2

(12) United States Patent
Ford et al.

(10) Patent No.: US 11,832,966 B2
(45) Date of Patent: Dec. 5, 2023

(54) METHODS AND MAGNETIC IMAGING DEVICES TO INVENTORY HUMAN BRAIN CORTICAL FUNCTION

(71) Applicant: Brain F.I.T. Imaging, LLC, Unadilla, NY (US)

(72) Inventors: John P. Ford, Unadilla, NY (US); Gustavo P. Sudre, Washington, DC (US)

(73) Assignee: BRAIN F.I.T. IMAGING, LLC, Unadilla, NY (US)

( * ) Notice: Subject to any disclaimer, the term of this patent is extended or adjusted under 35 U.S.C. 154(b) by 473 days.

(21) Appl. No.: 16/839,290

(22) Filed: Apr. 3, 2020

(65) Prior Publication Data
US 2020/0321124 A1    Oct. 8, 2020

Related U.S. Application Data

(60) Provisional application No. 62/828,687, filed on Apr. 3, 2019.

(51) Int. Cl.
*A61B 5/00* (2006.01)
*G16H 50/20* (2018.01)
(Continued)

(52) U.S. Cl.
CPC .............. *A61B 5/6803* (2013.01); *A61B 5/38* (2021.01); *A61B 5/4088* (2013.01); *G06N 20/00* (2019.01); *G16H 50/20* (2018.01)

(58) Field of Classification Search
CPC .......... G16H 50/20; G16H 40/60; A61B 5/38; A61B 5/4088; A61B 5/6803; A61B 5/246;
(Continued)

(56) References Cited

U.S. PATENT DOCUMENTS

| 3,445,760 A | 5/1969 | Zimmerman |
| 3,506,913 A | 4/1970 | Lambe et al. |

(Continued)

FOREIGN PATENT DOCUMENTS

| CN | 101583308 A | 11/2009 |
| CN | 101912255 A | 12/2010 |

(Continued)

OTHER PUBLICATIONS

Bagić et al., "Clinical Magnetoencephalography Practice in the United States Ten Years Later: A Survey-Based Reappraisal," Journal of Clinical Neurophysiology, Nov. 2020, vol. 37, Issue 6, pp. 592-598.

(Continued)

*Primary Examiner* — Molly Wilburn
(74) *Attorney, Agent, or Firm* — Fenwick & West LLP

(57) ABSTRACT

Techniques are described for determining cognitive impairment, an example of which includes accessing a set of epochs of magnetoencephalography (MEG) data of responses of a brain of a test patient to a plurality of auditory stimulus events; processing the set of epochs to identify parameter values one or more of which is based on information from the individual epochs without averaging or otherwise collapsing the epoch data. The parameter values are input into a model that is trained based on the parameters to determine whether the test patient is cognitively impaired. Graphical user interfaces are described for presenting MEG epoch data and a score that correlates to a likelihood of the test individual being cognitively impaired.

19 Claims, 67 Drawing Sheets

(51) Int. Cl.
 G06N 20/00 (2019.01)
 A61B 5/38 (2021.01)
(58) Field of Classification Search
 CPC .... A61B 5/7246; A61B 5/7267; G06N 20/00;
 G06N 20/20; G06K 9/6228; G06K
 9/00523
 See application file for complete search history.

(56) References Cited

U.S. PATENT DOCUMENTS

| | | | |
|---|---|---|---|
| 3,676,718 A | 7/1972 | Anderson et al. | |
| 3,689,780 A | 9/1972 | Meissner et al. | |
| 3,936,677 A | 2/1976 | Fulton et al. | |
| 4,736,751 A | 4/1988 | Gevins et al. | |
| 4,862,359 A | 8/1989 | Trivedi et al. | |
| 5,325,862 A | 7/1994 | Lewis et al. | |
| 5,326,764 A | 7/1994 | Milstone et al. | |
| 5,381,791 A | 1/1995 | Qian | |
| 5,713,354 A | 2/1998 | Warden | |
| 5,752,514 A | 5/1998 | Okamura et al. | |
| 6,192,276 B1 | 2/2001 | Strandberg | |
| 6,195,576 B1 | 2/2001 | John | |
| 6,230,037 B1 | 5/2001 | Tsukada et al. | |
| 6,256,531 B1 | 7/2001 | Ilmoniemi et al. | |
| 6,471,960 B1 | 10/2002 | Anderson | |
| 6,473,518 B1 | 10/2002 | Machida et al. | |
| 6,665,553 B2 | 12/2003 | Kandori et al. | |
| 6,724,188 B2 | 4/2004 | Butters et al. | |
| 6,745,063 B2 | 6/2004 | Tsukada et al. | |
| 6,784,663 B2 | 8/2004 | Sarwinski et al. | |
| 6,979,688 B2 | 12/2005 | Ford | |
| 6,995,165 B2 | 2/2006 | Ford | |
| 7,002,341 B2 | 2/2006 | Baudenbacher et al. | |
| 7,130,675 B2 | 10/2006 | Ewing et al. | |
| 7,197,352 B2 | 3/2007 | Gott et al. | |
| 7,368,456 B2 | 5/2008 | Ford | |
| 7,662,829 B2 | 2/2010 | Ford | |
| 7,812,030 B2 | 10/2010 | Ford | |
| 7,816,366 B2 | 10/2010 | Ford | |
| 8,030,710 B2 | 10/2011 | Pidin | |
| 8,258,147 B2 | 9/2012 | Ford | |
| 8,489,544 B2 | 7/2013 | Ford | |
| 8,653,090 B2 | 2/2014 | Ford | |
| 9,084,788 B2 | 7/2015 | Ford | |
| 9,095,266 B1 | 8/2015 | Fu | |
| 9,119,855 B2 | 9/2015 | Ford | |
| 9,286,443 B2 | 3/2016 | Ford et al. | |
| 10,588,576 B2 | 3/2020 | Phillips et al. | |
| 10,736,557 B2 | 8/2020 | Ford et al. | |
| 11,337,631 B2 | 5/2022 | Ford et al. | |
| 2002/0115927 A1 | 8/2002 | Tsukada et al. | |
| 2002/0175693 A1 | 11/2002 | Starr et al. | |
| 2003/0042898 A1 | 3/2003 | Sarwinski et al. | |
| 2003/0100844 A1 | 5/2003 | Miller et al. | |
| 2003/0158128 A1 | 8/2003 | Ford | |
| 2004/0002645 A1 | 1/2004 | Ewing et al. | |
| 2004/0145366 A1 | 7/2004 | Baudenbacher et al. | |
| 2004/0171960 A1 | 9/2004 | Musha et al. | |
| 2004/0254443 A1 | 12/2004 | Gott et al. | |
| 2005/0124863 A1 | 6/2005 | Cook | |
| 2005/0215514 A1 | 9/2005 | Ford | |
| 2007/0015728 A1 | 1/2007 | Ford | |
| 2007/0032737 A1 | 2/2007 | Causevic et al. | |
| 2007/0038067 A1 | 2/2007 | Kandori et al. | |
| 2008/0249430 A1 | 10/2008 | John | |
| 2009/0018431 A1 | 1/2009 | Feiweier et al. | |
| 2009/0062676 A1 | 3/2009 | Kruglikov et al. | |
| 2009/0232884 A1 | 9/2009 | Ford | |
| 2010/0203140 A1 | 8/2010 | Ford | |
| 2010/0280334 A1 | 11/2010 | Carlson et al. | |
| 2011/0077260 A1 | 3/2011 | Ford | |
| 2011/0190621 A1 | 8/2011 | Verdoorn et al. | |
| 2012/0084919 A1 | 4/2012 | McCroskey et al. | |
| 2012/0271148 A1 | 10/2012 | Nelson | |
| 2013/0041590 A1 | 9/2013 | Burich | |
| 2013/0245422 A1 | 9/2013 | D'Arcy et al. | |
| 2014/0000630 A1 | 1/2014 | Ford | |
| 2014/0081347 A1 | 3/2014 | Nelson et al. | |
| 2015/0313901 A1 | 11/2015 | Ford | |
| 2016/0045128 A1 | 2/2016 | Sitt et al. | |
| 2016/0081577 A1 | 3/2016 | Sridhar | |
| 2016/0157742 A1 | 6/2016 | Huang et al. | |
| 2017/0224241 A1 | 8/2017 | Chen | |
| 2017/0281071 A1* | 10/2017 | Ford | A61B 5/4088 |
| 2020/0164201 A1* | 5/2020 | Berenyi | A61N 1/3603 |

FOREIGN PATENT DOCUMENTS

| | | |
|---|---|---|
| CN | 105852885 A | 8/2016 |
| EP | 1447045 A1 | 8/2004 |
| EP | 1948014 B1 | 12/2017 |
| JP | 2015-527111 A | 9/2015 |
| WO | WO 2005/039585 A1 | 5/2005 |
| WO | WO 2007/008858 A2 | 1/2007 |
| WO | WO 2009/149246 A1 | 12/2009 |
| WO | WO 2013/155385 A1 | 10/2013 |
| WO | WO 2014/004365 A2 | 1/2014 |
| WO | WO 2017/172961 A1 | 5/2017 |
| WO | WO 2018/163178 A1 | 9/2018 |
| WO | WO 2019/070895 A1 | 4/2019 |

OTHER PUBLICATIONS

Kligfield et al., "Recommendations for the Standardization and Interpretation of the Electrocardiogram: Part I: The Electrocardiogram and Its Technology: A Scientific Statement From the American Heart Association Electrocardiography and Arrhythmias Committee, Council on Clinical Cardiology; the American College of Cardiology Foundation; and the Heart Rhythm Society Endorsed by the International Society for Computerized Electrocardiology," Circulation, vol. 115, Issue 10, Mar. 13, 2007, pp. 1306-1324.

Bardy, F. et al., "Deconvolution of magnetic acoustic change complex (mACC)," Clinical Neurophysiology, vol. 125, No. 11, 2014, pp. 2220-2231.

Barrows, parts of "Antineoplastic and Immunoactive Drugs," Chapter 86 in Remington: The Science and Practice of Pharmacy, 20th Edition, Gennaro et al. (eds.), Lippincott, Williams & Wilkins, Baltimore, MD, 2000, only pp. 1498 and 1815 supplied.

Beers et al. (eds.), Chapter 126 ("Malignant Tumors") in The Merck Manual of Diagnosis and Therapy, 17th Edition, Merck & Co., Inc., Rahway, NJ, Jan. 1999, only title pages and text pp. 842-843 supplied.

Berendse, H.W. et al., "Magnetoencephalographic Analysis of Cortical Activity in Alzheimer's Disease: a Pilot Study", Clinical Neurophysiology, 2000, pp. 604-612, vol. 111.

Bland J.M. et al., "Statistical Methods for Assessing Agreement Between Two Methods of Clinical Measurement," Lancet, 1986, pp. 307-310, vol. 327, No. 8476.

Boly, M. et al., "Preserved Feedforward but Impaired Top-Down Processes in the Vegetative State", Science, May 13, 2011, pp. 858-862, vol. 332.

Borg, X., "The Inverse Cube Law for Dipoles," The General Science Journal, Jan. 25, 2009, 2 pages, May be Retrieved at <URL:http://blazelabs.com/inversecubelaw.pdf>.

Calabresi et al., "Chemotherapy of Neoplastic Diseases," Goodman & Gilman's The Pharmacological Basis of Therapeutics, 9th Edition, 1996, Section X, pp. 1225-1229.

Cao et al., "5-Fluorouracil Prodrug: Role of Anabolic and Catabolic Pathway Modulation in Therapy of Colorectal Cancer," Clinical Cancer Research, 1995, pp. 839-845, vol. 1, No. 8.

Cheour, M. et al., "Magnetoencephalography is feasible for infant assessment of auditory discrimination," Sep. 15, 2004, Experimental Neurology, 190, S44-S51.

Childress, J. et al., "Cutaneous Hand and Foot Toxicity Associated with Cancer Chemotherapy," American Journal of Clinical Oncology, vol. 26(5), pp. 435-436, 2003.

(56) References Cited

OTHER PUBLICATIONS

Chua, D. et al., "Efficacy of Capecitabine Monotherapy in Patients with Recurrent and Metastatic Nasopharyngeal Carcinoma Pretreated with Platinum-Based Chemotherapy," Proc. Am. Soc. Clin. Oncol., vol. 22, p. 511, 2003.
Clarke, A. et al., "Predicting the Time Course of Individual Objects with MEG," Cerebral Cortex, Oxford Journals, Sep. 2014, 12 pages.
Ehrlanger et al., "Cutaneous Absorption and Urinary Excretion of 6-14C-5-5-Fluorouracil Ointment Applicated in an Ointment to Healthy and Diseased Human Skin," Dermatologies, vol. 140, Suppl. 1, pp. 129-136, 1970.
Elasmer et al., "Case Report: Hand-Foot Syndrome Induced by Oral Fluoropyrimidine S-1," Jpn. J. Clin. Oncol., vol. 3(4), p. 172-174, 2001.
Extended European Search Report, European Patent Application No. 17776577.3, dated Nov. 7, 2019, 8 pages.
Extended European Search Report, European Patent Application No. 18864067.6, dated Nov. 11, 2020, eight pages.
Findlay, M. et al., "Measurement of Plasma 5-Fluorouracil by High-Performance Liquid Chromatography with Comparison of Results to Tissue Drug Levels Observed Using in Vivo 19F Magnetic Resonance Spectroscopy in Patients in Protracted Venous Infusion with or without Interferon-α," Annals of Oncology, vol. 7(47-53), pp. 111-117, 1996.
Fischel, J-L. et al., "Experimental Arguments for a Better Understanding of Hand-Foot Syndrome Under Capecitabine", Proceedings of the American Association for Cancer Research, 2004, p. 487 (Abstract #2119), vol. 45.
Fujii, S. et al., "Effect of Coadministration of Uracil or Cytosine on the Anti-Tumor Activity of Clinical Doses of 1-(2-Tetrahydrofuryl)-5-Fluorouracil and Level of 5-Fluorouracil in Rodents," Gann., vol. 70, pp. 209-214, 1979.
Fukushima, S. et al., "Carcinogenicity of Uracil, a Nongenotoxic Chemical, in Rats and Mice and Its Rationale", Cancer Research, 1992, pp. 1675-1680, vol. 52.
Gallen, C.C. et al., "Magnetoencephalography and Magnetic Source Imaging: Capabilities and Limitations", Functional Neuroimaging, 1995, pp. 227-249, vol. 5.
Gallo, R. et al., "The Enzymatic Mechanisms for Deoxihymidine Synthesis in Human Leukocites," The Journal of Clinical Investigation, vol. 48, pp. 82-93, 1969.
Georgopoulos, A. et al., "Synchronous Neural Interactions Assessed by Magnetoencephalography: A Functional Biomarker for Brain Disorders", Journal of Neural Engineering, 200, pp. 349-355, vol. 4.
Giani, A.S. et al., "Detecting Tones in Complex Auditory Scenes," NeuroImage, 2015, vol. 122, pp. 203-213.
Gmehlin, D. et al., "Age Effects on Preattentive and Early Attentive Auditory Processing of Redundant Stimuli: Is Sensory Gating Affected by Physiological Aging?" Journal of Gerontology A Biol. Sci. Med Sci., 2011, pp. 1043-1053, vol. 10.
Golubic, SJ et al., "MEG biomarker of Alzheimer's disease: Absence of a prefrontal generator during auditory sensory gating," Hum. Brain Mapp., 2017, vol. 38, pp. 5180-5194.
Gramfort, A., et al. "Graph-Based Variability Estimation in Single-Trial Event-Related Neural Responses," IEEE Trans. on Biomedical Engineering, May 2010, vol. 57, No. 5, pp. 1051-1061.
Gramfort, A., et al., "MEG and EEG data analysis with MNE-Python," Frontiers in Neuroscience, 2013, vol. 7, Article 267, pp. 1-13.
Hamalainen, M. et al., "Magnetoencephalography—Theory, Instrumentation, and Applications to Noninvasive Studies of the Working Human Brain", Reviews of Modern Physics, Apr. 1993, pp. 413-497, vol. 65, No. 2.
Hari, R., "The Neuromagnetic Method in the Study of the Human Auditory Cortex," Auditory Evoked Magnetic Fields and Electric Potentials, by Grandori et al. ed., Karger: Basel, Switzerland, 1990, pp. 222-282.

Hartmann, H.R. et al., "Modulation of the Effects of Fluoropyrimidines on Toxicity and Tumor Inhibition in Rodents by Uridine and Thymidine," Med. Oncol. & Tumor Pharmacother., vol. 3(2), pp. 111-118, 1986.
Harvey, S.C., "Drug Absorption, Action and Disposition," Chapter 35 in Remington's Pharmaceutical Sciences, 18th Ed., Gennaro et al. (eds.), 1990, Mack Publishing Co., Easton, PA, pp. 697-724.
Harvey, S.C., "Topical Drugs," Chapter 38 in Remington's Pharmaceutical Sciences, 18.sup.th Ed., Gennaro et al. (eds.), 1990, Mack Publishing Co., Easton, PA, pp. 757-773.
Hatfield, D. et al., "Synthesis of (3-Ribosyluric Acid) 5-Phosphate and (3-Ribosylxanthine) 5-Phosphate by a Pyrimidine Ribonucleotide Pyrophosphorylase of Beef Erythocytes," The Journal of Biological Chemistry, pp. 60-66, 1964.
Hejna, M. et al., "Decrease of Duration and Symptoms in Chemotherapy-Induced Oral Mucositis by Topical GM-CSF: Results of a Prospective Randomised Trial," European Journal of Cancer, vol. 37(16), pp. 1994-2002, 2001.
Hirata, K. et al., "Pharmacokinetic Study of S-1, A Novel Oral Fluorouracil Antitumor Drug," Clinical Cancer Research, Aug. 1999, pp. 2000-2005, vol. 5.
Hoff, P., "The Tegafur-Based Dihydropyrimidine Dehydrogenase Inhibitory Fluoropyrimidines, UFT/Leucovorin (ORZEL.TM.) and S-1: A Review of Their Clinical Development and Therapeutic Potential," Investigational New Drugs, 2000, pp. 153-163, vol. 18.
Ichikawa, W. et al., "Both Gene Expression for Orotate Phosphoribosyltransferase and its Ratio to Dihydropyrimidine Pehydrogenase Influence Outcome Following Fluoropyrimidine-Based Chemotherapy for Metastatic Colorectal Cancer," British Journal of Cancer, 2003, pp. 1486-1492, vol. 89.
Ikenaka, K. et al., "Effect of Uracil on Metabolism of 5-Fluorouracil In Vitro," Gann., vol. 70, pp. 353-359, 1979.
International Search Report and Written Opinion, Patent Cooperation Treaty Application No. PCT/IB2020/053219, dated Sep. 4, 2020, seventeen pages.
International Search Report and Written Opinion, Patent Cooperation Treaty Application No. PCT/US2013/047289, dated Feb. 11, 2014, 12 pages.
International Search Report and Written Opinion, Patent Cooperation Treaty Application No. PCT/US2017/024813, dated Aug. 14, 2017, seventeen pages.
International Search Report and Written Opinion, Patent Cooperation Treaty Application No. PCT/US2018/054228, dated Dec. 11, 2018, eighteen pages.
Jacobi, M., "Brainwaves and Consciousness—Brainwaves (1) Beta, Alpha, Theta and Delta," 2002-2014, May be Retrieved at <URL:http://www.hirnwellen-und-bewusstsein.de/brainwaves_1.html, Jan. 18, 2008.
Johnson, M.R. et al., "Life Threatening Toxicity in a Dihydropyrimidine Dehydrogenase-Deficient Patient After Treatment with Topical 5-Fluorouracil," Clinical Cancer Research, Aug. 1999, pp. 2006-2011, vol. 5.
Kawaguchi, Y. et al., "Studies on the Metabolism of 1-(2-Tetrahydrofuryl)-5-Fluorouracil and Uracil Co-Administered Orally to Tumor-Bearing Rats," Gann., vol. 19, pp. 869-899, 1980.
Knuutila, J. et al., "Large-Area Low-Noise Seven-Channel de SQUID Magnetometer for Brain Research," Rev. Sci. Instrum., Nov. 1987, pp. 2145-2156, vol. 58.
Kowanko et al., Prevention and Treatment of Oral Mucositis in Cancer Patients, Best Practice, 1998, pp. 1-6, vol. 2, Issue 3. Available at http:/Joralcancerfoundation_org/dental/pdf/mucositis.pdf, 6 pages.
Largillier, R. et al., "Prospective Analysis of Dihydropyrimidine Dehydrogenase (DPD) Activity for Predicting Capecitabine-Related Toxicities in Metastatic Breast Cancer Patients," (Roser Abstract), p. 39, 2002.
Laukka, E.J. et al., "Effects of Between-Person Differences and Within-Person Changes in Symptoms of Anxiety and Depression on Older Age Cognitive Performance," Psychological Medicine, 2017, pp. 1350-1358.
Leo, S. et al., "Dermatological Toxicity from Chemotherapy Containing 5-Fluorouracil," Journal of Chemotherapy, vol. 6(6), pp. 2-5, 1994.

(56) References Cited

OTHER PUBLICATIONS

Levy, S. et al., "A Pharmacokinetic Evaluation of 0.5% and a 5% Fluorouracil Topical Cream in Patients with Actinic Keratosis," Clinical Therapeutics, vol. 23(6), pp. 908-920, 2001.

Luccioni et al., "Pyrimidine Nucleotide Metabolism in Human Colon Carcinomas: Comparison of Normal Tissues Primary Tumors and Xenografts," Int. J. Cancer, vol. 58, p. 32-.

Mackean, M. et al., "Phase I and Pharmacologic Study of Intermittent Twice-Daily Oral Therapy with Capecitabine in Patients with Advanced and/or Metastatic Cancer," Journal of Clinical Oncology, vol. 16(9), pp. 2977-2985. 1998.

Maehara, Y. et al., "Scientific Basis for the Combination of the Tegafur with Uracil," Oncology, vol. 11(9), Supplement No. 10, pp. 14-21, 1997.

Makris, N. et al., "Human Cerebral Cortex: A System for the Integration of Volume- and Surface-Based Representations," NeuroImage, pp. 139-153, 2006, vol. 33.

Malet-Martino, M. et al., "Clinical Studies of Three Oral Prodrugs of 5-Fluorouracil KCapecitabine, UFT,S-1): A Review," The Oncologist, 2002, pp. 288-323, vol. 7.

Miller, G., "Feedback from Frontal Cortex May Be a Signature of Consciousness," Science, May 13, 2011, p. 779, vol. 332.

Mountz, J.M. et al., "Comparison of Qualitative and Quantitative Imaging Characteristics of [$^{11}$C]PiB and [$^{18}$F]flutematamol in normal control and Alzheimer's subjects," NeuroImage Clinical, 2015, pp. 593-598, vol. 9.

Naguib, F.N.M. et al., "Enzymes of Uracil Catabolism in Normal and Neoplastic Human Tissues," Cancer Research, Nov. 1985, pp. 5405-5412, vol. 45.

Nairn, J. G., "Solutions, Emulsions, Suspensions and Extracts," Chapter 83 in Remington's Pharmaceutical Sciences, 18$^{th}$ Edition, Gennaro et al.(eds.), Mack Publishing Co., Easton, PA, 1990, only pp. 1519-1544 supplied.

Nesselroade, J.R. et al., "Methodological and Theoretical Implications of Intraindividual Variability in Perceptual-Motor Performance," Journal of Gerontology, 2004, vol. 59B, No. 2, pp. P49-P55.

Niedzwicki, J. et al., "Structure-Activity Relationship of Pyrimidine Base Analogs of Ligands of Orotate Phosphoribosyltransferase," Biochemical Pharmacology, vol. 33(15), pp. 2383-2395, 1984.

Park, D. et al., "Activation of CaMKIV by Soluble Amyloid-β1-42 Impedes Trafficking of Axonal Vesicles and Impairs Activity-Dependent Synaptogenesis," Science Signaling, Jul. 11, 2017, vol. 10, No. 487, 12 pages.

Partial Supplementary European Search Report for EP13810531.7, dated Feb. 10, 2016, 7 pages.

Pekkonen, E. et al., "Impaired Preconscious Auditory Processing and Cognitive Functions in Alzheimer's Disease," Clinical Neurophysiology, 1999, vol. 110, pp. 1942-1947.

Powis, G., "Anticancer Drugs: Antimetabolite Metabolism and Natural Anticancer Agents," International Encyclopedia of Pharmacology and Therapeutics, pp. 42-50, 1994.

Pugh et al. (eds.), Stedman's Medical Dictionary, 27th Edition, Lippincott Williams & Wilkins, Baltimore, MD, 2000, see pp. 365, 613-617 & 620 ("carcinoma," "dermatitis," "dermatosis & dermatoses").

Roberts, T.P.L. et al., "MEG Detection of Delayed Auditory Evoked Responses in Autism Spectrum Disorders: Towards an Imaging Biomarker for Autism", Autism Research, Feb. 2010, pp. 8-18, vol. 3, No. 1.

Sabbagh, M.N. et al., "Increasing Precision of Clinical Diagnosis of Alzheimer's Disease Using a Combined Algorithm Incorporating Clinical and Novel Biomarker Data," Neurol. Ther., 2017, vol. 6, (suppl 1), pp. S83-S95.

Samid, D., "Important Information About Xeloda (Capecitabine) Tablets," Roche Laboratories Inc., 2003, pp. 29-31.

Sawada, N. et al., "Induction of Thymidine Phosphorylase Activity and Enhancement of Capecitabine Efficacy by Taxol/Taxotere in Human Cancer Xenografts," Clinical Cancer Research, Apr. 1998, pp. 1013-1019, vol. 4.

Schilsky, R.L. et al., "Sixty-Third Meeting of the Oncologic Drug Advisory Committee," Food and Drug Administration Center for Drug Evaluation and Research, 1999.

Senff, H. et al., "Topical 5-Fluorouracil Solution in the Treatment of Warts—Clinical Experience and Percutaneous Absorption," British Journal of Dermatology, vol. 118, pp. 409-414, 1968.

Sigma U.S. Catalog, "Biochemical and Reagents for Life Science Research," St. Louis, MO, 2000-2001 edition, only p. 1000 supplied.

Sludden, J. et al., "Liver Dihydropyrimidine Dehydrogenase Activity in Human, Cynomolgus Monkey, Rhesus Monkey, Dog, Rat and Mouse," Pharmacology, pp. 276-280, 1998.

Spicer, E. et al., "Toxicity Study of Uracil in Dogs," Journal of Applied Toxicity, vol. 5, pp. 199-204, 1985.

Stein, J.H. et al., Editor-in-Chief, Internal Medicine, 4th Edition, Chapters 71 and 72, pp. 699-715, 1994.

Stokes, M. G., et al. "Simple Metric for Scaling Motor Threshold Based on Scalp-Cortex Distance: Application to Studies Using Transcranial Magnetic Stimulation," Journal of Neurophysiology, 2005, pp. 4520-4527, vol. 94, No. 6.

Sweatt, J.D., "Creating Stable Memories," Science, Feb. 18, 2011, pp. 869-870, vol. 331.

Swinyard, E.A. et al., "Pharmaceutical Necessities," Chapter 66 in Remington's Pharmaceutical Sciences, 18th Ed., Gennaro et al. (eds.), 1990, Mack Publishing Co., Easton, PA, pp. 1286-1329.

Taulu, S. et al., "Removal of Magnetoencephalographic Artifacts with Temporal SignalSpace Separation: Demonstration with Single-Trial Auditory-Evoked Responses," Human Brain Mapping, 2009, pp. 1524-1534, vol. 30.

Taulu, S. et al., "Spatiotemporal Signal Space Separation Method for Rejecting Nearby Interference in MEG Measurements," Physics in Medicine and Biology, 2006, 11 pages, vol. 51, No. 7.

Taulu, S. et al., "Suppression of Interference and Artifacts by the Signal Space Separation Method," Brain Topography, Summer 2004, pp. 269-275, vol. 16, No. 4.

U.S. Appl. No. 60/355,764, filed Feb. 12, 2002, Inventor John P. Ford [Copy Not Enclosed].

U.S. Appl. No. 60/697,910, filed Jul. 8, 2005, Inventor John P. Ford [Copy Not Enclosed].

U.S. Appl. No. 60/933,038, filed Jun. 4, 2007, Inventor John P. Ford [Copy Not Enclosed].

U.S. Appl. No. 61/069,031, filed Mar. 12, 2008, Inventor John P. Ford [Copy Not Enclosed].

U.S. Appl. No. 61/666,171, filed Jun. 29, 2012, Inventor John P. Ford [Copy Not Enclosed].

U.S. Appl. No. 62/315,376, filed Mar. 30, 2016, Inventor John P. Ford [Copy Not Enclosed].

Vanden Heuvel, J.P. et al., "Differential Nucleobase Protection Against 5-Fluorouracil Toxicity for Squamous and Columnar Cells: Implication for Tissue Function and Oncogenesis," Investigational New Drugs, Jul. 1, 2015, pp. 1003-1011, vol. 33.

Venes et al.(eds.), Taber's Cyclopedic Medical Dictionary, 21st Edition, F. A. Davis Co., Philadelphia, PA, 2009, see pp. 285-289 ("carcinoma").

Wang, J. et al., "Oral 5-FU is a More Effective Antimetastatic Agent than UFT," Anticancer Research, 2004, pp. 1353-1360, vol. 24.

Weast et al., CRC Handbook of Chemistry and Physics, Boca Raton, FL, 1981, only p. C-536 supplied: see entry for "Uracil.".

Williamson, S.J. et al., "Biomagnetism," Journal of Magnetism and Magnetic Materials, 1981, pp. 129-201, vol. 22, No. 2.

Xeloda (Capecitabine) Tablets Product Label Insert, Roche Pharmaceuticals, 2003, 47 pages.

Zamrini, E. et al., "Magnetoencephalography as a Putative Biomarker for Alzheimer's Disease," International Journal of Alzheimer's Disease, 2011, pp. 1-10, vol. 2011.

Zografi et al., "Disperse Systems," Chapter 19 in Remington's Pharmaceutical Sciences, 18.sup.th Ed., Gennaro et al. (eds.), 1990, Mack Publishing Co., Easton, PA, only pp. 257-309 supplied. See in particular p. 302 ("Emulsifying Agents").

Extended European Search Report, European Patent Application No. 20782636.2, 9, dated Dec. 9, 2022, 14 pages.

(56) References Cited

OTHER PUBLICATIONS

International Search Report and Written Opinion, Patent Cooperation Treaty Application No. PCT/US2022/045839, dated Jan. 27, 2023, 23 pages.
Nichols, T., et al., "Nonparametric permutation tests for functional neuroimaging: A primer with examples", Human Brain Mapping, vol. 15, Issue1, Jan. 2002, pp. 1-25, XP055291962, ISSN: 1065-9471, DOI: 10.1002/hbm.1058.
United States Office Action, U.S. Appl. No. 17/745,115, filed Nov. 18, 2022, 7 pages.
Demopoulos, C., et al., "Magnetoencephalographic Imaging of Auditory and Somatosensory Cortical Responses in Children with Autism and Sensory Processing Dysfunction," Frontiers in Human Neuroscience, May 2017, vol. 11, Article 259, pp. 1-15.
Baillet, S., "Magnetoencephalography for brain electrophysiology and imaging," Nature Neuroscience, vol. 20, No. 3, Mar. 2017, pp. 327-339.
Brookes, M.J. et al. "Magnetoencephalography with optically pumped magnetometers (OPM-MEG): the next generation of functional neuroimaging," Trends in Neurosciences, vol. 45, No. 8, Aug. 2022, pp. 621-634.
Grubbs, F.E., "Sample Criteria for Testing Outlying Observations," The Annals of Mathematical Statistics, vol. 21, No. 1, Mar. 1950, pp. 27-58.
Hanna-Pladdy, B. et al., "Functional Magnetic Resonance Imaging Biomarkers Predicting Cognitive Progression in Parkinson Disease: Protocol for a Prospective Longitudinal Cohort Study," JMIR Research Protocols, vol. 8, Iss. 4:e12870, Apr. 2019, pp. 1-13.
Hurd, M.D et al., "Monetary Costs of Dementia in the United States," The New England Journal of Medicine 368(14), Apr. 2013, pp. 1326-1334.
Joshi, A. et al., "Reducing between scanner differences in multicenter PET studies," NeuroImage, vol. 46, Feb. 6, 2009, pp. 154-159.
Krashes, M.J. et al., "Rapid, reversible activation of AgRP neurons drives feeding behavior in mice," The Journal of Clinical Investigation, vol. 121, No. 4, Apr. 2011, pp. 1424-1428.
Lezak, M., "Neuropsychological Assessment," Fifth Edition, Oxford, UK: Oxford University Press, Mar. 22, 2012 (table of contents only).
Logothetis, N.K. "What we can do and what we cannot do with fMRI," Nature, vol. 453(7197), Jun. 12, 2008, pp. 869-878.
López-Sanz, D. et al., "Magnetoencephalography applied to the study of Alzheimer's disease," Progress in Molecular Biology and Translational Science, vol. 165, 2019, pp. 25-61.
Mason, J.W. et al., "Recommendations for the Standardization and Interpretation of the Electrocardiogram," Circulation, vol. 115, Iss. 10, Feb. 23, 2007, pp. 1325-1332.
Medina, R. et al., "Electrophysiological Brain Changes Associated with Cognitive Improvement in a Pediatric Attention Deficit Hyperactivity Disorder Digital Artificial Intelligence-Driven Intervention: Randomized Controlled Trial," Journal of Medical Internet Research, vol. 23, No. 11:e25466, Nov. 2021, pp. 1-18.
Nunez, P. et al., "Electric Fields of the Brain: The Neurophysics of EEG," Second Edition, Oxford, UK: Oxford University Press, 2006 (table of contents only).
Poldrack, R.A., "Inferring Mental States from Neuroimaging Data: From Reverse Inference to Large-Scale Decoding," Neuron, vol. 72, No. 5 Dec. 8, 2011, pp. 692-697.
Ramirez, S. et al., "Creating a False Memory in the Hippocampus," Science, vol. 341(6144), Jul. 26, 2013, pp. 387-391.
Sherkow, J.S., "CRISPR: Pursuit of profit poisons collaboration," Nature, vol. 532(7598), Apr. 14, 2016, pp. 172-173.
Vogel, J.W. et al., "Four distinct trajectories of tau deposition identified in Alzheimer's disease," Nature Medicine, vol. 27(5), Apr. 29, 2021, pp. 871-881.
Wang, Y. et al., "Viral vectors as a novel tool for clinical and neuropsychiatric research applications," General Psychiatry 31(2), Oct. 2018, pp. 1-9.

* cited by examiner

MMS: 30  
onset B: 100 ms

MMS: 30  
onset B: 95 ms

P017    P019

NV

MMS: 21  
onset B: 128 ms

MMS: 23  
onset B: 120 ms

P015    P024

CI

METHODS AND MAGNETIC IMAGING DEVICES TO INVENTORY HUMAN BRAIN CORTICAL FUNCTION

CROSS REFERENCE TO RELATED APPLICATION

This application claims benefit to U.S. Provisional Application No. 62/828,687, filed on Apr. 3, 2019, entitled "Methods and Magnetic Imaging Devices to Inventory Human Brian Cortical Function," which is hereby incorporated by reference in its entirety for all purposes.

FIELD OF THE ART

The present description is directed to the field of medical imaging. More particularly, this description pertains to systems and methods of detecting and evaluating electromagnetic activity in the brain.

BACKGROUND

Despite rapidly increasing societal burden, progress in developing treatments for neurodegenerative disorders, such as Alzheimer's disease ("AD"), remains slow.

Part of the challenge in developing effective therapeutic agents is the requirement that the molecule cross the blood-brain barrier ("BBB") in order to engage a disease-relevant target. Another challenge, particularly relevant to efforts to develop disease-modifying agents, is the need for noninvasive techniques that can repeatedly be used to monitor disease status and progression. Although several imaging approaches have been used to monitor efficacy of potential disease-modifying antibodies in AD clinical trials—notably positron emission tomography ("PET") detection of β-amyloid plaque burden—these radioisotopic imaging techniques detect a presumptive pathophysiological correlate of disease and do not directly measure the primary symptom, the loss of cognitive function.

Existing approaches to measuring brain function are likewise poorly suited to monitoring neurodegenerative disease status and progression.

Cerebral cortex functional imaging approaches currently in clinical use do not image neural function directly: functional magnetic resonance imaging ("fMRI") images blood flow; positron emission tomography ("PET"), when used to monitor glucose consumption, images metabolism.

In addition, there can be a mismatch between the temporal resolution of certain functional imaging approaches and the duration of signaling events in the brain. fMRI, for example, is sensitive on a time frame of seconds, but normal events in the brain occur in the time frame of milliseconds ("msec"). Although electroencephalography ("EEG") is sensitive to events in a millisecond time frame, unpredictable signal attenuation by the tissues that surround the brain cause both near and far signals to be commingled. This problem is compounded when there are multiple current sources (e.g., both primary and secondary cortical sources).

There thus exists a need in the art for noninvasive techniques for imaging brain cortical function that can be used to detect and monitor changes in function. There is a particular need for noninvasive functional imaging approaches that can be used to detect, stage, and monitor progression of neurodegenerative disorders with statistically significant classification accuracy.

SUMMARY

In using magnetoencephalography ("MEG") to detect cognitive impairment (CI), we have discovered that statistically meaningful differences between normal and diseased brain responses to a repeated stimulus are found in the relative presence and intensity of certain parameters, which may also be referred to as features, in an individual's evoked responses across multiple distinct evoked responses; this distributional information has previously been discarded in an early step of signal analysis through signal processing. Accordingly, we have now developed models that are capable of noninvasively detecting, staging, and monitoring progression of neurodegenerative disorders with statistically significant classification accuracy.

The models separate patients having a cognitive dysfunction from patients with a normal cognitive function based on test MEG data collected from test patients' brain activity. The models are developed by collecting model MEG data from a pool of test patients having a range of cognitive function states that have been preferably objectively evaluated by an alternative protocol such as the Mini Mental State Exam ("MMSE"). The model MEG data is collected using at least one superconducting quantum interference device ("SQUID") sensor detecting signals from the brain of test patients under a data collection protocol. The MEG measures the relative extent of brain activation, excitation, and/or response. The MEG data from at least one SQUID sensors, generally no more than one, or generally no more than a handful, is subsequently analyzed. Candidate parameters in the form of differences between the MEG scans of dysfunctional test patients and normal test patients are identified. The candidate parameters are developed to quantify these differences and to show that the activation, excitation, and/or response occurs progressively differently with progressive cognitive dysfunction. Specific ones of the candidate parameters are then selected for inclusion in one of the models as model parameters. Data science techniques of varying complexity, from regressions to machine learning and deep learning algorithms, are used to train the model for use in recognizing, quantifying, and categorizing patients outside the test set.

As a specific example, a CI model is able to separate test patients with normal cognitive function from those with cognitive dysfunction characteristic as measured by one or more psychiatric tests. To train the models, MEG with a set of SQUID sensors is used to detect signals from the brain following an auditory stimulus in a set of test patients. The test patients have a range of cognitive function states that have been preferably objectively evaluated by an alternative protocol. The MEG measures, after an auditory stimulus, the relative extent of brain activation/excitation and subsequent response to the activation. Subtle differences between the MEG scans of CI test patients (cognitively impaired test patients) and "normal" (NV) test patients were identified. Discrete candidate parameters of the model MEG data were identified as model parameters and were developed to quantify these subtle differences. The models and their constituent model parameters have been shown to robustly distinguish between normal and CI patients, with performance varying from perfect categorization of the test patients downward depending on how many model parameters are used. In implementation, models may be built from among a range of possible model parameters, which concordantly have a range of performance in ability to distinguish normal and CI patients.

Other features and advantages of the present invention will be apparent from the following more detailed description, taken in conjunction with the accompanying drawings which illustrate, by way of example, the principles of the invention.

FIT. 36 shows example heatmaps of different subjects with epochs sorted based on the feature of signal similarity in C peak windows, according to an embodiment.

Figure 37:
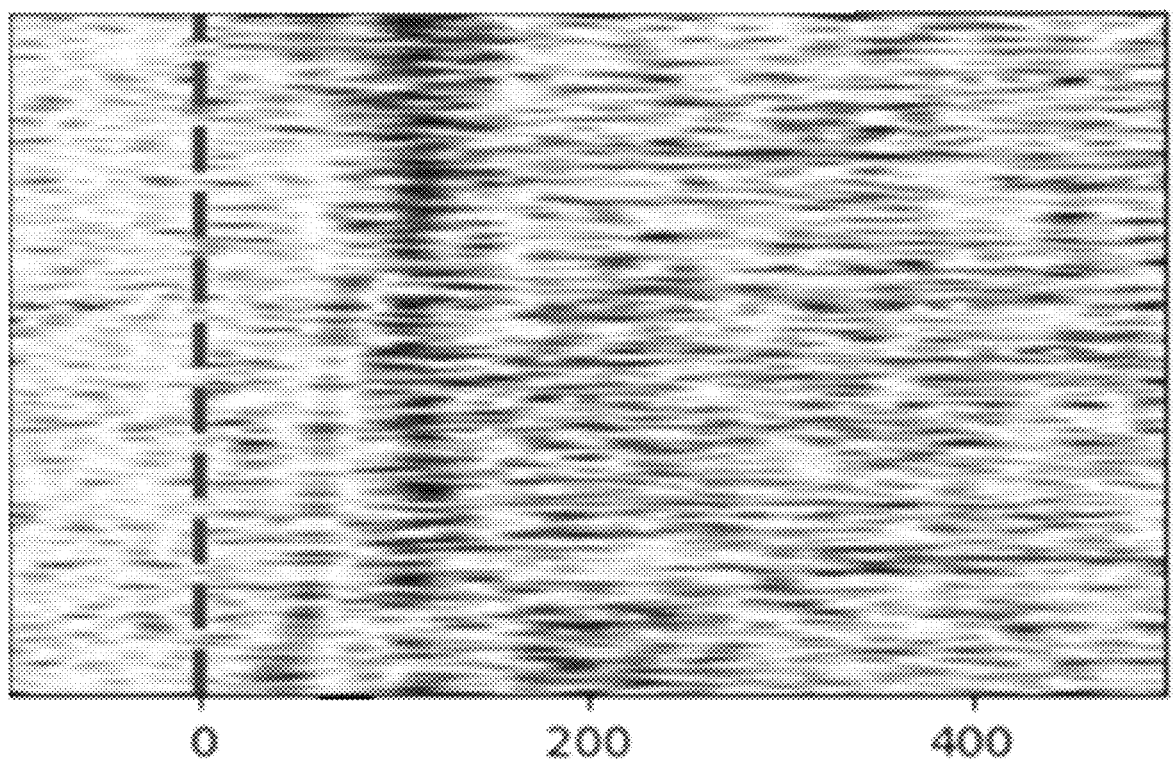

FIG. 37 is a heatmap of epochs from a first run sorted on the latency of the A peak for a patient exhibiting normal cognitive function.

Figure 38:
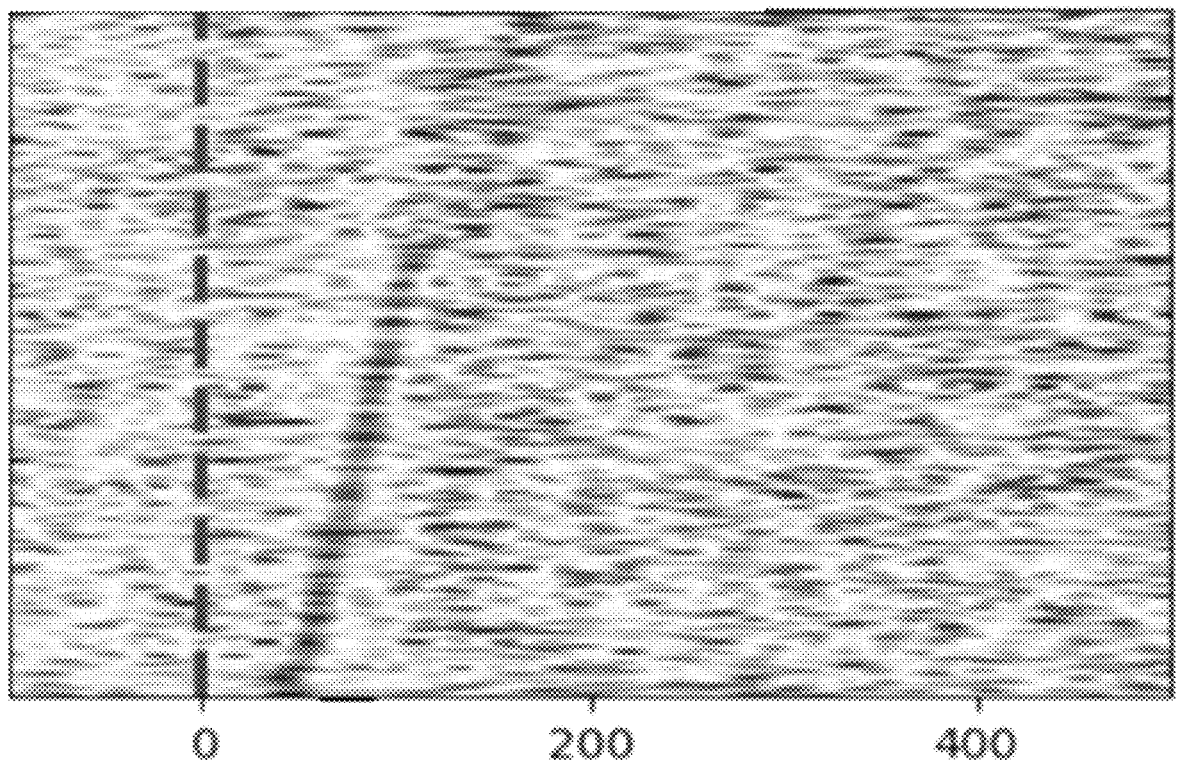

FIG. 38 is a heatmap of epochs from a first run sorted on the latency of the A peak for a patient exhibiting impaired cognitive function.

Figure 39:
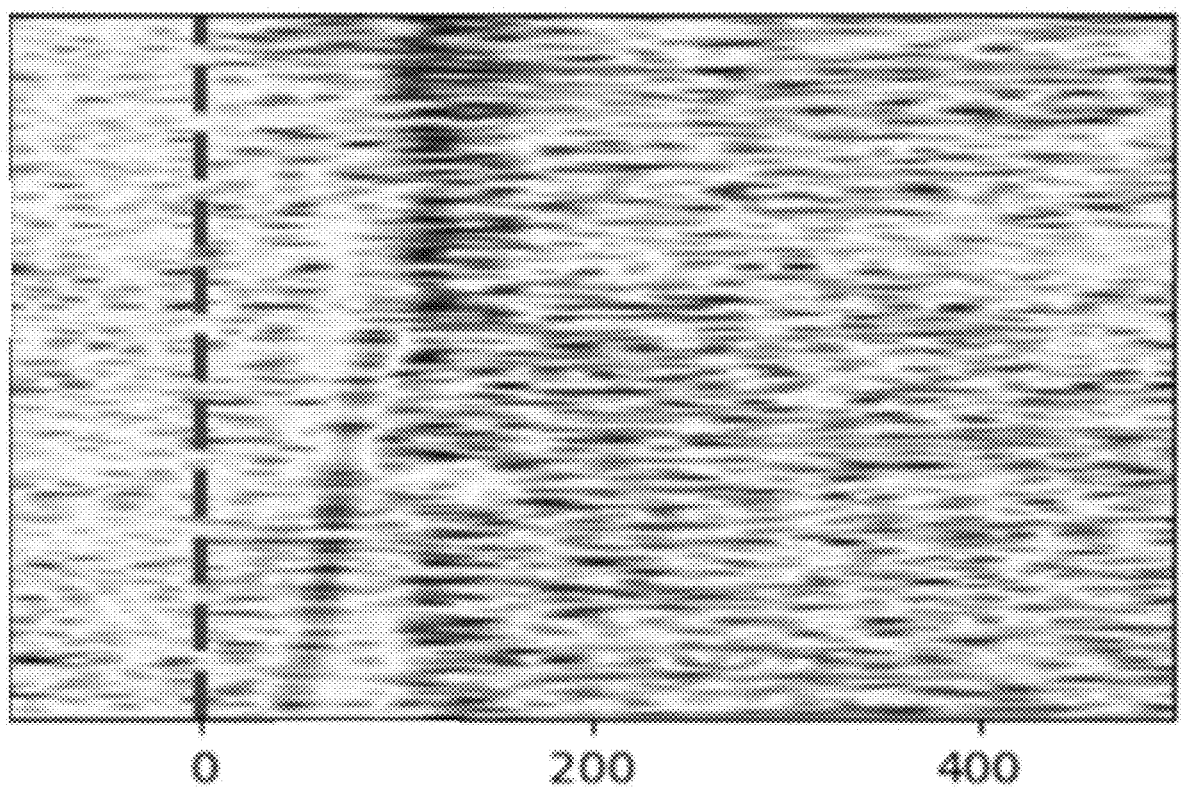

FIG. 39 is a heatmap of epochs from a second run sorted on the latency of the A peak for the patient exhibiting normal cognitive function.

Figure 40:
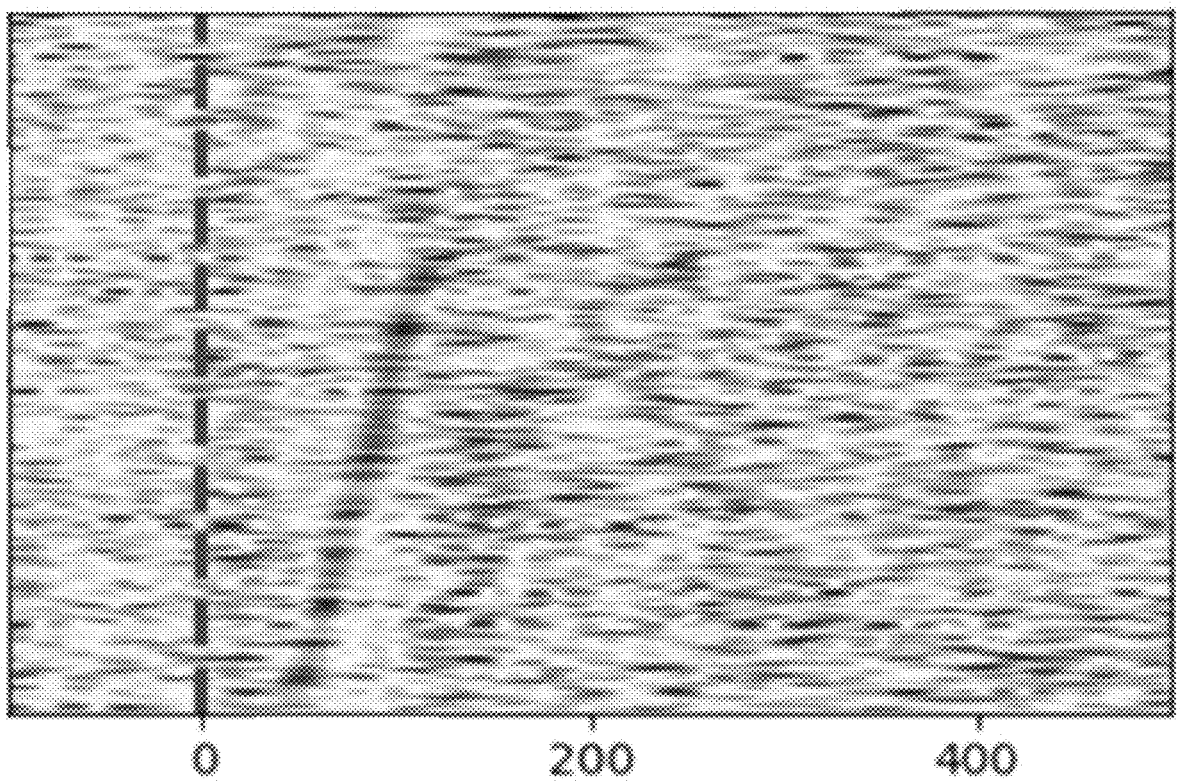

FIG. 40 is a heatmap of epochs from a second run sorted on the latency of the A peak for the patient exhibiting impaired cognitive function.

Figure 41:
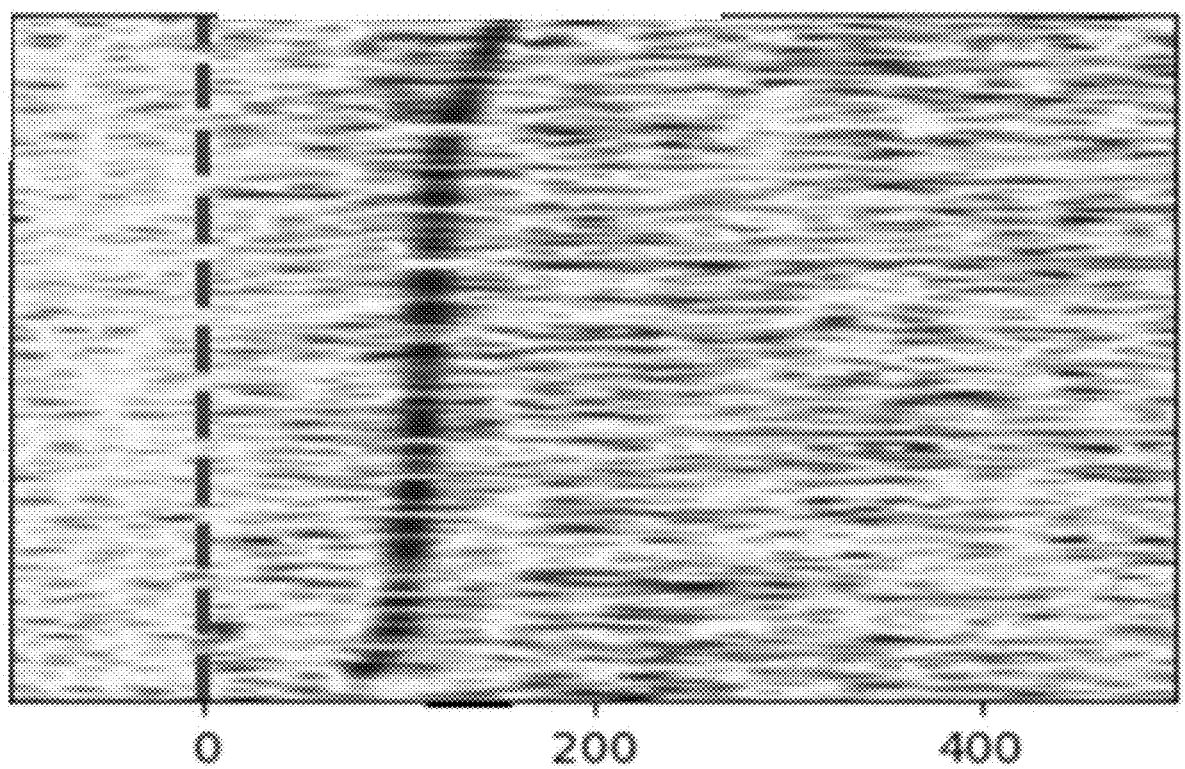

FIG. 41 is a heatmap of epochs from a first run sorted on the latency of the B peak for the patient exhibiting normal cognitive function.

Figure 42:
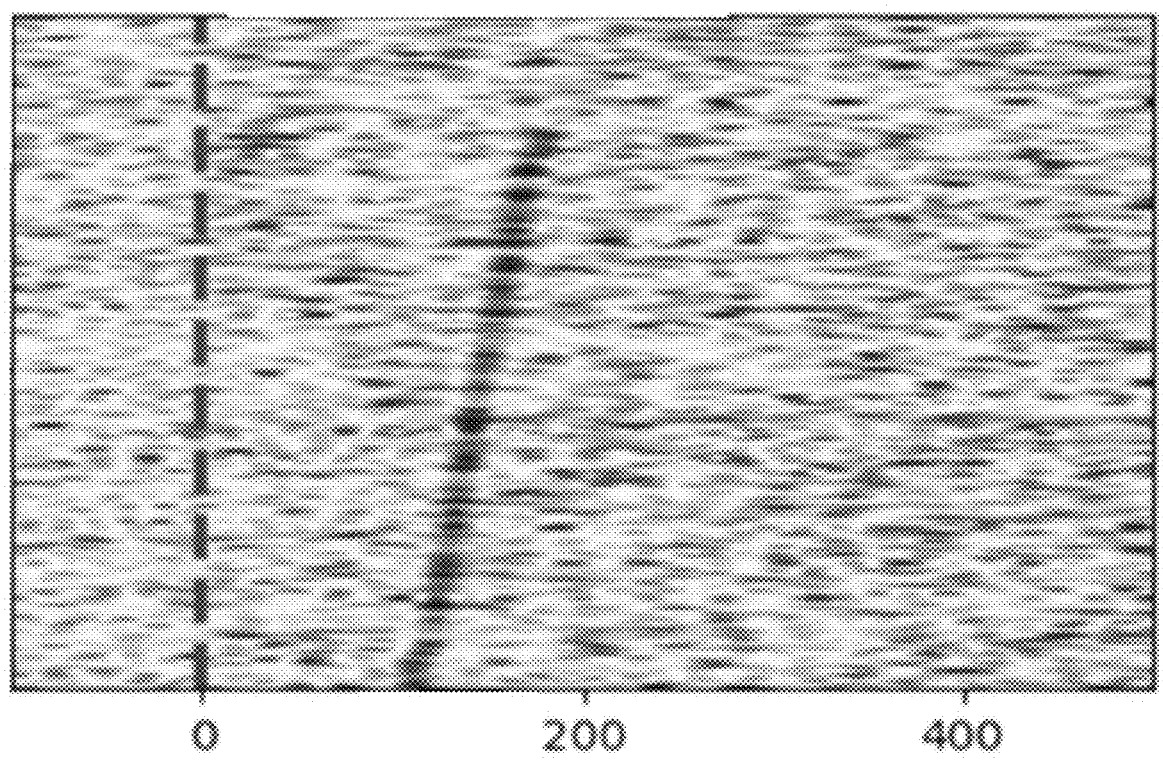

FIG. 42 is a heatmap of epochs from a first run sorted on the latency of the B peak for the patient exhibiting impaired cognitive function.

Figure 43:
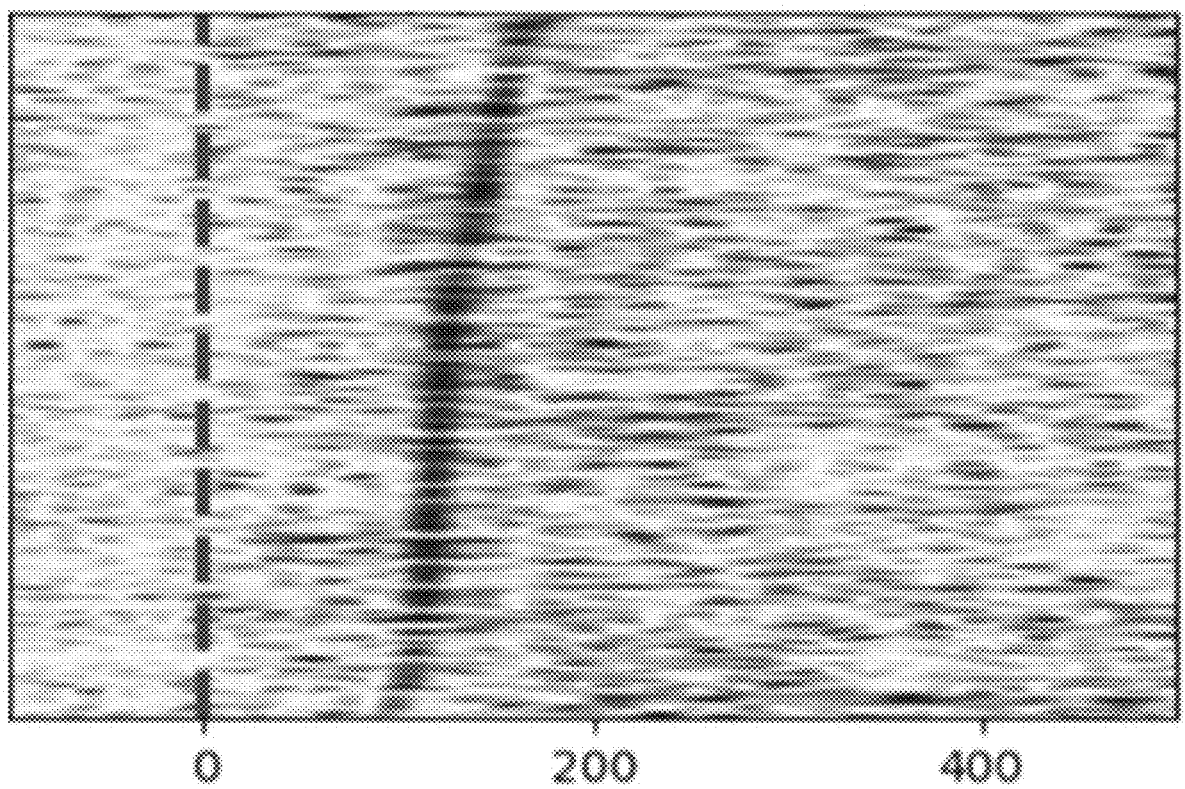

FIG. 43 is a heatmap of epochs from a second run sorted on the latency of the B peak for the patient exhibiting normal cognitive function.

Figure 44:
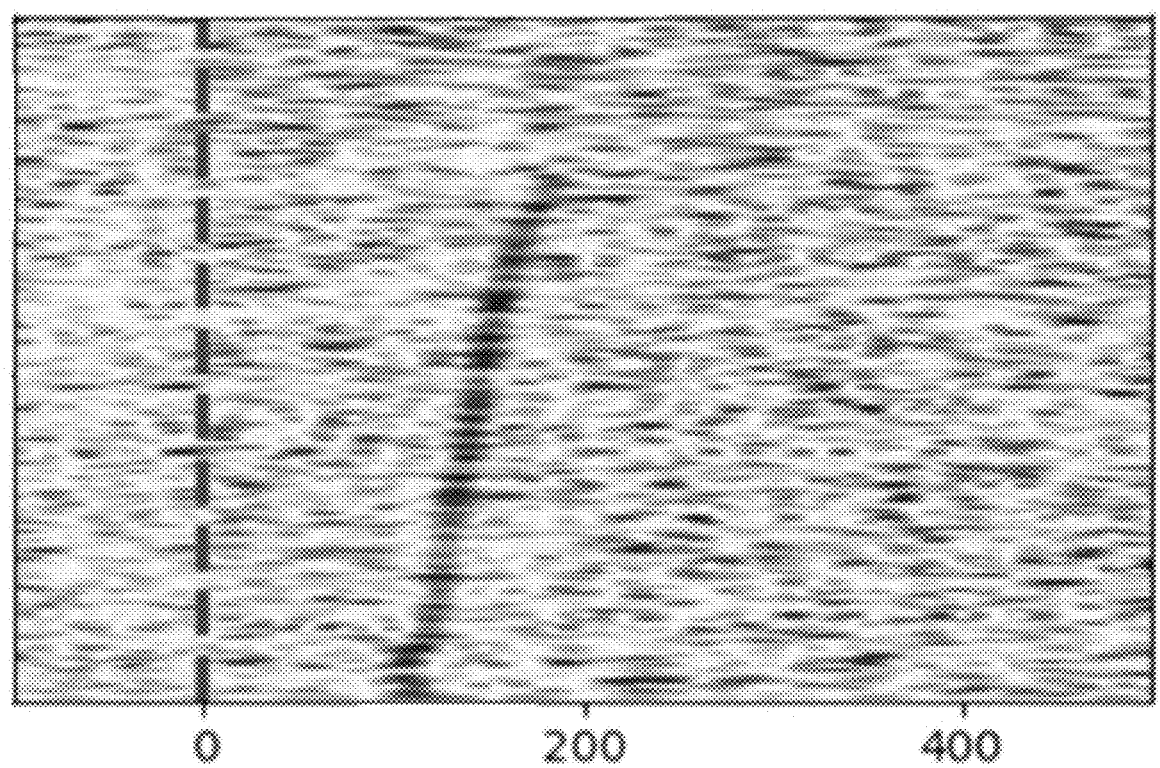

FIG. 44 is a heatmap of epochs from a second run sorted on the latency of the B peak for the patient exhibiting impaired cognitive function.

Figure 45:
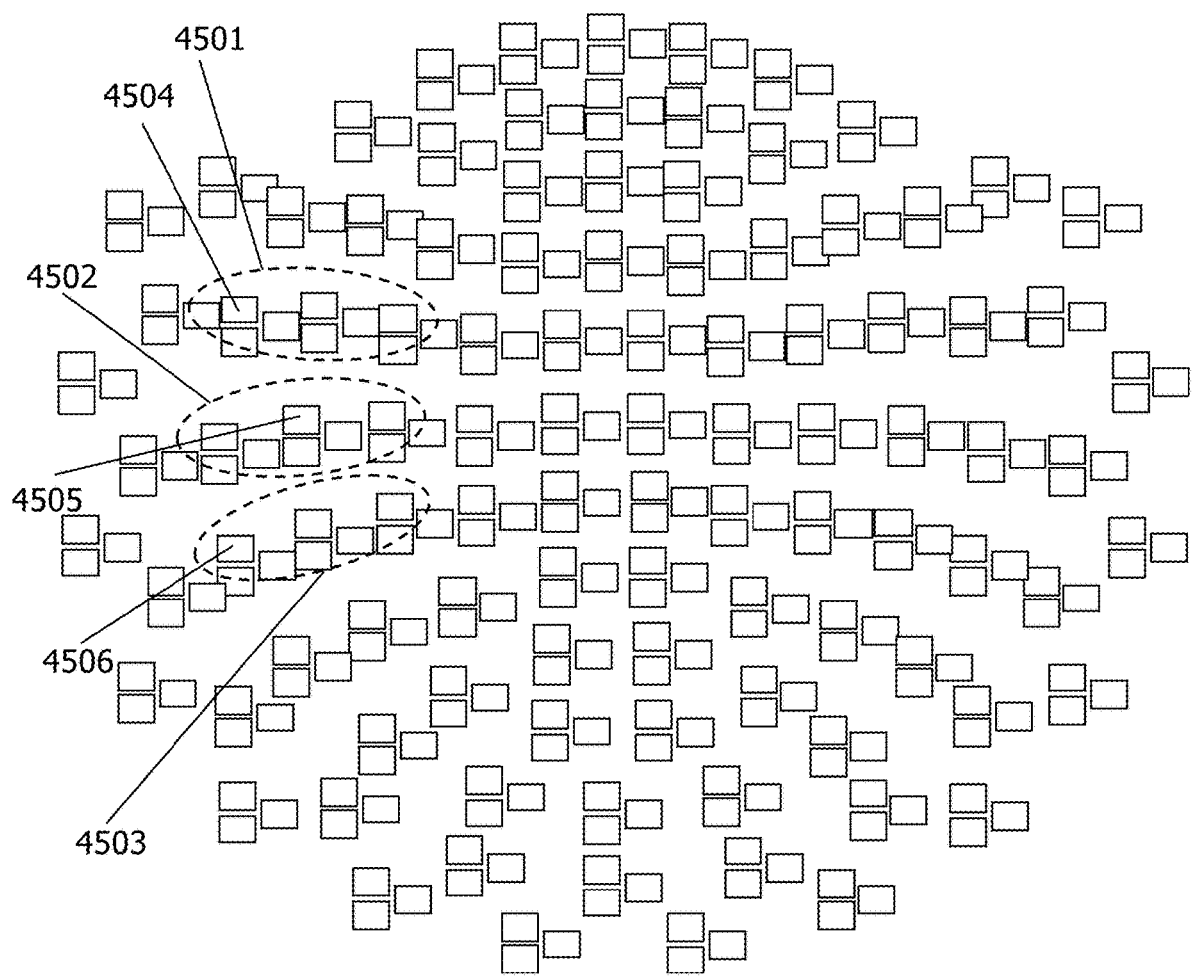

FIG. 45 shows schematically the relative locations of the magnetoencephalography (MEG) sensors from which the MEG data for certain heatmaps was drawn.

Figure 46:
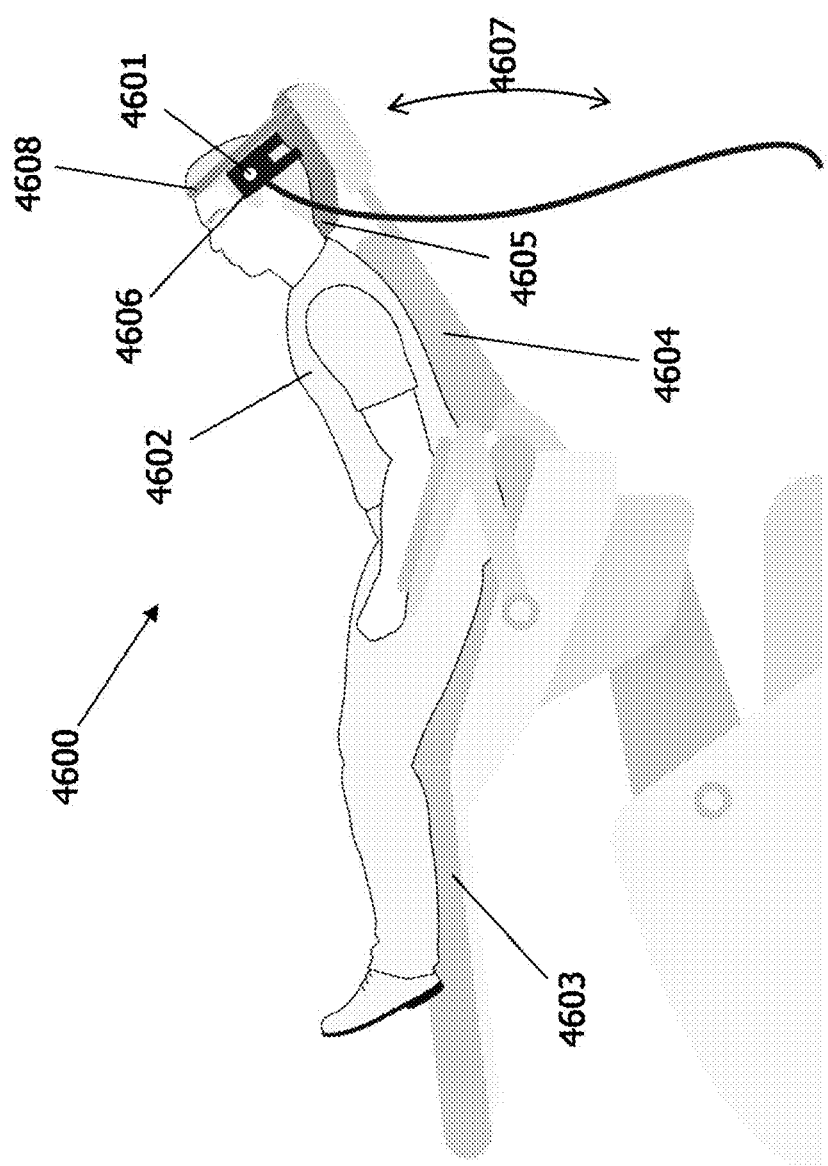

FIG. 46 shows schematically a side view of a MEG device in an embodiment of the present disclosure.

Figure 47:
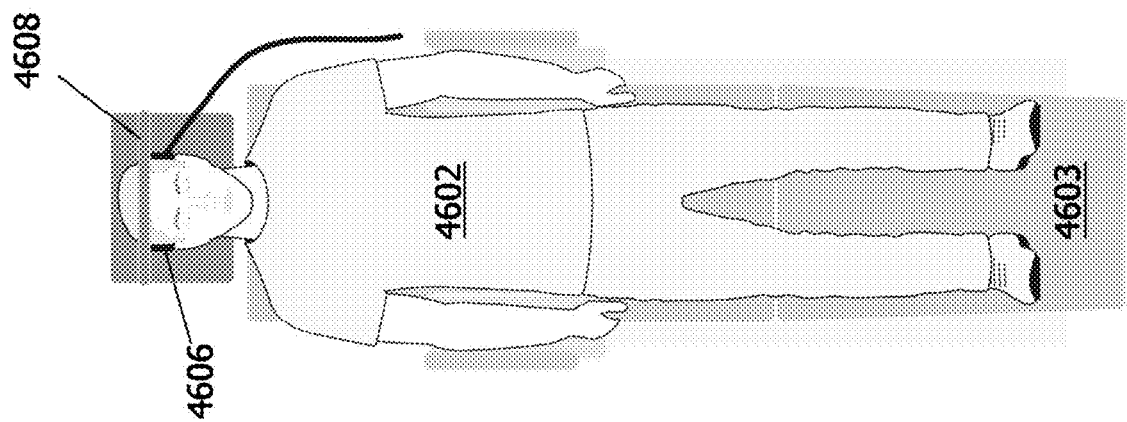

FIG. 47 shows schematically a top view of the MEG device of FIG. 46.

Figure 48:
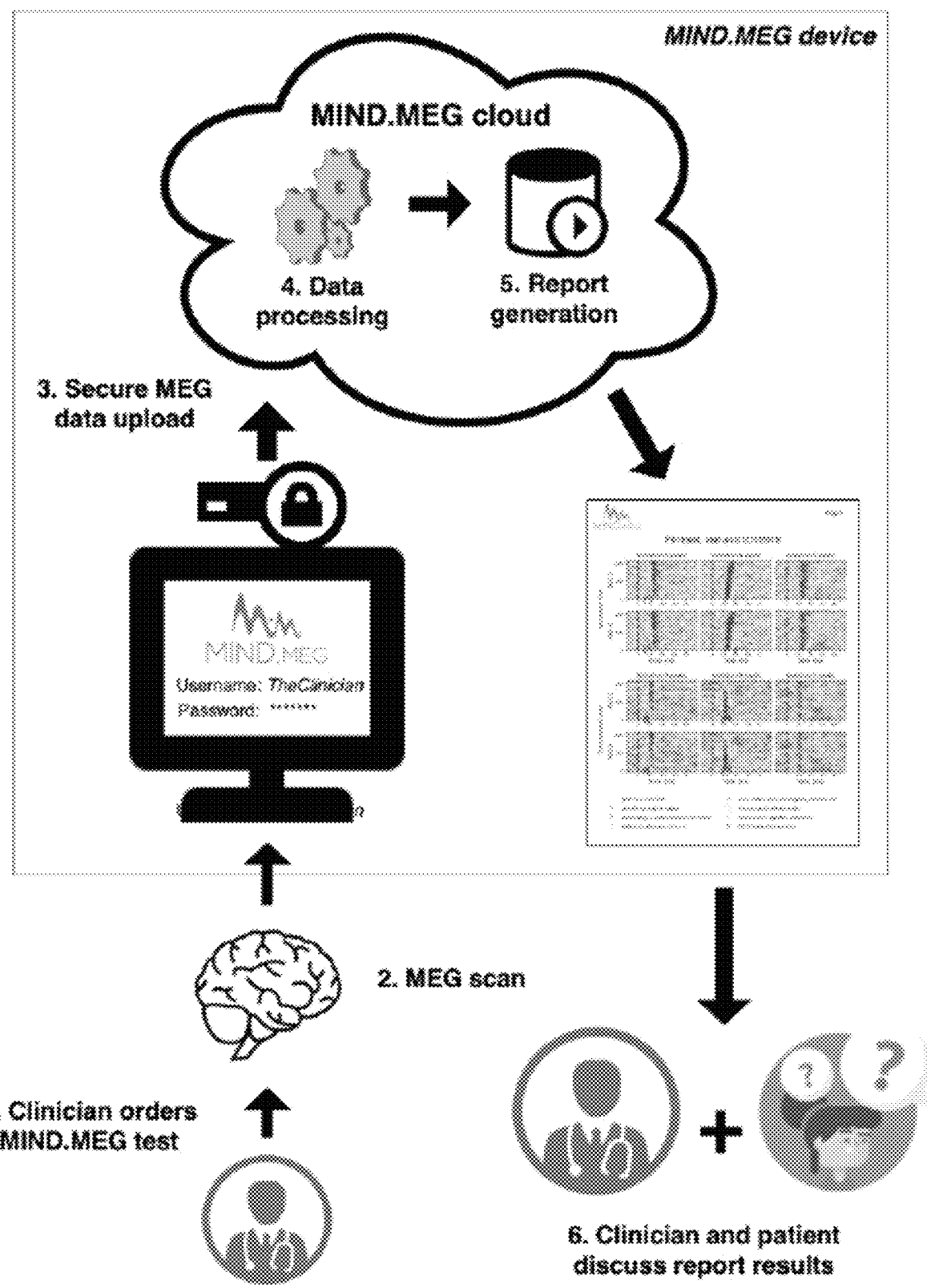

FIG. 48 shows schematically a process of inventorying human brain cortical function in an embodiment of the present disclosure.

Figure 49:
Figure 49:
Figure 49:
Figure 49:
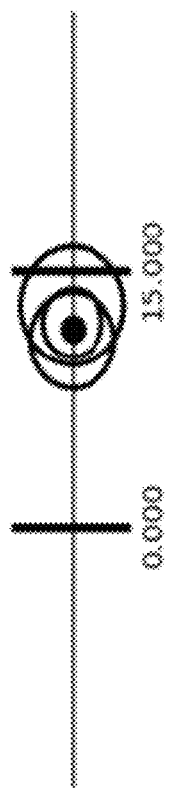

FIG. 49 shows schematically a partial display of a report of results of inventorying human brain cortical function in an embodiment of the present disclosure.

Figure 50:
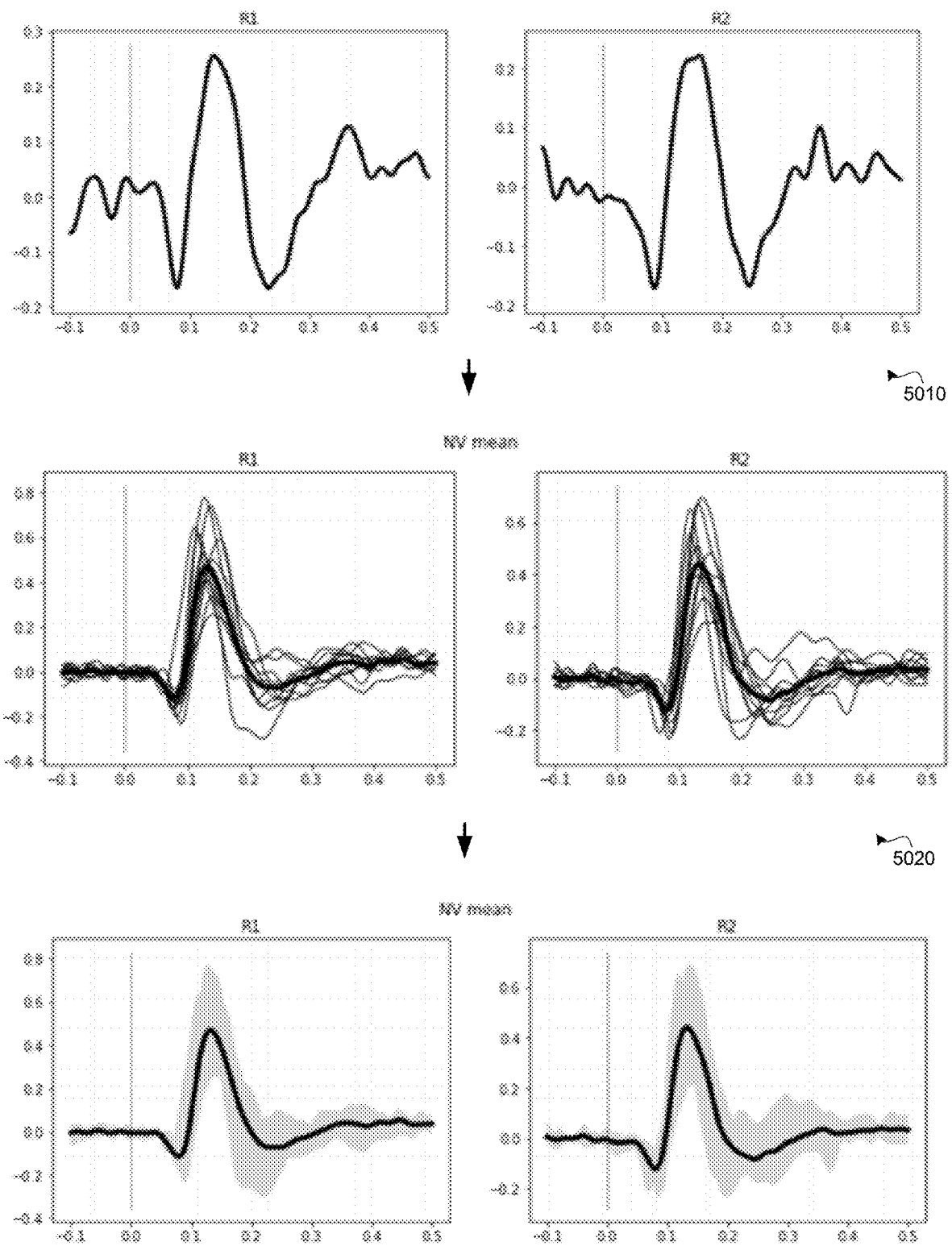

FIG. 50 is a conceptual diagram illustrating a computer-implemented process of generating a background of the normal range of evoked potential of normal volunteers, according to an embodiment.

Figure 51:
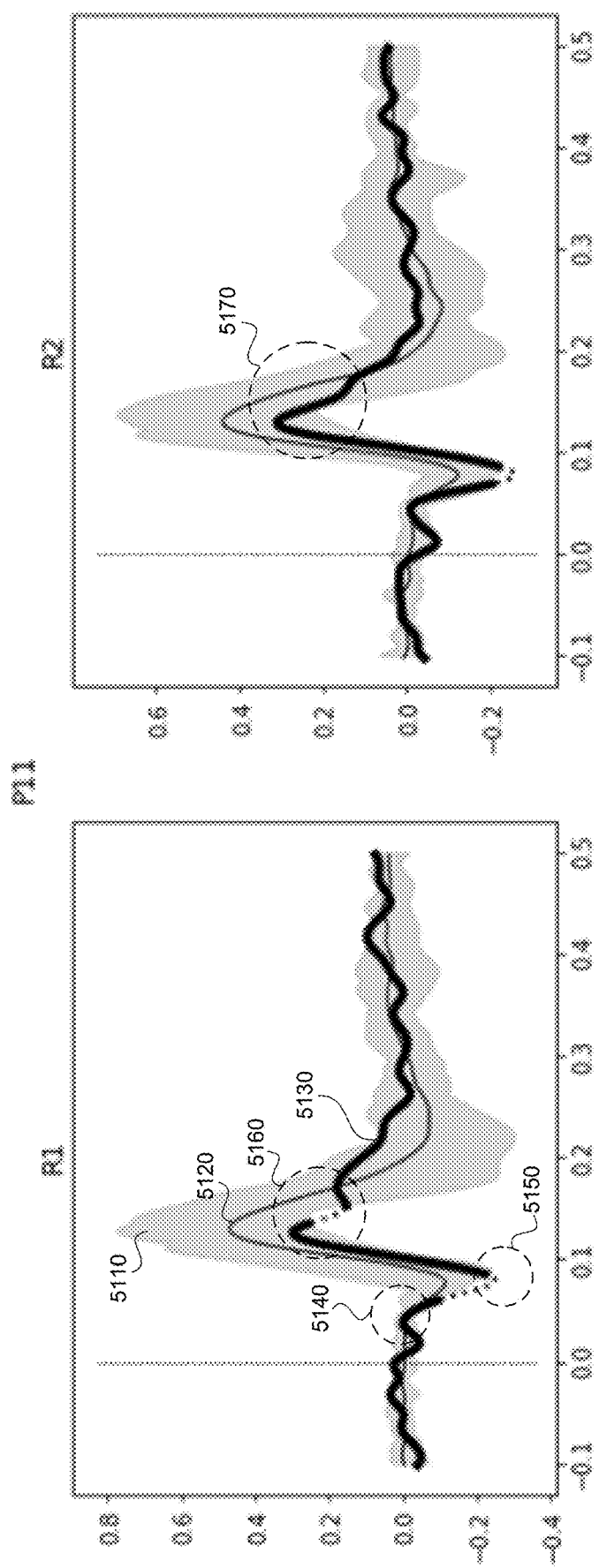

FIG. 51 shows two example summary plots of a test patient P11 for the first run and the second run.

Figure 52:
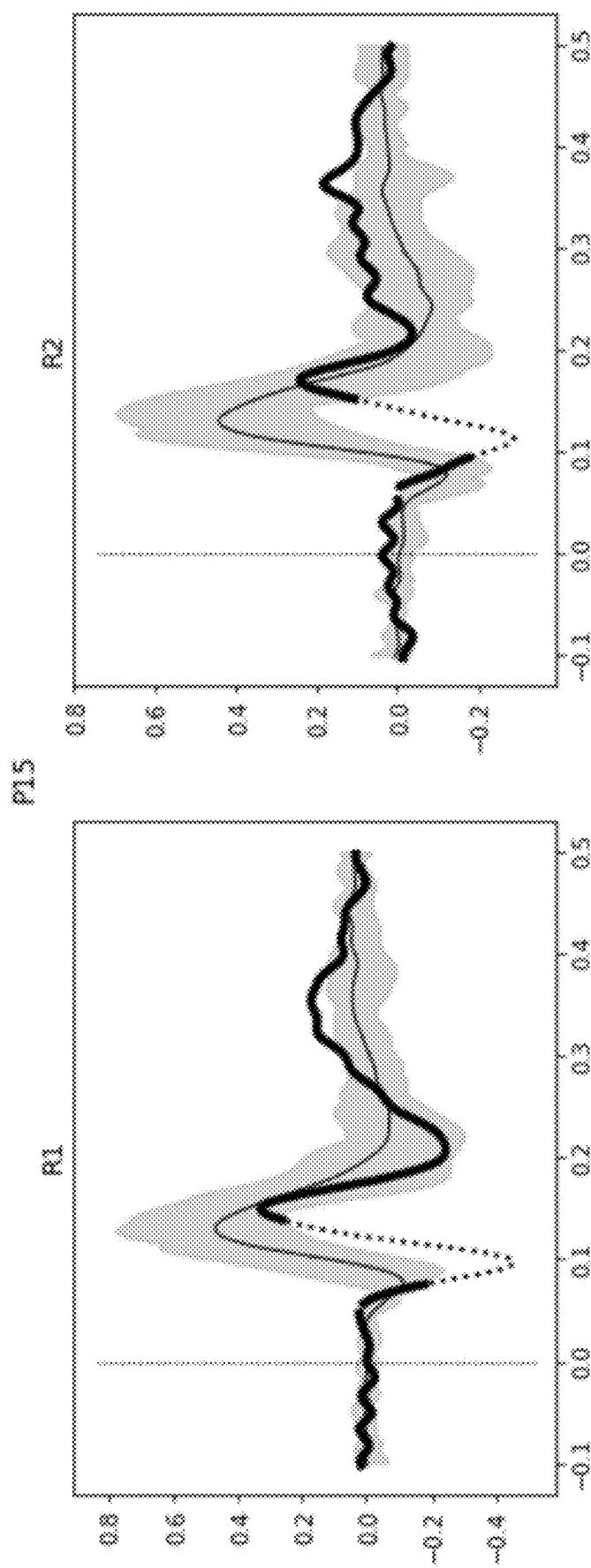

FIG. 52 shows two example summary plots of a test patient P15 for the first run and the second run.

Figure 53:
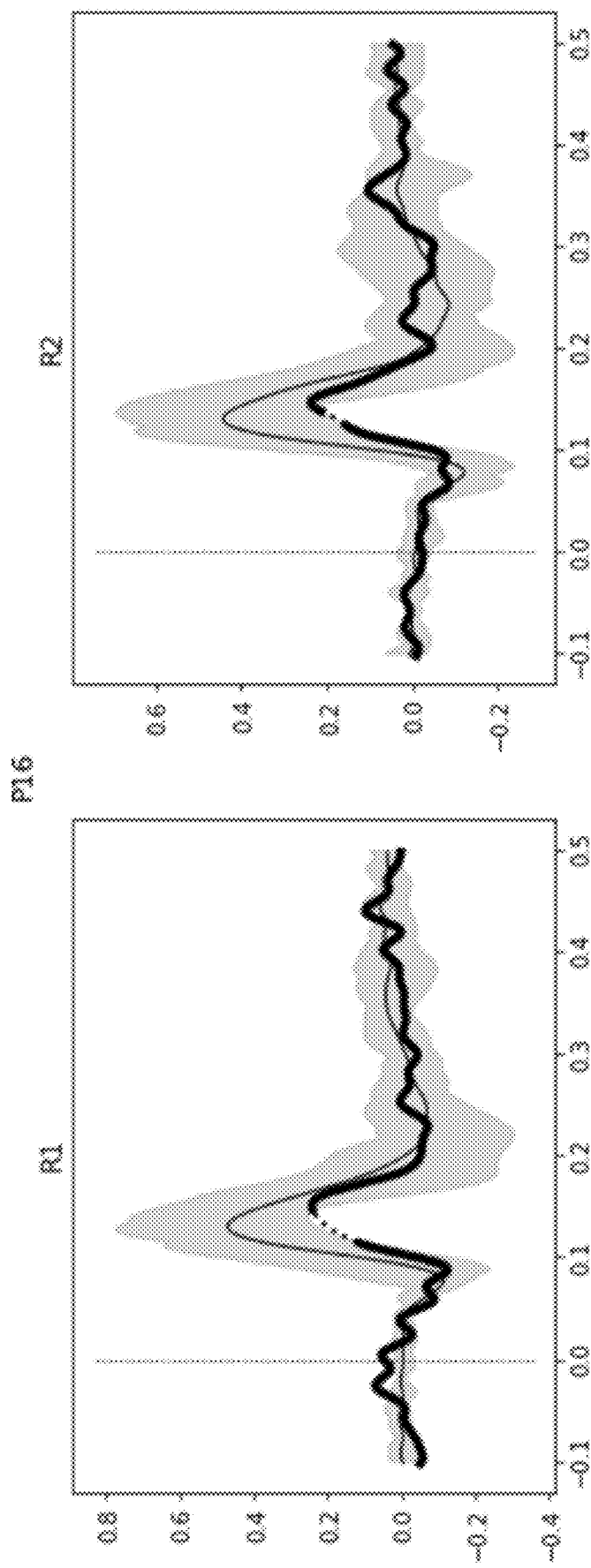

FIG. 53 shows two example summary plots of a test patient P16 for the first run and the second run.

Figure 54:
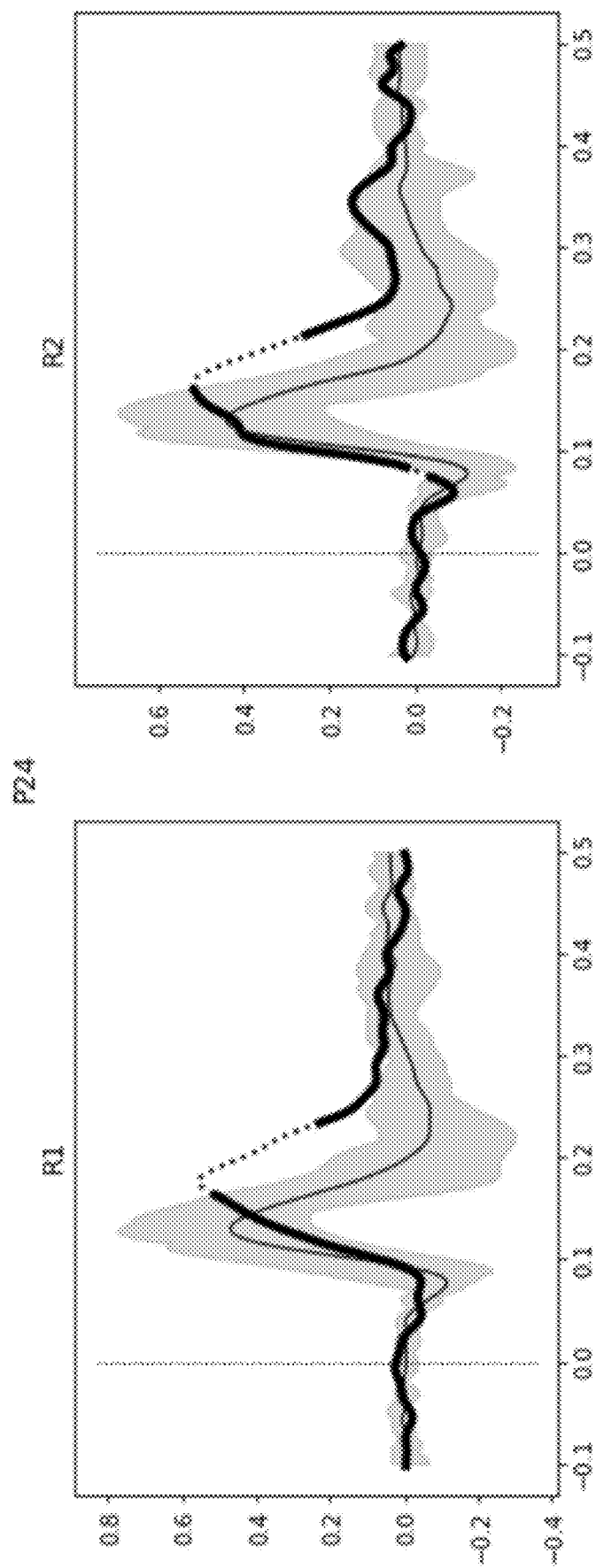

FIG. 54 shows two example summary plots of a test patient P24 for the first run and the second run.

Figure 55:
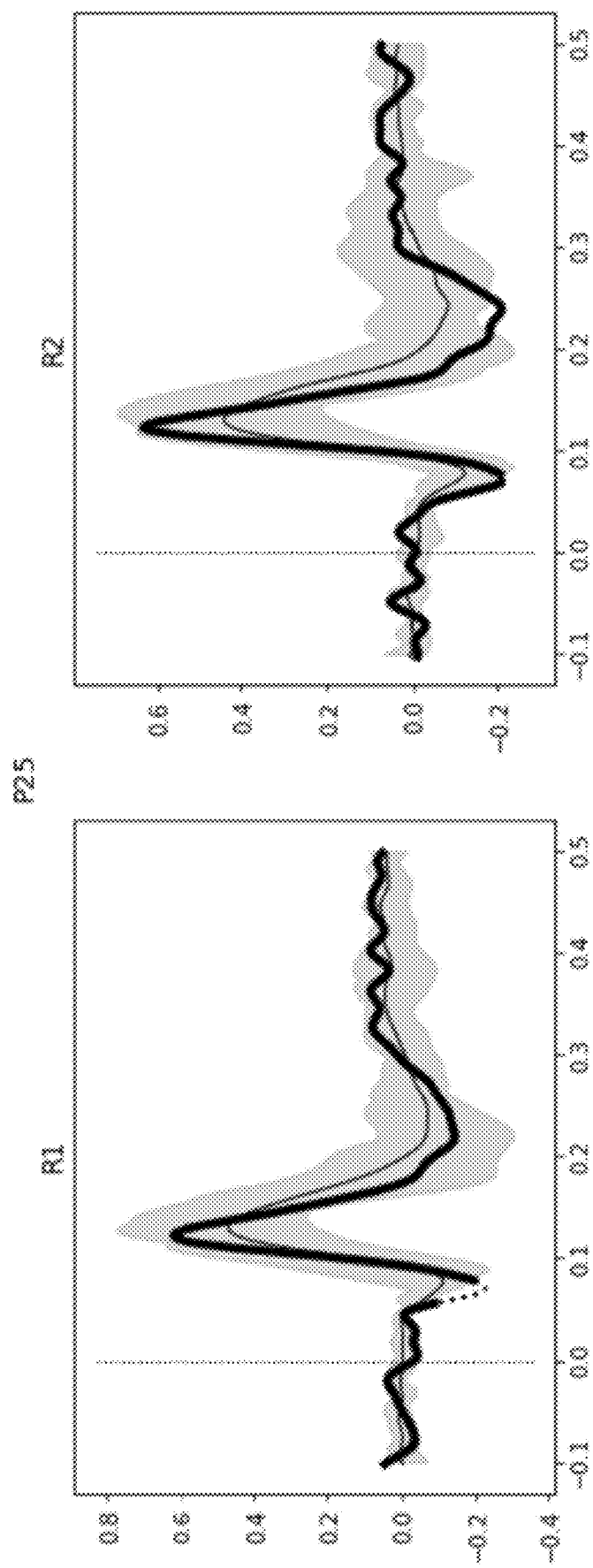

FIG. 55 shows two example summary plots of a test patient P24 for the first run and the second run.

Figure 56:
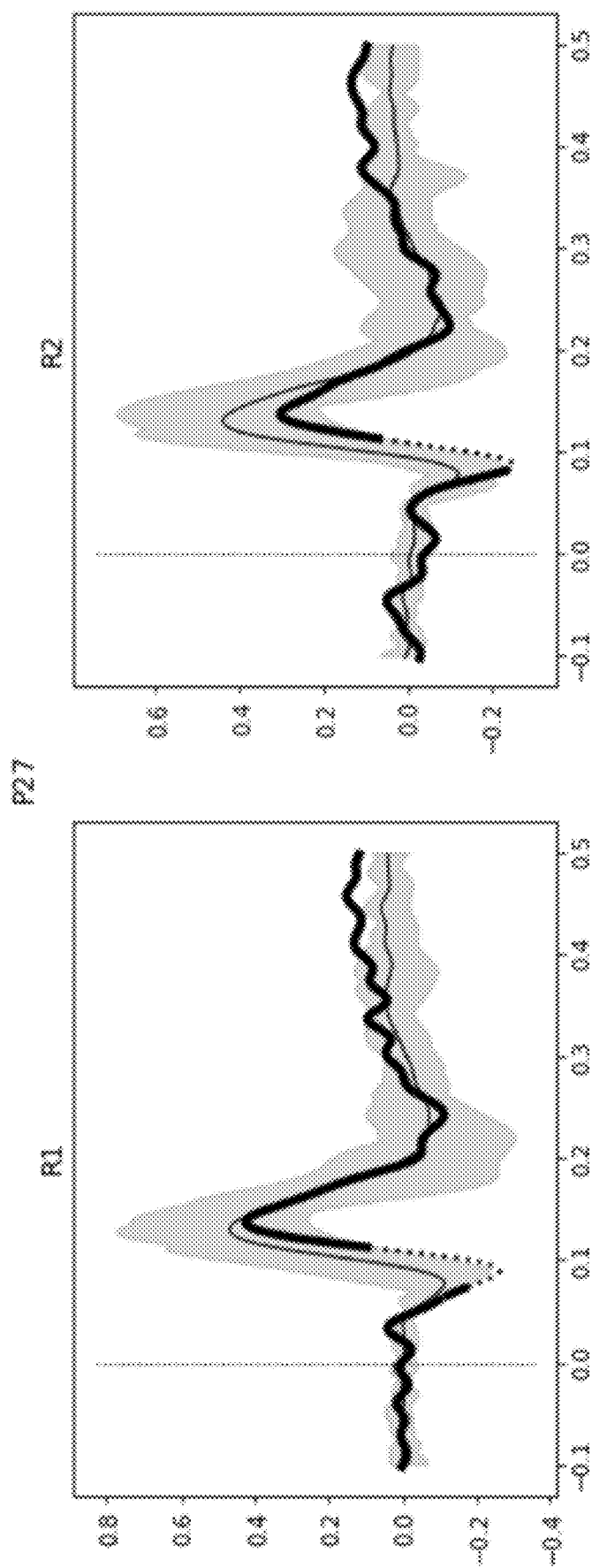

FIG. 56 shows two example summary plots of a test patient P27 for the first run and the second run.

Figure 57:
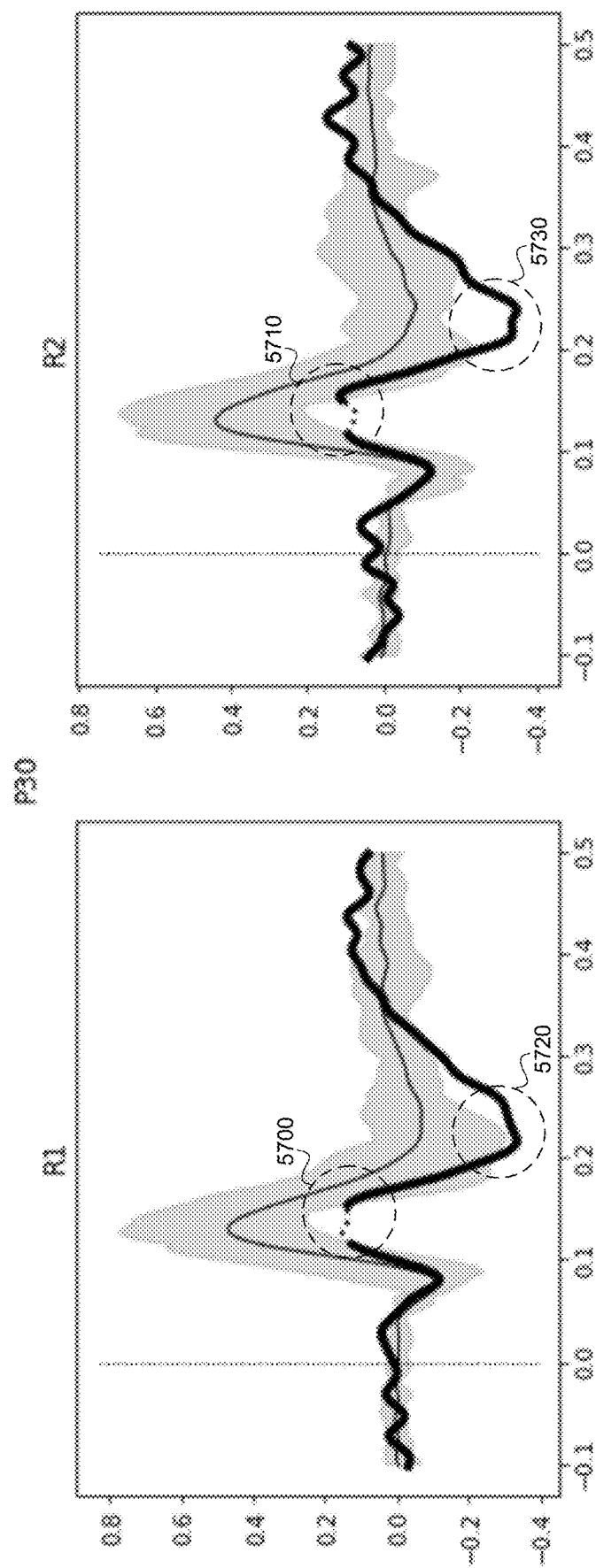

FIG. 57 shows two example summary plots of a test patient P30 for the first run and the second run.

Figure 58:
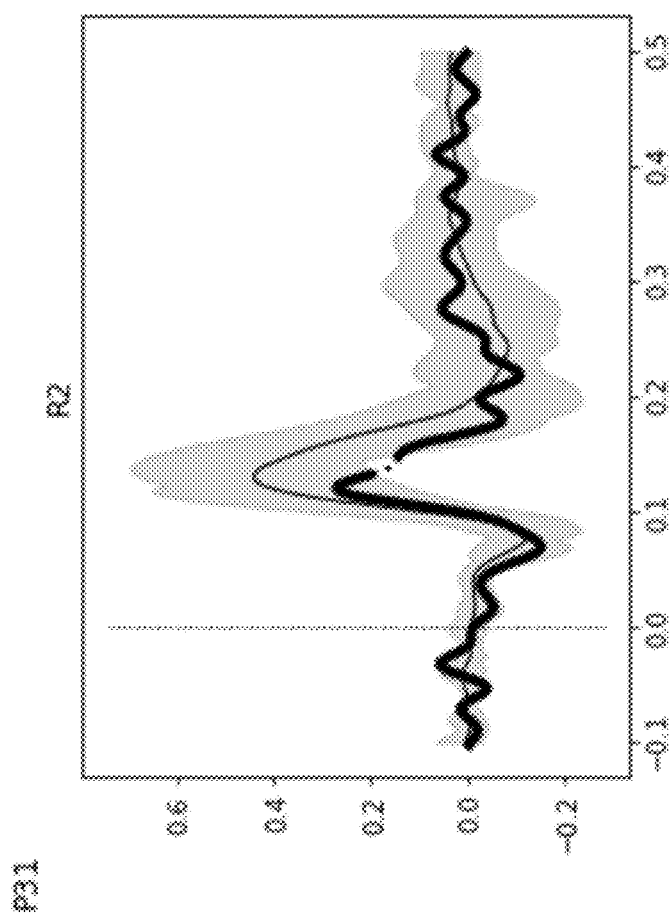
Figure 58:
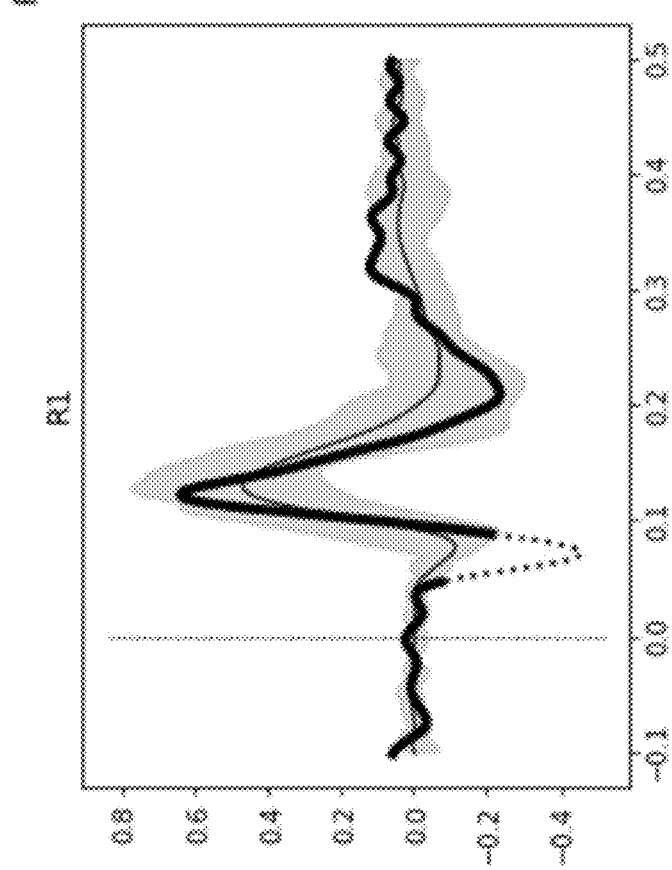

FIG. 58 shows two example summary plots of a test patient P31 for the first run and the second run.

Figure 59:
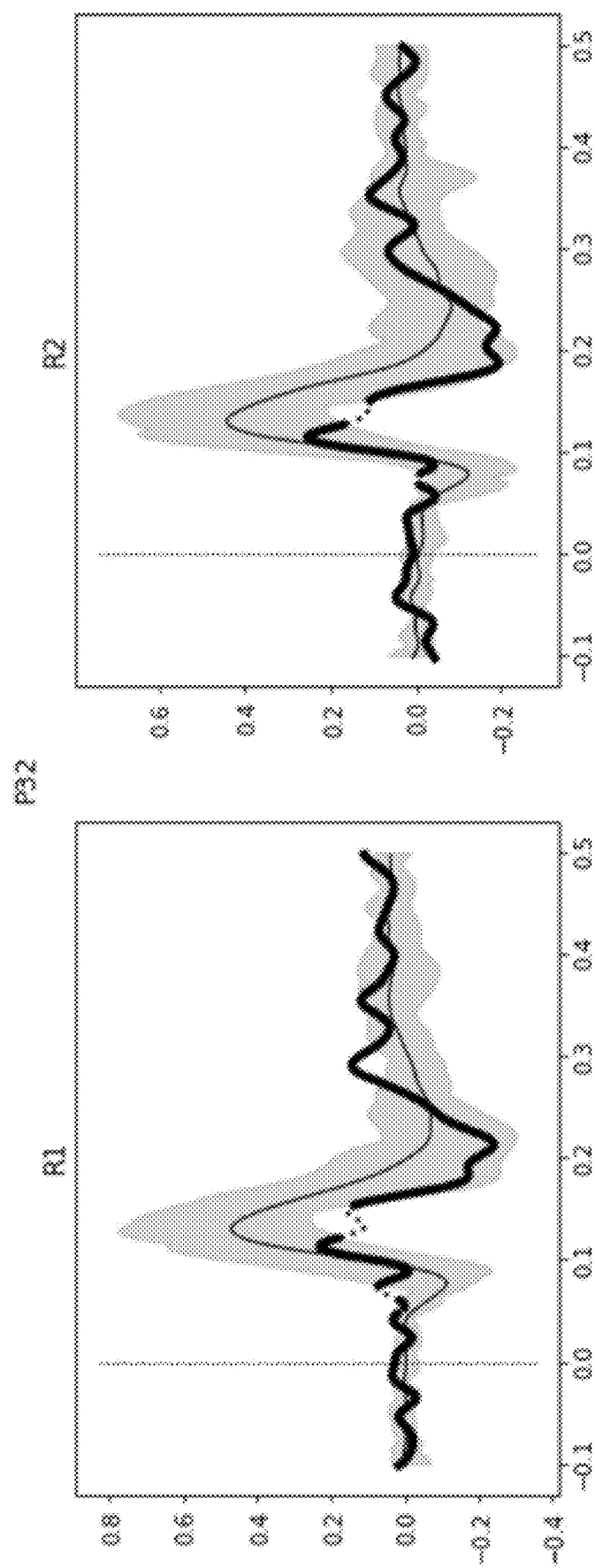

FIG. 59 shows two example summary plots of a test patient P32 for the first run and the second run.

Figure 60:
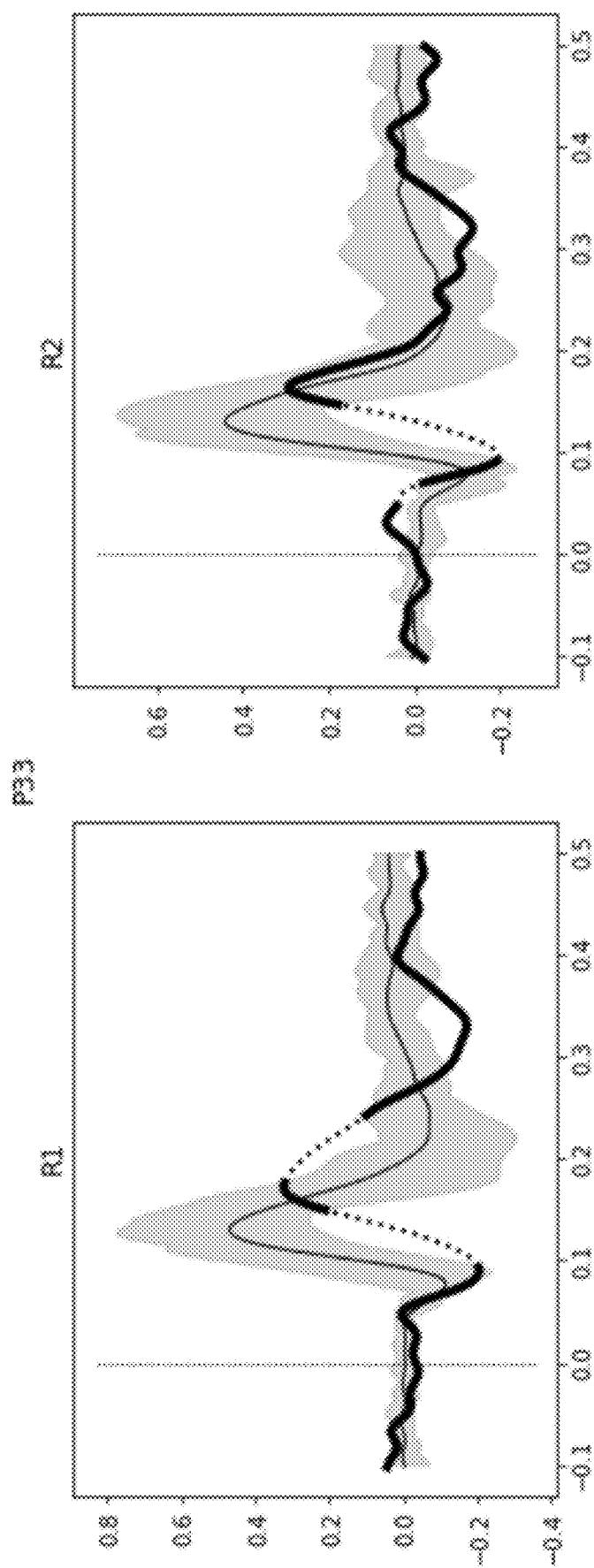

FIG. 60 show two example summary plots of a test patient P33 for the first run and the second run.

Wherever possible, the same reference numbers will be used throughout the drawings to represent the same parts.

DETAILED DESCRIPTION

I. Measurement Setup

Figure 1A:
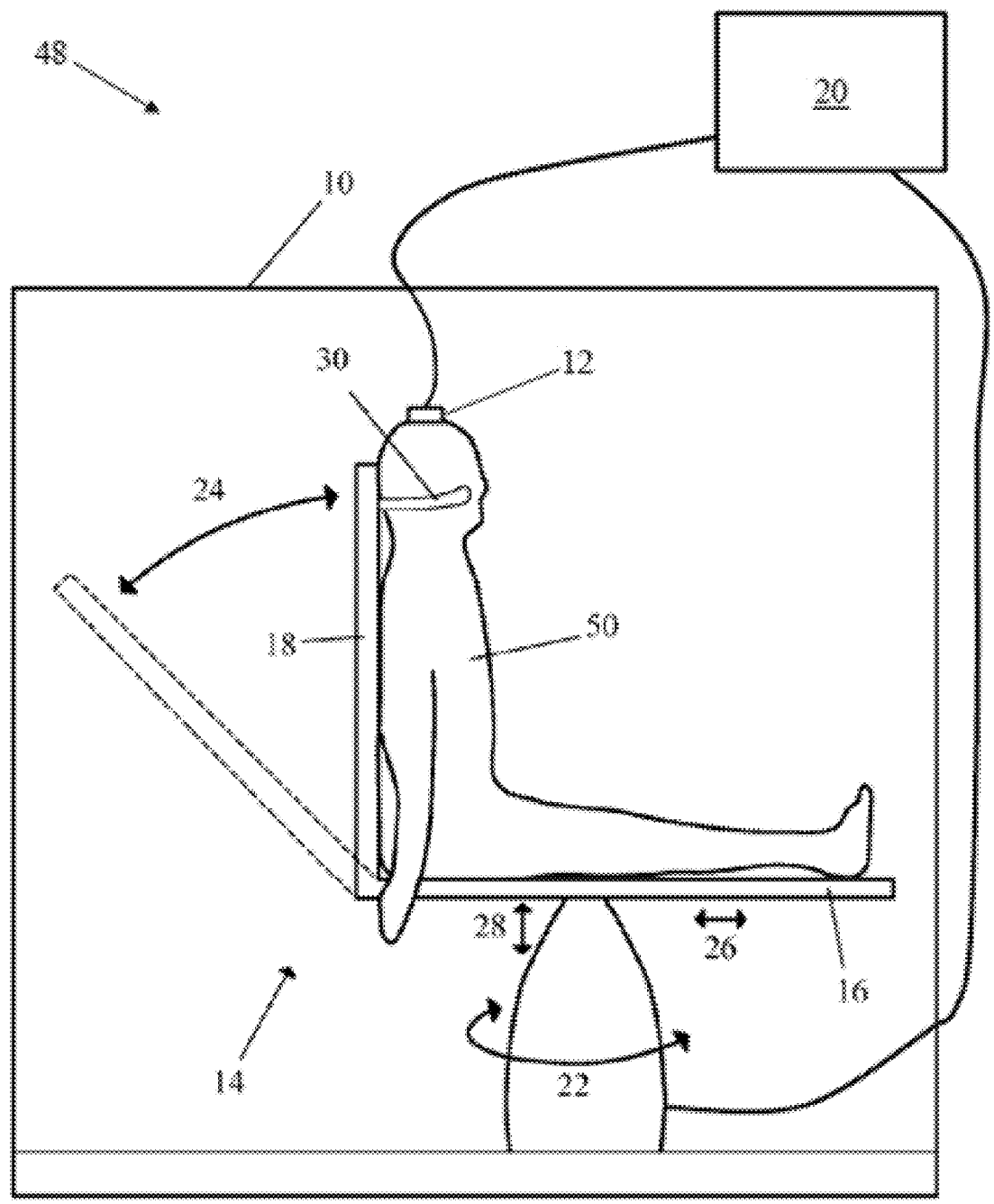
FIG. 1A shows schematically a test patient in a movable patient support device for a magnetoencephalography ("MEG") system in one embodiment.

FIG. 1A shows a Magnetoencephalography ("MEG") system 48 to detect electrical activity in the human brain, in the form of the magnetic fields generated by the electrical activity, according to one embodiment. A test patient 50 is seated in a patient support device 14. A Faraday cage 10 surrounds the test patient 50 and the patient support device 14 to block external environmental magnetic fields. The sensor head 12 and the associated Dewar housing 40 (see FIG. 1C) to cool the sensors 32 (see FIG. 1B) are fixed in space. The sensor head 12 and the patient support device 14 are in communication with and controlled by a computer 20, which is located outside the Faraday cage 10.

The patient support device 14 includes a seat portion 16 and a back portion 18. The patient support device 14 is rotatable 22 at least a full 360°, with the back portion 18 being reclinable 24, preferably from a vertical position to a position about 45° from vertical. The patient support device 14 is also controlled horizontally 26 and vertically 28 in order to maintain the sensor head 12 in contact with the head of the test patient 50, as the angle of inclination of the patient support device back 18 is simultaneously changed or the patient support device 14 is simultaneously rotated. The patient support device 14 also includes a head stabilizer 30 to maintain the head in a predetermined fixed position with respect to the patient support device back 18. The head stabilizer 30 contacts the cheeks of the test patient 50 to immobilize the cheek bones, thereby immobilizing the head.

The vertical, horizontal, rotational, and recline adjustments to the patient support device 14 may be automated and controlled by the computer 20. Alternatively, the adjustments may be manual or automated by the patient support device 14 itself. The SQUID electronics includes a monitor and a computer 20 with software for operation of the SQUID sensors 32 and control of the position of the patient support device 14. If the vertical, horizontal, rotational, and recline adjustments are done manually or independently of the computer 20, a location sensor may be used to determine the location of the head surface of the test patient 50 with respect to the SQUID sensors 32.

Figure 1B:
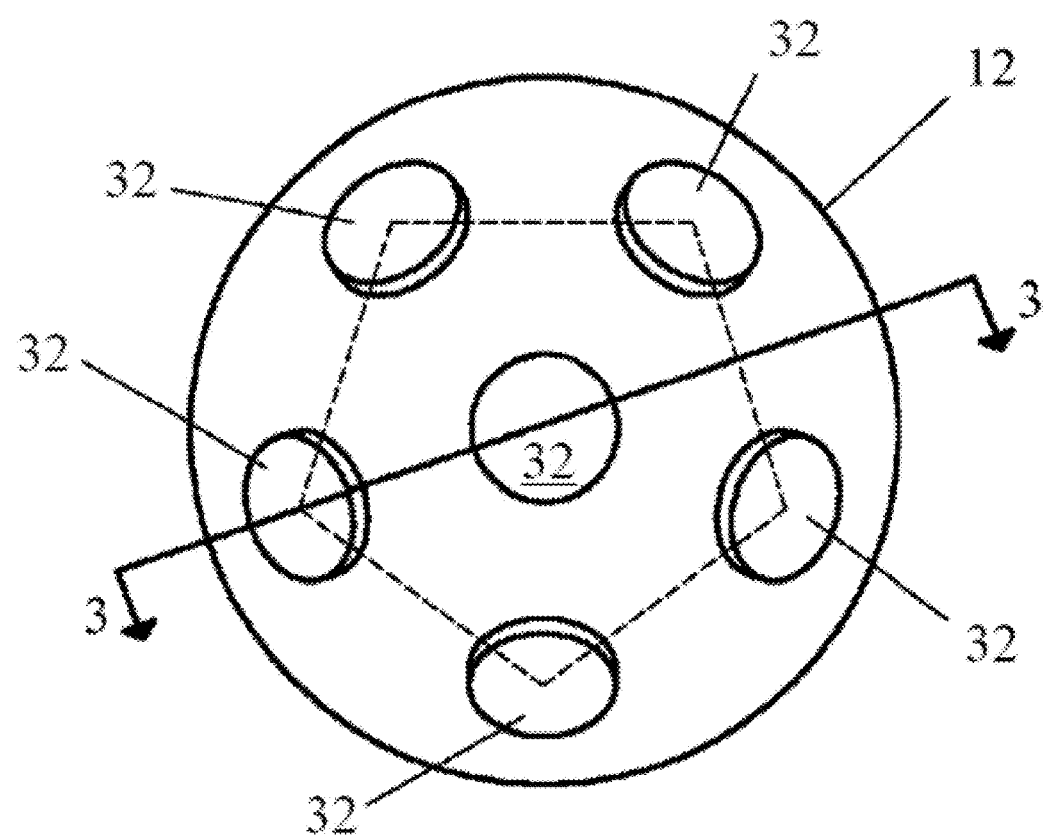
FIG. 1B shows schematically a top view of an example sensor head with an array of superconducting quantum interference device ("SQUID") sensors with the five surrounding sensors focused to an area about two to four centimeters below the central sensor in one embodiment.

FIG. 1B shows a top view of an example SQUID sensor head 12 with five SQUID sensors 32 in an array around a sixth central SQUID sensor 32, according to one embodiment. The central SQUID sensor 32 is flat with the five surrounding SQUID sensors 32 oriented at a fixed angle toward the central SQUID sensor 32. The fixed angle in FIG.

1B is about 45°. In other embodiments, other counts, orientations, and relative arrangements of SQUID sensors 32 may be used.

Although the measurement setup may comprise a currently manufactured MEG device such as an Elekta Neuromag® 306 channel (306 MEG sensor) MEG device with associated other hardware, the measurement setup may alternatively be an MEG device comprising fewer sensors and a relatively simplified measurement setup as will be further described below. This is advantageous for numerous reasons, one of which is cost. An Elekta Neuromag® 306 channel setup costs $2,000,000 at the time of this writing, whereas one embodiment of the simplified measurement setup would only cost approximately $200,000 at the time of this writing.

In some embodiments of a simplified measurement setup, the system preferably uses a single wire Faraday cage 10 for magnetic isolation. The Faraday cage 10 is a wire enclosure formed by a mesh of conducting material and blocks external static and non-static electric fields by canceling out their effects on the interior of the Faraday cage 10. The Faraday cage 10 surrounds the test patient 50 and sensor head 12.

In some embodiments of a simplified measurement setup, relatively few SQUID sensors 32, down to as few as a single sensor, are used, which reduces the equipment cost. One, two, three, four, five, six, seven, eight, or nine sensors may be used. In some embodiments, a movable patient support device 14, movable manually or by a software program, is used in conjunction with the relatively small array of SQUID sensors 32. This allows the brain region of interest (desired to be analyzed) to be precisely determined and defined (e.g., the superior temporal gyms). This helps ensure that those few SQUID sensors that are used are placed at a location around the brain identified as generating the signals desired to be analyzed. The small array SQUID sensor head 12 is lower in cost not only because of the reduced sensor count, but also because of commensurately reduced volume of liquid helium in a stationary Dewar housing 40 (see FIG. 1C) relative to the movable Dewar housing of, for example, the Elekta Neuromag® 306 system or equivalents. Further, by having SQUID sensors 32 that are not constrained to discrete, fixed locations with respect to the head of the test patient 50, the system described herein may also be able to provide significantly better images of the cortical region of interest relative to the more expensive system.

The patient support device 14 is non-magnetic and non-paramagnetic (ideally completely of plastic components) to prevent any interference with the SQUID device.

In one specific embodiment, the array of SQUID sensors 32 is fixed at a predetermined angle with respect to vertical. The predetermined angle is about 50° or less. As a specific example, the array of SQUID sensors 32 is fixed at an angle of about 45° from vertical with five SQUID sensors 32 at the points of a pentagon, each about 2 cm from a central sixth SQUID sensor 32. Each SQUID sensor 32 is about 1.5 cm in diameter. The peripheral SQUID sensors 32 are aimed at a point about 2 cm below the central SQUID sensor 32. The MEG system 48 includes a Dewar flask with a small liquid helium reservoir. The test patient 50 sits in the patient support device 14 that is tiltable up to about 45° or 50° from vertical and rotatable at least 360°, similar to a dentist chair, but with precise control of the orientation and tilt of the patient support device 14. The precise location (including both tri-axis position and orientation) of the patient support device 14 is communicated to the software of the computer 20 directing the data acquisition. The patient support device 14 stabilizes the head of the test patient 50 by a cushioned support on each maxilla. The test patient 50 and sensor head 12 are housed completely in a Faraday cage 10 to shield environmental magnetic flux. Such a device may be used anywhere, i.e., it is easily physically portable between rooms, and is expected to cost only about $200,000 at the time of this writing.

The array of SQUID sensors 32 is placed over the area(s) of interest of the brain. The array of SQUID sensors 32 may be placed over the inferior frontal gyms to detect the "top down" response from the cortical executive region. The latter part of the 500-msec signal over the auditory cortex may likely also capture some of this information. The same strategy may be used for visual, sensory, motor, and cognitive inventory. Data collected from the array of SQUID may be used to create a regional magnetic cortical surface map to inventory the function of hearing, sight, touch, movement, and cognition of a normal healthy brain. This information may allow the analysis of individuals in disease states or other conditions of interest.

Generally, each SQUID sensor 32 in an array may function as an axial gradiometer to attenuate the environmental magnetic noise. The position of the array of SQUID sensors 32 can be correlated by an imaging of the head to give a precise location of the array of SQUID sensors 32 relative to the brain structures. Any imaging technique may be used that distinguishes the physical location and shape of the brain, including, but not limited to ultrasound and magnetic resonance imaging ("MRI"). In this case, only detected signals that demonstrate the expected strength decay laterally between SQUID sensors 32, consistent with a superficial signal origin, are scored. Software directs the movable array of SQUID sensors 32 to refine the image in order to provide a robust surface map of the surface sulcal activity, thereby specifically creating a map of basal neural activity or "noise".

In another specific embodiment, an array of three to nine or more SQUID sensors 32, about one centimeter in size with a fixed radial geometry, may be used to image the brain or the surface of the brain via a computer-directed movable C-arm.

Figure 1C:
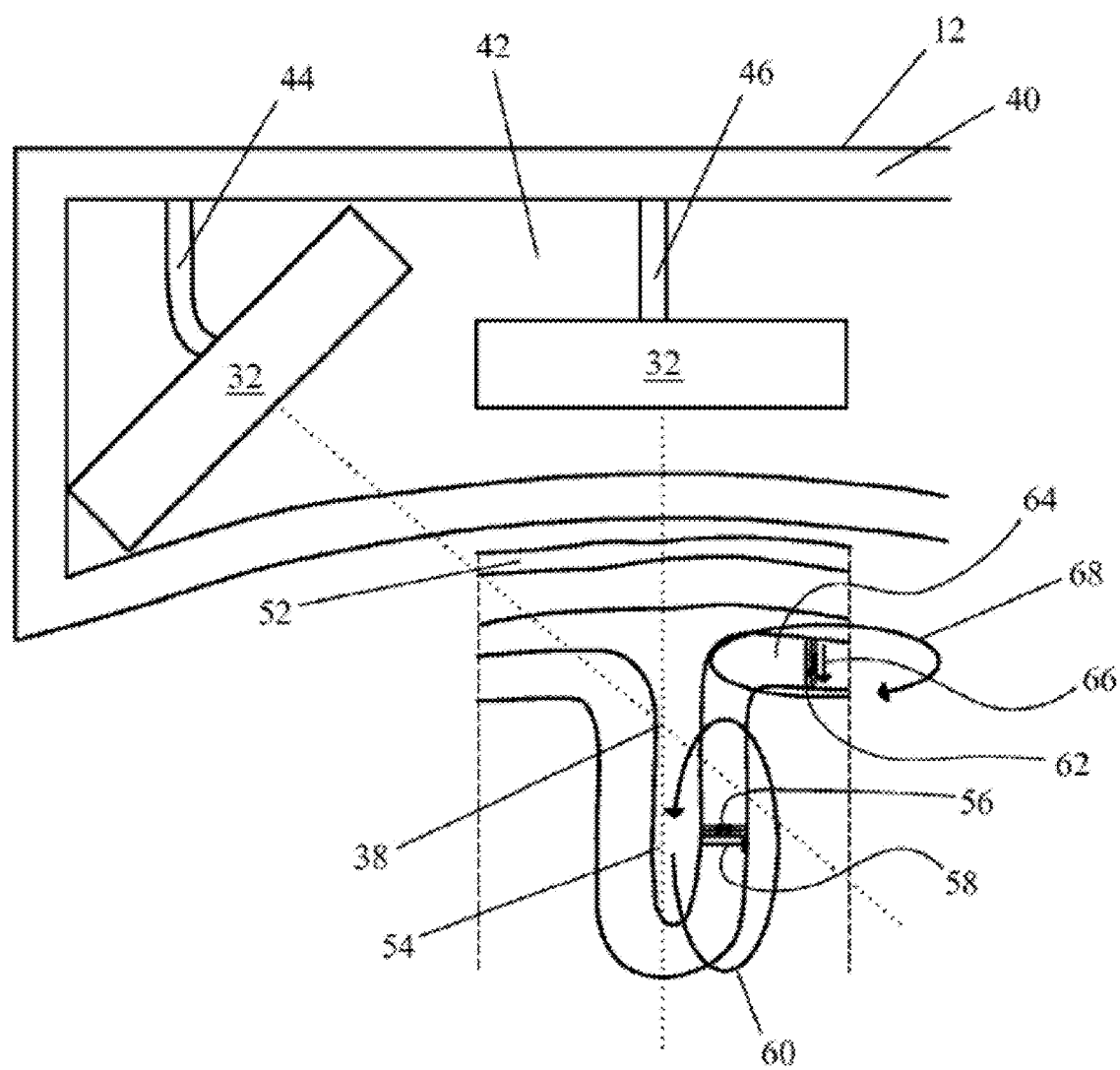
FIG. 1C shows a cross section of the SQUID sensor head of FIG. 1B along line 33 with the sensor head oriented to detect a magnetic field generated by electrical signals near a sulcus of a brain in one embodiment.

FIG. 1C shows the SQUID sensor head 12 placed against the scalp 52 of the test patient 50 above a sulcus 54 of interest, according to one embodiment. The peripheral SQUID sensors 32 (see also FIG. 1B) and the central SQUID sensor 32 converge on a focal point 38 about two to four centimeters below the central sensor 32. The sensor head 12 includes a Dewar housing 40 for the sensors. The Dewar housing 40 holds the liquid helium in the enclosed portion 42 of the sensor head 12 to maintain the SQUID sensors 32 at superconducting temperatures and insulates the SQUID sensors 32 and the liquid helium from the environment and the head of the test patient 50. Electrical wiring 44, 46 powers each of the SQUID sensors 32. The neuronal structures 56, and hence the electrical impulses, in the sulcal wall are oriented substantially parallel 58 to the scalp 52, thereby generating a magnetic field 60 in a plane substantially perpendicular to the scalp 52. In contrast, the neuronal structures 62, and hence the electrical impulses, of the gyms 64 are oriented substantially perpendicular 66 to the scalp 52, thereby generating a magnetic field 68 in a plane substantially parallel to the scalp 52. The magnetic field 60 generated from electrical activity in the sulcus 54 therefore is much more easily detected than the magnetic field 68 generated from electrical activity in the gyms 64 with the sensor head 12 located as shown in FIG. 1C.

The location of the source of a magnetic signal may be estimated by the SQUID sensors 32, and when the source of the magnetic signal is expected to be at a sulcus 54, the sulcus 54 location may be estimated directly from the SQUID signals. For example, when the right index finger is stimulated, the SQUID signal maximum is over the left sensory cortex, where sensory input from the finger is registered.

More generally, the sulcus 54 represents a physical boundary and an absolute limit to current transmission and thus to magnetic field transmission. That is, a SQUID sensor 32 placed contralateral to a sulcus-generated signal detects signals from, effectively, a point source, and the signal strength decreases as the inverse cube of the distance from the source. A SQUID sensor 32 placed ipsilateral to a sulcus-generated signal has characteristics of a dipole such that the signal strength decreases as the inverse square of the distance from the source. The SQUID sensors 32 contralateral to the gyms 64 of interest demonstrate a decay in intensity as the cube function of distance. In this configuration, the output is thus markedly simplified for interpretation but not degraded.

The measurement setup may also include an MRI device for collection of MRI data. This MRI data may be used to perform source localization within the brain; however, as described above, source localization may be estimated without the MRI data, such as when the magnetic signal is a well-known response from a well-known stimulus.

Figure 1D:
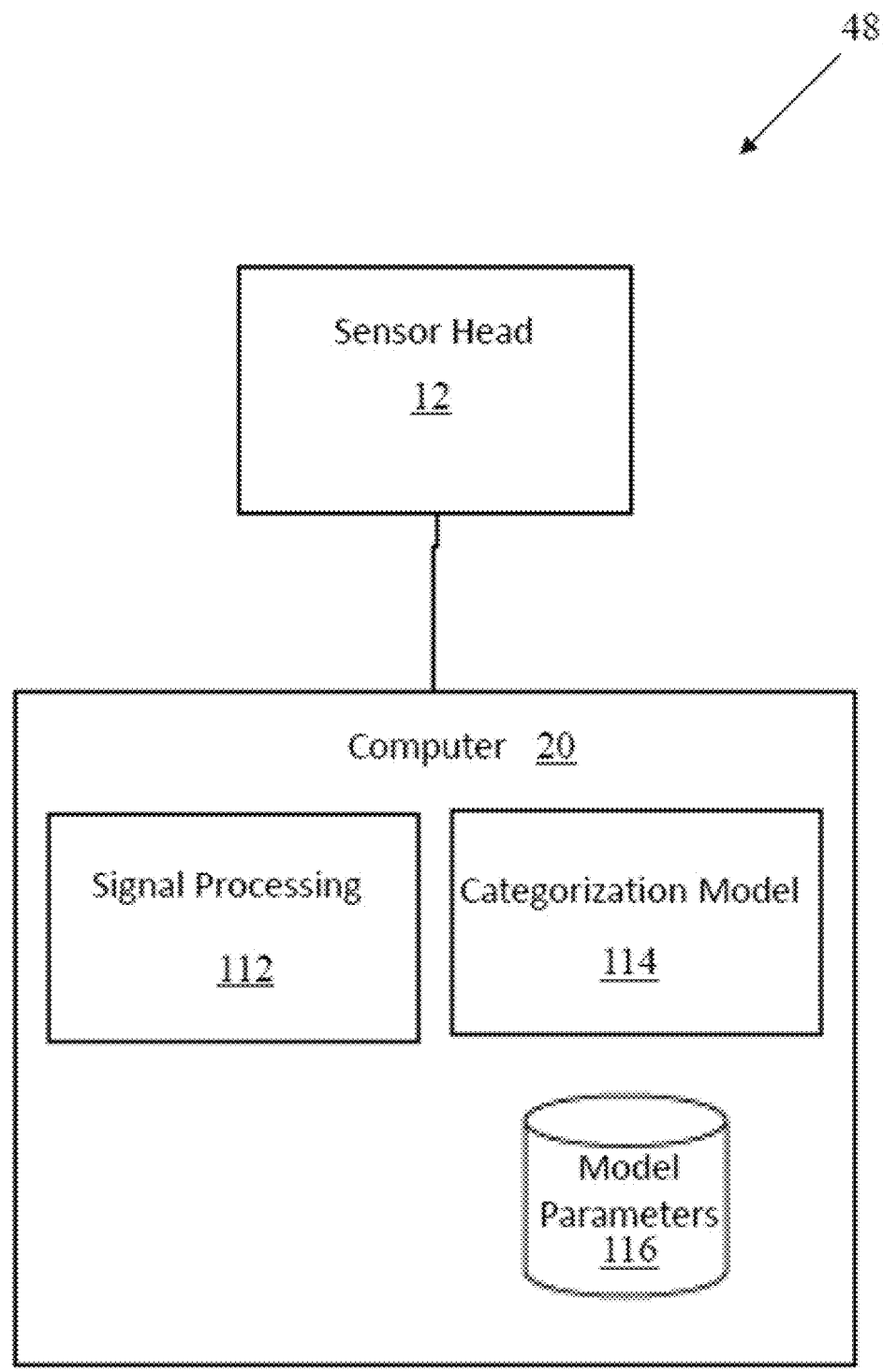
FIG. 1D shows a logical component diagram of an MEG system in one embodiment.

Referring to FIG. 1D, the MEG system 48 includes a sensor head 12 in communication with a computer 20. The computer 20 includes signal processing 112 and a categorization module 114 for determining weights of the candidate parameters of the model, and the computer 20 stores model candidate parameters 116. Parameters may also be referred to as features.

II. Meg Signal Measurements

The MEG system 48 described above detects signals from the brain using one or more SQUID sensors 32 as discussed above. In one series of embodiments, these signals are captured following an auditory stimulus provided to a human patient. Generally, the models described herein are built using and can evaluate patients based on providing multiple iterations of an auditory stimulus to the patient. An "epoch", as used herein, refers to a single measured response or single output over a single predetermined period of time, such as with respect to a single stimulus event. As a specific example, to build an Alzheimer's Disease Detection ("ADD") or Cognitive Impairment (CI) model or evaluate any given patient with respect to the ADD model or CI model, generally multiple epochs are collected. In the experimental Example described in Section IV below the number of epochs collected was approximately 250, however this may vary by implementation.

The frequency of auditory stimulus, duration of stimulus, and pattern of stimulus may vary by implementation. For example, the patients who contributed MEG data for the generation of the example models in Section IV below were presented with a series of 700 Hz standard tones of 50 msec duration, spaced every 2500 msec. With a proportion of 1 to 5, a deviant tone (600 Hz) was randomly presented. All tones were presented to the test patient's left ear, for a total of 250 samples. Test patients were scanned in three different runs, with two of those runs being performed during the same visit. In one embodiment, only the responses to standard tones were analyzed, and responses to deviant tones were discarded.

Although specific tone frequencies, tone durations, inter-trial intervals, and numbers of epochs were used to collect the MEG data described herein, it will be appreciated that a range of values may be selected for each. The tone frequencies may be in the range of 500 to 1000 Hz or alternatively in the range of 600 to 700 Hz. The tone duration may be in the range of 25 to 75 msec. The inter-trial intervals may be at least 500 msec or alternatively in the range of 500 to 3000 msec. The total number of epoch collected in a single session may be at least 200 or alternatively at least 250.

The measurement setup and computer 20 particularly may map the magnetic field strength to the surface of the cerebral cortex. The array of SQUID sensors 32 are located over the cortical region controlling the function to be inventoried. For auditory evoked potential, the sensor heads 12 are placed over the superior temporal gyms to record initial response to a repeated sound stimulus. The patient support device 14 may be moved to refine the topological image quality. The contour maps of magnetic field intensity may be collected over a 500-600 msec epoch after a defined stimulus (e.g., pitch, intensity, duration, and repetition). To achieve adequate data homogenization in order to render the content of the collected MEG data understandable without degrading it, the data collection may be limited to neural transmission originating in the most superficial neurons lining the sulci of the relevant gyms of the human cortex. These processes were carried out with respect MEG data that served as the basis for the generation of the example models of Section IV below. The output may be presented as a contour map with no attempt being made to determine the underlying dipole or current structure.

Data collected from the MEG system that is passed to the computer 20 may be band-pass filtered, for example by retaining frequencies in the range of 1-30 Hz and removing frequencies outside that range. This helps keep most of the variance in the power of the recordings and also to remove any slow drifts in the data, normally related to recording artifacts. The data may also be otherwise processed, one example of which is segmenting an incoming data stream into separate epochs by time. For example, the computer 20 may determine the timing of the presentation of each standard tone, and data in the 100 msec preceding the presentation, and 500 msec after, may be recorded and averaged over all presentations. This procedure results in one time series per channel, containing 600 samples from −100 msec to 500 msec, where time zero determined the presentation of the standard tone. These processes were carried out with respect to MEG data that served as the basis for the generation of the example models of Section IV below. In one example scenario used to build the test CI model described in Section IV below, the number of averaged presentations was between 207 and 224, depending on patients and runs.

Other types of signal processing may also be performed. For example, data collected by the Elekta Neuromag® 306 channel system may be further processed using Elekta Neuromag's Maxfilter™ software to remove sources of outside noise. This signal processing was carried out with respect MEG data that served as the basis for the generation of the example models of Section IV below. Depending upon the physical setting of data collection and specific data collection tools used, additional or even fewer signal processing steps than described herein may be helpful as well, particularly due to variation based on the physical location of the recording (e.g. the amount of external noise in the site). Thus, signal processing may not be necessary based on the recording instrument and site used in future applications of this description.

Figure 2A:
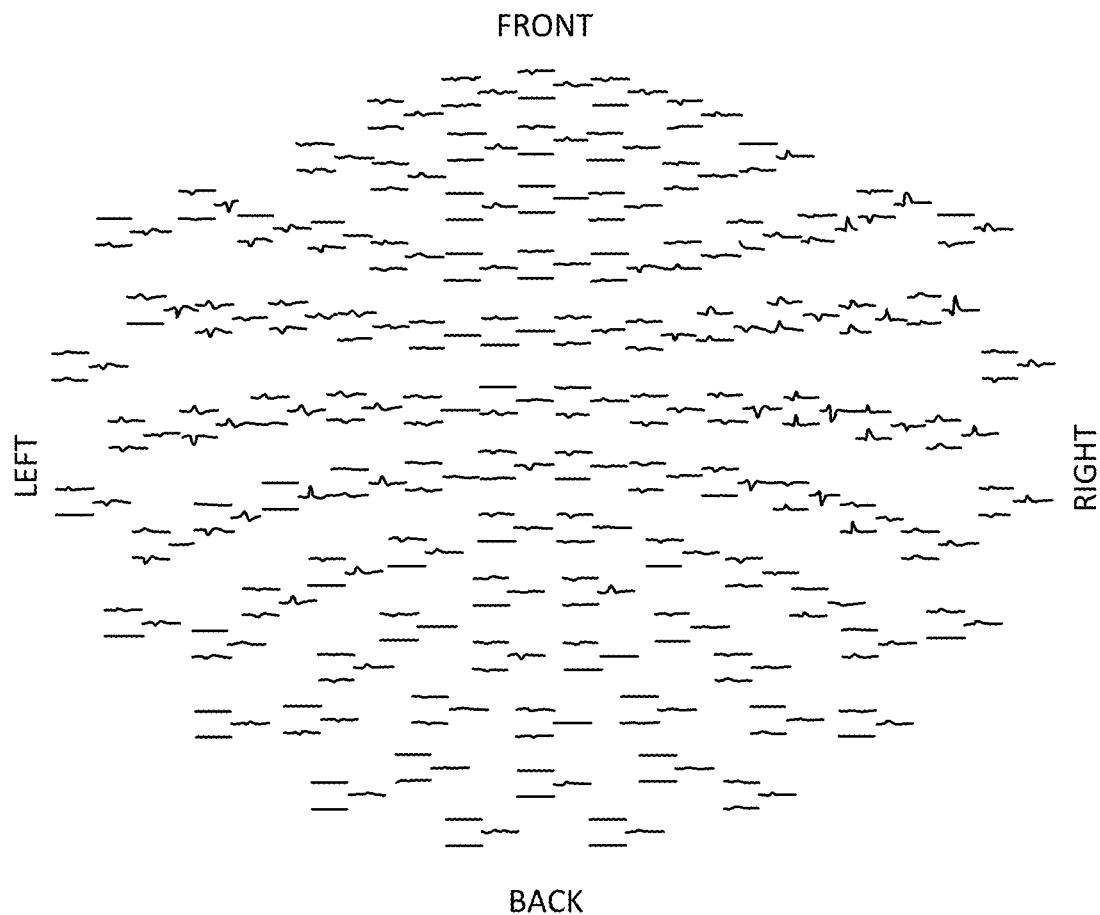
FIG. 2A shows example averaged responses to a stimulus for each of a number of SQUID sensors.

FIG. 2A illustrates the averaged response of a signal (a "signal illustration") to the standard tone for each SQUID sensor 32, both gradiometers and magnetometers, with each signal illustration being arranged in a location in FIG. 2A corresponding to the relative location of the SQUID sensor 32 in the array in the sensor head 12, according to one embodiment. Each signal illustration in FIG. 2A represents one of the 306 sensors (not separately labeled), where the horizontal axis goes from −100 to 500 msec, where 0 represents the time at which the tone was presented to the patient. As discussed above, the Y axis value for signal received from the SQUID sensor 32 is a quantification of magnetic activity measured in a particular part of the brain, as indicated by magnetic fields detected by the SQUID sensors 32.

Figure 2B:
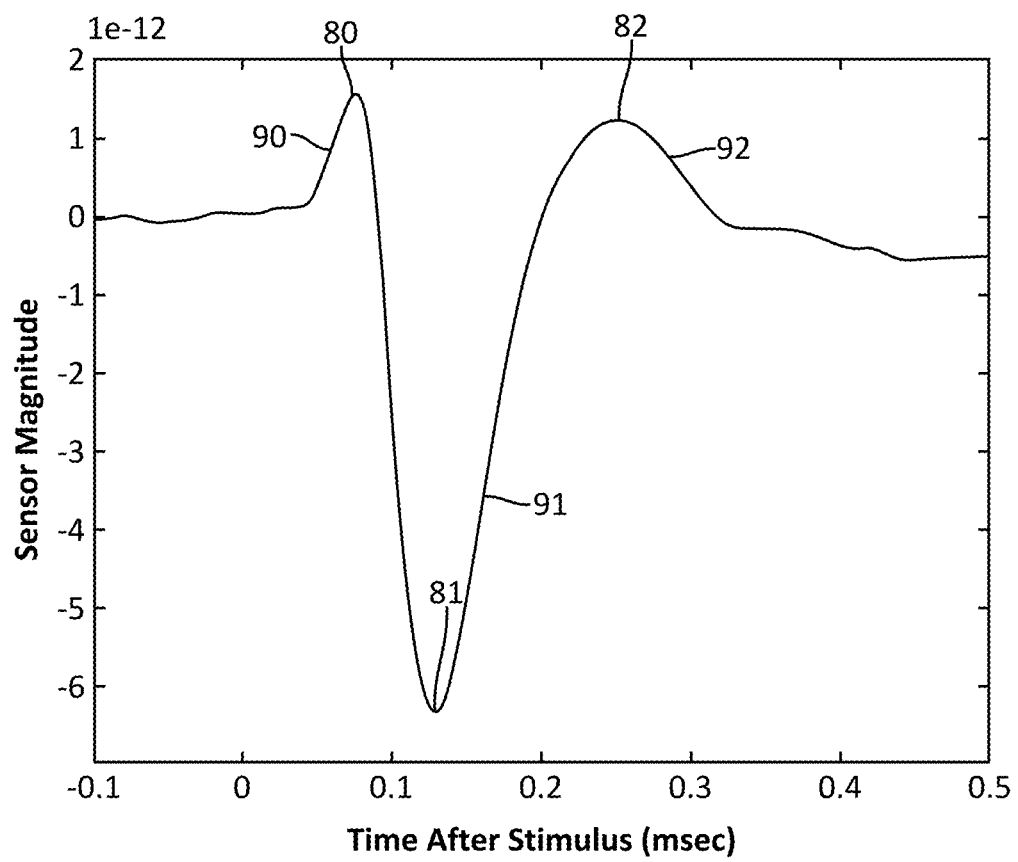
FIG. 2B shows an example averaged response for a single SQUID sensor.

Zooming in on an example SQUID sensor's response provides a prototypical waveform pattern such as shown in FIG. 2B, which shows an example of an averaged evoked stimulus response in an area of interest in the brain as measured by a single SQUID sensor 32 of the sensor head 12. The positive and negative sensor magnitude depends on the position of the sensor and are therefore arbitrary, but peak B 92 is shown and described as a negative peak throughout the present disclosure for consistency. The example waveform pattern of FIG. 2B was collected from a test patient with no measured cognitive dysfunction.

The human brain's response to the auditory stimulus, on average and for particularly placed SQUID sensors 32, includes several curves that peak, that is they have values of zero for their first derivative at some point after stimulus. These peaks include a peak A 90 defining a first local maximum 80, followed by a peak B 91 defining a local minimum 81, followed by a peak C 92 defining a second local maximum 82, followed by a return to a baseline. Peak A 90 is commonly known in the EEG literature as "P50" or "m50". Peak B 91 is commonly known in the EEG literature as "N100", "m100", or an awareness related negativity ("ARN") peak. Peak C 92 is commonly known in the electromagnetic literature as "P200". On average, the first local maximum 80 is generally observed within about 50 to 100 msec after the stimulus, which was presented at time zero in FIG. 2B. The local minimum 81 is generally observed between about 100 and 150 msec after the stimulation. The second local maximum 82 is generally observed between about 200 and 400 msec after the stimulation event.

Throughout the remainder of this description and in the claims, it is sometimes useful to refer to these peaks without reference to which specific peak is intended. For this purpose, the terms "first peak", "second peak", and "third peak" are used. Where the "first peak" is either peak A 90, peak B 91, or peak C 92, the "second peak" is a different one of the peaks from the "first peak", and the "third peak" is the remaining peak different from the "first peak" and the "second peak". For example, the "first peak" may be arbitrarily associated with peak B 91 for this example, with the "second peak" being peak A 90 and the "third peak" being peak C 92, and so on.

III. Model Development

Once MEG signals have been collected from a set of test patients 50 as model MEG data, possible candidate parameters of the model MEG data may be identified, analyzed, and selected to determine the model parameters that will make up the CI model. The heatmaps introduced in Section III.B. provide one way in which the MEG data may be analyzed for use in performing these tasks.

III.A. Sensor Selection

In developing the CI model, consideration is given to specific signals in the sensor head 12 that are used to train and use the model. For example, for models in Section IV (except for Section IV.E) below, a pool of channels of SQUID sensors 32 located ipsilaterally to the tone presentation, where the most discriminating parameters between the two groups were initially identified, were reviewed. Within that channel pool, in one implementation the channel with the least variability in the latency of peak A 90 was chosen. Specifically, the latency of peak A 90 (e.g., the time point from stimulus presentation to maximal deflection within the expected peak A 90 timeframe) was calculated for the data from each of a group of channels previously identified to capture the ipsilateral response. That process was repeated two thousand times, sampling the epochs with replacement (bootstrap) in each iteration. This procedure yielded a distribution of latencies of peak A 90 for each channel in the pool, and the channel with smallest variability in the latency of peak A 90 was selected.

In other implementations, other or additional factors may be used to identify one or more channels whose test data will be analyzed to build the CI model. Examples of these factors and example models built using these factors are discussed in Section IV.E below.

In other models, other criteria may be used to select one or more SQUID sensors 32 whose test data will be analyzed to build the CI model, such as, for example, the best match to the expected 3-peak pattern (peak A 90, peak B 91, and peak C 92) or the strongest peak B 91 when responding to auditory tones.

III.B. Candidate Parameter Identification

There is a great deal of information that can be obtained from the recorded epochs of MEG signal data. On an individual epoch level or after averaging many epochs, the following pieces of information may be determined for use as candidate parameters themselves, or as precursor information towards the determination of other candidate parameters. The computer 20 may determine maximum 80 (or maximum "strength") of peak A 90, the maximum 81 of peak B 91, and the maximum 82 of peak C 92, in either absolute units of magnetic field strength, electrical activity, in some other units, or on a relative scale such as % of largest recorded epoch for that patient or relative to some baseline. The computer 20 may also determine an associated time of occurrence of each peak after stimulation, which are referred to hereafter as latency A, latency B, and latency C, respectively. Latencies may also be computed in other forms, for example the latency of peak B 91 may be calculated relative to the average peak A 90 latency, for that patient or for a population, and so on. The computer 20 may also determine an area under the curve with respect to a baseline, relative to that patient or relative to a population, for peak A 90, peak B 91, and peak C 92. The onset and offset of each peak 90, 91, 92, calculated, for example, as mean (baseline)+/−2 standard deviations, may also be useful in candidate parameter identification.

There can be various candidate parameters (features). Some of the features are peak latency, which may be length of time between stimulus application and the brain signal achieving its maximum absolute value, and Peak B onset and offset, which may be the time point after stimulus application when the absolute value of the signal became more than twice the standard deviation of the baseline (time <0), within a 100 to 190 ms window after stimulus application. Another parameter may be the percentage of epochs with one of the three peaks, which may be the percentage of the total number of standard epochs showing any of the 3 peaks. After computing which epochs have each of the 3 peaks, the percentage of epochs with a combination of the peaks captures how many epochs have a combination of 2 or 3 peaks. Area of A and C may be related to looking at the heatmap as a regular image. The area of A and C may be the amount of blue (negative polarity) in the trials detected to contain A and C peaks, respectively. Strong and weak A peaks with B may be the number of B peaks in the first half (strong) epochs with A peaks, and then the second half (weak) of epochs with A peaks. Strong and weak A peaks with C may be similar to the one above, but the number of C peaks in epochs with strong and weak A peaks. Peak B amplitude in strong and weak A epochs may be similar to the one above, but it is based on the average peak B amplitude (i.e. amount of red) in epochs with strong A and also in epochs with weak A peaks. In other words, the amount of red (positive polarity) within the B peak time window, for the first and seconds halves of epochs with A peaks.

Due to the variation across epochs, valuable additional information may be obtained by analyzing the MEG data in heatmaps. Visualizing this MEG data in the form of a heatmap, such as the one shown in FIG. 3A, allows visual inspection of the set of raw epoch data to identify trends and parameters that are hidden or lost in averaged or otherwise collapsed or conflated MEG data. In such a heatmap, each of the responses, or epochs, is plotted as a horizontal line with a color scale representing the strength of the measured magnetic field. These heatmaps allow visual interpretation of the set of raw epoch data that the computer 20 processes in generating and using the CI model. Although for convenience some of the following descriptions of the generation and use of the CI model are described with respect to calculations that may be performed with respect to and on the data in these heatmaps, those of skill in the art will appreciate that in practice the computer 20 performs calculations with respect to the data itself, without regard to how it would be visualized in a heatmap.

Many candidate parameters were identified by observation of an apparent correlation between the candidate parameter and the Mini-Mental State Examination ("MMSE") score of the test patient. The apparent correlations were mostly initially identified by visual inspection of the heatmaps of model MEG data. For example, it was observed that the CI test patients (i.e., test patients with lower MMSE scores) tended to have more epochs with peak A 90 than normal test patients 50. It was also observed that normal test patients (i.e., with higher MMSE scores) tended to have more epochs with all three peaks. The weaker peak A 90 half of the epochs that have peak A 90 were observed to have a higher amplitude of peak B 91 in normal test patients than CI test patients. Finally, the number of epochs with peak C 92 in the weaker peak A 90 half of the epochs that have peak A 90 were observed to be within an intermediate range for normal test patients.

Figure 3A:
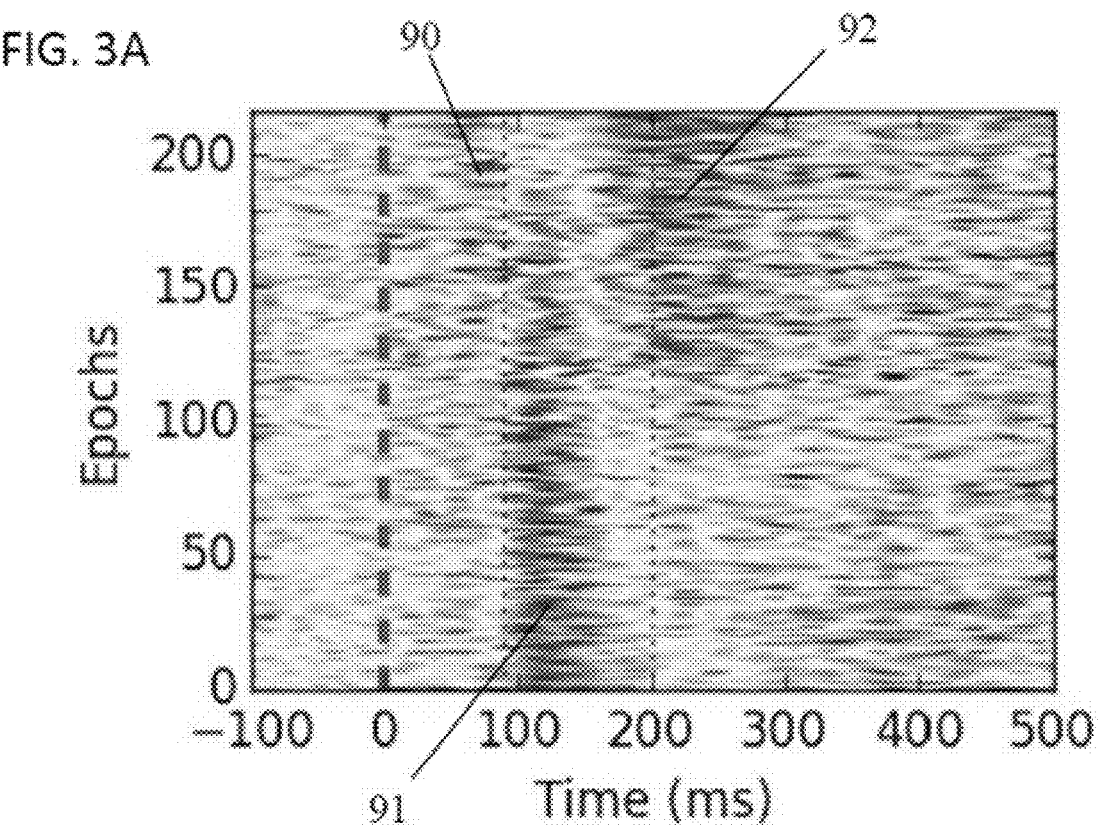
FIG. 3A shows an example heatmap of the epochs of a magnetoencephalography ("MEG") set of scans from a single session for a single SQUID sensor for a first normal patient.
Figure 3B:
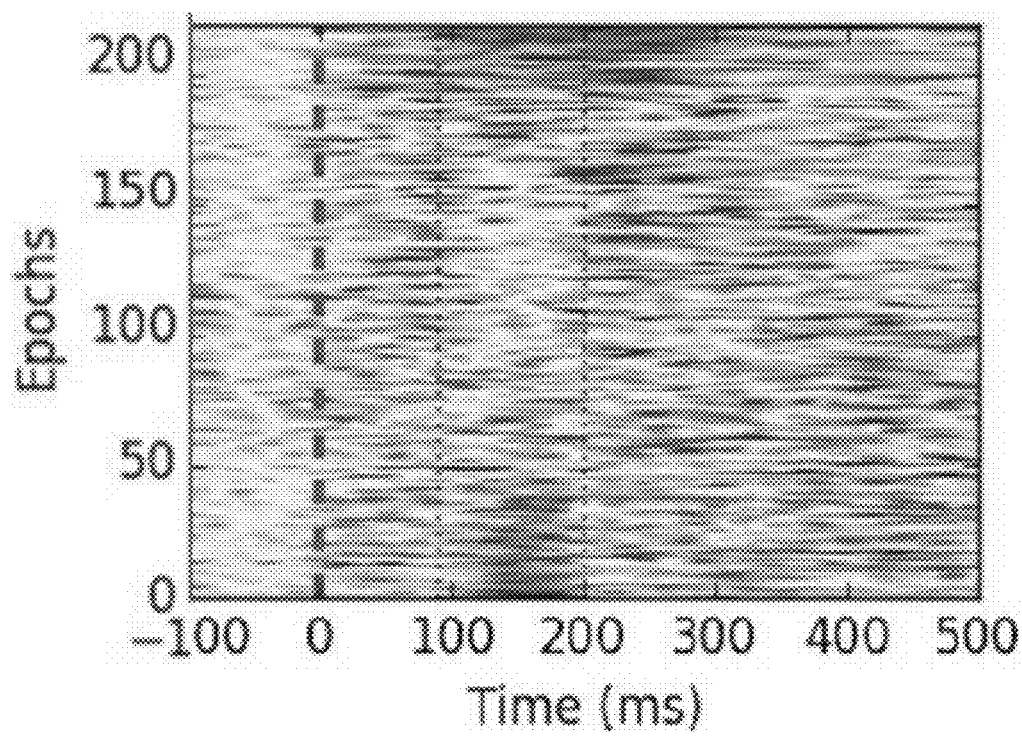
FIG. 3B shows an example heatmap of the epochs of a MEG set of scans from a single session for a single SQUID sensor for an Alzheimer's Disease ("AD") patient.
Figure 3C:
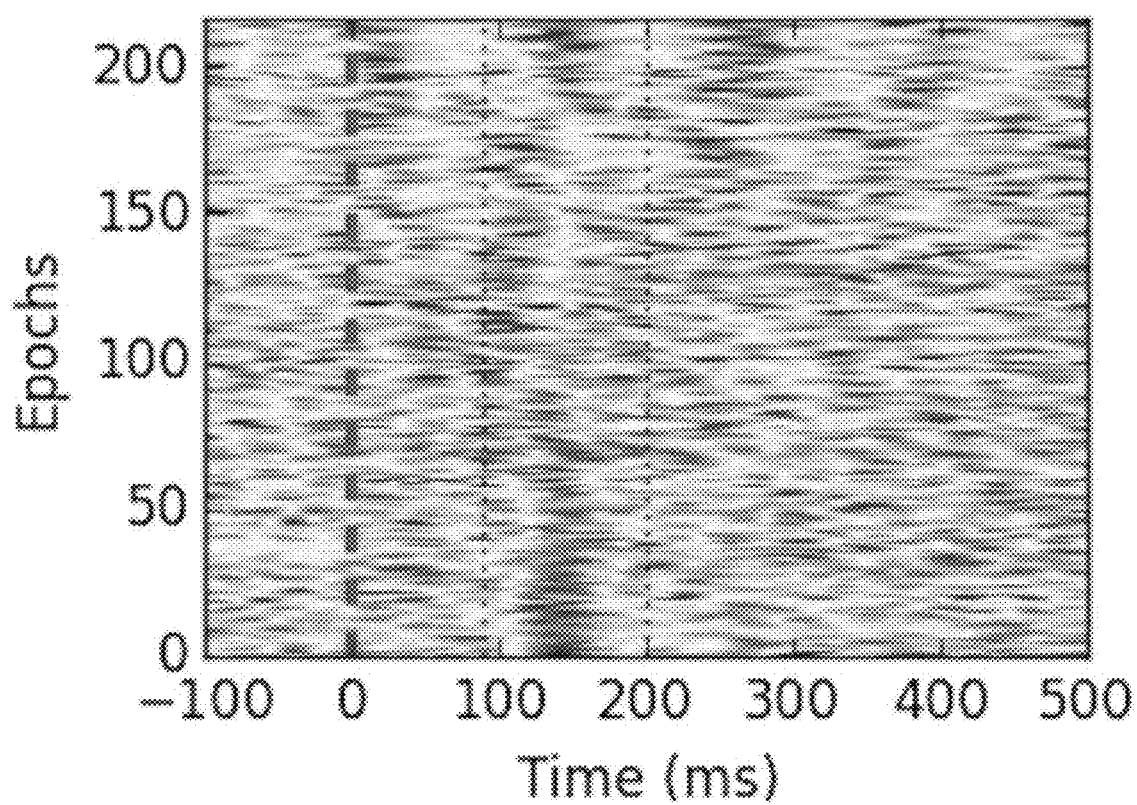
FIG. 3C shows an example heatmap of the epochs of a MEG set of scans from a single session for a second normal patient.

FIG. 3A through FIG. 3C illustrate several example heatmaps, with epochs on the y-axis and time with respect to the stimulus time on the x-axis. Each heatmap represents one complete auditory stimulation test run for one patient. Each epoch represents a response to a single stimulus. In these heatmaps, white refers to a neutral (close to baseline) magnetic or electrical field as measured by one of the SQUID sensors 32, while red arbitrarily refers to a positive magnetic or electrical field and blue arbitrarily refers to a negative magnetic or electrical field. For each epoch, the color scale is normalized from blue to red based on the data in the epoch. The relative intensity of the positive or negative field is indicated by the intensity of the red or blue color, respectively. The epochs in the heatmaps of FIG. 3A, FIG. 3B, and FIG. 3C are not ordered chronologically but rather by a similarity metric of the signal within the window of peak B 91. Any one of a number of different sorting metrics may be used. For example, the epochs in the heatmap may be sorted based on the duration of one of the three peaks 90, 91, 92, the maximum of one of the three peaks 90, 91, 92, or the latency of one of the three peaks 90, 91, 92. After the sorting of all epochs is done, for visual representation the highest peak B 91 is placed at the bottom in FIG. 3A through FIG. 3C.

FIG. 3A shows a heatmap of the MEG data from a normal patient. Peak B 91, represented in blue between about 90 and 200 msec, has a uniform, well-defined onset and leads to a strong peak C 92, represented in red and appearing after peak B 91. In contrast, FIG. 3B shows the MEG data for an AD patient having a peak B 91 with a less-uniform, less-defined onset. In this case, the peak B 91 is not particularly strong, and although the peak C 92 is not very uniform or well-defined, it is still clearly present. Not all AD patient MEG data, however, showed this same type of deviation. The MEG data (not shown) from one AD patient shows a stronger peak B 91 with a less-uniform, less-defined onset and a peak C 92 that is barely noticeable. MEG data (not shown) for two other AD patients shows a much stronger peak A 90 than for the MEG data of the normal patient shown in FIG. 3A. The onset of the peak B 91 was fairly uniform and well-defined for those AD patients but was delayed in comparison to peak B 91 of the normal patient, and peak C 92 was visible but weak. Finally, FIG. 3C shows MEG data for another normal patient, but the data is very atypical in comparison to the observed MEG data of the other normal patients. Peak A 90, peak B 91, and peak C 92 are fairly weak and poorly-defined in the MEG data in FIG. 3C, with peak B 91 starting later and ending earlier than for other normal patients. Collectively, these heatmaps illustrate that reliance on averaged or otherwise aggregated epoch data alone obscures the variety in stimulus responses that will occur in actual patients, and thus is likely to alone be insufficient to generate a model for discriminating between normal and AD patients.

At least some of the candidate parameters for the CI model were identified or are more easily explained by looking at the non-averaged epochs of MEG data organized in heatmaps. Some of these candidate parameters include a percentage of epochs having a particular peak or combination of peaks. The determination of whether or not a given epoch has a given peak can be based on any one of a number of calculations, examples of which are described further in the following subsections of Section IV.

Additional candidate parameters include identified subsets of epochs in a given set of scans from a single session for a given SQUID sensor. Specifically, two (or more) subsets may be identified for a given test patient dividing the epochs based on any one of the candidate parameters or some other aspects. For example, two subsets may be identified, based on a candidate parameter such as presence of one of the peaks where presence is a relative measure of magnetic field strength relative to the other epochs for that test patient. In this example, the subset with the peak being present may be divided into two further subsets of a "stronger" subset including some threshold proportion of the epochs (e.g., 50%) with the higher (or stronger, or strongest) relative presence of the peak, and also of a "weaker" subset including the remaining proportion of the epochs with the lower (or weaker, or weakest) relative presence of peak (or absence thereof). Other candidate parameters or aspects of the epoch data may also be used to generate subsets, such as strong and weak subsets, including, for example, peak timing and variability, and peak amplitude and variability.

Yet additional candidate parameters may be determined based on those identified subsets. For example, any given candidate parameter mentioned in Section IV may be determined with respect to an identified subset of epochs. For example, if a strong peak A 90 subset is identified, which may represent 50% of the epochs in the set of scans from a single session of a patient having the strongest relative presence of peak A 90 compared to a weak peak A 90 subset, another candidate parameter may be the mean or median amplitude (in terms of magnetic field strength) of the peak B 91 in the strong subset. One of skill in the art will appreciate the wide variety of possible candidate parameters that may possibly be generated by dividing the epoch data from the set of scans from a single session of a patient and sensor according to one aspect/candidate parameter, and then calculating another candidate parameter based on an identified subset.

III.B.1. Candidate Timing Parameters

Some of the candidate parameters may be generally categorized as peak timing parameters, including peak latency parameters, peak onset parameters, peak offset parameters, and peak duration parameters. Each of these candidate parameters may be calculated for each of peak A 90, peak B 91, and peak C 92. For these candidate parameters, the values of the candidate parameters for the CI model are determined based on epochs from test patient training data that are determined to include all three peaks 90, 91, 92, herein referred to as the tri-peak subset. Thus, instead of using all epochs from the scan session of a test patient 50 of a SQUID sensor 32 to calculate the value of the timing parameter for each peak, it was first determined which epochs had each peak, and then the value for the timing parameter for each peak was calculated. The average and variability of the value of each timing parameter was calculated through bootstrapping, and these averages and variabilities are additional possible CI model candidate parameters. Additional parameters may also include the values of the timing parameters (and their averages and variabilities) as instead calculated from averaged response MEG data (i.e., the average of all epochs together per SQUID sensor per patient).

Each of various peak latency parameters may be estimated in accordance with the length of time between stimulus application and an epoch achieving its maximum (or minimum) absolute value. For example, the latency of peak B 91 may be estimated as a time point in each epoch at which the signal displayed its maximum absolute value. The values of the peak B 91 latency average ["latencyB (mean)"] and variability ["latencyB (var)"] candidate parameters for a particular model patient may be calculated based on the data set of the individual peak B 91 latency points for the epochs under consideration (e.g., those having all three peaks) for that particular model patient in the training set. The resulting candidate parameter values may then be fed into the CI model for training.

The latency of peak A 90 may be estimated based on the time point in each epoch at which the first time derivative of the signal became zero, counting backwards from the latency of peak B 91. The values of the peak A 90 latency average ["latencyA (mean)"] and variability ["latencyA (var)"] candidate parameters may be determined based on the time points for these epochs under consideration for each patient in the training set.

Again, starting at the latency of peak B 91 and going backwards, the onset of peak B 91 may be estimated based on the time point in each epoch at which the absolute value of the signal became more than a predetermined number of the standard deviation (e.g., twice the standard deviation) of the baseline signal (for time <0). The values of the peak B 91 onset average ["onsetB (mean)"] and variability ["onsetB (var)"] candidate parameters may be determined based on the time points for these epochs under consideration for each patient in the training set.

Similar to the onset of peak B 91, the time point in each epoch for the offset of peak B 91 may be estimated using the same criteria but counting forward from the latency of peak B 91. The values of the peak B 91 offset average ["offsetB (mean)"] and variability ["offsetB (var)"] candidate parameters may be determined based on these time points for the epochs under consideration for each patient in the training set.

Starting at the latency of peak A 90 and going backwards in time, the onset of peak A 90 may be estimated as the time point in each epoch at which the first time derivative of the signal changes sign. The values of the peak A 90 onset average ["onsetA (mean)"] and variability ["onsetA (var)"] candidate parameters may be determined based on these time points for the epochs under consideration for each patient in the training set. Note that the onset of peak B 91, as defined herein, may be the same as the offset of peak A 90. Similarly, the offset of peak B 91, as defined herein, may be the same as the onset of peak C 92.

The offset of peak C 92 was calculated as the first time point in each epoch when the signal returns to the same value as in the offset of peak B 91, or some threshold time (e.g., 450 msec post stimulation), whichever occurs sooner. The value of the peak C 92 offset average ["offsetC (mean)"] and variability ["offsetC (var)"] candidate parameters may be determined based on these time points for the epochs under consideration for each patient in the training set.

The duration of peak B 91 in each epoch is the offset of peak B 91 minus the onset of peak B 91. The values of the peak B 91 duration average ["duration (mean)"] and variability ["duration (var)"] candidate parameters may be determined based on these time points for the epochs under consideration for each patient in the training set.

For each of these timing parameters, a particular process for calculating the value of the candidate parameter is provided above, however those of skill in the art will appreciate alternative mechanisms of calculating these quantities may be established.

III.B.2. Candidate Subset Parameters

The determinations of the values of other candidate parameters for the test patients in the training set involves further processing of the epochs of the MEG data. As above, illustration by heatmap is useful in conceptualizing these candidate parameters. One type of processing includes determining which epochs include one or more of the peaks. This calculation can be used for determining a number of candidate parameters, including those based on strong/weak subsets of epoch as introduced in Subsection III.B.1 above.

In one embodiment, to perform this processing and/or identify candidate parameters, the epochs in the heatmap are sorted based on similarity within specific time windows. Often, though not necessarily, the sorting is with respect to a particular "sorting" peak. For example, the epochs in FIG. 3A may be sorted based on the time window of sorting peak B 91, such that epochs at the bottom of the plot look more similar, and are more likely to have a peak B 91, than epochs at the top. To do the sorting, initial peak boundaries are first estimated using all epochs for a test patient, and those initial estimates are used to sort the heatmap and count the epochs that displayed each peak. In one embodiment, sorting is performed using spectral embedding that transforms the data to a single dimension, after applying a radial basis function ("RBF") kernel with a gamma value such as gamma=0.1.

After the epochs are sorted based on their similarity within a time window related to peak A 90, peak B 91, or peak C 92, a cutoff epoch for delineating between which epochs are determined to have and to not have the sorting peak is selected that maximizes the correlation of the sorted area within the time window. In one embodiment, an ideal linear signal decay function is used to determine the maximum of the correlation within the time window. For example, assume peak A 90 is the sorting peak and there are a total of 200 epochs. When visually examining the heatmap sorted in the initial guess for peak A 90, only about the bottom 30% of the epochs had peak A 90 in one case. Computationally, to determine the cutoff epoch, the computer 20 may create 200 different images where the signal in the time window for peak A 90 linearly decays from the "bottom" of the heatmap to one of the 200 epochs, and remains zero after it ends its decay. The image that has the highest correlation with the actual heatmap is considered the image where the zero is around the 30% mark.

Figure 3D:
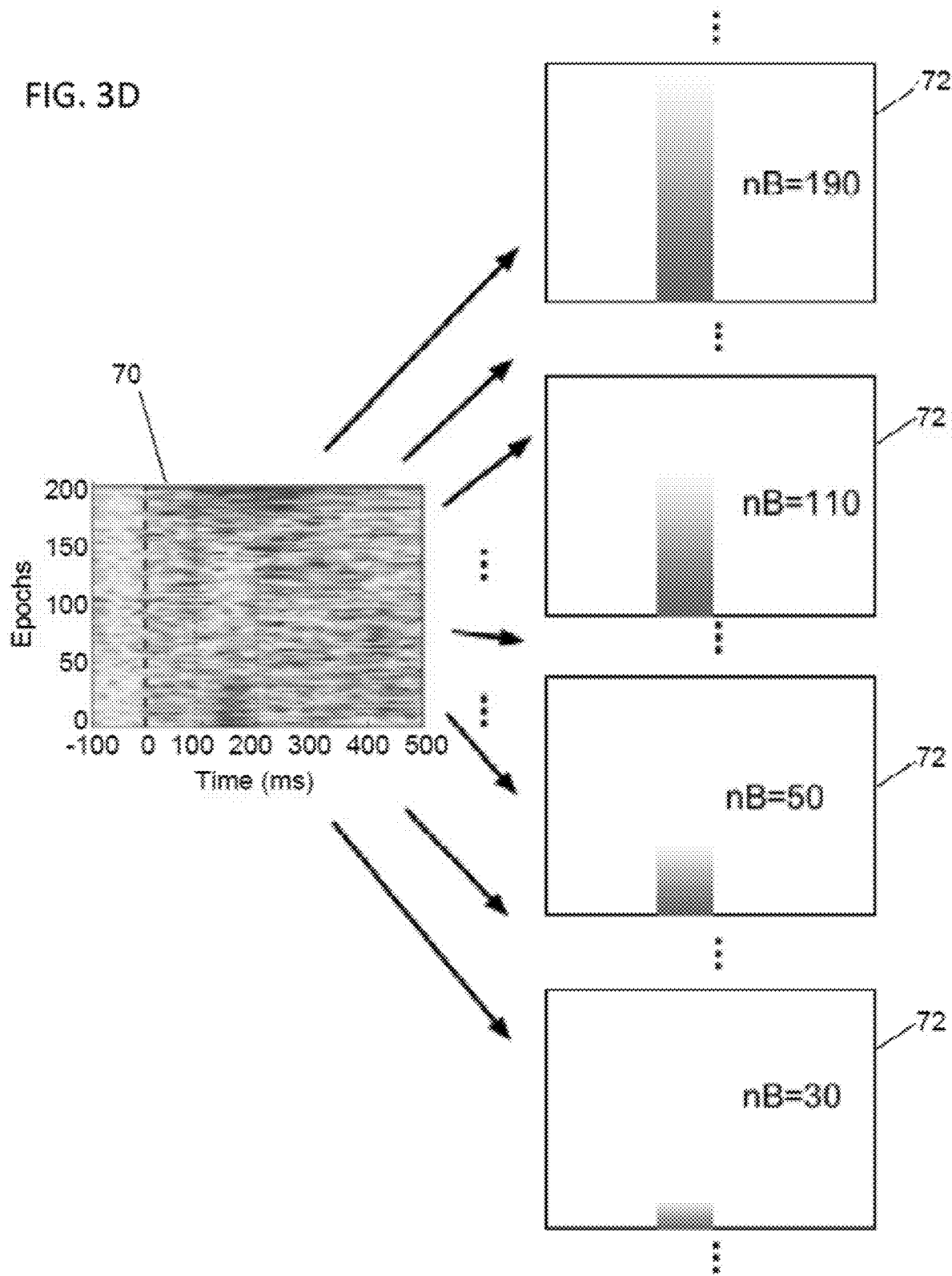
FIG. 3D shows a procedure for estimating the candidate parameter nB.

FIG. 3D schematically shows the determination of the nB value for a sample set of scans from a single session. The real heatmap 70 is spatially correlated with every possible ideal heatmap 72 from no epochs having peak B 91 up to all of the epochs having peak B 91. Each epoch is assigned a normalized maximum value based on the maximum value of the strongest peak B 91. For a given sample set, the peak latencies, onsets, and offsets are determined using bootstrapping. Those three timing variables are then used in determining nB (or nA or nC). The sorting of the heatmap is done using only the data within the onset-to-offset time window of the peak being analyzed. After nB (or nA or nC) is determined, all of the epochs from 1 to nB (or nA or nC) are classified as having peak B 91 (or peak A 90 or peak C 92).

The ideal heatmaps 72 for nB=30, nB=50, nB=110, and nB=190 are shown in FIG. 3D for the real heatmap 70 having about 200 epochs. Each ideal heatmap 72 has a linear gradient within the peak B 91 window, where epoch one has a value of one (e.g., dark blue) and epoch nB has a value of zero (e.g., white). The nB value for the ideal heatmap 72 with the highest correlation to the real heatmap 70 is assigned as the nB value for the real heatmap 70. A similar approach is used to assign the values for nA and nC.

Using these approaches, it can be determined which specific epochs have (or lack) each of the three peaks 90, 91, 92, and the number of epochs with each peak can be calculated, as well as how many epochs have every possible combination of the three peaks 90, 91, 92. Said differently, the tri-peak subset of epochs can be determined. Additionally, the values for a number of the candidate parameters for each patient in the training set can be determined, including the candidate parameter regarding the number of epochs with peak A 90 [nA], the candidate parameter regarding the number of epochs with peak B 91 [nB], the candidate parameter regarding the number of epochs with peak C 92 [nC], the candidate parameter regarding the number of epochs with peak A 90 and peak B 91 [A*B], the candidate parameter regarding the number of epochs with peak A 90 and peak C 92 [A*C], the candidate parameter regarding the number of epochs with peak B 91 and peak C 92 [B*C], and the candidate parameter regarding the number of epochs with peak A 90, peak B 91, and peak C 92 [A*B*C]. The values for these candidate parameters may be determined as a number count, or as a fraction of the total number of epochs for that test patient. The candidate parameters may also be determined using percentage of epochs with one or more of the three peaks. For example, the percentage of epochs having peak A [pctA] may be expressed as 73%. The candidate parameters may also be expressed as the percentage of epochs having peaks A and B, having peaks A, B, and C, having peaks A or C, having peak A but not C, etc.

The values of other candidate parameters may also be determined for each test patient 50 in the training set. The values of the area of peak A and C [area A and C], area of peak B [areaB] are respectively the aggregated area under the heatmap (e.g., heatmap shown in FIG. 3A) that is blue (i.e., with positive magnetic field signal) and the aggregated area under the heatmap that is red (i.e., with negative magnetic field signal). The value of an area ratio candidate parameter (e.g., [areaAandC/areaB]) is the ratio of these two numbers.

The values of other candidate parameters may be determined by creating strong and weak subsets, as introduced above. The value of the candidate parameter for the strong peak A 90 epochs containing peak B 91 is based on the number of epochs having a peak B 91 in the strong peak A 90 subset (e.g., half/50% cutoff) of epochs ["strongA_Bnum"]. Similarly the value of the candidate parameter for the weak peak A 90 epochs containing peak B 91 is based on the number of epochs having a peak B 91 in the weak peak A 90 subset ["weakA_Bnum"]. The value of the candidate parameter for the amplitude of peak B 91 in the strong peak A 90 epochs is based on the average amplitude (e.g., amount of red) of peak B 91 in the epochs in the strong peak A 90 ["strongA_Bamp"] subset. The value of the candidate parameter for the amplitude of peak B 91 in the weak peak A 90 epochs are based on the average amplitude (e.g., amount of red) of peak B 91 in the epochs in the weak peak A 90 ["weakA_Bamp"] subset. In other embodiments, these candidate parameters measuring amplitude may be based on another factor other than average, such as median and generally, any measure of amplitude may be used.

Values for other similar candidate parameters may also be calculated for the reverse situation of subsets including peak B 91, with values based on peak A 90 amplitude or number ["strongB_Anum", "weakB_Anum", "strongB_Aamp", "weakB_Aamp"]. Further values for candidate parameters may also be calculated based on any permutation of a given subset of epochs (e.g., strong or weak) containing a peak (e.g., A, B, or C), and some measure of a quantity of the epochs in that subset (e.g., amplitude or count of another one of peak A 90, peak B 91, or peak C 92).

III.B.3. Other Candidate Parameters

The feature ratio area under the curve ["rAUC"] is calculated as the ratio of the area under the curve ("AUC") of peak C 92 to the AUC of peak A 90 from the averaged MEG data. The boundaries of peaks A and C are defined manually for each run, based on when each peak started and finished with respect to the horizontal baseline. Boundaries are straight vertical lines crossing the time chosen for the beginning and end of each peak. The area is then calculated by creating a straight baseline from the starting point of the boundary to the ending point of the boundary and summing the magnitude of the signal with respect to this baseline. Finally, the ratio between the two areas under the curves is calculated. In exemplary experiments, rAUC tended to be greater in normal test patients than cognitively-impaired test patients.

For the ratio latency ["rLat"], the latency of each peak from the averaged MEG data is determined by finding the time of the highest absolute magnitude of the signal within the three sets of pre-determined boundaries. Then, the difference between the latency of peak C 92 and latency of peak B 91 is calculated, and similarly, the difference between latency of peak B 91 and latency of peak A 90. The ratio of these differences is the value for rLat. In exemplary experiments, rLat tended to be lower for the cognitively-impaired test patients and was particularly low for one such test patients.

After an initial identification of the rAUC and rLat candidate parameters and investigation of their potential as model parameters, a more thorough identification and investigation was performed. As discussed previously, this included not just looking at averaged MEG data from numerous scans but also investigating the distribution of the activation over epochs in the heatmaps of the model MEG data.

Other candidate parameters based on evaluating the heatmaps included ["areaA_ratio"], which is the ratio of the area of peak A 90 in the weak peak A 90 epochs to the area of peak A 90 in the strong peak A 90 epochs; ["Bamp_ratio"], which is the ratio of the overall amplitude of peak B 91 in the stronger half of peak A 90 epochs to the overall amplitude of peak B 91 in the weaker half of peak A 90 epochs (a similar parameter can be determined and used for the C peaks ["Camp_ratio"], and similarly for any permutation of the peaks used to determine the weak and strong subsets, and the peak used to determine the ratio); ["Bnum sA/wA"], which is the ratio of the number of epochs having peak B 91 in the stronger half of peak A 90 epochs to the number of epochs having peak B 91 in the weaker half of peak A 90 epochs; ["Camp_ratio"], which is the ratio of the overall amplitude of peak C 92 in the stronger half of peak A 90 epochs to the overall amplitude of peak C 92 in the weaker half of peak A 90 epochs (a similar parameter can be used for the B peak ["Bamp_ratio"], and similarly for any permutation of the peaks used to determine the weak and strong subsets, and the peak used to determine the ratio); and ["Cnum sA/wA"], which is the ratio of the number of epochs having peak C 92 in the stronger half of peak A 90 epochs to the number of epochs having peak C 92 in the weaker half of peak A 90 epochs. Generally, further permutations of the above parameters are also possible. For example, any parameter including a ratio can also be calculated by inverting the values described above as making up the ratio.

Another candidate parameter, [badInPool], that can be added is a summation of how many candidate parameters in the pool were outside the range for normal test patients. For example, if the pool includes 17 candidate parameters, the value of [badInPool] is in the range of 0 to 17, depending on how many of the 17 candidate parameters a given CI test patient has a value outside the Gaussian distribution fitted to the normal test patient values. In other words, for each of the 17 candidate parameters, the normal values are gathered and fit to a Gaussian distribution. For each candidate parameter, if the value of the candidate parameter for an CI test patient has a probability of being in that distribution that is smaller than the smallest normal test patient probability, then a value of one is added to the [badInPool] candidate parameter. In other words, the less likely the excluded CI test patient was to be part of the normal distribution, the higher the value of the [badInPool] parameter.

To determine the [badInPool] candidate parameter, a separate calculation is made for each of the candidate parameters already in the CI model. For a given candidate parameter, the MEG data for all normal test patients according to an already-determined cutoff for that model parameter (based on whether the MEG data comes from a normal test patient) is fit to a distribution, such as a normal (Gaussian) distribution. That distribution is used to estimate the smallest probability among normal test patients to be part of the normal test patients, where that value is used as a cutoff to mark the value of a given parameter as "bad" or not. In a leave-one-out cross-validation framework, the left-out patient is not used when estimating the normal distribution (although if the left-out patient were an AD patient, the value would not be used anyway).

The value of the [badInPool] candidate parameter for each patient is a simple summation of how many other candidate parameters for that test patient had smaller probabilities of being in the distribution for normal test patients than the smallest normal test patient probability. In an example CI model having six other candidate parameters aside from [badInPool], [badInPool] can go from 0 to 6.

Another possible, similar candidate parameter is [weightInPool], which is a more detailed version of [badInPool]. The weight for [weightInPool] is a summation of the absolute differences between the smallest normal test patient probabilities and that test patient's corresponding probability of being in the distribution for normal test patients, summed over the set of candidate parameters in the model (other than [badInPool]). [badInPool] and [weightInPool] are both posthoc parameters.

III.B.4. Specific Examples of Parameters

In certain embodiments, various exemplary parameters represent different measurements of one or more peaks in the epochs. One example parameter includes area under the curve of peak X, where peak X may be peak A, B, or C. This parameter measures the amount of blue or red signals between onset and offset of peak A, B, or C. Another example parameter includes the percentage of epochs with peaks X. This parameter measures the number of epochs identified to have peaks X as a percentage of the total number of epochs.

Example parameters further include the percentage of epochs with both peaks X and peaks Y, where a peak Y is another peak A, B, or C different from peak X. This parameter measures the number of epochs identified to have both peaks X and Y as a percentage of the total number of epochs. Example parameters further include the percentage of epochs with X or peaks Y. This parameter measures the number of epochs identified to have either X, Y, or both peaks as a percentage of the total number of epochs. Example parameters further include the percentage of epochs with peaks X among epochs with strong peaks A. By way of example, epochs with peaks A may be sorted from strongest to weakest peak A, and the number of epochs with peaks X among the stronger half of the epochs with peaks A is counted. Example parameters further include the percentage of epochs with peaks X among epochs with weak peaks A. By way of example, epochs with peaks A are sorted from strongest to weakest peak A, and the number of epochs with peaks X among the weaker half of the epochs with peaks A is counted.

Example parameters further include the average normalized AUC of peaks X among epochs with weak peaks A. By way of example, epochs with peaks A are sorted from strongest to weakest peak A, and the average amplitude of the peak X is computed among the weaker half of the epochs with peaks A that also have peaks X. Example parameters further include the average normalized AUC of peaks X among epochs with strong peaks A. By way of example, epochs with peaks A are sorted from strongest to weakest peak A, and the average amplitude of the peak X is computed among the stronger half of the epochs with peaks A that also have peaks X.

Example parameters further include the average latency in peak X. This parameter measures the time in which the peak X reaches its maximal absolute amplitude. Example parameters further include the variability in the latency of the peak X. This parameter measures the variability in the time in which the peak X reaches its maximal absolute amplitude. Example parameters further include the average duration of the peak X. This parameter is the average difference between peak X offset and onset. Example parameters further include the variability of the duration of the peak X. This parameter measures the variability of the difference between peak X offset and onset. Example parameters further include the average onset for peak X. This parameter measures the average time in which the peak X surpasses a certain number of standard deviations (e.g., 2 standard deviations) of the baseline signal. Example parameters further include the variability of the onset for peak X. This parameter measures the variability of the time in which the peak X surpasses a certain number of standard deviations (e.g., 2 standard deviations) of the baseline signal. Example parameters further include the standard deviation of the latency of X across all epochs. The time point in which peak X reaches its maximum absolute value is calculated in each epoch. The standard deviation over epochs is reported.

Example parameters further include the average amplitude of the peak X. This parameter measures the average of the maximum absolute value reached by the peak X across epochs. Example parameters further include the variability in the maximum absolute amplitude of the peak X. This parameter measures the variability of the maximum absolute value reached by the peak X across epochs. Example parameters further include the average offset for peak X. This parameter measures the average time in which the peak X returns to a value below a certain number of standard deviations (e.g., 2 standard deviations) of the baseline signal. Example parameters further include the variability of the offset for peak X. This parameter measures the variability of the time in which the peak X returns to a value below a certain number of standard deviations of the baseline signal (e.g., 2 standard deviations). Example parameters further include a change in peak X time shift. This parameter computes how many time points peak X went above a certain number of standard deviation of baseline (e.g., 1 standard deviation), and divides it by the total number of time points between onset and offset (0 to 1, closer to one means less variable). This parameter may serve as a proxy to how "diagonal" the peak is, from the bottom of the heatmap to the top. The more consistent in time across epochs (i.e., the less diagonal), the closer the parameter is to 1.

Example parameters further include peak X amplitude ratio between epochs with strong and weak peaks A. Epochs with peaks A are sorted from strongest to weakest peak A, the average amplitude of the peak X is computed among the epochs that also have peaks X. The ratio of that amplitude between strong and weak A epochs is calculated. Example parameters further include the rate of increase of the peak X. This parameter measures the slope of the line that goes from peak X onset to peak X latency time points. Example parameters further include the rate of decrease of the peak X. This parameter measures the slope of the line that goes from peak X latency to peak X offset time points. Example parameters further include the ratio between peak A AUC in strong over weak peaks A. The amount of blue signal is calculated for weak and strong A epochs, and the ratio is calculated. Example parameters further include the ratio between peak A AUC and peak C AUC. This parameter measures the amount of positive polarity signal in peak A epochs over the amount of positive polarity signal in C peak epochs Example parameters further include the ratio of number of epochs with peaks X between strong and weak peak A epochs. By way of example, epochs are split into weak and strong peaks A, and the number of epochs with peak X in each group is compared against each other.

III.C. Model Parameter Selection

Figure 3E:
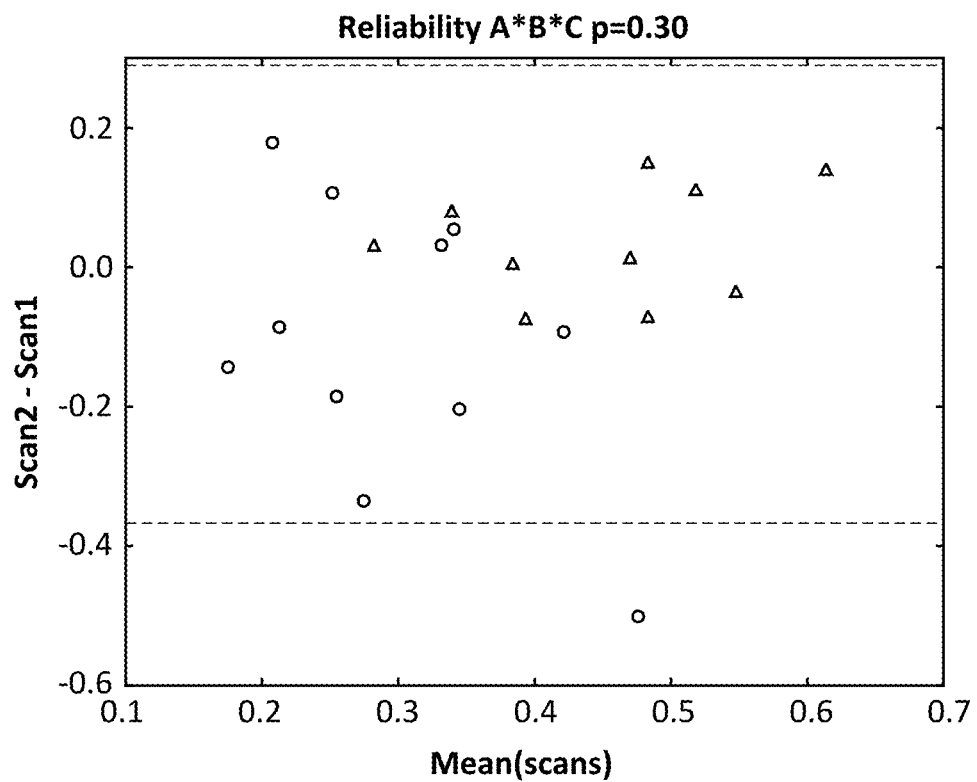
FIG. 3E shows an example Bland-Altman reliability plot for the candidate parameter A*B*C for an example set of test patients.
Figure 3F:
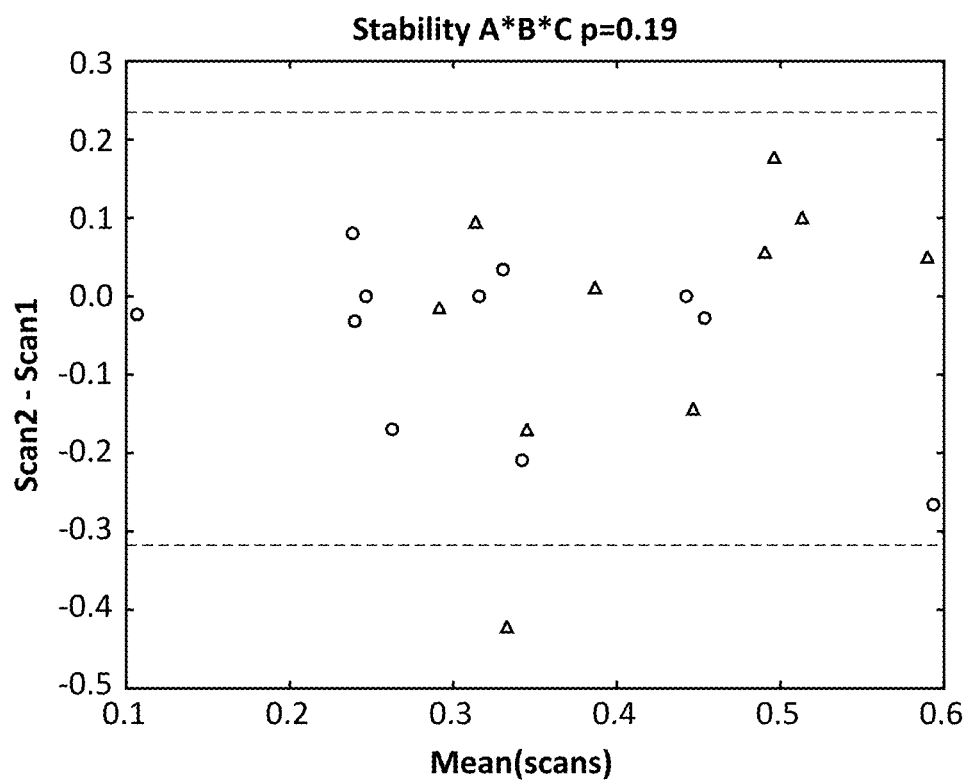
FIG. 3F shows an example Bland-Altman stability plot for the candidate parameter A*B*C for an example set of test patients.

The candidate parameters were evaluated based on whether they were reproducible within and across test patient visits (each visit generating a set of epochs) for reliability and stability, respectively. Bland-Altman plots were used to measure those characteristics. Two such plots appear in FIG. 3E and FIG. 3F, where the triangles are associated with MEG data from normal test patient and the circles are associated with MEG data from CI test patients. FIG. 3E shows a Bland-Altman plot of the reliability of the A*B*C candidate parameter. FIG. 3F shows an example Bland-Altman plot of the stability of the A*B*C candidate parameter for a set of test patients. In short, these plots compare the mean of two measurements and their standard deviation. The horizontal lines in FIG. 3E and FIG. 3F are 95% confidence interval lines, and any candidate parameter that had more than one patient outside the confidence boundaries for the reliability or the stability was deemed unsatisfactory.

In other embodiments, other criteria and methods may be used to evaluate the reliability and stability of candidate parameters, including, but not limited to, intraclass correlation coefficient ("ICC") and regression analysis.

Among the wide variety of possible candidate parameters that may be used to build the CI model, thirty-seven candidate parameters were identified from visual analysis of MEG data to build one implementation of a CI model. The subtle differences between the MEG scans of CI test patients and "normal" test patients described above were identified by careful manual visual review and observation and not by a computer algorithm. The 37 candidate parameters, previously described in Section III.B, include (as ordered from best to worst in terms of excluding CI test patients from the distribution for normal test patients) as weakA_Bamp, strongA_Bnum, nA, weakA_Camp, A*B*C, strongA_Bamp, B*C, areaC, duration (var), Cnum sA/wA, areaA, A*C, weakA_Cnum, nC, areaA_ratios, latencyA (var), onsetA (var), A*B, nB, offsetB (mean), strongA_Cnum, offsetB (var), Bnum sA/wA, Bamp_ratio, areaA/areaC, latencyB (mean), areaA/areaC, latencyB (var), offsetC (var), latencyA (mean), Camp_ratio, onsetA (mean), onsetB (mean), onsetB (var), duration (mean), strongA_Camp, and offsetC (mean).

Some of these candidate parameters were selected for further analysis based on being reliable and stable candidate parameters. Further analysis included determining the correlation between the candidate parameter and the MMSE score of the test patient 50. The selection of which reliable and stable candidate parameters became model parameters was based, at least in part, on the weights the linear and non-linear models assigned to the model parameters.

It is important to note that two patients with very similar MMSE scores were found to have very different peak C 92 amplitudes, which highlights how these candidate parameters may offer new insights into the disease that were hidden by just looking at MMSE scores.

In some embodiments, a certain number of parameters (e.g., 100 parameters) specified in Section III.B.4 are generated. In one embodiment, roughly half of the parameters are selected from each side of the head. For example, in some embodiments, 50 of the parameters are contralateral features while other 50 of the parameters are ipsilateral features. To select the parameters, the stability of the parameters across different patient visits are determined for those 100 features. The stability is measured based on correlation, which is discussed in further detail in Section VII.C. By way of example, for each of the features, a scatter plot may be created among multiple patients. In the scatter plot, the X axis is the parameter value at the first run of a patient and the Y axis is the parameter value at the second run of the patient. The runs may be generated during the same or different patient visits. Multiple points can be plotted based on the two-run plots of different patients. The more stable the feature is, the closer to a diagonal line the plot will be. In other words, using techniques such as linear regression, a diagonal line of slope 1 may be fit through a scatter plot using data among different patients for a stable feature. For the scatter plots, additional dimensions (e.g., additional patient visits or additional runs) may be added if the stability across more than two runs is determined. The most stable features may be selected given a preset threshold (e.g., $p<0.05$, false discovery rate $q<0.05$). The selection process may reduce the set of features to 35 out of the initial 100. In turn, the within-day variability in absolute value for each of the selected features (e.g., the 35 selected features) may be determined. A total of 70 features are may be selected (e.g., 35 selected features and 35 variability values determined from the selected features) for further analysis such as training and testing of the CI model.

III.D.1. Model Training

Once CI model parameters are selected, the CI model is trained to classify patients based on their MEG data. A wide variety of machine learning techniques can be used to create the CI model, examples of which include Random Forest Classifiers ("RFC"), Random Classifier Regressors, Gradient Boosting, Support Vectors (also known as Support Vector Machine or "SVM"), Linear SVM, Radial basis function kernel SVM ("RBF SVM"), Linear Regression, Logistic Regression, and other forms of regressions. This list is not exhaustive, and one of skill in the art will appreciate that other machine learning techniques may also be used, including techniques in the field of deep learning such as Neural Networks.

Generally, training these models generates a set of coefficients, which may also be referred to as weights, that represent directly or indirectly how the values for the various model parameters correspond to either a cumulative score that correlates (positively or negatively) with CI or a classification of CI. For example, in one embodiment, the cumulative score may measure a value that is negatively correlated with the chance of a patient having some form of CI. Put differently, the lower the cumulative score, the more likely that the patient having the cumulative score is detected with one or more forms of CI. In one implementation of any of the example models described in Section IV below, a set of model test patients were selected to include a subset having no known cognitive dysfunction and a subset showing a range of severity of symptoms of cognitive dysfunction, specifically cognitive dysfunction associated with CI. However, in practice the principles described herein may also be applicable to a variety of other diseases and conditions, including, but not limited to, mild cognitive disorder. In the case of a CI example model generated using RFC with one-step classification, the coefficients may also be referred to as "critical values", as used in the literature regarding RFC models, in this case for categorizing the values of particular model parameters for a given patient as being normal or CI-indicative.

What the model is trained to detect may vary by implementation. Examples include a two-step classification and a one-step classification. In a two-step classification, a first model is used to predict the cumulative score for a patient, and then a second model is used to categorize or quantify a patient with respect to a particular disease or CI based on the predicted cumulative score. In a one-step classification, a single model categorizes or quantifies a patient with respect to CI directly.

For two step classifications, the first step uses a linear/non-linear model, generally a linear or non-linear regression, although in alternate implementations more complicated algorithms may be used. After the cumulative score has been predicted, the second step includes using a simple cutoff to classify whether the test patient is a normal test patient or an CI test patient. For example, a set of predicted cumulative scores of test patients is fit to a linear model and one or more weights is determined that correlates the predicted cumulative scores with a categorization.

The CI model may be a static model or a living model. In a static model, the model parameters and their weights are not changed as the model is used to evaluate and assess new patients. For example, in the RFC example, the normal value limits are calculated by fitting a Gaussian distribution to the set of normal patients minus whatever patient is left out in the cross validation. In a living model, new MEG data that has been collected from some or all new patients becomes additional model MEG data used to further train the weights of the candidate parameters or to add, delete, or change candidate parameters and thereby update the model. For a progressive disease, such as AD, the CI model may also be fine-tuned by monitoring the patients and collecting model MEG data over time and re-evaluating the earlier CI model MEG data, such as if a particular normal test patient begins to show symptoms of the progressive disease, to add, delete, or change candidate parameters and/or retrain the CI model to re-determine the model weights, and thereby update the model.

In some embodiments, both the selection of features for use in training the CI model and the training of the CI model may be conducted through a cross-validation process. For example, in one embodiment, a random set of 5 features out of 70 features pre-selected (as discussed in Section III.C) are used in training the CI model. In an example cross-validation process, a random set of 5 features are selected out of the 70 features. The test patients are divided into a training set and a testing set. For example, in a collection of 20 test patients, 19 out of the 20 test patients may be classified as the training set and the last test patient is held out and used as the testing set. Other combinations of numbers in the training set and testing set are also possible. The testing set is used to train the weights of the CI model for the random set of 5 features for a weighted combination of features to predict the cumulative score. The CI model may be a linear or non-linear model. In one embodiment, the CI model is a linear model. After it is trained, the CI model is used to predict the cumulative score of the testing set and compute the error of the testing set. For example, the error may be computed by determining the difference between the actual cumulative score and the predicted score.

The cross-validation process may be repeated for additional rounds by using different training and testing sets. Other combinations of training sets and testing set are repeated to train the CI model and determine the error computed by the CI model. For example, in each round, a different test patient is held out as the testing set and the training is conducted using the rest of the patients. After the error values for different test patients are determined, an error metric such as a mean-square error is computed across all rounds. The error metric may represent the mean error of the 5 features selected for the CI model.

In addition to using different training sets, the cross-validation process may be repeated for additional sessions for using different features. In another session of training, a different set of 5 features may be selected and the cross-validation process is repeated to determine the error metrics for this particular set of 5 features. The training and cross-validation processes may further be repeated until other possible combinations of 5 features are tested. In some embodiments, a combination of 2, 3, 4, 6 features, or other suitable numbers, may also be tested. In some embodiments, a limited number of features are used to train the CI model to achieve a balance between having sufficient features to describe an accurate story with a satisfactory error and avoiding excessive number of features that make the model narrative become difficult to understand and that could overfit the data.

In some embodiments, the cross-validation process that includes leaving one test patient out as a testing set may be referred to as leave one out cross validation ("LOOCV").

In some embodiments, in addition to features used in the training the CI model and predicting the cumulative score, additional features that best correlate (either individually or collectively) with the cumulative score may also be reported in a clinical display that is to be discussed in further detail in Section VII.F. The additional features may be reported even though they are not included in training the CI model or the predication of the cumulative score.

III.D.2. Example Cumulative Score

In one embodiment, the model is trained to predict a combined score, which may also be referred to as a cumulative score or an integrated neurocognitive test score (INTS). The cumulative score may be developed to reflect a combination of multiple cognitive test scores of test patients, instead of focusing on a single cognitive domain (e.g., compared to only the MMS score). In one embodiment, the score may be defined by the first component of a principal component analysis that takes into consideration different neuropsychiatric scores.

Figure 13A:
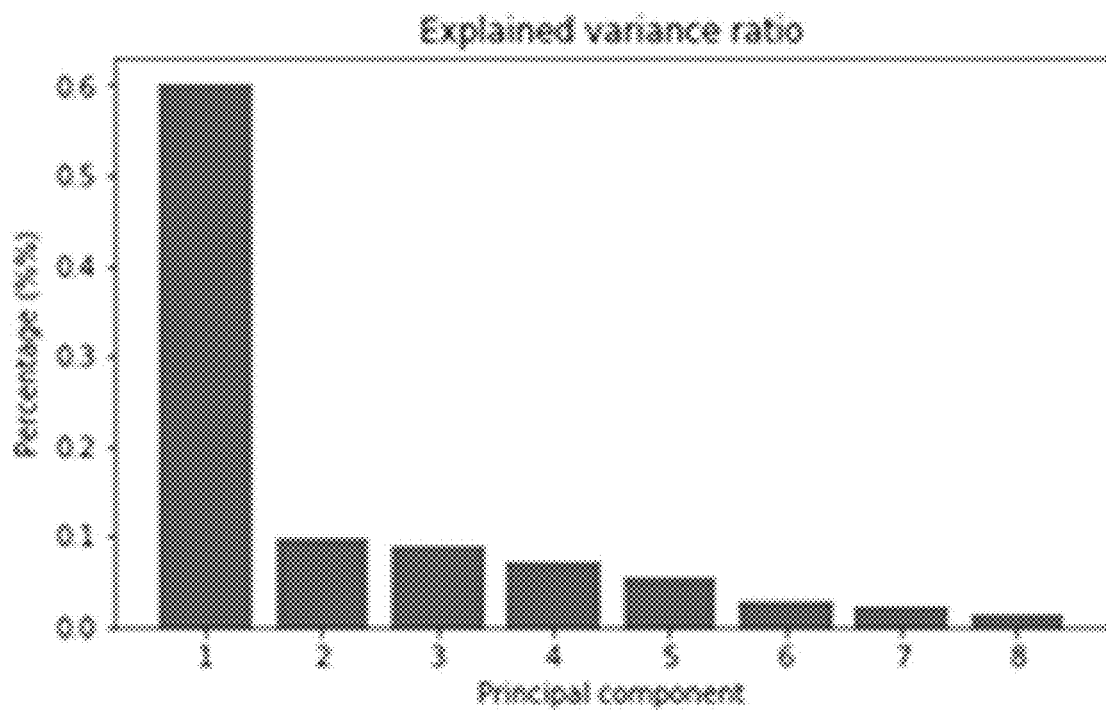
FIG. 13A illustrates a plot of variance ratio of a principal component analysis, according to one embodiment.
Figure 13B:
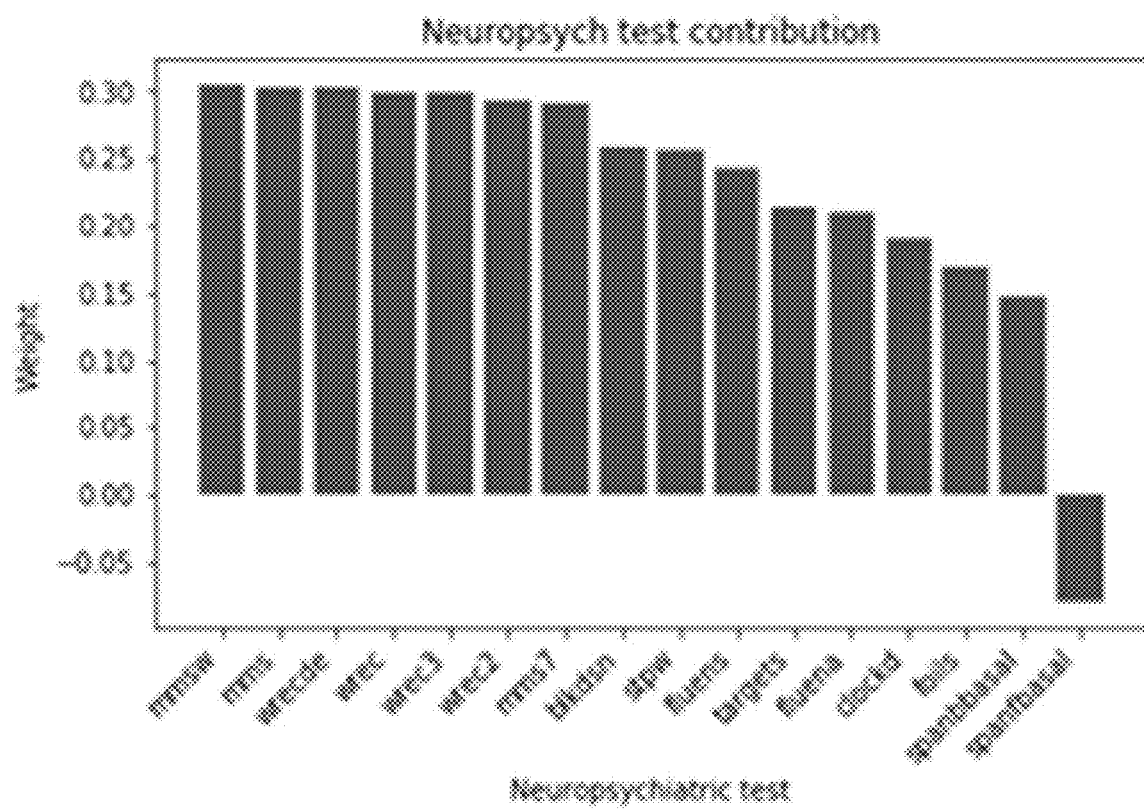
FIG. 13B illustrates a plot of different neuropsychiatric test score contribution to a cumulative score, according to one embodiment.

FIGS. 13A and 13B shows that the cumulative score predicted by the trained CI model according to an embodiment is a reasonable representation of the combination of multiple cognitive test scores. Principal component analysis was performed by taking into consideration 16 different neuropsychiatric scores that are listed in Section VII.X. The 16 scores are mms, mms7, mmsw, wrec, wrec2, wrec3, wrecde, targets, foils, fluena, fluens, spanfbasal, clockd, blkdsn, and stpw. In carrying out the principal component analysis, the tests were originally chosen from an initial set of 42 tests, which were filtered to exclude tests that had zero or low variance in the dataset that was used, or that were not completed by all of the test patients in the dataset. The cumulative score was the first component of the principal component analysis.

FIG. 13A illustrates the contribution of each component to the overall variance in the neuropsychiatric test data. FIG. 13A shows that the first component, which represents the cumulative score, corresponds to most of the variance in the neuropsychiatric test data (over 60%). The next most important component only explains fewer than an additional 10% of the variance. In this embodiment, the principal component analysis showed that the cumulative score is a good representation of the combined results of various neuropsychiatric tests. FIG. 13B shows the weight of the individual contribution of each of the 16 tests to the first principal component. There are similar contributions by most tests to the cumulative score.

In one embodiment, the cumulative score may be normalized to be within a range from 50 to 100. A score of 50 may represent a low cognitive ability (e.g., a high likelihood of CI). A score of 100 may represent a high or normal cognitive ability (e.g., a high likelihood of normal cognitive ability). The lower boundary of the range may be determined based on the lowest score observed across the samples in the MMS scale. This may represent the cognitive abilities found in the test data as related to the general population.

IV. Examples

IV.A. Test Measurement Setup and Example Data Collection Protocol

An Elekta Neuromag® 306 channel MEG system 48 was used to record whole brain signals. The system had a total of 306 SQUID sensors 32, with each of the 102 locations having three different SQUID sensors 32: two planar gradiometer SQUID sensors 32 and one magnetometer SQUID sensor 32.

Figure 4A:
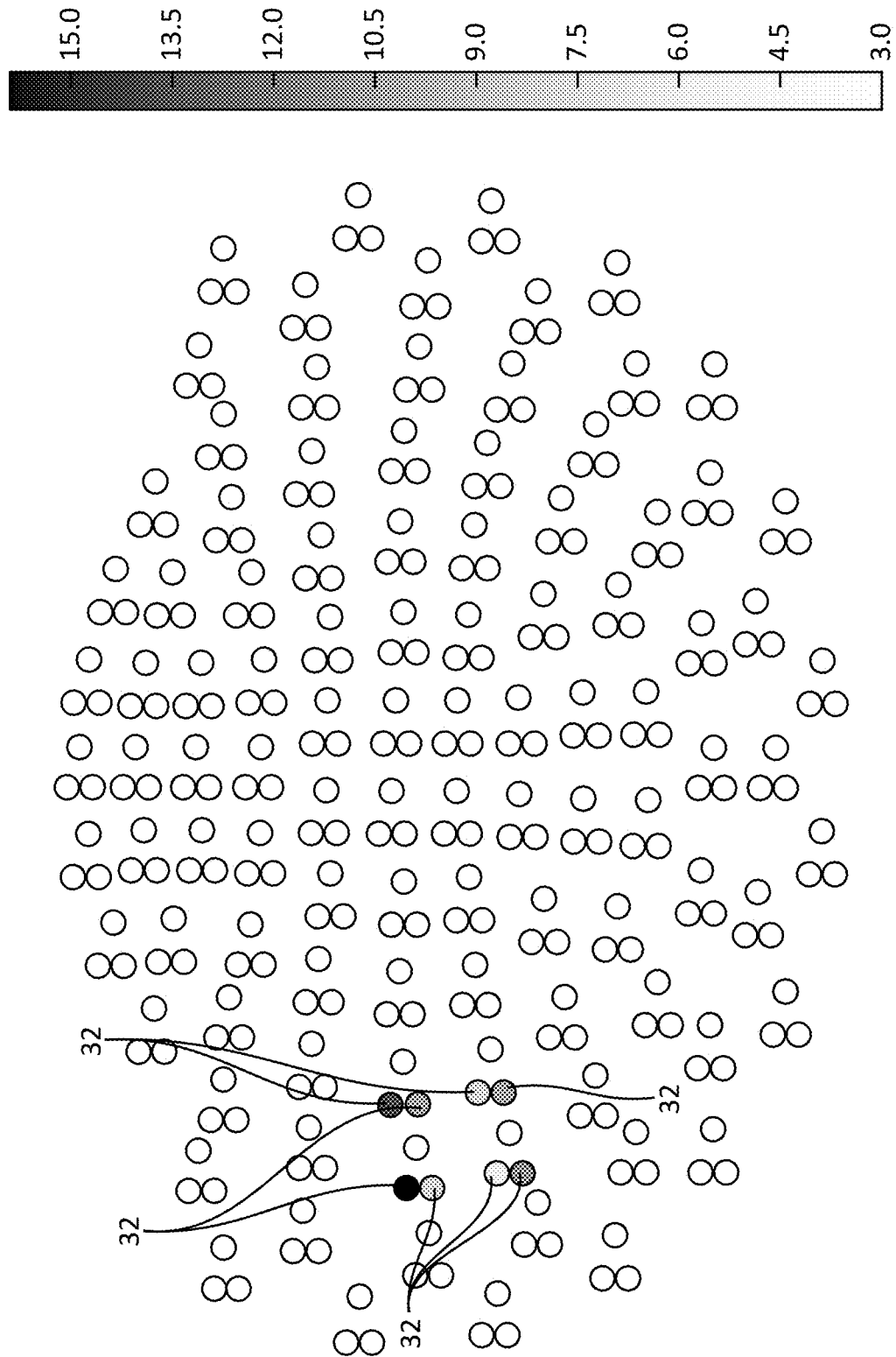
FIG. 4A shows schematically a gradiometer and magnetometer orientation of SQUID sensors in one embodiment.

FIG. 4A shows the array of SQUID sensors 32 for the Elekta Neuromag® MEG apparatus, with the shaded circles representing the generally most informative SQUID sensors 32, out of a pool of gradiometers located on the ipsilateral side of the helmet, for the CI models described herein. Each circle in FIG. 4A represents a gradiometer or a magnetometer. As shown in FIG. 4A, the gradiometer SQUID sensors 32 are paired and are sensitive to magnetic fields that are at 90 degrees to each other. Also shown but not labeled in FIG. 4A, a magnetometer SQUID sensor 32 was associated with each pair of gradiometer SQUID sensors 32 in the MEG apparatus.

Gradiometer SQUID sensors 32 and magnetometer SQUID sensors 32 are structurally and functionally different from each other. Magnetometers measure the amplitude of the magnetic field (e.g. in Tesla units, T) at a certain point in space. Gradiometers measure the difference or gradient between magnetic fields (e.g. in Tesla/meter units, T/m) in two different points in space. These two points in space may be across the same spatial plane (e.g., a spatial gradiometer as in the Elekta system used herein), or along the same (Z) axis (e.g., an axial gradiometer).

The informative gradiometers used to generate the example models in this section tended to be at the eight locations of SQUID sensors 32 labeled in FIG. 4A, and only the data from these eight SQUID sensors 32 was used. These eight SQUID sensors 32 are most known for receiving signals from the left temporal region of the brain. These included sensors MEG0233, MEG0242, MEG0243, MEG1612, MEG1613, MEG1622, and MEG1623 of the Elekta Neuromag® 306 channel system. The colors in FIG. 4A represent the frequency of use in the CI models described herein. There were a total of 63 sessions. The frequency of use from top to bottom of the four sensors in the left column was 16, 4, 3, and 9. The frequency of use from top to bottom of the four sensors in the right column was 13, 7, 4, and 7. This indicates that a much smaller SQUID sensor head 12 may be used if placed at the proper location on the head of the patient.

The experimental setup discussed above was used to capture the MEG data used to generate the models in this section. The specific details of the capture of the MEG data is discussed above in Section II, and is not repeated here for clarity and to condense this description.

The same set of test patients was used to build the example CI models in this section. The set of test patients included twenty-one test patients, including ten normal test patients with no indication of cognitive impairment and eleven test patients who had already been diagnosed as having CI. An MRI was collected for each subject. Scans to record auditory evoked fields were run on the test patients in accordance with the setup and MEG data gathering steps discussed above. MEG recordings were performed in a magnetically-shielded room. All test patients except for one cognitively-impaired patient also received an MMSE score based on an administered MMSE test. Data from the test patient without an MMSE score was not used in the regression model but was used for the one-step classification tasks.

All of the test patients were white except for one black normal test patient and one black CI test patient. The normal test patient pool included five men and five women in an age range of 64 to 84 years, with a median age of 72 and a mean age of 73.9. The CI test patient pool included eight men and three women in an age range of 62 to 84 years, with a median age of 78 and a mean age of 76.2.

Figure 4B:
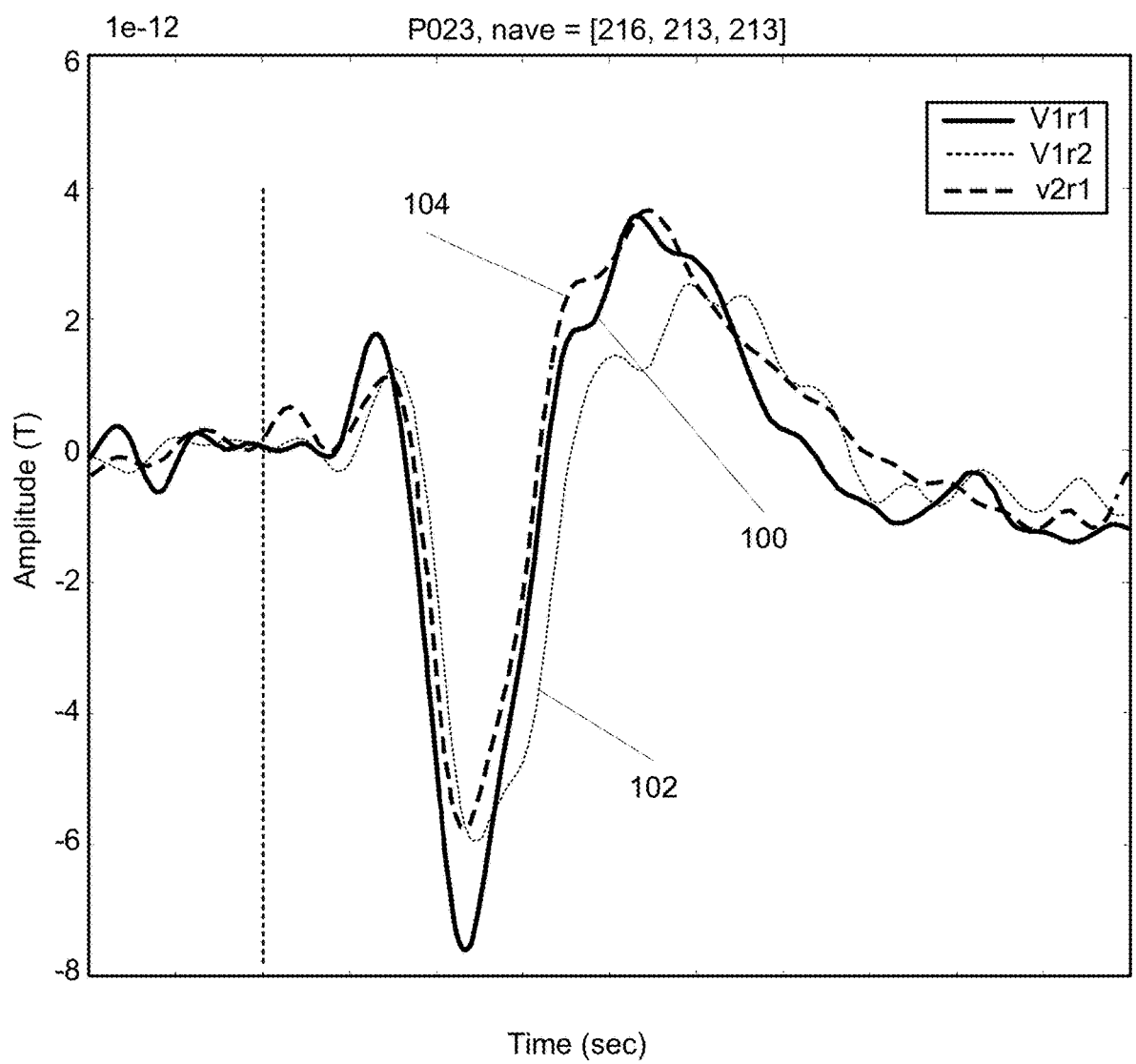
FIG. 4B shows example response signals from three different sessions on a representative normal patient.

FIG. 4B shows the three averaged response signal curves 100, 102, 104 from three example auditory stimulation test sessions, two done on the same day and the third being done on a different day, on a representative normal patient. These curves illustrate the general reproducibility between test runs for normal patients. However, they also highlight that there is a significant amount of non-uniformity between individual epochs even for normal patients, which the example CI models described in this section are able to quantify and capture.

Figure 4C:
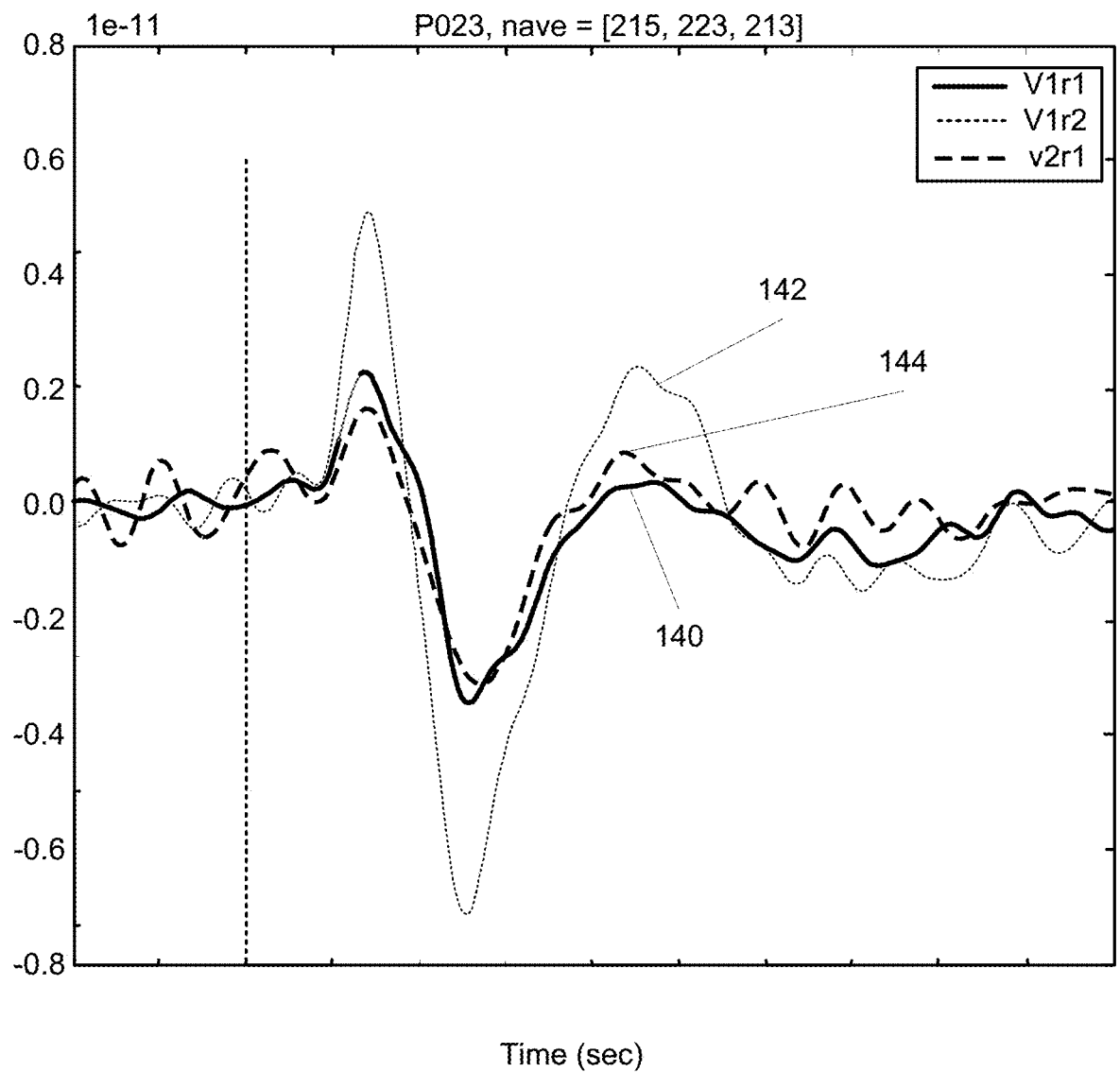
FIG. 4C shows example response signals from three different test sessions on an AD patient.

FIG. 4C shows the three averaged response signal curves 140, 142, 144 from three example auditory stimulation test sessions, two done on the same day and the third being done on a different day, on a representative CI patient. Although two of the curves are very similar, the peaks and valley of the third are significantly greater in magnitude. These curves illustrate the relative lack of reproducibility between test runs for CI patients. However, like the normal patient curves they also highlight that there is a significant amount of non-uniformity between individual epochs for CI patients as well, again which the example CI models described in this section are able to quantify and capture.

The MEG data used to produce the averaged MEG data curves shown in FIG. 2A, FIG. 2B, FIG. 4B, and FIG. 4C may come from hundreds of repetitions of an evoked response from a single test session. Visualizing this MEG data in the form of a heatmap, such as the one shown in FIG. 3A, allows visual inspection of the set of raw epoch data to identify trends and parameters that are hidden or lost in the averaged or otherwise collapsed MEG data. In such a heatmap, each of the responses, or epochs, is plotted as a horizontal line with a color scale representing the strength of the measured magnetic field.

In developing the example model described in this section, gradiometer SQUID sensors 32 (i.e. only 204 out of the 306 SQUID sensors 32) were used, since those SQUID sensors 32 had the best power in discriminating between the two groups. These SQUID sensors 32 were selected on the basis of having minimum variability in peak A 92. For other models, however, the magnetometers (i.e. the other 102 out of the 306 SQUID sensors 32) may be used in place or in addition to the above-mentioned 204 SQUID sensors.

IV.B.1. Example CI Model 1

For a first example CI model, a set of 17 candidate parameters that were both reliable and stable (see Section III.C.) were called "good" parameters, which were carried on for future analysis. Although many of the candidate parameters that failed the reliability and stability test were good at discriminating between normal and CI test patients, they were not selected for this particular CI model as model parameters, because the candidate parameters were not sufficiently reproducible in other recording sessions of the same test patient.

From the good candidate parameters, normal distributions were established based on the mean and standard deviations of normal test patient values for each candidate parameter, and the number of CI test patients having probabilities lower than the lowest normal test patient of being part of the distribution was determined. In other words, the candidate parameter correctly sorted the CI test patient if the CI test patient's probability of being in the normal test patient distribution was smaller than the probability of the least likely normal test patient. The parameters were then scored based on how many CIs were outside the distribution for normal test patients (i.e., how many test patients were correctly marked as CI patients). That score (i.e. the number of CI test patients outside the distribution) was used as a preliminary rank of the good parameters.

The ranked set of 17 good candidate parameters were then selected to identify the candidate parameters that were included as model parameters in this CI model. In this example embodiment, the candidate parameter that marked the most CI test patients correctly was selected first, added to the CI model and considered the best model parameter. Each subsequent model parameter that was selected and added if it added the most information to that previous information (i.e. captured CI test patients not captured by previous candidate parameters). When two model parameters marked the same number of CI test patients (or same number of additional test patients), both were added together. This procedure was employed to minimize the number of candidate parameters used and therefore reduce the chances of overfitting. The model parameter selection continued until no more CI test patients were left to be marked.

This procedure selected the following six model parameters: the number of epochs with all three peaks 90, 91, 92 ["A*B*C"], the number of epochs with peak A 90 ["nA"], the amplitude of peak C 92 in the weak peak A 90 epochs ["weakA_Camp"], the amplitude of peak B 91 in the weak peak A 90 epochs ["weakA_Bamp"], the number of strong peak A 90 epochs with a peak B 91 ["strongA_Bnum"], and the variability of the duration of peak B 91 ["duration (var)"]. To this set of six candidate parameters, the [weight-InPool] candidate parameter was also added. Thus, this example CI model had seven model parameters in total.

The CI model was then trained using a linear model on those seven parameters to predict cumulative score. A hard cutoff on predicted cumulative score was then used to classify the test patient as normal or CI. No cross validation was used, and thus the same data was used for both training and testing.

The result of the model was the predicted cumulative score, which was then split to classify the data. The model was able to perfectly distinguish between normal test patients and CI test patients based on predicted cumulative score.

IV.C Example CI Model 2

Another CI model was built using the same seven candidate parameters from the prior example CI model (example CI model 1) plus the posthoc [badInPool] candidate parameter for a total of eight model parameters.

Although very good correlation with cumulative score and group separation was shown in this model, each candidate parameter does not provide an answer in isolation. A very high correlation with cumulative score may be achieved, in one embodiment, by combining the best candidate parameters using a non-linear model (random classifier regressor) to predict cumulative scores, which are used to discriminate between normal test patients and CI test patients. This work makes it clear that while some test patients are marked as CI based on many candidate parameters, some others depend on characteristics of a smaller set of candidate parameters. This shows how a varied set of candidate parameters is effective at discriminating test patients. It further shows that candidate parameters derived from individual aspects of data from individual epochs are important in discriminating test patients, rather than, for example, entirely relying on data that aggregates, collapses or conflates MEG response data from multiple epochs together, such as by averaging data from multiple epochs.

IV.D. Alternative Modeling Technique CI Example Models

Different machine learning methods and model designs were tested using the full set or a subset of the 17 good candidate parameters described above. A summary of these results is shown in Table 1. For each of these model designs/method, both a two-step classification (regression to determine a hypothetical cumulative score, and then classification as CI or normal) and a simple classification as CI or normal between the two groups were tried. The hyperparameters for each machine learning method were left at default for each of these models. One of skill in the art will appreciate that tuning these hyper parameters will generally lead to improvement in the predictive power of these example CI models.

Table 1 illustrates a number of example CI models built using different sets of candidate parameters and trained using different machine learning techniques. As a key to the following table, "Two-step" and "One-step" denote whether two step classification or one step classification was used per the previous paragraphs. The example machine learning techniques used included Random Forest, Gradient Boosting, Support Vectors (also known as Support Vector Machine or "SVM"), Linear SVM, Radial basis function kernel SVM ("RBF SVM"), a Linear Regression, and a Logistic Regression. All example CI models in Table 1 were trained using leave one out cross validation ("LOOCV").

The sets of model parameters used include "all" (all 17 good candidate parameters) with the [badInPool] and [weightInPool] parameters making 19 model parameters total, and all 17 good candidate parameters without the [badInPool] and [weightInPool] parameters making 17 model parameters, labeled in the table as "no InPool."

In Table 1, "r" denotes the correlation coefficient for all test patients and accuracy denotes the performance of the model in correctly categorizing the twenty test patients as normal or CI (e.g., 1 means all twenty test patients were categorizing correctly, etc.). For all of the two-step models, Pearson correlation coefficients (r) and p-value (p), as well as the Spearman correlation coefficient (r) and p-value (p), were calculated separately for both normal ("NV") and CI test patients. All such values in Table 1 are rounded to two decimal points.

TABLE 1

Machine Learning Method Results

| Method | r | Accuracy | NV | | AD | |
|---|---|---|---|---|---|---|
| | | | Pearson | Spearman | Pearson | Spearman |
| Two-step Random Forest (all) | 0.8932 | 1.0 | r = 0.28 (p = 0.43) | r = −0.04 (p = 0.92) | r = 0.07 (p = 0.84) | r = 0.11 (p = 0.76) |
| Two-step Random Forest (no InPool) | 0.6685 | 0.75 | r = 0.77 (p = 0.01) | r = 0.71 (p = 0.02) | r = −0.34 (p = 0.33) | r = −0.40 (p = 0.26) |
| Two-step Gradient Boosting (all) | 0.9091 | 1.0 | r = −0.23 (p = 0.52) | r = −0.03 (p = 0.94) | r = 0.29 (p = 0.42) | r = 0.17 (p = 0.64) |
| Two-step Gradient Boosting (no InPool) | 0.3651 | 0.65 | r = 0.14 (p = 0.70) | r = 0.20 (p = 0.58) | r = −0.18 (p = 0.62) | r = −0.13 (p = 0.73) |
| Two-step Support Vectors (all) | 0.4435 | 0.5 | r = 0.29 (p = 0.41) | r = 0.40 (p = 0.25) | r = −0.34 (p = 0.33) | r = −0.24 (p = 0.50) |

TABLE 1-continued

Machine Learning Method Results

| Method | r | Accuracy | NV Pearson | NV Spearman | AD Pearson | AD Spearman |
|---|---|---|---|---|---|---|
| Two-step Support Vectors (no InPool) | 0.2582 | 0.5 | r = 0.17 (p = 0.64) | r = 0.18 (p = 0.63) | r = −0.37 (p = 0.30) | r = −0.33 (p = 0.35) |
| One-step Linear SVM (all) | | 0.9047 | | | | |
| One-step Linear SVM (no InPool) | | 0.8571 | | | | |
| One-step RBF SVM (all) | | 0.8571 | | | | |
| One-step RBF SVM (no InPool) | | 0.7143 | | | | |
| One-step Logistic Regression (all) | | 0.9524 | | | | |
| One-step Logistic Regression (no InPool) | | 0.8571 | | | | |

The results of these models illustrate several points. First, the two posthoc parameters, [badInPool] and [weightInPool] provide a substantial improvement to a model's performance. The ensemble non-linear models (RF and GBM) tend to outperform the others, given the current set of model parameters. High classification accuracies may also be obtained without taking the intermediate step of predicting cumulative scores. However, for reasons already stated herein, this is a highly useful characteristic of the models, for example, for use in evaluating for the presence or progression of other diseases.

IV.E. Example CI Models Based on Other Channel Selection Criteria

To evaluate the effect of the SQUID sensor 32 selection criterion, other selection criteria were tested. The tested criteria included selecting the SQUID sensor 32 that had the highest percentage of epochs having peak A 90 ("most peak A"), selecting the SQUID sensor 32 that had the highest percentage of epochs having peak B 91 ("most peak B"), and selecting the SQUID sensor 32 that had the highest intensity for peak A 90 ("highest peak A") using all epochs.

Once the sensor selection was made, the 37 candidate parameters were calculated based on the MEG data from those selected SQUID sensors 32, and the stability and reliability of each candidate parameter was evaluated independently to determine which candidate parameters were good. The most peak A 90, most peak B 91, and most intense peak A 90 sensor selection criteria produced 9, 17, and 11 good candidate parameters, respectively. Example CI models were then developed using a two-step classification based on all of the good candidate parameters, and no InPool parameters. Again, RFC was used to predict cumulative scores and a regular cutoff on the predicted value was used to classify as normal or CI for the two-step classification. The results of this evaluation are shown in Table 2.

TABLE 2

ADD Model Results with Alternative Sensor Selection Criteria

| Sensor Criterion | r | Accuracy | NV Pearson | NV Spearman | CI Pearson | CI Spearman |
|---|---|---|---|---|---|---|
| Most peak A (all) | 0.3290 | 0.6 | r = 0.63 (p = 0.05) | r = 0.68 (p = 0.03) | r = −0.27 (p = 0.45) | r = −0.23 (p = 0.52) |
| Most peak A (no InPool) | −0.1564 | 0.45 | r = 0.34 (p = 0.34) | r = 0.29 (p = 0.42) | r = −0.10 (p = 0.79) | r = −0.09 (p = 0.82) |
| Most peak B (all) | 0.5614 | 0.65 | r = 0.26 (p = 0.47) | r = 0.37 (p = 0.30) | r = 0.35 (p = 0.32) | r = 0.23 (p = 0.53) |
| Most peak B (no InPool) | 0.2784 | 0.55 | r = 0.11 (p = 0.77) | r = 0.08 (p = 0.84) | r = 0.48 (p = 0.16) | r = 0.43 (p = 0.21) |
| Highest peak A intensity (all) | 0.6105 | 0.9 | r = 0.44 (p = 0.21) | r = 0.35 (p = 0.32) | r = −0.39 (p = 0.27) | r = −0.37 (p = 0.29) |
| Highest peak A intensity (no InPool) | 0.4665 | 0.6 | r = 0.35 (p = 0.32) | r = 0.42 (p = 0.23) | r = 0.40 (p = 0.25) | r = 0.39 (p = 0.27) |

Based on the test data presented herein, none of these alternative sensor criteria provided results as good as using the least variability in the latency of peak A 90 as the sensor selection criterion. However, it is clear that other alternative sensor criteria are still predictive and may be a viable substitute to minimizing peak A 90 latency variability. While there are many ways in which a single channel may be selected for use in extracting the features, the characteristic of peak A has yielded the best classifier results so far. That may be because of actual characteristics of peak A, or the number of stable and reliable features such selection scheme yields, compared to other methods.

IV.F. Additional CI Model Examples

In order to test how the number of model parameters affects the CI model, a large number of additional example CI models were created, where the number of good candidate parameters being used was varied for the Random Forest Regressor (RFR) CI model in the leave-one-out cross validation framework described above in Section IV.E.3. Two-step classification was performed: as above, first predicting the cumulative score, second using the cumulative score to classify the patient between normal and CI. As above, the Random Forest Regressor uses its default parameters, and no hyperparameter optimization was performed. Two versions of each such CI model were created, one with and one without the posthoc parameters ([badInPool] and [weightInPool]).

The number of CI model parameter chosen at random from the pool of 17 good candidate parameters was fixed. Then, those model parameters were chosen randomly from the pool of good candidate parameters 200 different times, and histograms were created for the regression coefficient and accuracy. This produced 16 sets of histogram pairs (i.e., choosing one parameters at random, all the way to 17). Note that the variability of choosing one parameter at random (after 17 iterations), and 17 parameters (always the same ones, as there are only 17 parameters), comes from the Random Forest algorithm, which has a random component in splitting the trees.

Figure 4D:
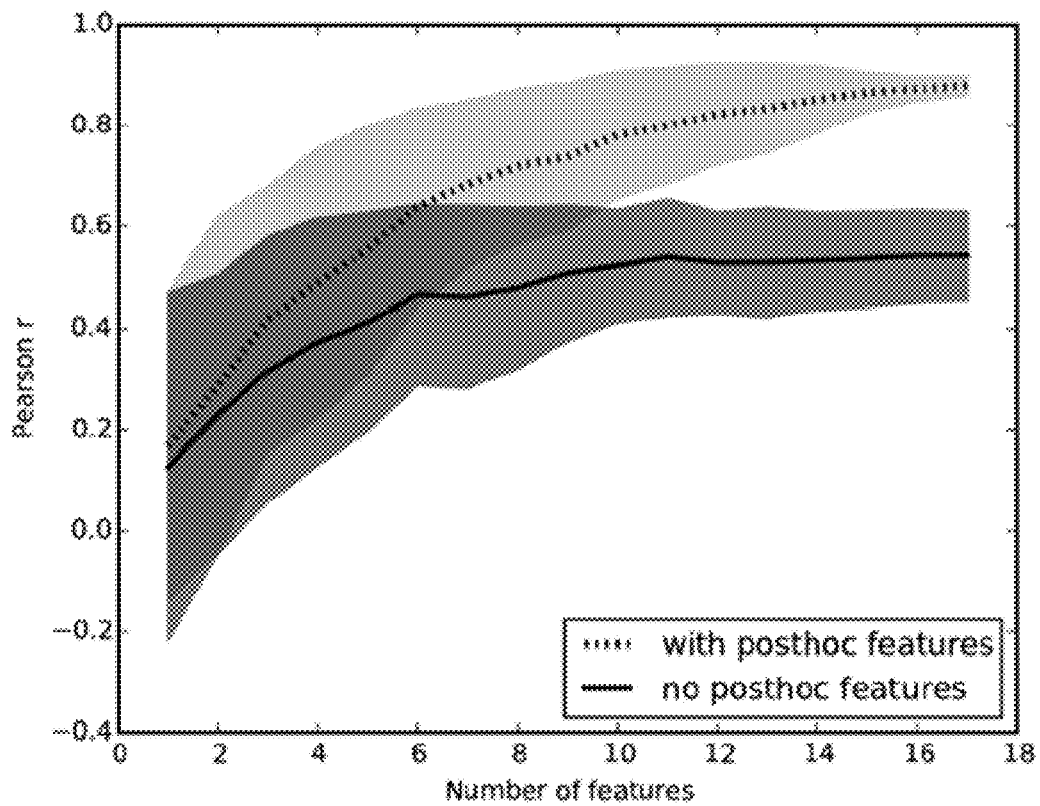
FIG. 4D shows the mean and standard deviation of the Pearson r value as a function of the number of candidate parameters used in a CI model.

FIG. 4D shows the average and standard deviation for the Pearson r value (y-axis) as a function of the number of good candidate parameters (x-axis) included in the example CI models both with and without posthoc parameters. In FIG. 4D, the average is illustrated as a solid line, and the standard deviation is illustrated as an envelope around that line.

Figure 4E:
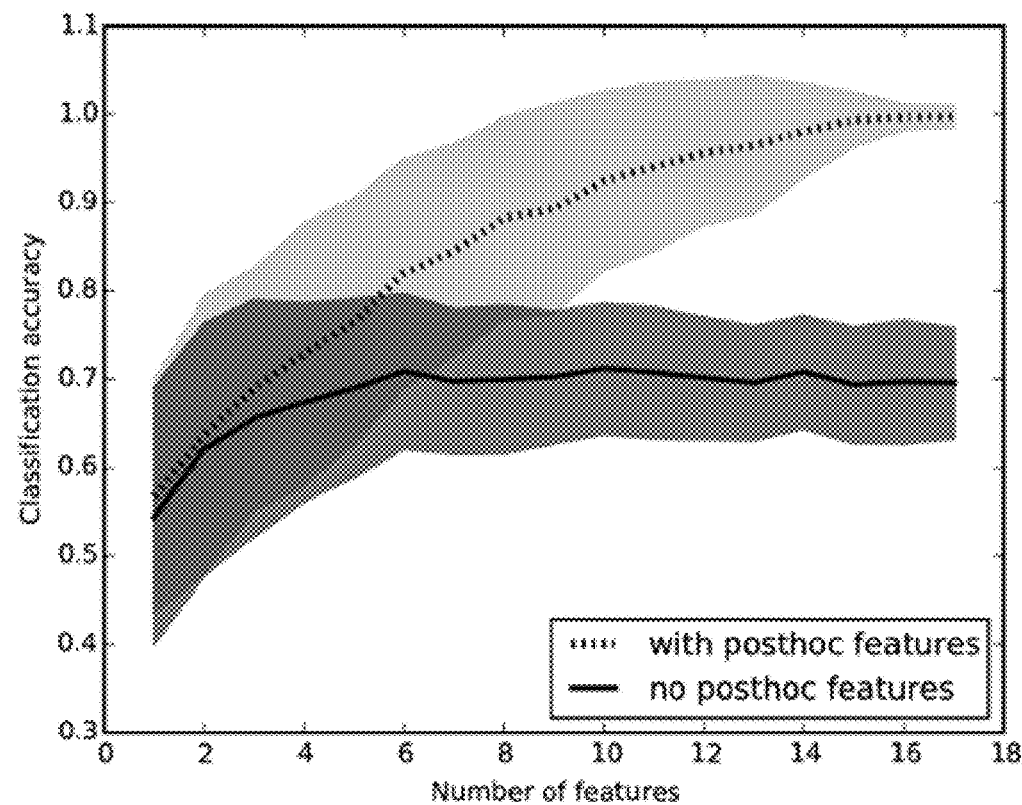
FIG. 4E shows the mean and standard deviation of the classification accuracy as a function of the number of candidate parameters used in a CI model.

FIG. 4E shows the average and standard deviation for the classification accuracy as a function of the number of good candidate parameters included in the example CI model both with and without posthoc parameters. FIG. 4E is otherwise illustrated similarly to FIG. 4D.

FIG. 4D and FIG. 4E show that the more of the good candidate parameters that are used, the better the performance of the resulting CI model. They further illustrate that the two posthoc parameters are powerful. Further, the variance between posthoc and no posthoc parameters increases as the number of model parameters increases. Again, the deviation when all 17 good candidate parameters are used in the CI model is a result of the randomization component of the Random Forest Regressor.

V. Model Use

A developed model, for example one of the CI models mentioned above with a particular set of candidate parameters, may be applied to other "new" patients who were not part of the training set. The "new" MEG data is collected from the new patients in the same manner as the model MEG data was collected from the test patients. The new MEG data is then analyzed to determine the values of the model parameters for the model for the new patient. The values of the new patient's model parameters are compared to the model values for the model parameters, and an assessment of the new patient is provided. The assessment of the new patient relates to the medical condition that the model was developed to evaluate. The common example throughout this description is for discrimination of CI; however the processes throughout this description are applicable to other medical conditions.

The computer 20 calculates the model parameter values from the new patient MEG data, when possible, but human input may be helpful for the determination of some model parameter values, depending on the nature of the process to determine the model parameter value. After analysis of the new MEG data is complete, the results are provided.

Figure 5:
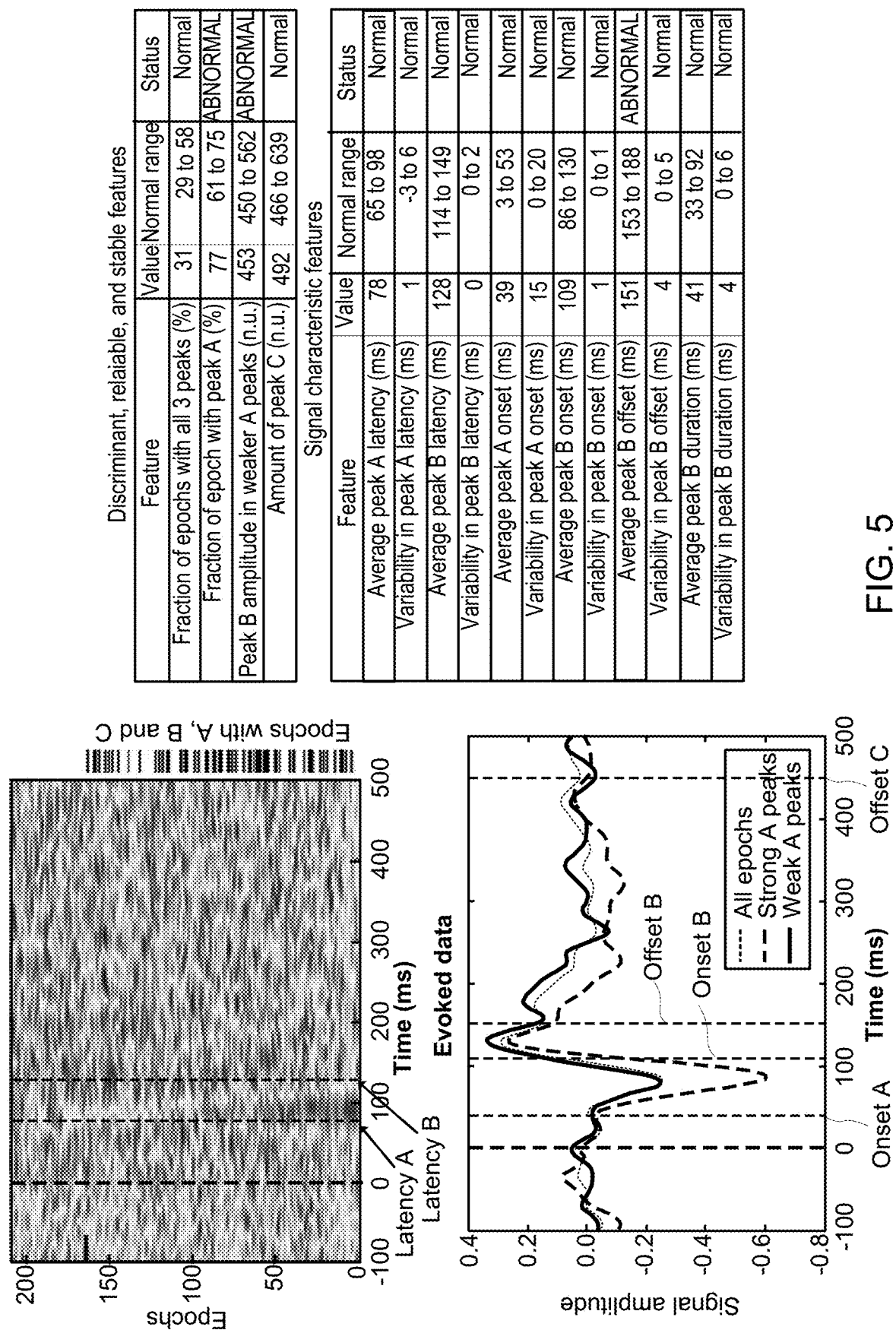
FIG. 5 shows an example graphical user interface for presentation on a computer display to provide results from use of a CI model on a test patient.

FIG. 5 illustrates an example graphical user interface display that a doctor may use to quickly analyze the new patient after the collection of the MEG data. The upper left portion of the example display of FIG. 5 shows an example heatmap of the new MEG data. The lower left portion of the example display of FIG. 5 shows curves of averaged MEG data for all epoch, strong peak A 90 epochs, and weak peak A 90 epochs, along with the estimates for the values of onsets and offsets. The upper right portion of the example display of FIG. 5 shows an example chart listing the model parameters of the model, the patient's values for those model parameters, and the normal values for those model parameters, along with highlighting of any abnormal results. The lower right portion of the example display of FIG. 5 shows an example chart that lists other candidate parameters, the patient's values for those candidate parameters, and normal values, and highlights any abnormal results. The example patient in FIG. 5 would be considered to have CI based on the information in FIG. 5.

Regarding the highlighting of abnormal parameters, the individual values for each model parameter contributing to the [badInPool] and [weightInPool] parameters as discussed above in Section III.B.3 can be used as part of a presented graphical user interface (GUI) display to determine which parameter values to highlight. Generally, when a given patient's value for a given model parameter is outside the range that is expected from a distribution of normal test patients, the value for that model parameter may be marked as abnormal in the GUI. For example, if, as above, the normal test patient values for all test subjects are used for model parameter A*B*C, and a distribution (e.g., a normal distribution) is estimated from that. Assume for this example that the smallest probability among normal test patients to be in that distribution is calculated as 0.2. Consequently any patient with probability <0.2 of being in the distribution for normal test patients will have the model parameter A*B*C marked in some distinguishing manner (e.g., in red as presented in FIG. 5).

Models that are trained based on the parameters to determine whether a patient is cognitively impaired can be used in methods of diagnosing cognitive impairment in a patient.

Models that are trained based on the parameters to determine whether a patient is cognitively impaired and to discriminate degrees of cognitive impairment can be used in methods of staging the extent of cognitive impairment in the patient. Such models can also be used in methods of monitoring progression of disease. In methods of monitoring disease progression, at least a first determination and a second determination of the degree of cognitive impairment are obtained at a spaced time interval, and the change in degree of cognitive impairment between first and second determinations is calculated.

Models that are trained based on the parameters to determine whether a patient is cognitively impaired and to discriminate cognitive impairment caused by neurodegeneration from cognitive impairment of other etiology can be used in methods of diagnostically discriminating cognitive impairment in a patient caused by neurodegeneration from cognitive impairment of other etiology.

The models can also be used in a method of treating a patient having cognitive impairment, the method comprising administering a therapeutically effective amount of an anti-cognitive impairment therapeutic agent to a patient who has been determined through use of the model to have cognitive impairment.

In some embodiments, the anti-cognitive impairment therapeutic agent is a disease-modifying anti-neurodegeneration agent. In some embodiments, the anti-cognitive impairment therapeutic agent is a cognitive symptom enhancement agent.

In certain embodiments, the disease-modifying anti-neurodegeneration agent binds to one or more of beta-secretase 1 (BACE-1), gamma secretase, Tau, Aβ, amyloid precursor protein (APP), α-synuclein, leucine rich repeat kinase 2 (LRRK2), parkin, presenilin 1, presenilin 2, apolipoprotein E4 (ApoE4), huntingtin, p75 neurotrophin receptor (p75NTR), CD20, prion protein (PrP), and death receptor 6 (DR6).

In specific embodiments, the anti-cognitive impairment therapeutic agent is selected from Table 3.

TABLE 3

| Agent (target or mechanism of action) | Company |
| --- | --- |
| ALKS 7119 (CNS modulator) | Alkermes |
| ALZ-801 (amyloid beta-protein inhibitor) | Alzheon |
| ALZT OP1 (amyloid beta-protein inhibitor) | AZTherapies |
| ANAVEX ™ 2-73 | Anavex Life Sciences |
| ANAVEX ™ Plus (ANAVEX 2-73/donepezil) | Anavex Life Sciences |
| apabetalone (RVX-208) (BET protein inhibitor) | Resverlogix |
| ARC-029 (nilvadipine) | Archer Pharmaceuticals |
| ASP3662 (11-beta-HSD1 inhibitor) | Astellas Pharma US |
| AVN-101 (serotonin 6 receptor antagonist) | AllaChem & Avineuro Pharmaceuticals |
| AVN-322 (serotonin 6 receptor antagonist) | AllaChem & Avineuro Pharmaceuticals |
| AVP-786 (dextromethorphan)analogue/quinidine) | Avanir Pharmaceuticals & Concert Pharmaceuticals |
| AVP-923 (dextromethorphan/quinidine) | Avanir Pharmaceuticals |
| AXS-05 (bupropion/dextromethrophan) | Axsome Therapeutics |
| AZD3293 (BACE inhibitor) | AstraZeneca & Eli Lilly |
| azeliragon (TTP488) (RAGE antagonist) | vTv Therapeutics |
| BACE inhibitor | Eli Lilly |
| BAN2401 (humanized anti-amyloid beta mAb) | Biogen | Eisai |
| bexarotene (RXR-selective retinoid analogue) | ReXceptor |
| BI 409306 (phosphodiesterase 9A inhibitor) | Boehringer Ingelheim Pharmaceuticals |
| bisnorcymserine (butyrylcholinesterase inhibitor) | QR Pharma |
| BPN14770 (type 4 cyclic nucleotide phosphodiesterase inhibitor) | Tetra Discovery Partners |
| brexpiprazole (dopamine partial agonist) | Lundbeck & Otsuka Pharmaceutical |
| bryostatin 1 (protein kinase C stimulant) | Neurotrope BioScience |
| CAD106 (beta-amyloid protein inhibitor) | GlaxoSmithKline |
| CNP 520 (BACE1 protein inhibitor) | Amgen & Novartis Pharmaceuticals |
| CPC-201 (donepezil/peripherally acting cholinergic blocker fixed-combination)dose) | Chase Pharmaceuticals |
| CPC-212 (next-generation acetylcholinesterase inhibitor) | Chase Pharmaceuticals |
| crenezumab (beta-amyloid protein inhibitor) | Genentech |
| CSP-1103(amyloid beta-protein inhibitor) | CereSpir |
| donepezil transdermal patch | Corium International |
| E2027 | Eisai |
| E2609 (BACE1 protein inhibitor) | Biogen & Eisai |
| ELND005 (amyloid beta-protein inhibitor) | Transition Therapeutics |
| gantenerumab (amyloid beta-protein inhibitor) | Genentech |
| GC021109 (purinoceptor P2Y6 agonist) | GliaCure |
| GSK933776 (amyloid beta-protein inhibitor) | GlaxoSmithKline |
| idalopirdine (serotonin 6 receptor antagonist) | Lundbeck & Otsuka Pharmaceutical |
| immune globulin | Grifols USA |
| INP-102 intranasal | Impel NeuroPharma |
| JNJ-54861911 (BACE inhibitor) | Janssen Research & Development & Shionogi |
| LY3002813 (N3pG-amyloid beta mAb) | Eli Lilly |
| MEDI1814 (anti-amyloid beta mAb) | MedImmune |
| memantine transdermal patch | Corium International |
| MER 5101 (vaccine with beta-amyloid protein fragment) | MerciaPharma |
| MK-7622 (muscarinic M1 receptor modulator) | Merck |
| MSDC-0160(mTOT modulator) | Metabolic Solutions Development |
| NGP 555 (amyloid precursor protein secretase modulator) | NeuroGenetic Pharmaceuticals |

TABLE 3-continued

| Agent (target or mechanism of action) | Company |
| --- | --- |
| NIC-515 (amyloid precursor protein secretase inhibitor) | Humanetics |
| NTC-942 (serotonin 4 receptor agonist) | Nanotherapeutics |
| PF-05251749 | Pfizer |
| PF-06648671 | Pfizer |
| PF-06751979 | Pfizer |
| pioglitazone (insulin sensitizer) | Takeda Pharmaceuticals |
| piromelatine (melatonin agonist) | Neurin Pharmaceuticals |
| Posiphen ® (R-phenserine) | QR Pharma |
| rilapladib (Lp-PLA2 inhibitor) | GlaxoSmithKline |
| RVT-101 (serotonin 6 receptor antagonist) | Axovant Sciences |
| SAR228810 (anti-protofibrillar AB mAb) | Sanofi US |
| solanezumab (amyloid beta protein inhibitor) | Eli Lilly |
| SUVN-502 (serotonin 6 receptor antagonist) | Suven Life Sciences |
| SUVN-D4010 (serotonin 4 receptor agonist) | Suven Life Sciences |
| T-817MA (amyloid beta-protein inhibitor) | Toyama Chemical |
| T3D-959 (PPAR-delta/gamma agonist) | T3D Therapeutics |
| TGF-beta agonist | Stanford University & SRI Bioscience |
| TPI 287 (next-generation taxane) | Cortice Biosciences |
| TRx0237 (tau protein aggregation TDP-43 aggregation inhibitor)inhibitor/ | TauRx Pharmaceuticals |
| UB-311 (amyloid beta-protein inhibitor vaccine) | United Biomedical |
| verubecestat (MK-8931) (BACE1 protein inhibitor) | Merck |
| VX-745 (p38 mitogen-activated protein kinase inhibitor) | EIP Pharma |

Models that are trained based on the parameters to determine whether a patient is cognitively impaired and to discriminate degrees of cognitive impairment can also be used in methods of setting the dosage of an anti-cognitive impairment therapeutic agent in a patient having cognitive impairment. In typical embodiments, the method comprises determining the degree of cognitive impairment, and then setting the dosage of the anti-cognitive impairment therapeutic agent based on the determined degree of the patient's cognitive impairment.

Models that are trained based on the parameters to determine whether a patient is cognitively impaired and to discriminate degrees of cognitive impairment can also be used in methods of titrating the dosage of an anti-cognitive impairment therapeutic agent in a patient having cognitive impairment. In typical embodiments, a first determination and a second determination of the degree of cognitive impairment are determined at a spaced interval during which interval the patient has been receiving an anti-cognitive impairment therapeutic agent at a first dosage level, and the dosage is increased to a second dosage level if the degree of cognitive impairment has increased between the first and second determinations.

VI. Model Performance & Observations

Additional analysis may be done to evaluate the performance of a model once the model has been developed. To evaluate the example models described herein, the highest scoring good candidate parameters were used to predict the cumulative score of each test patient. Those calculations were performed using the entire dataset and also using cross-validation. In cross validation, one of the test patients is left out and the model is trained using all of the remaining test patients. The trained model is then used to predict the cumulative score of the left-out test patient. That evaluation was done for each test patient as the left-out test patient.

Figure 6A:
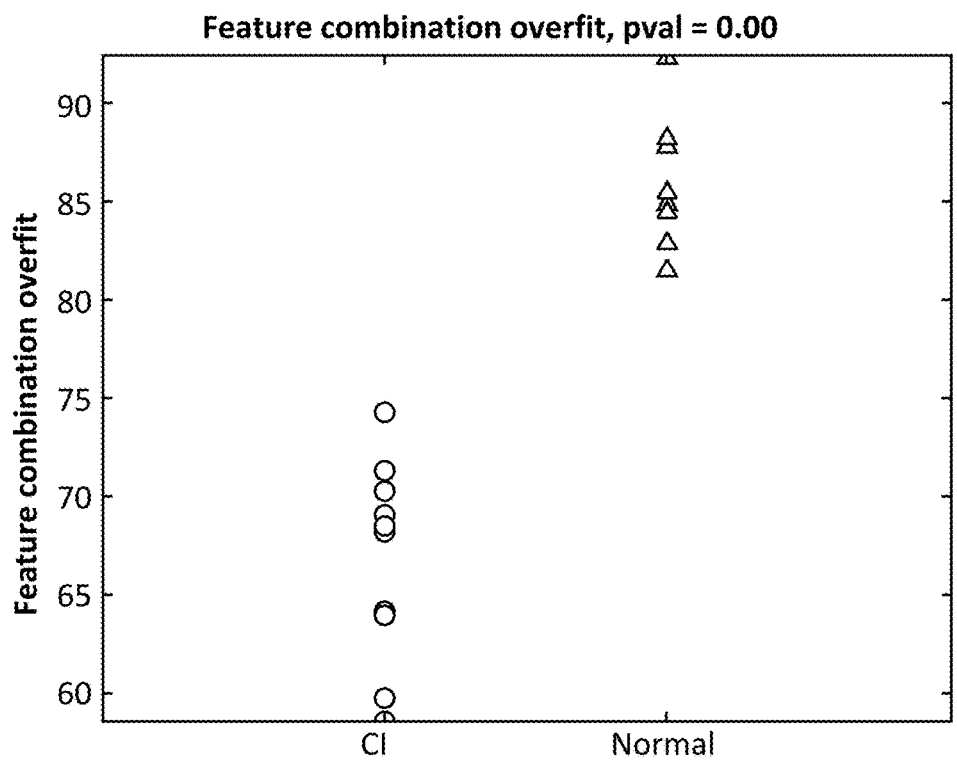
FIG. 6A shows separation of patients by patient group for a linear CI model of seven model parameters.
Figure 6B:
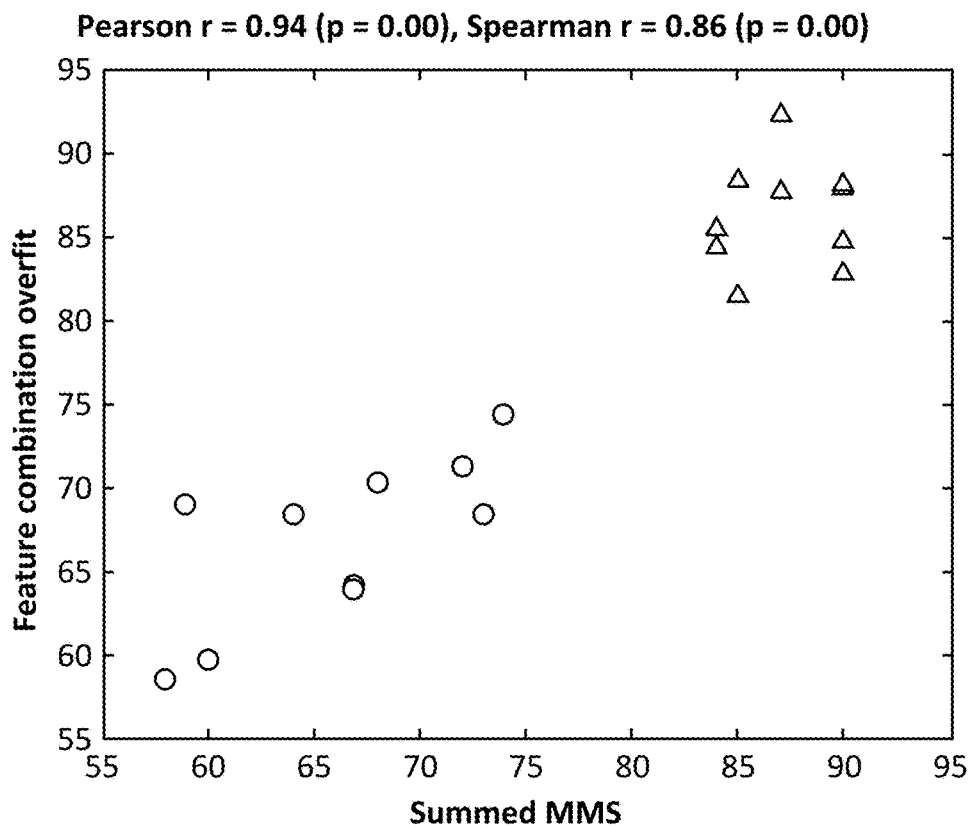
FIG. 6B shows separation of patients by summed Mini-Mental State Examination ("MMSE") score for the linear CI model associated with FIG. 6A.
Figure 6C:
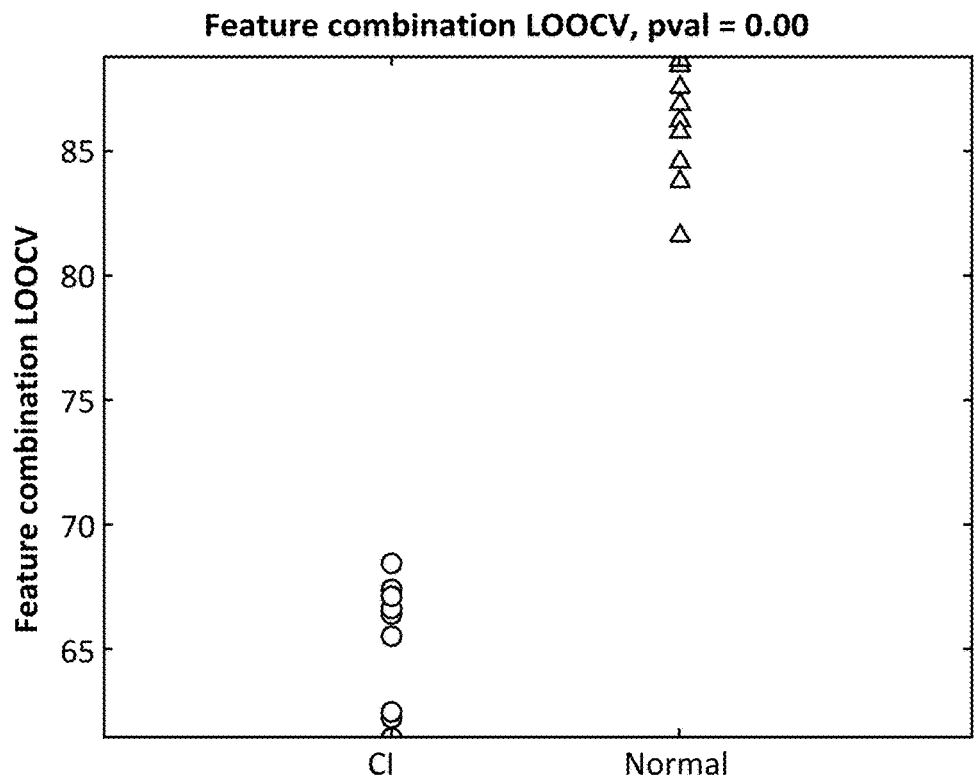
FIG. 6C shows separation of patients by patient group for a non-linear CI model of eight model parameters.
Figure 6D:
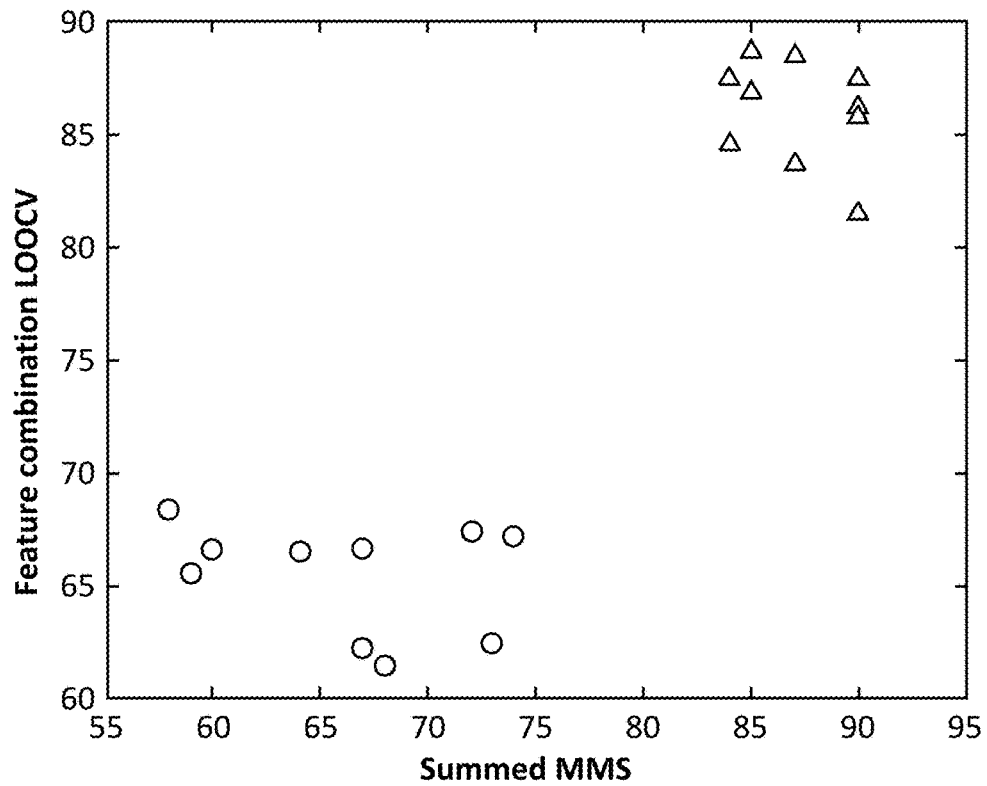
FIG. 6D shows separation of patients by summed MMSE score for the non-linear CI model associated with FIG. 6C.

In the one-step classification model, the left-out test patient was classified directly as a normal test patient or an CI test patient, without predicting an cumulative score. In the two-step model, the left-out test patient was classified as a normal test patient or an CI test patient based on the predicted cumulative score. Referring to FIG. 6A and FIG. 6B, the seven candidate parameter Example CI Model 1, implemented as a linear model as described above without using LOOCV, provides a very good prediction of the cumulative score ($r=0.94$, $p<0.001$) for the left-out test patient. In this simulation of a clinical environment in which the status of the test patient is unknown, the model was able to perfectly discriminate between normal test patients and CI test patients. Referring to FIG. 6C and FIG. 6D, the eight candidate parameter Example CI Model 2 using LOOCV, implemented as a non-linear model as described above, is still able to perfectly distinguish between normal and CI, but does not predict the cumulative score ($r=0.88$, $p<0.001$) as well as Example CI Model 1. Specifically, a Random Forest Regressor was trained for the non-linear model using all good candidate parameters of the test patients and predicted the cumulative score of the left-out test patient. In other words, when using a leave-one-out cross validation with the non-linear model, the reliable and stable model parameters predict whether the left-out test patient was normal or CI with 100% accuracy (perfect sensitivity and specificity).

Although the model was developed using normal test patients and CI test patients, the model may allow for the identification of test patients with an intermediate level of cognitive function ("minimal cognitive impairment" or "MCI") between that of normal test patients and that of test patients with CI.

In the MEG data described herein, it appears that the peak A 90 is setting the "time lock" of the first note of the response for the peak B 91. The peak B 91 is then generated, with it being suspected that the peak B 91 is shared by signal connectivity with the frontal cortex and the peak C 92 then helps to characterize the peak B 91. A missing peak C 92 may be associated with a prolonged peak B 91 but is not a requirement for a correctly timed peak B 91.

The model may be used to detect temporal changes in a magnetic cortical surface map as a result of application of one or more controlled stimuli to a human patient as described herein. The results may be used to give a better understanding of the correlation between stimuli and human brain activity.

Figure 15A:
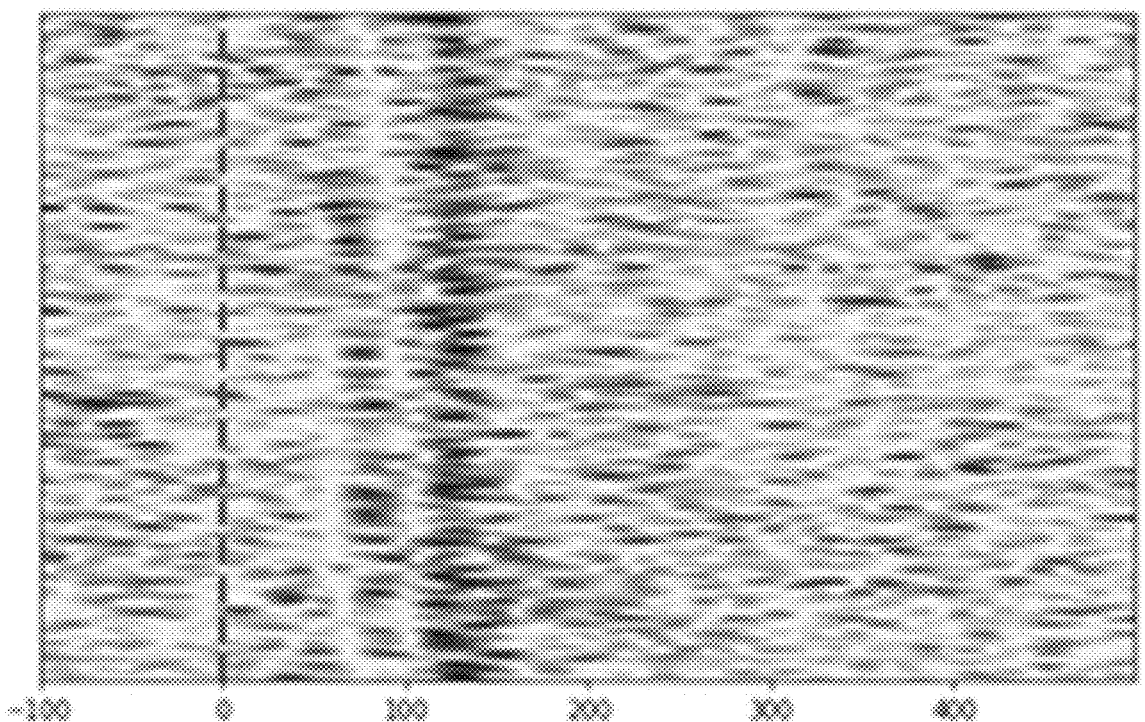
FIGS. 15A and 15B illustrate example heatmaps of different CI test patients, according to one embodiment.
Figure 15B:
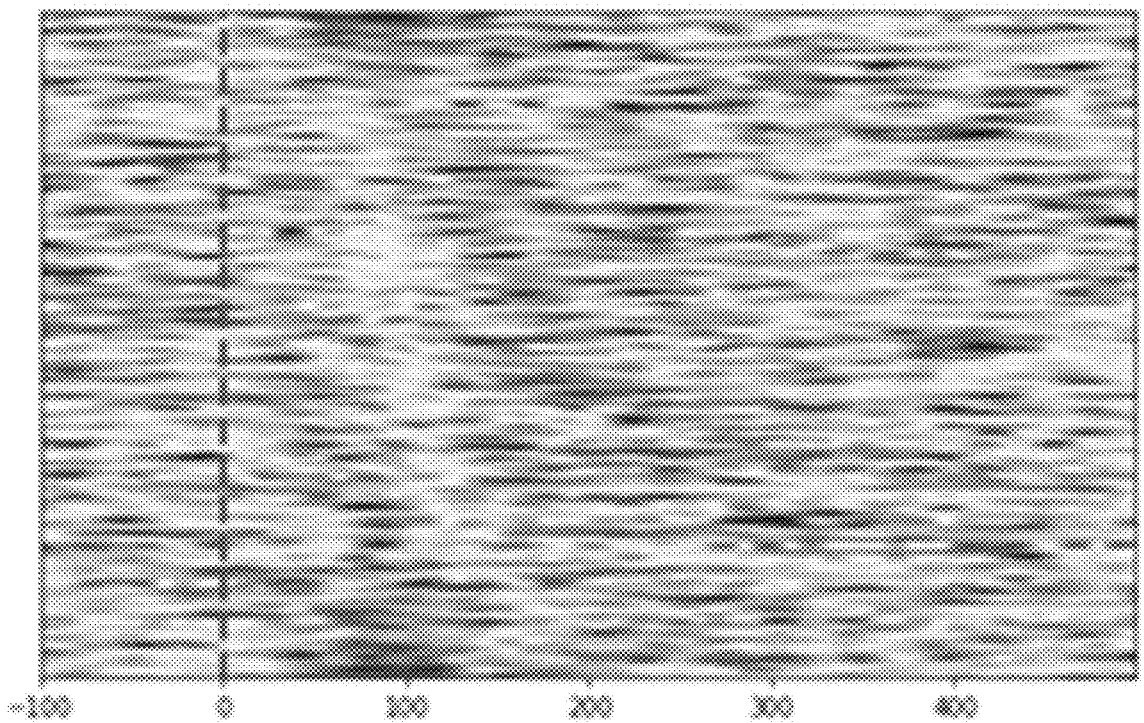

Various CI models described in this disclosure capture differences in cognitive activity for patients who have similar standard neurocognitive test results. The CI models are useful for detecting different patterns of cognitive activity, which may respond to different types of treatment. This is evident in a comparison of FIGS. 15A and 15B. FIG. 15A is a heatmap of a first CI test patient and FIG. 15B is a heatmap of a second CI test patient. The heatmaps are quite different but the standard tests yield similar results. The heatmaps are sorted based on signal similarity in peak A window.

Figure 16:
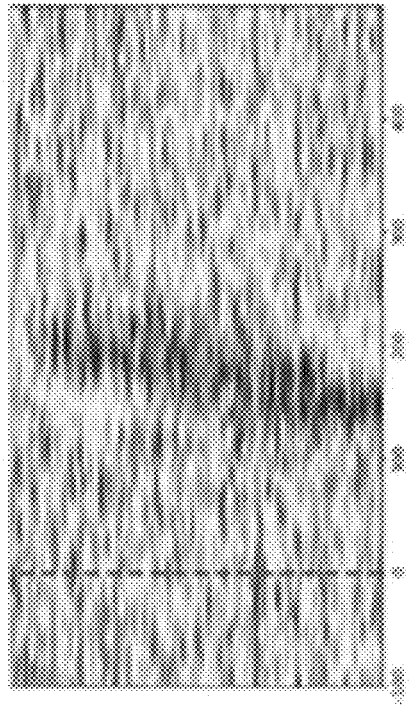
FIG. 16 illustrates example heatmaps of two different patients across patient visits.
Figure 16:
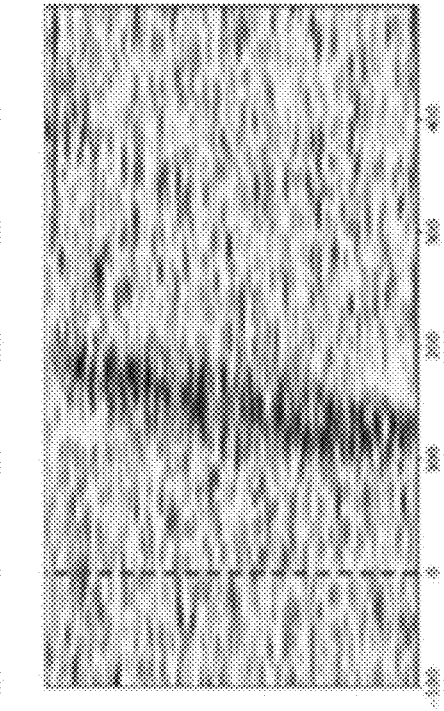
Figure 16:
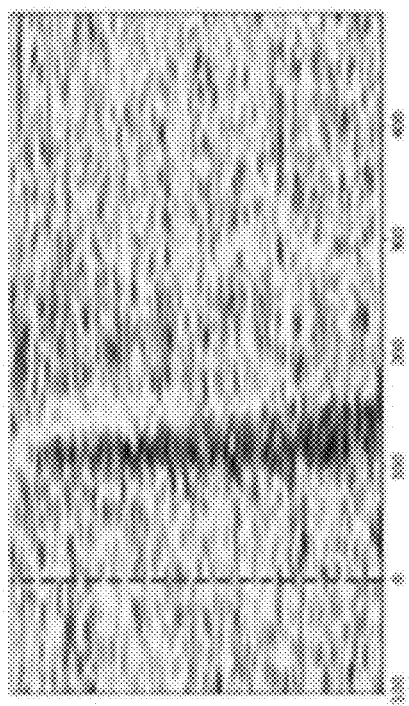
Figure 16:
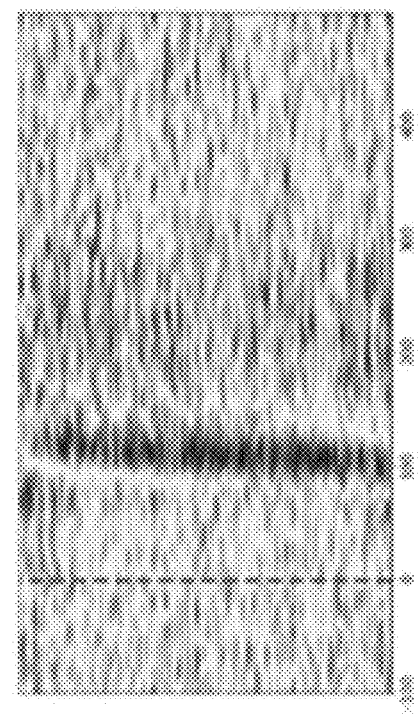

The features displayed in a CI model in accordance with an embodiment also shows stability over a short time interval within individuals (2 weeks between tests). FIG. 16 shows heatmaps of two different patients across patient visits that are two weeks apart. Each heatmap is sorted based on signal similarity in peak B window. As shown in FIG. 16, the heatmaps for a NV test patient is consistently "normal" while the heatmaps for a CI test patient is consistently "not normal", with invariably prolonged B peak duration in both visits.

VII. Additional Cognitive Impairment Models

VII.A. Summary

Additional embodiments beyond discussed with respect to the CI model and examples of Section IV above are also possible. For compactness of description, the following examples described only those aspects that have changed from previous examples, unless otherwise stated, example patient data, model development including sensor selection, parameter selection, model training, and inference is the same as discussed above in Sections III and IV.

For convenience of description, the models of Section V may be referred to as Cognitive Impairment (CI) models to illustrate the applicability of the model to any disease that affects cognitive impairment. In practice, both the previous CI models of Section IV and the CI models of this section both function to identify presence and progression of cognitive diseases. In one specific embodiment, both CI and ADD models may characterize a cognitive impaired subject as someone having an MMS score below 26. Other embodiments may use other tests other than MMS and other thresholds as baselines against which to label cognitive impairment.

The CI models of this section include several aspects that vary versus the examples in the prior sections. First, they include additional within-day variability features that represent and capture evidence of instability in short-term cognitive function of individuals with cognitive impairment. Implicit in these features is that multiple scans acquired for a patient are useful in evaluating cognitive function. Second, they exclude features that were not stable across multiple (across-day) visits by an individual, thus removing features that were not reliable indicators of cognitive impairment. They also include contralateral channel features, in addition to ipsilateral channel features used in the CI models.

VII.B. Sensor Selection

While in the CI models the sensor from which features were created was selected based on a stability metric, the current models achieve superior results by selecting the sensor based on a metric of signal deflection. Specifically, the algorithm chooses the channel from a pool of a plurality (e.g., 12) of channels (ipsilateral or contralateral) that has the highest absolute signal deflection in the heatmap, within a time window (e.g., 50 to 250 ms) (herein referred to as the mostDef method). The example 50 ms to 250 ms time window was selected because it comfortably accounts for both A and B peaks in most subjects, regardless of latency drifts across epochs, or inter-subject variability. In other embodiments, other sensor selection methods (e.g., sensor stability as discussed previously) may be used in place of the mostdef method.

In one embodiment, sensors are selected with the maximum absolute deflection between 50 and 250 ms. The absolute value of the heatmap within that time window is taken to generally encapsulate both the A and B peaks. The signal may be averaged across time and epochs. The sensor in each side with the maximum score is selected.

VII.B. Within-Day Variability Features

The inventors recognized that the within-day variability for many features correlated with cognitive function. Computing the absolute difference between two scans of a patient captured on the same day illustrated this in test data. The difference in time within the day between the two scans may vary. For the example data discussed below, the two scans were about 45 minutes apart.

Figure 7:
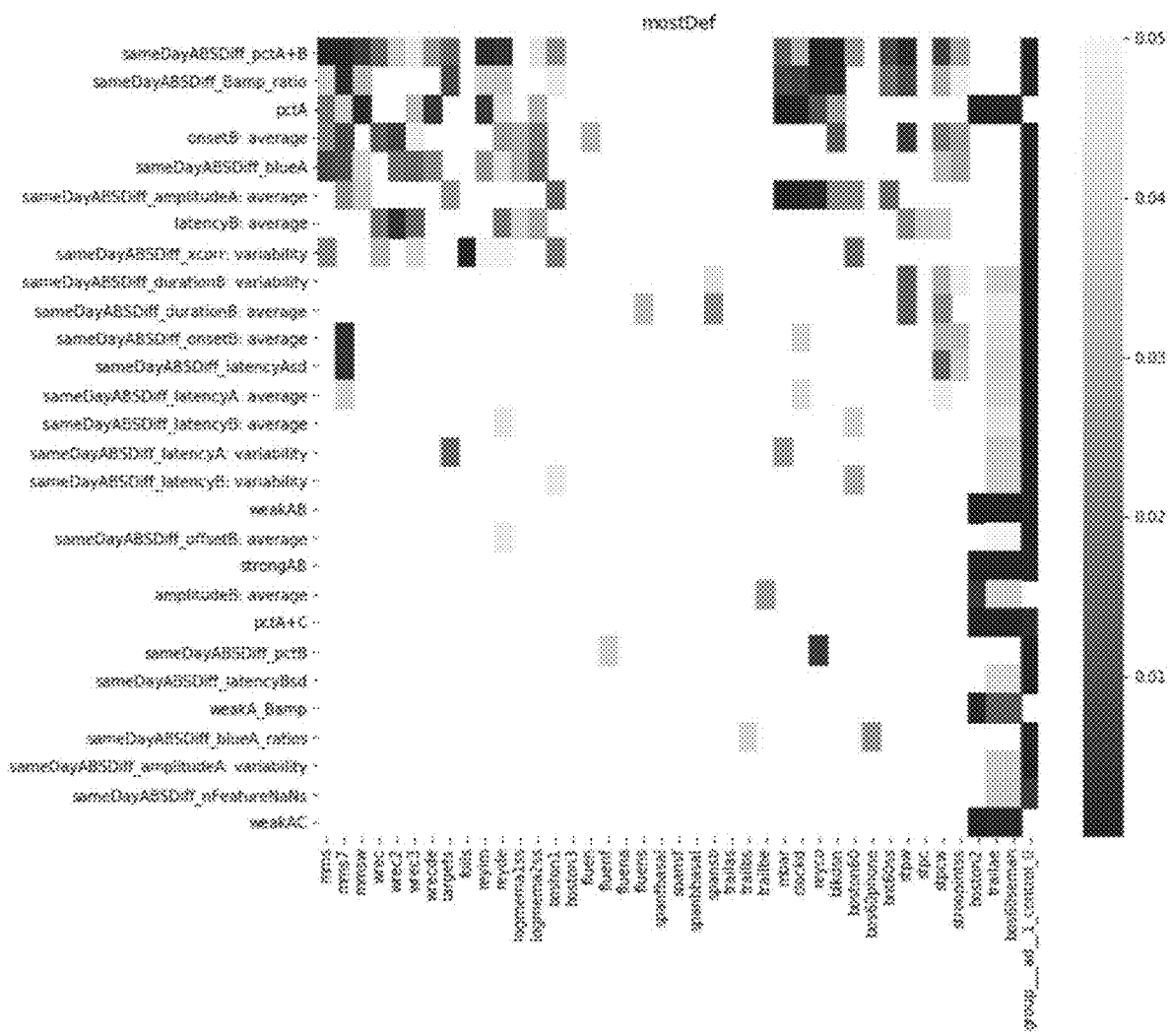
FIG. 7 illustrates a correlation matrix between ipsilateral features (vertical) and different psychiatric tests for evaluating cognitive impairment (horizontal), according to one embodiment.

FIG. 7 illustrates a correlation matrix between ipsilateral features (vertical) and different psychiatric tests for evaluating cognitive impairment (horizontal), according to one embodiment. CI model features indicating information about same-day variability have the prefix "sameDay-ABSDiff." A full key for abbreviations in the figures can be found in Sections VII.X. and VII.Y below.

Within FIG. 7, the value of each cell illustrates the p-value of Pearson correlation tests between one of the features and one of the many known tests for cognitive impairment. The darker the color of the cell, the higher the association between the feature and the test. The CI models discussed in prior sections focused on the first column (MMS score), and the last one (group separation between CI and NV), but FIG. 7 illustrates that features in both models are also related to other tests commonly used to evaluate cognitively impaired patients.

Figure 8A:
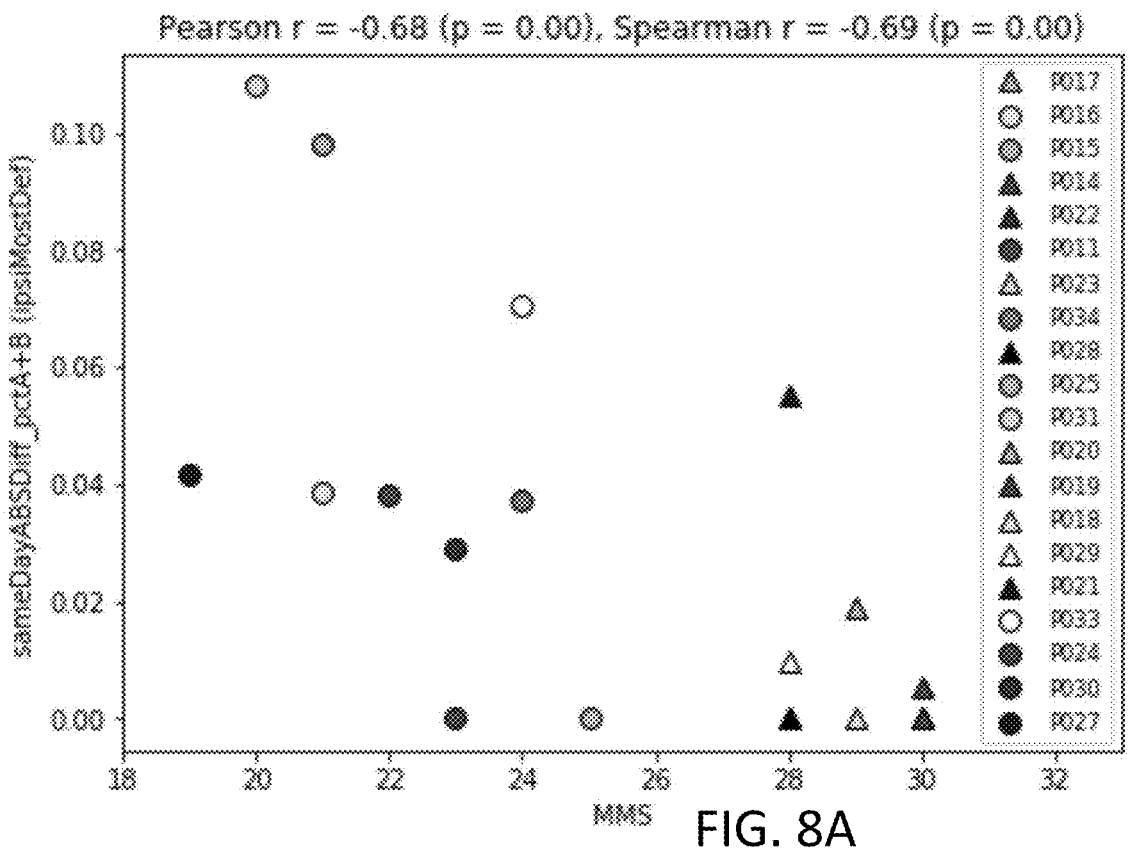
FIGS. 8A, 8B, and 8C illustrate scatterplots of within-day feature variability for three possible model features, according to one embodiment.
Figure 8B:
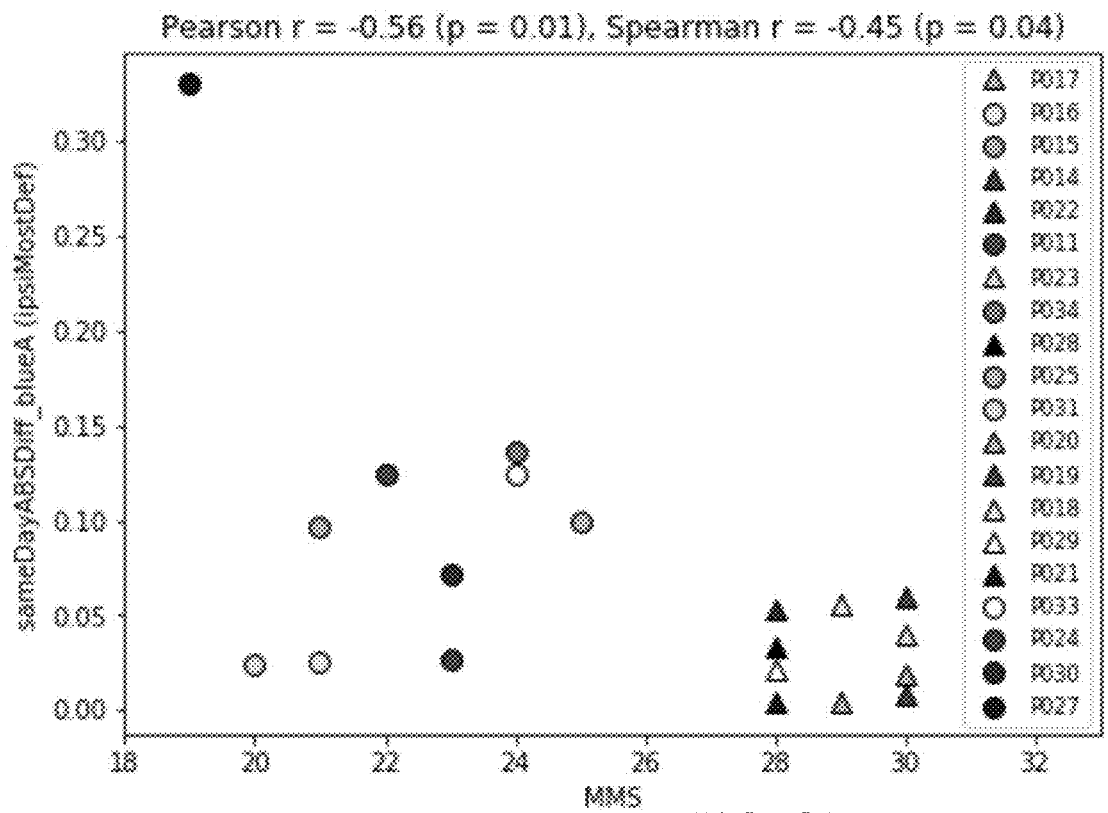
Figure 8C:
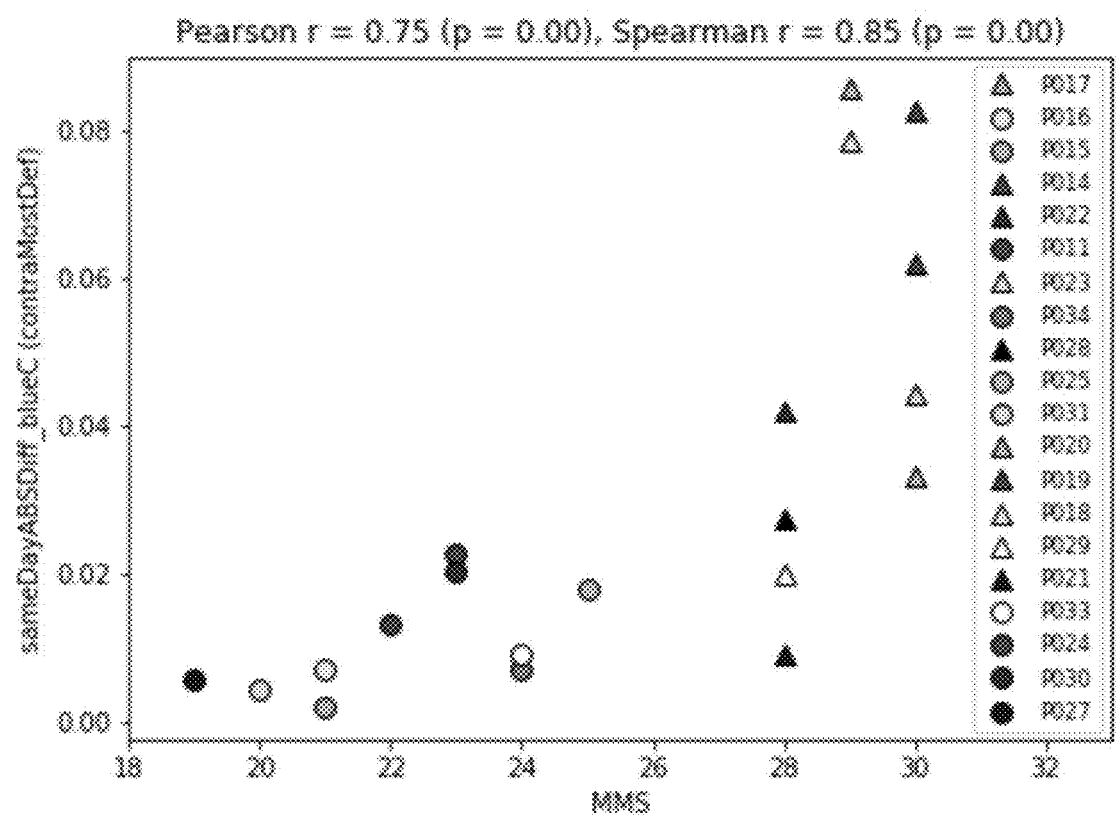

FIGS. 8A, 8B, and 8C illustrate scatterplots of within-day feature variability for three possible model features, according to one embodiment. FIG. 8A specifically plots MMS for a number of the test patients against within-day variability (sameday ABSdiff) in the number of A or B peaks for that patient. FIG. 8B specifically plots MMS for a number of the test patients against within-day variability in the area under the curve for peaks A for that patient. Both FIGS. 8A and 8B illustrate that there is a significant amount of within-day variability for these features for patients exhibiting cognitive impairment (e.g., MMS <26) as compared to NV patients.

FIG. 8C illustrates a scatter plot of same-day feature variability in area under the curve for C peaks plotted against MMS score, according to one embodiment. FIG. 8C specifically illustrates an example feature where NV patients have high same-day variability whereas CI patients have low within-day variability.

In one embodiment of the CI model discussed in Section IV above, a second scan acquired on the same day is used to establish feature reliability (for example, using Bland-Altman plots). Alternately, in one embodiment of the CI model, the second scan on the same day is instead used to compute feature variability. Further, one or more of the features of the CI model may be a feature that quantifies the variability of scan data (e.g., number of peaks A) which itself may be another feature in the model.

VII.C. Restricting Same Scan Features to Ones Stable Across Visits

Figure 9:
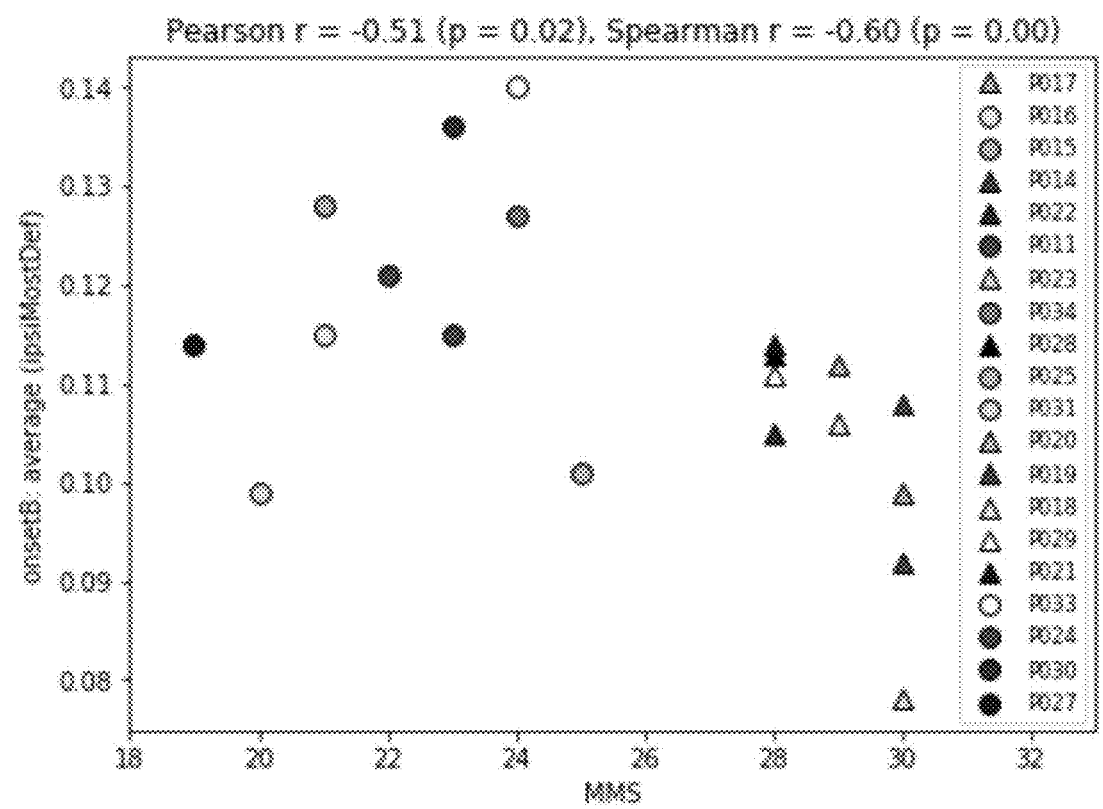
FIG. 9 illustrates a scatterplot of one such example feature where the average onset of the B peak shows an inverse correlation with a patient's MMS score, according to one embodiment.

Further, the inventors recognized that while adding within-day variability features enhanced model performance, many features derived from single scans still provided meaningful boosts to model performance. FIG. 9 illustrates a scatterplot of one such example feature where the average onset of the B peak shows an inverse correlation with a patient's MMS score, according to one embodiment.

However, not all features were sufficiently stable across separate tests on separate days for NV patients as well as CI patients to merit inclusion in the model. In order to make sure features included in a model were stable across evaluations, the correlation between features was measured across separate MEG scans on separate days. The number of days between scans may vary, but is generally short compared to the typical scale of the cognitive disease being studied, which are generally on the order of months if not years. For the example data discussed below, the two scans were about two weeks apart.

In one embodiment, a first vector was constructed using a separate data point from each of the test patients for a given feature for a first visit and scan (visit 1, scan 1). A second vector was constructed using the same data points of the same feature for the set of test patients for a second visit and scan (visit 2, scan 2). Features considered for inclusion in a model were those that had a statistically significant correlation ($p<0.05$, corrected using False Discovery Rate at $q<0.05$) between the two vectors. Those of skill in the art will appreciate that many other similar tests may be used to evaluate which features to carry through to a model based on inter-day feature stability.

VII.D. Adding Contra-Lateral Features

Further, the inventors recognized that model performance could be improved by including MEG sensor data from contralateral to the ear that received the auditory stimulation, in addition to sensor data from sensors ipsilateral to the ear that received the auditory stimulation.

Figure 10:
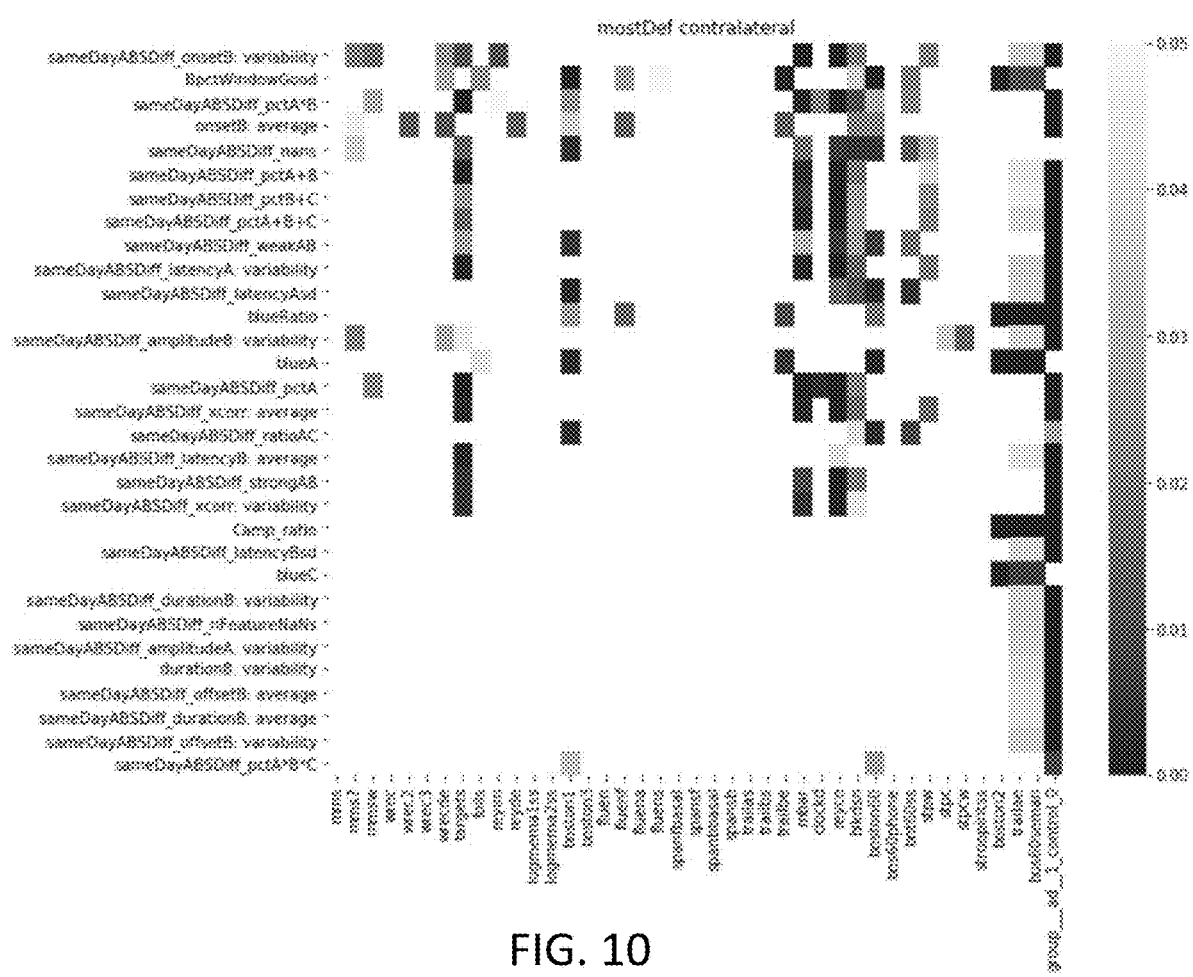
FIG. 10 illustrates a correlation matrix between contralateral features (vertical) and different psychiatric tests (horizontal), according to one embodiment.

FIG. 10 illustrates a correlation matrix between contralateral features (vertical) and different psychiatric tests (horizontal), according to one embodiment. The features and psychiatric tests in FIG. 10 are the same as in FIG. 7. Comparing FIGS. 7 (ipsilateral features) and 10 (contralateral features) illustrates that the two different sets of features have a different pattern of related psychiatric tests that are related. In particular, while the tests on the left of the matrix are more related to ipsilateral features, tests on the right are more related to the contralateral features. As a specific example, contralateral features correlate well with ReyCo and MBAR, both alternate tests of higher cognitive function and abstract reasoning.

Because of this complementary pattern, one embodiment of the CI model includes at least one feature from at least one contralateral sensor channel in addition to at least one feature from an ipsilateral sensor channel. In another embodiment, a CI model may be built using features based on solely contralateral sensor channels.

VII.E. Example CI Models

In one embodiment, one or more linear CI models are constructed. Each CI model can be constructed to include different subsets of features from each other model based on how well they predict MMS for a test set of patients. The linear CI models output a predicted MMS score which can be used to classify between CI and NV groups by comparing against a threshold MMS score (e.g., 26). In other embodiments, other CI models may be constructed including different features. The CI models may be linear or non-linear functions of the feature weights and values. Additionally, the CI models may be constructed to predict one or more different psychiatric test values, such as any of the psychiatric tests listed in Section VII.X. below.

The CI models were evaluated in a leave-one-out cross validation (LOOCV) framework to select up to 5 features. The CI models used features from both ipsilateral and contralateral sides. In this specific embodiment, two sensor channels were used: one in each side of the helmet based on the mostDef method. Although this approach increases the number of features used in total, it is advantageous as it likely captures different types of information. In this embodiment, the CI models were trained on 19 out of 20 patients, and the MMS score was predicted on the remaining patient. The predicted score was used to place the patient in either the NV or CI group. This process for each patient in the leave-out position to produce predictions for all patients.

In other embodiments, further features beyond 5 may be used. Generally, the number of features is restricted to avoid overfitting, however in practice additional or fewer features may be used based on a variety of factors, such as the psychiatric tests used for training and inference, the amount of training data available, and the sensors used to collect data (e.g., contralateral, ipsilateral). Training more than one CI model can be advantageous as it provides multiple predictions/scores that can be aggregated (e.g., average, median) or provided as part of a comprehensive report on the presence or absence of cognitive impairment in a patient.

Figure 11A:
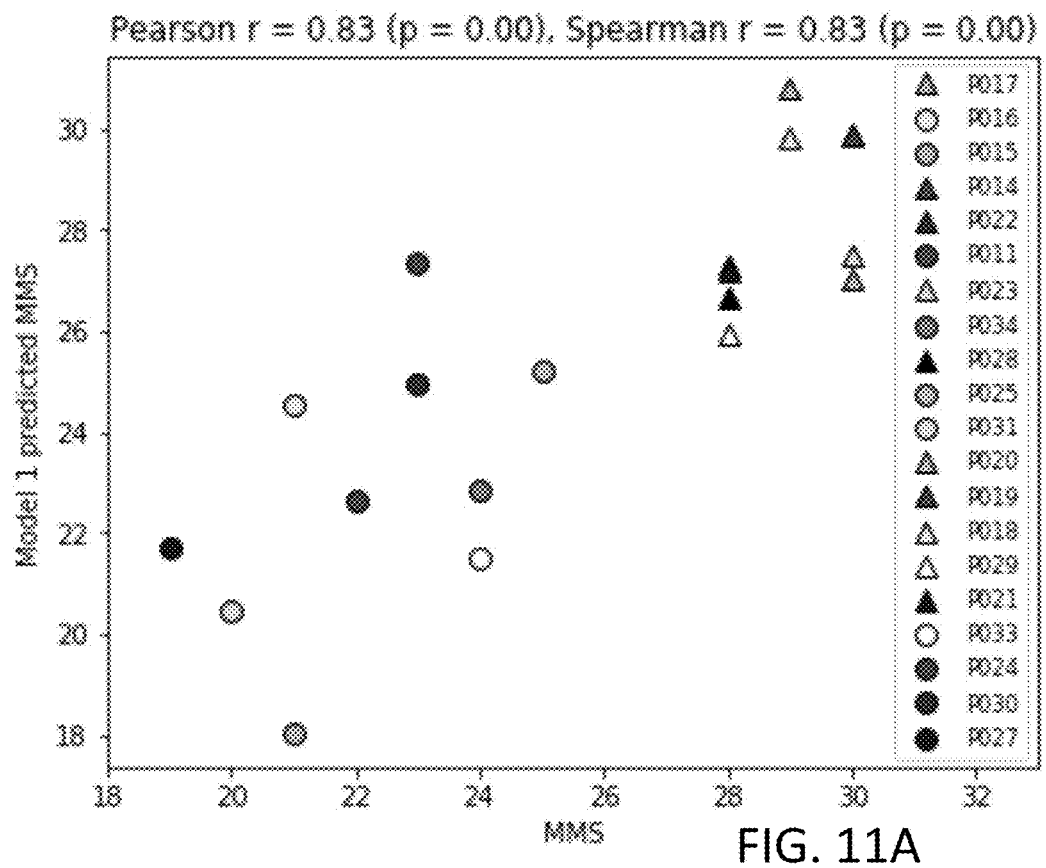
FIGS. 11A and 11B plot predicted and actual MMS scores for two types of dual-channel CI models, according to one embodiment.
Figure 11B:
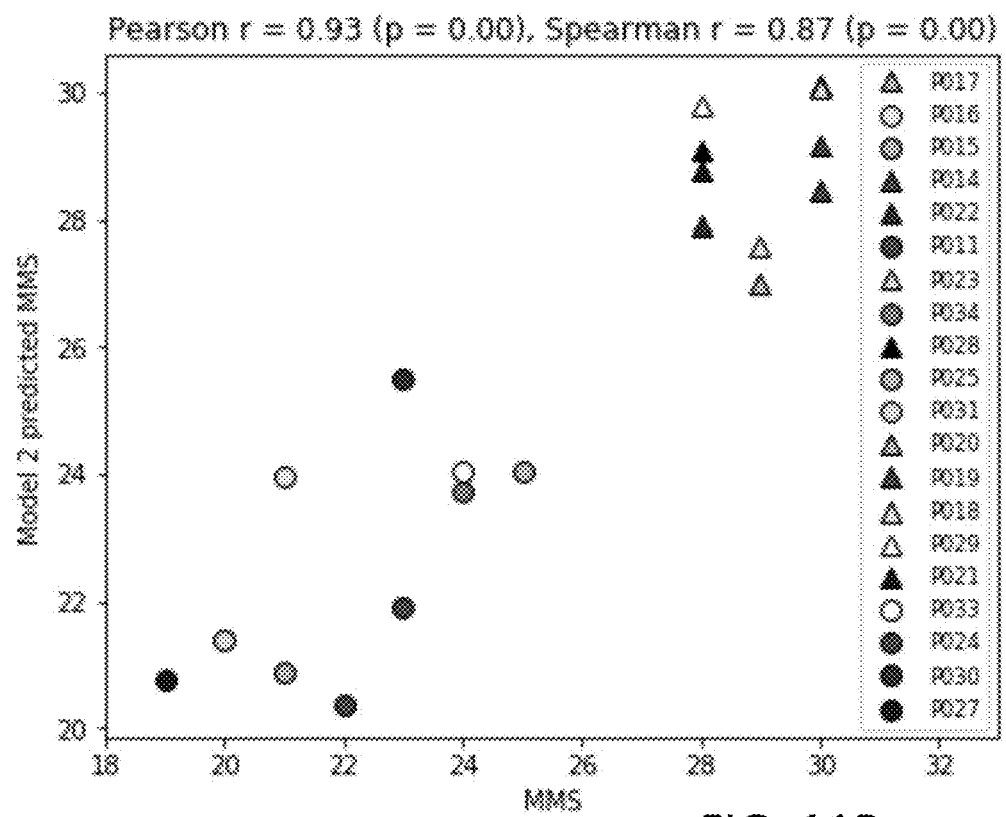

FIGS. 11A and 11B plot predicted and actual MMS scores for two types of dual-channel CI models, according to one embodiment. FIG. 11A illustrates an example CI model where the candidate features included only features significantly correlated to MMS ($p<0.05$, for a total of 16 features). Stated differently, the example CI model of FIG. 11A chooses the best linear combination of five or less features among all features significantly correlated to MMS. Example CI model 1 selected features [sameDayABSDiff_blueA.ipsi, sameDayABSDiff_blueC.contra, sameDayABSDiff_durationB: variability.ipsi, sameDayABSDiff_pctA+B.ipsi, and sameDayABSDiff_strongAB.ipsi], and the predicted scores using LOOCV achieved 90% a classification accuracy (mean-squared error 4.28).

FIG. 11B, by contrast, illustrates an example CI model where features correlated to any of the neuropsychiatric tests were included. Stated differently, the example CI model of FIG. 11B chooses the best linear combination of five or less features among all features significantly correlated to any of the neuropsychiatric tests evaluated. In this example, this included features corresponding to any of the dark squares in FIGS. 7 and 10, for a total of 78 features. Example CI model 2 used features [latencyB: average.ipsi, sameDayABSDiff_ApctWindowGood.ipsi, sameDayABSDiff_amplitudeA: average. contra, sameDayABSDiff_blueA.ipsi, and sameDayABSDiff_strongA_Camp.contra] and achieved a classification accuracy of 100% (mean-squared error 1.96).

The results discussed herein, as well as the features chosen to be used in the CI models are robust to exactly which channels were selected. Comparing the ADD and CI models, the two sets of models employ different channel selection techniques and different features, and correspondingly different values of evoked responses. Although the CI models outperform the ADD models in predictive performance, both types of models are predictive. This is a both a reflection of the spatial resolution of single sensors in MEG, and also that the processes described herein to are somewhat regional across the brain. This observation inform designed of the reduced sensor-count array discussed above, as precise positioning of the device may strictly necessary for the models to generate a predictive result.

In one embodiment, a CI model may be trained using the cross-validation process described in Section III.C. A set of 6 features are selected as weighted features in the CI model. The features are (1) the percentage of epochs with peaks A in ipsilateral responses, (2) the percentage of epochs with peaks B in ipsilateral responses, (3) the average latency in peaks B in ipsilateral responses, (4) a change in the percentage of epochs with peaks C among epochs with weak peaks A in ipsilateral responses, (5) a change in the average amplitude of peaks B, and (6) a change in the ratio between peak A AUC and peak C AUC in contralateral responses. The six features are extracted from a training set of multiple test patients to train the weights of the CI model. The CI model, after training, may be used to predict the cumulative score of incoming patients.

Figure 14:
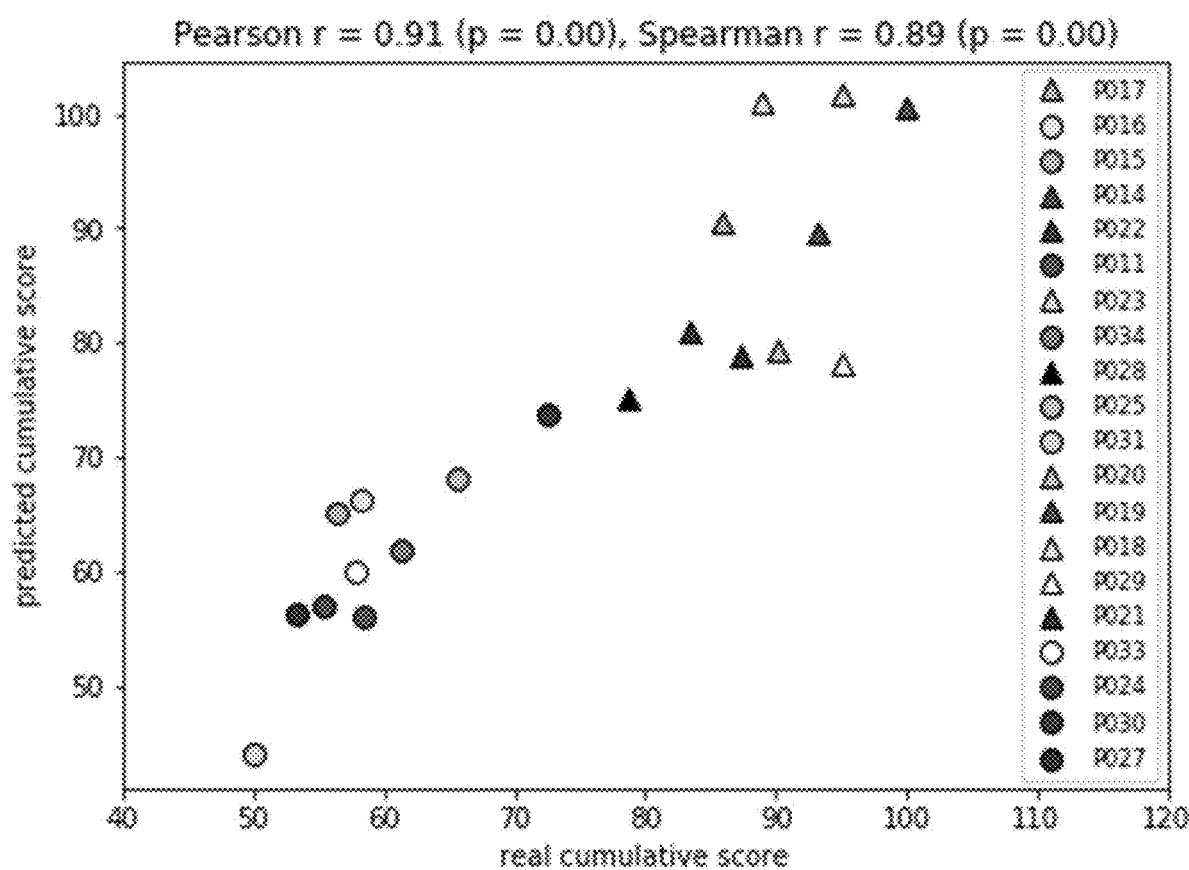
FIG. 14 illustrates a scatter plot of predicted and actual cumulative score of a CI model, according to one embodiment.

FIG. 14 shows a scatter plot of predicted cumulative scores predicted by the CI models and actual cumulative scores of the test patients. In generating the data in FIG. 14, the test patient for which the cumulative score is being predicted is not used when training the CI model. The circular points represent CI test patients while the triangular points represent NV test patients. This CI model using the six features identified above achieves a correlation between predicted and actual cumulative score of $r=0.91$ ($p<10^{-5}$), and a mean-squared error of 46.67.

VII.F. Examples of Clinical Display

Figure 12:
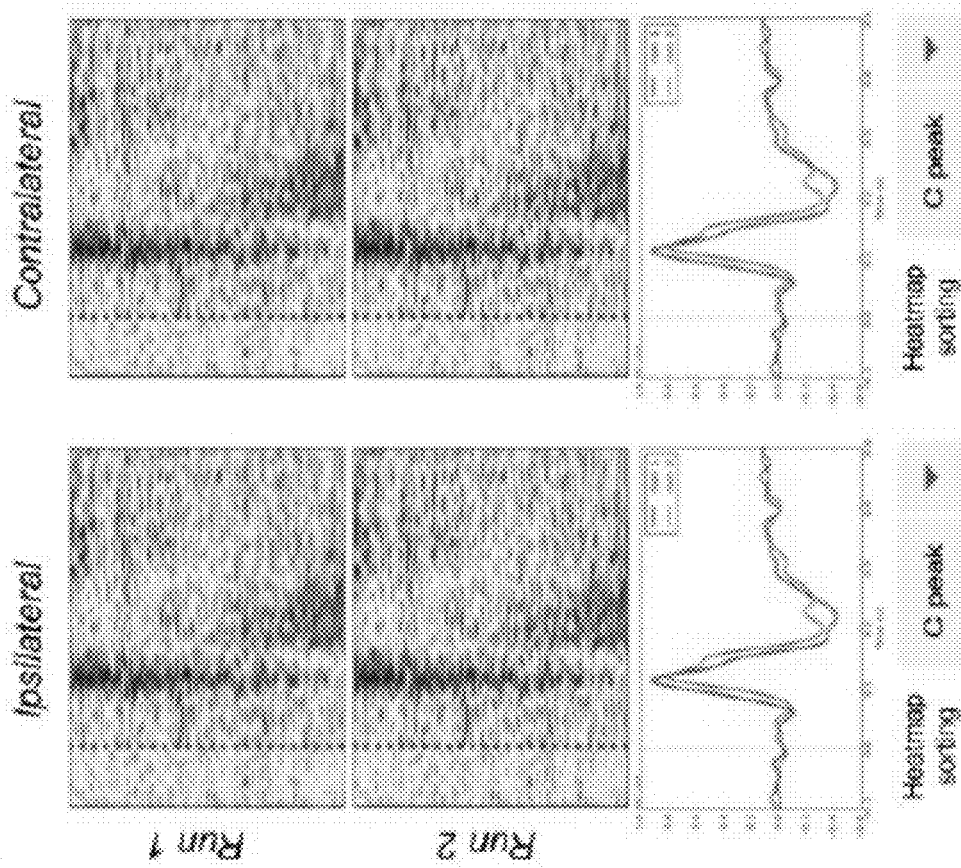
FIG. 12 illustrates a graphical user interface for presenting the results of scans and the prediction of a CI model, according to one embodiment.

FIG. 12 illustrates a graphical user interface (GUI) for presenting the results of scans and the prediction of a CI model, according to one embodiment. The graphical user interface is visually presented on a display of a computing device. The GUI may illustrate color-coded epoch data (heatmaps) and may also show evoked (averaged) response (e.g., blue for positive signal values, red for negative signal values, the degree of saturation of a color corresponding to amplitude). The heatmaps can be sorted based on different peaks using the buttons on the bottom of the display. The GUI may illustrate the sensor channels used, whether they are ipsilateral or contralateral, the features correspond to each sensor, the value corresponding to each feature, and the normal range for each feature value. Separate tabs in the GUI may permit switching between the data of different runs, or switch to showing features based on within-day feature variability. Interactive buttons permit transitioning between different views of the GUI, such as between runs or features.

Another button on the GUI opens display options, examples of which include but are not limited to: list of features to show (with option to get back to defaults), list of annotations to show (e.g. vertical lines for onset, offset, latency, with option to get back to defaults), whether or not to display the CI model prediction, thresholds to highlight features in the table in red. For example, outside the range, less than X % of being in the normal distribution, etc., a show "more details" button. Further, each feature in the table can have a "more details" button next to it, that when interacted with displays the single feature distribution, with a short description of the feature.

Figure 17A:
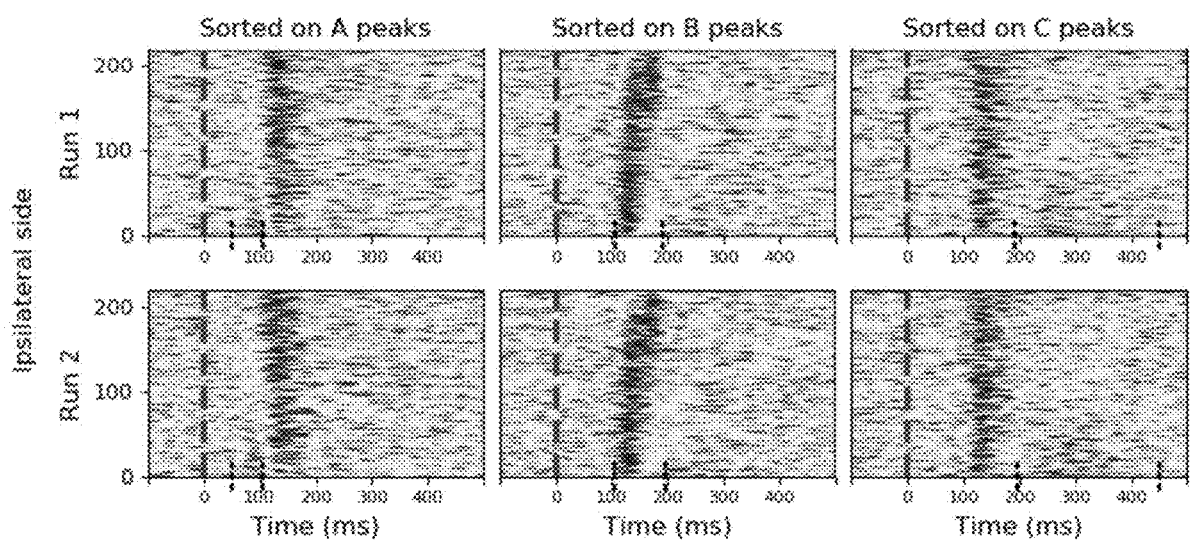
FIGS. 17A and 17B illustrate example graphical user interfaces for presenting the results of MEG scans, according to an embodiment.
Figure 17B:
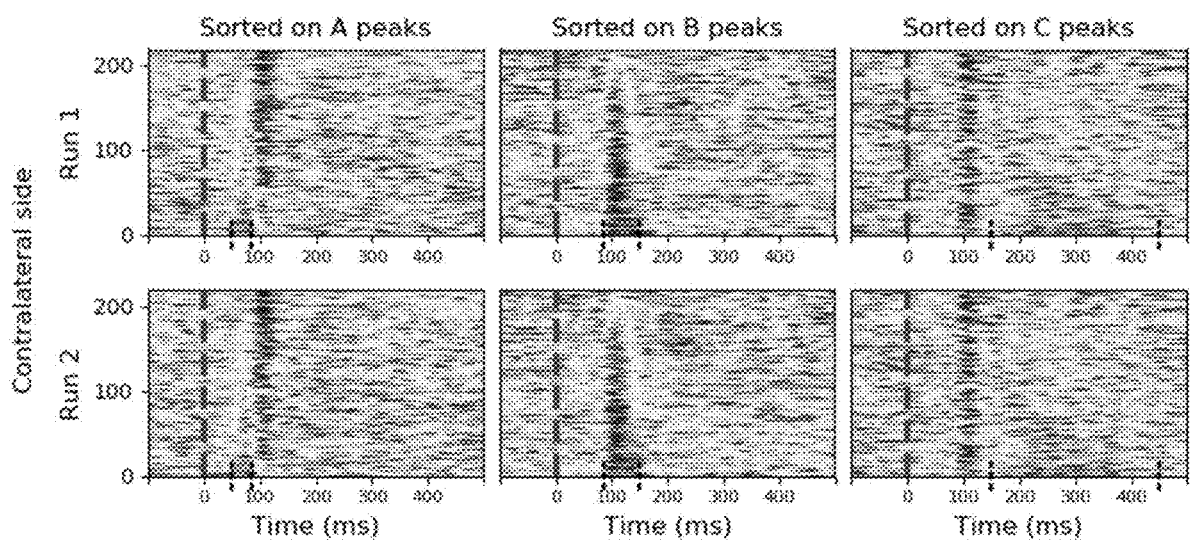
Figure 18A:
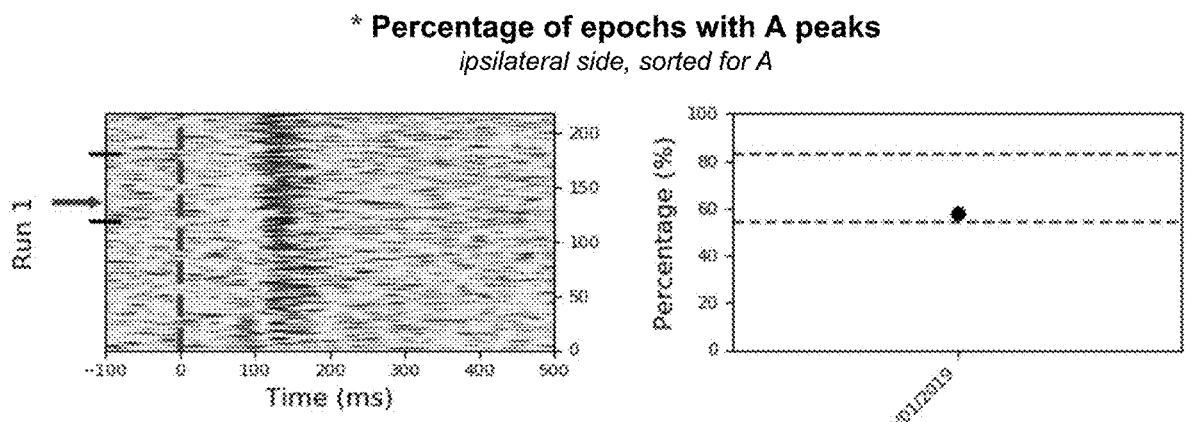
FIGS. 18A, 18B, and 18C illustrate graphical user interfaces for presenting features and heatmaps, according to an embodiment.
Figure 18B:
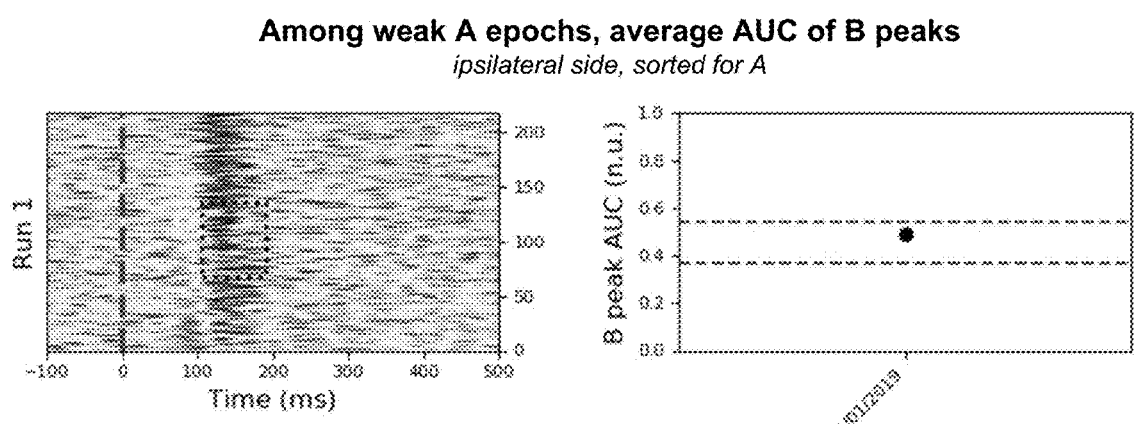
Figure 18C:
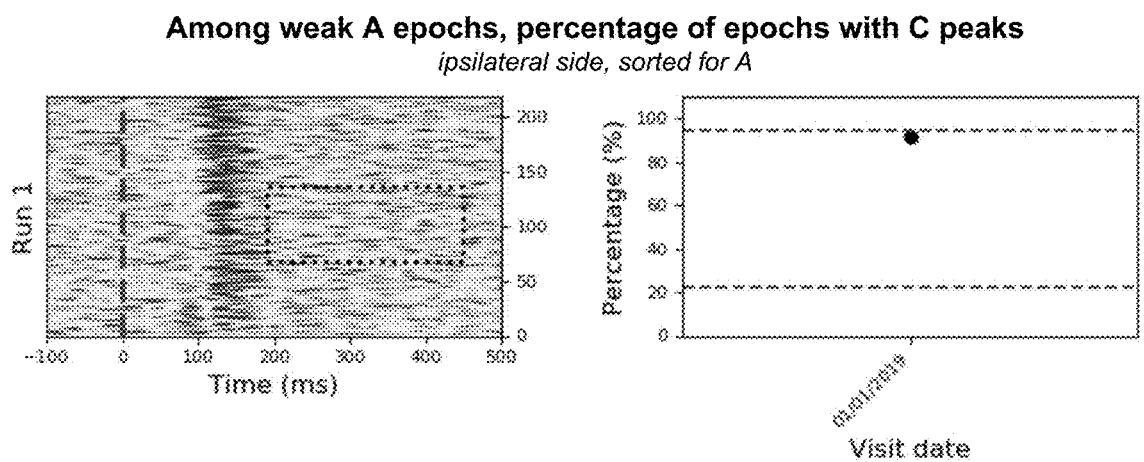
Figure 19:
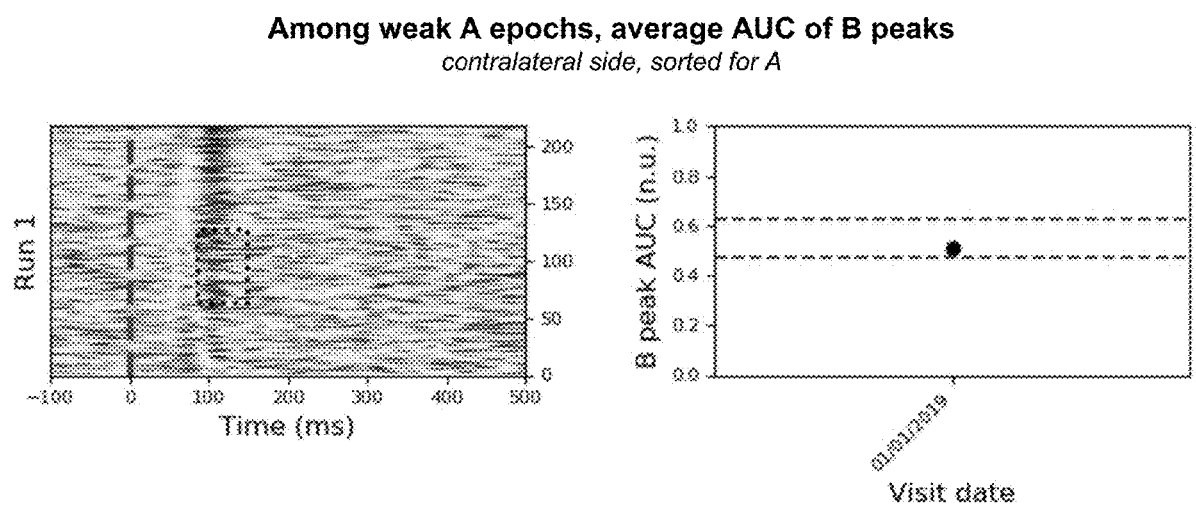
FIG. 19 illustrates a graphical user interface for presenting a feature and a heatmap, according to an embodiment.
Figure 20A:
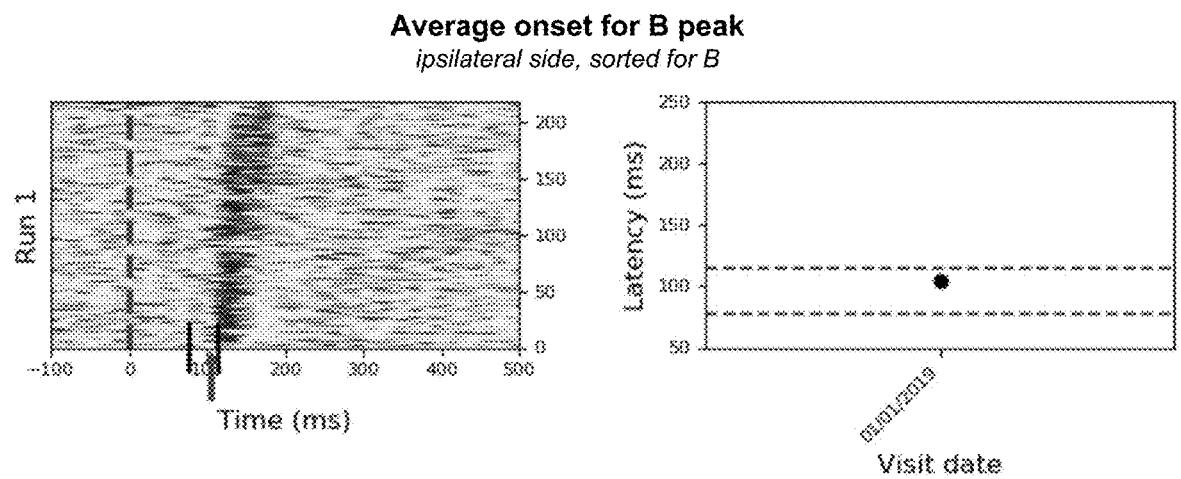
FIGS. 20A, 20B, and 20C illustrate graphical user interfaces for presenting features and heatmaps, according to an embodiment.
Figure 20B:
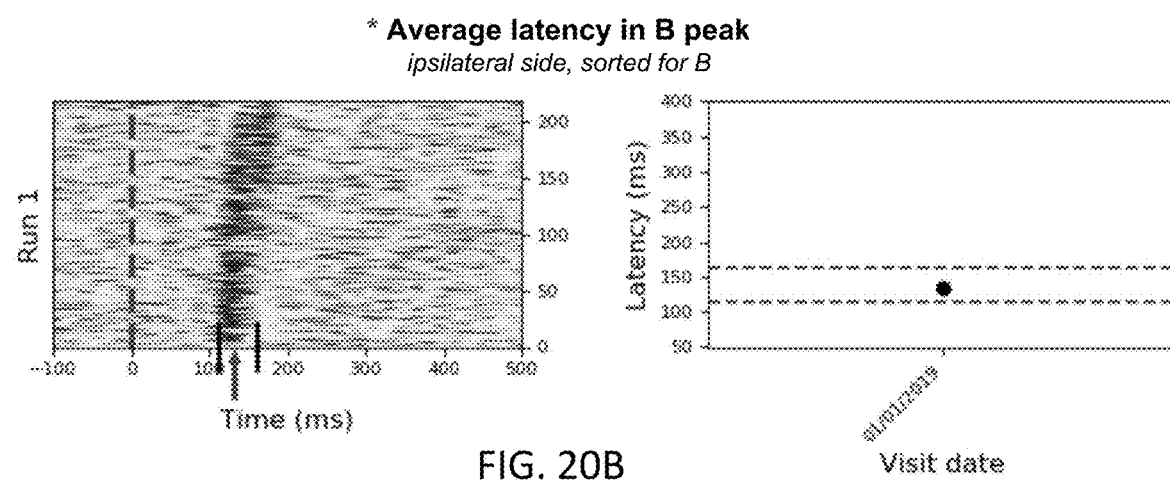
Figure 20C:
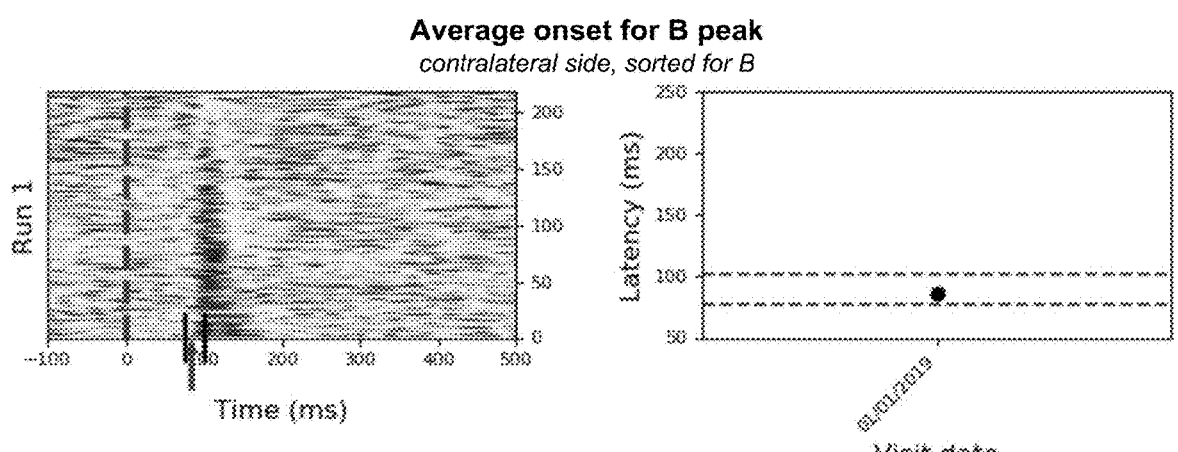
Figure 21:
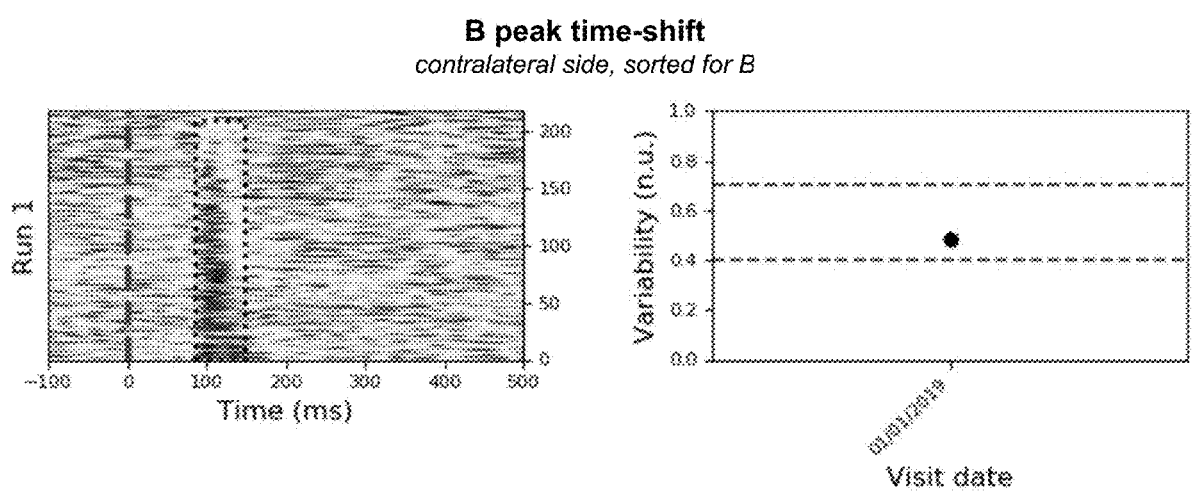
FIG. 21 illustrates a graphical user interface for presenting a feature and a heatmap, according to an embodiment.

FIGS. 17A and 17B illustrate an embodiment of a clinical display that may take the form of a GUI, according to an embodiment. The GUI may display a plurality of heatmaps of a patient that are separated by ipsilateral responses and contralateral responses and sorted by peak A, peak B and peak C. The GUI may also display a second set of heatmaps from a second run, as denoted as "Run 2" in the figures. The epochs are grouped in the heatmaps. In each heatmap, the vertical axis corresponds to individual epochs. The horizontal axis represents time, where the starting time represents the onset of the auditory stimulus. Different colors represent different signal polarity. For example, a blue color represents positive signal polarity and a red color represents negative signal polarity, or vice versa. In another embodiment, the color that represents the signal polarity is based on the peak type that is used to sort the epochs. For example, when peak A, which has a positive signal polarity, is used to sort the epochs, the positive polarity is represented by red color in a first heatmap. In a second heatmap that sorts the epochs by peak B, which has a negative signal polarity, the negative polarity is represented by red color. Other suitable ways to use the colors in the GUI are also possible.

Each of the heatmaps in the GUI simultaneously displays a plurality of epochs. For example, the vertical axis label "200" indicates that 200 epochs are displayed in the heatmap. Time, in milliseconds, is represented as progressing from left to right and the polarity of pulse in each epoch being represented by colors. In one embodiment, the sorting of the epochs across the vertical axis is not based on data acquisition sequence. In other words, epoch #200 is not necessarily collected after epoch #199 was collected during the run that collects data for a plurality of epochs. Instead, in one embodiment, the sorting of the epochs may be based on signal similarity within a predetermined timing window (e.g., 80-150 ms) after the auditory stimulus. For example, in a heatmap that is sorted by peak A, the epochs may be sorted by ascending or descending order of the amplitude of peak A in each epoch. The GUI may have a button to select the sorting options of the epochs to generate different version of heatmaps of the same underlying set of epochs. The GUI may also have a button to select the color options for each heatmap. The GUI may further have a button to toggle between ipsilateral responses and contralateral responses. The GUI may further have a button to select an individual display of a single heatmap or a series of heatmaps as shown in FIGS. 17A and 17B.

Referring to FIG. 18A through FIG. 26B, a clinical display that may take the form of a GUI may allow an operator to select different versions of heatmaps sorted by a type of peak and also displays a particular feature discussed in Section III.B.4. For example, a GUI may have one or more buttons that allow an operator to select the sorting option of the epochs (e.g., sorted by peak A, peak B, or peak C), the data source (e.g., whether ipsilateral responses or contralateral responses), and the feature to display. The feature may be a feature that is used in a CI model to generate the cumulative score or may be another relevant feature but is not directly used in the CI model. Referring specifically to FIG. 26A, the GUI 2600 may include a first display area 2610 for displaying a heatmap selected by the operator and a second display area 2620 for displaying a change in the selected feature value across different visits.

Figure 22A:
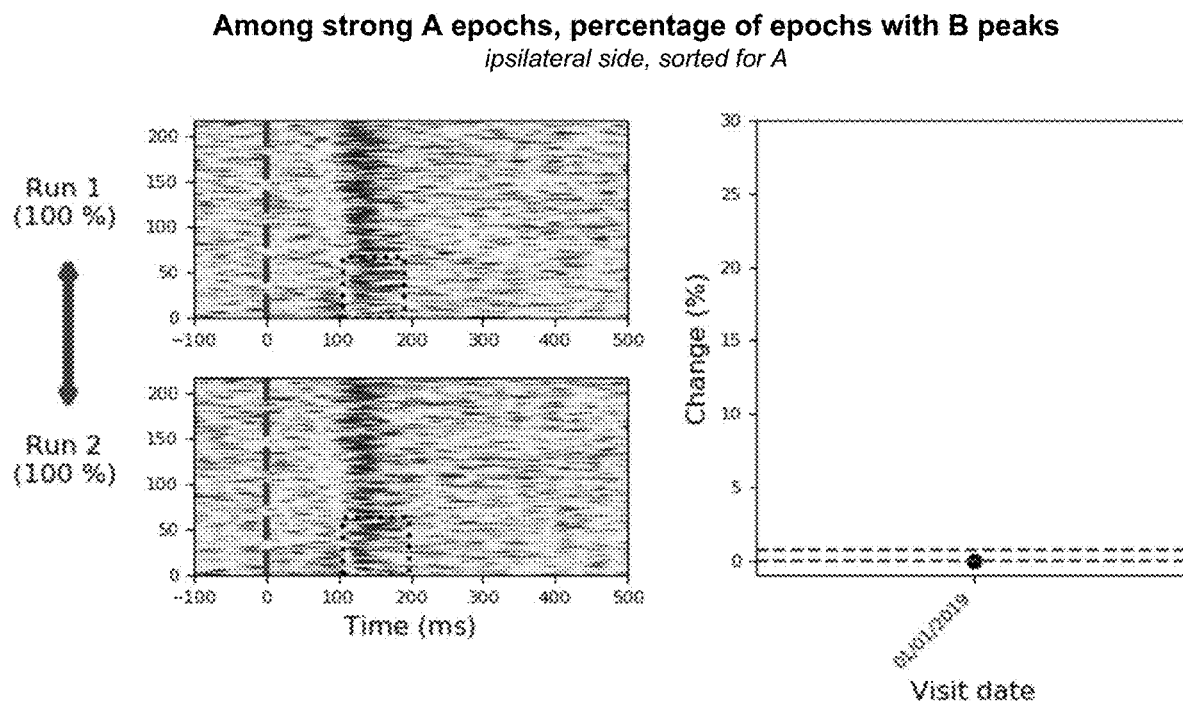
FIGS. 22A and 22B illustrate graphical user interfaces for presenting features and comparing multiple heatmaps, according to an embodiment.
Figure 22B:
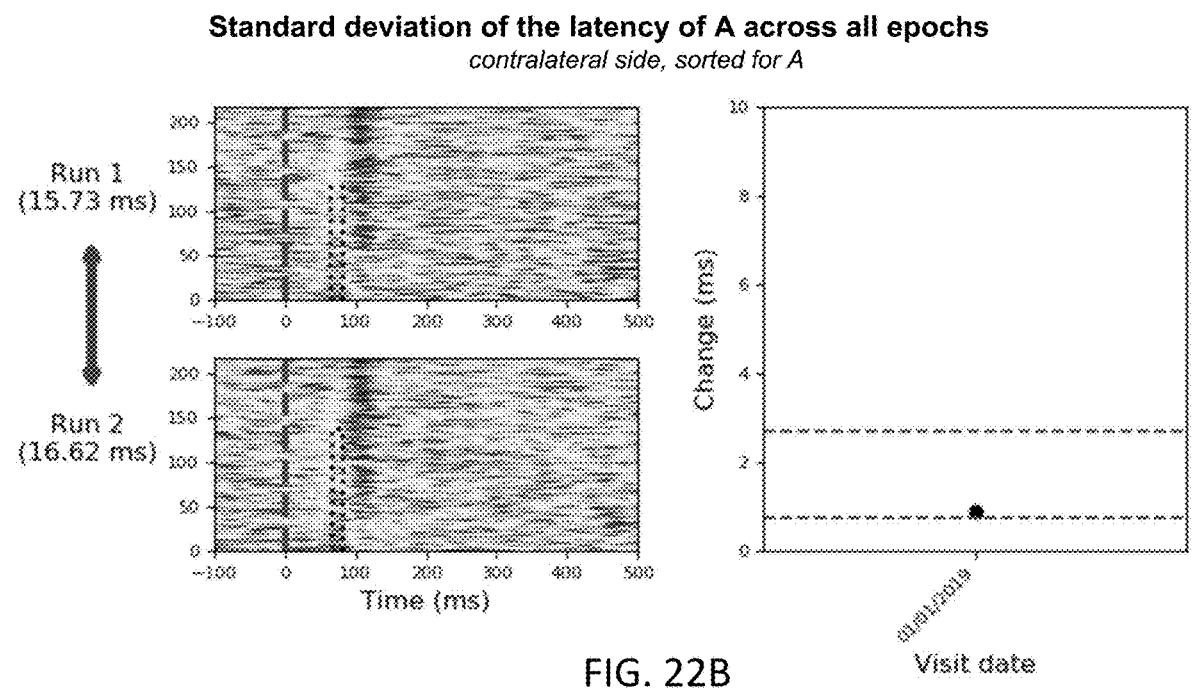
Figure 23A:
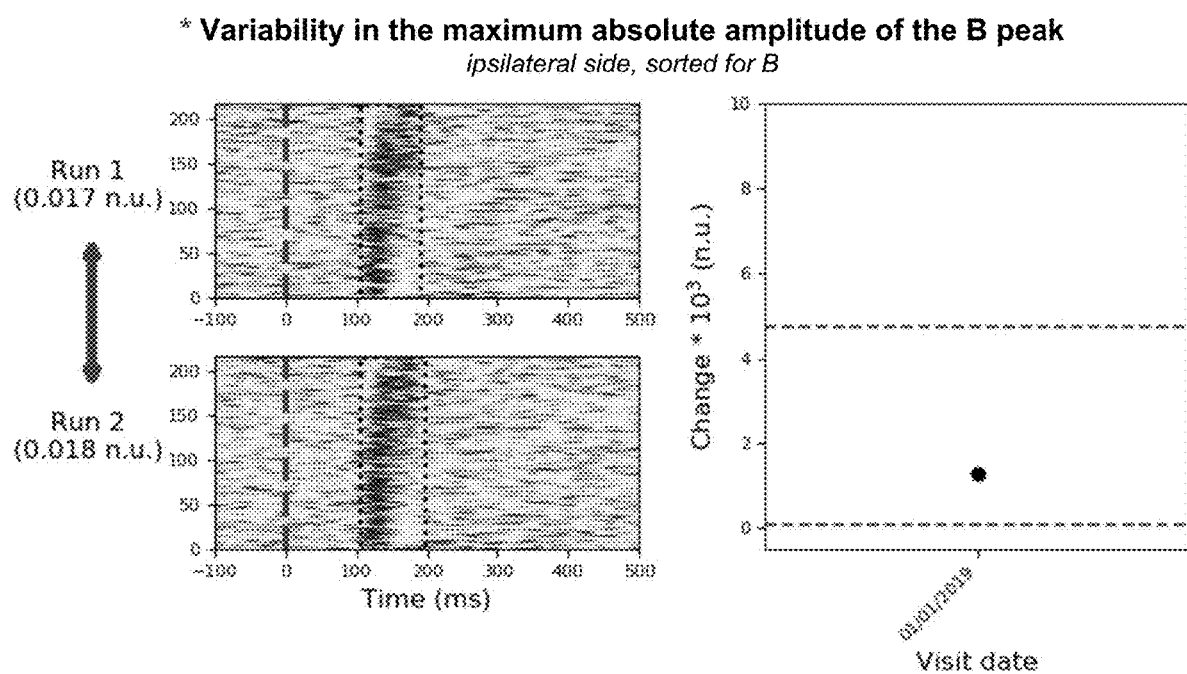
FIGS. 23A and 23B illustrate graphical user interfaces for presenting features and comparing multiple heatmaps, according to an embodiment.
Figure 23B:
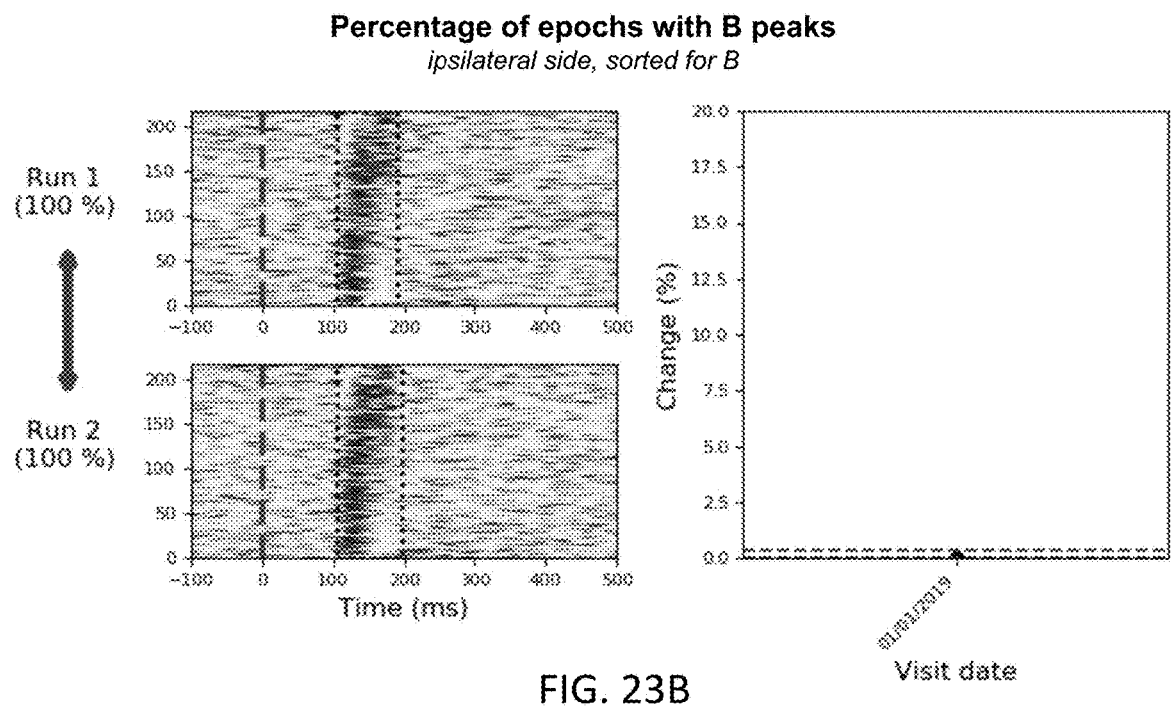
Figure 24A:
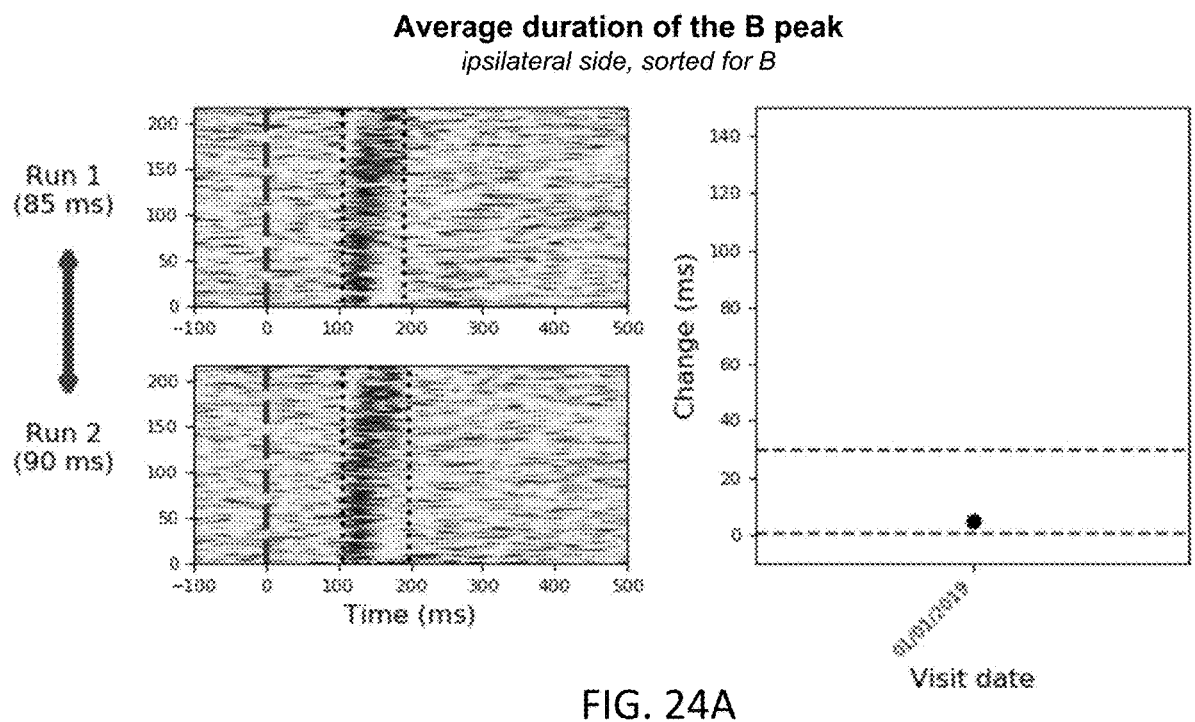
FIGS. 24A and 24B illustrate graphical user interfaces for presenting features and comparing multiple heatmaps, according to an embodiment.
Figure 24B:
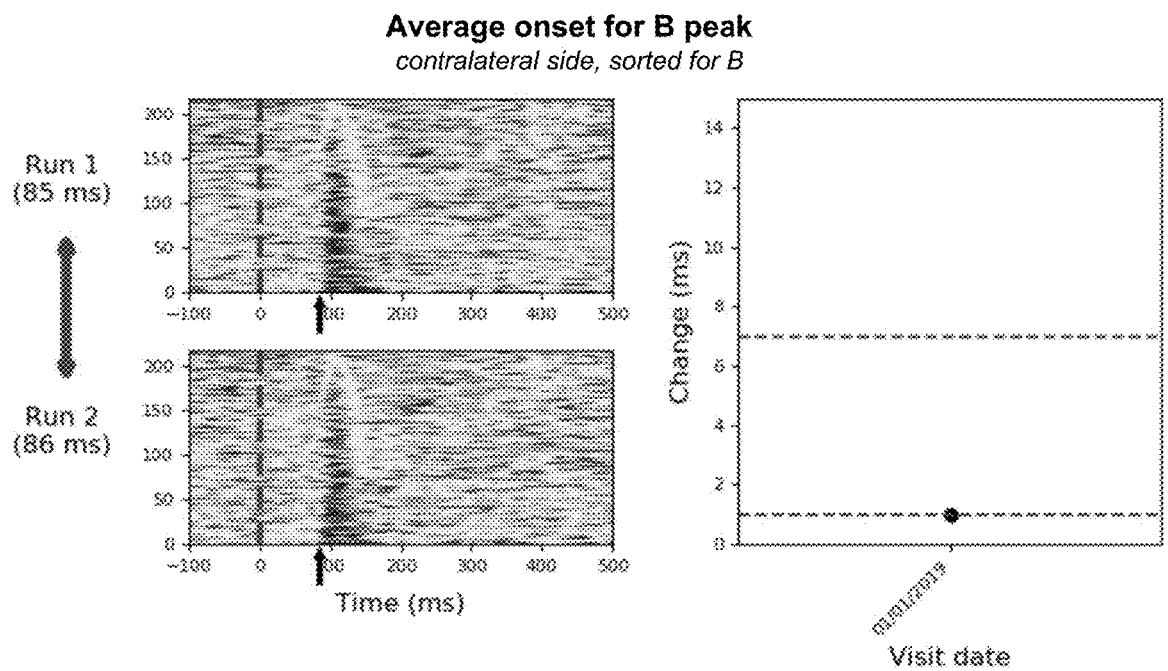
Figure 25:
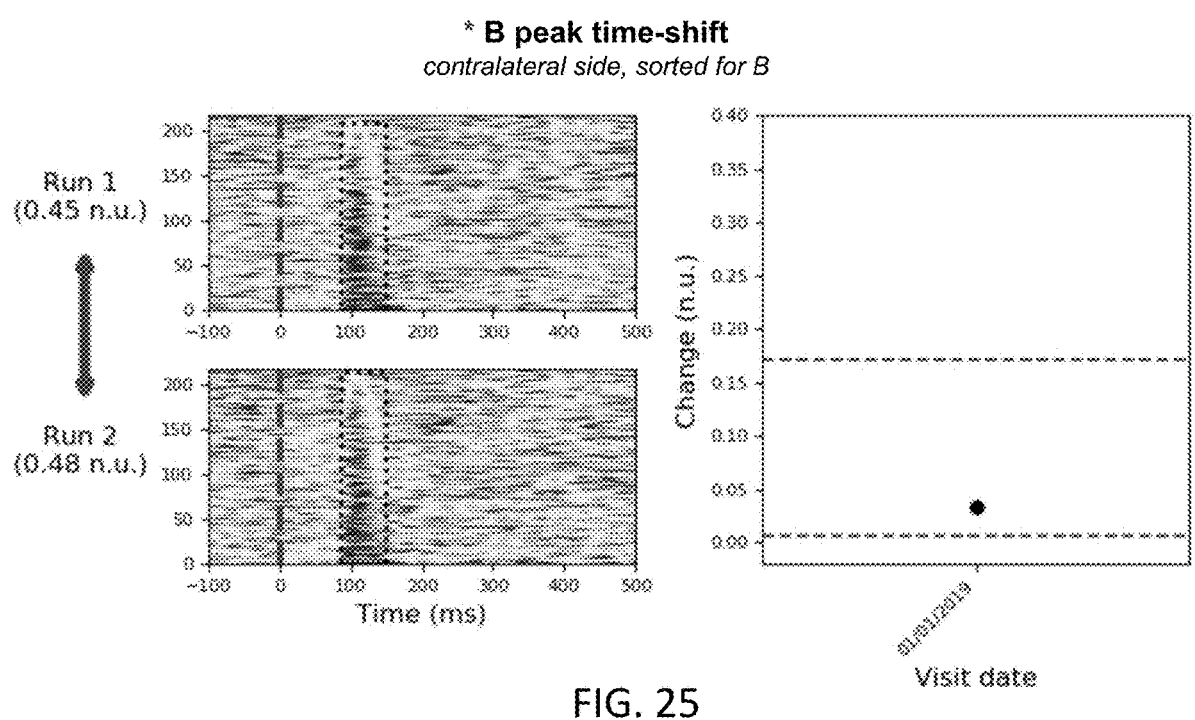
FIG. 25 illustrates a graphical user interface for presenting a feature and comparing multiple heatmaps, according to an embodiment.
Figure 26A:
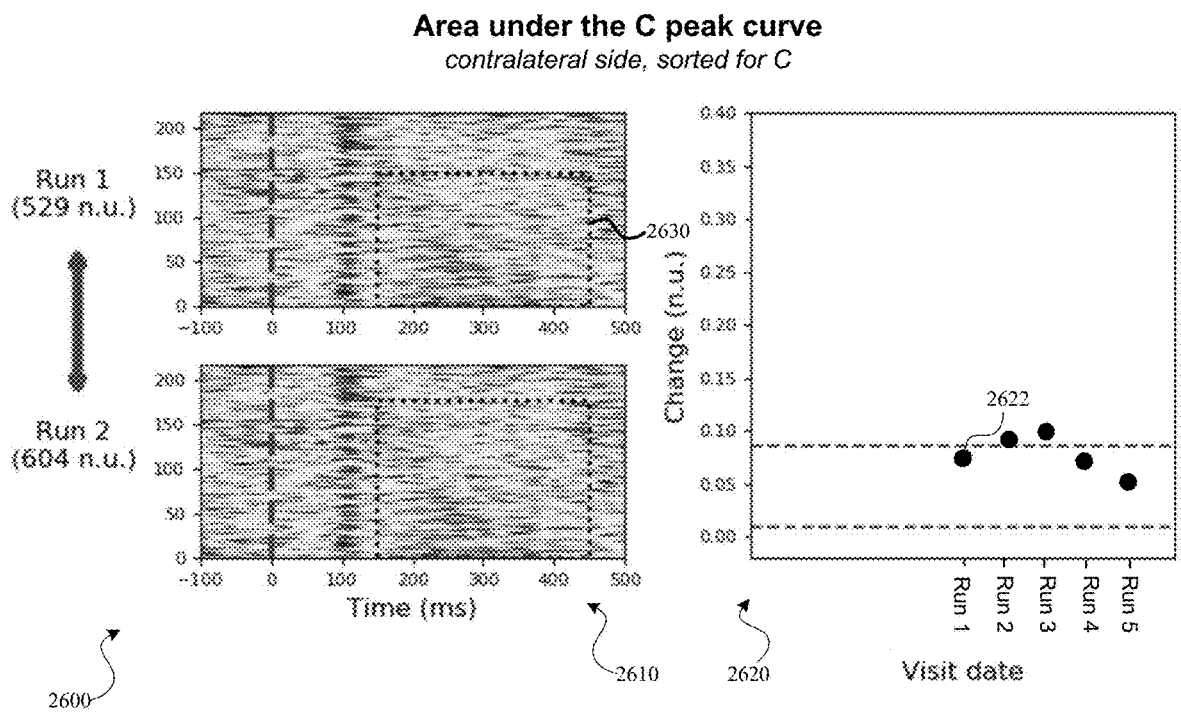
FIGS. 26A and 26B illustrate graphical user interfaces for presenting features and comparing multiple heatmaps, according to an embodiment.
Figure 26B:
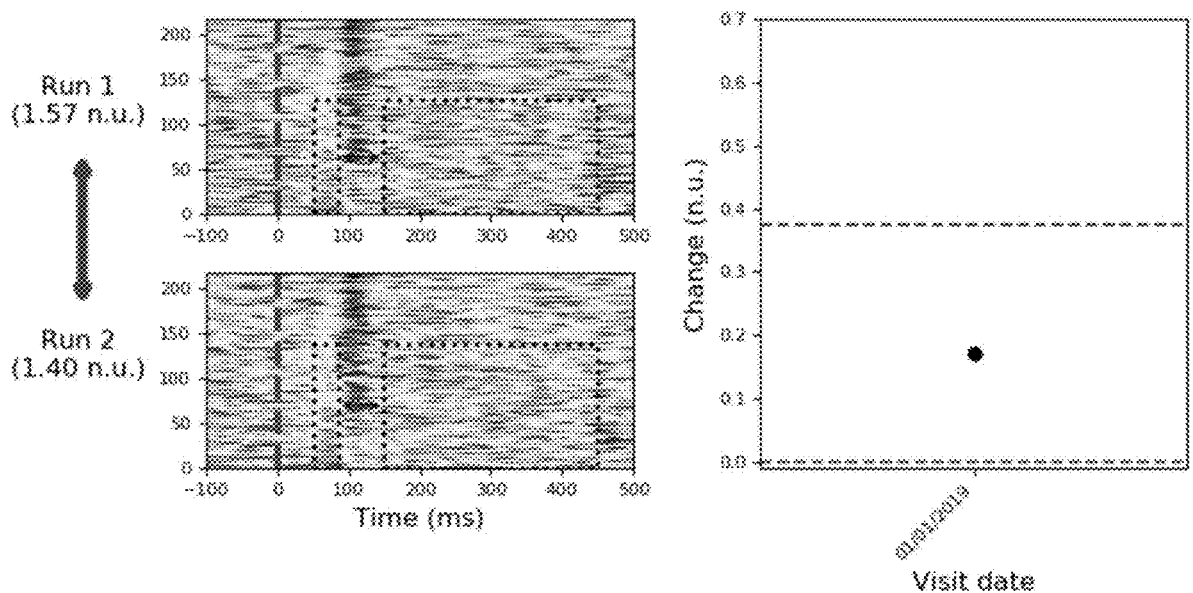

In the first display area 2610, the GUI 2600 displays one or more graphical elements 2630 at the heatmap in a location that corresponds to the feature selected. The graphical element 2630 represents an area of the heatmap that corresponds to a measurement for the feature in the heatmap. The feature selected may be related to one type of peak and may represent a measurement (e.g., amplitude, AUC, latency, etc.) of the type of peak. The graphical element 2630 may point to or otherwise emphasize an area in the heatmap that is related to the type of the peak associated with the selected feature and to the measurement. For example, in FIG. 26A, the feature selected is the area under the C peak curve. The graphical element 2630 is a dash lined rectangle that encloses an area in the heatmap that represents the area used to calculate the feature. In FIG. 26B, the feature selected is the ratio between peak A AUC and peak C AUC, the graphical elements may be two dash lined rectangles that respectively enclose the peak A location and the C peak location. For different features selected, different types of graphical elements may be used. For example, in FIGS. 18A and 20A, the graphical element is an arrow. In FIG. 22B, the graphical element is two parallel dashed lines.

In the second display area 2620, the GUI may display a plot of feature values across different runs that generate the epoch data (e.g., each run may correspond to a patient visit that captures MEG data or a patient visit may generate multiple runs). The second display area 2620 may also be referred to as a timeline of values over different runs. The second display area 2620 may include two dashed lines that indicate a normal range of values of the selected feature for NVs. A plurality of points 2622 each indicate the value of the selected feature of a particular run. In one embodiment, the GUI, by default, displays in the first display area 2610 the heatmap of the last run that is plotted at the second display area 2620. An operator of the GUI may select a different point in the second display area 2620 to change the heatmap. The heatmap displayed is generated based on the MEG epoch data that is collected during the particular run selected in the second display area 2620. In one embodiment, the GUI may include a button for selecting more than one run in the second display area 2620. Based on the selection, the GUI displays a plurality of heatmaps in the first display area 2610 to allow users of the GUI to compare heatmaps generated based on MEG data collected at different time.

The heatmaps shown in the GUI 2600 may be sorted by different options. The GUI 2600 may include a button for selecting a sorting of the plurality of epochs by peaks A, peaks B, or peaks C. For some selected features, the location of the graphical element 2630 may change based on the sorting option to represent different aspects of the measurement of the feature under different sorting. The GUI may also include another button for selecting ipsilateral data or contralateral data in displaying the heatmap.

Figure 27:
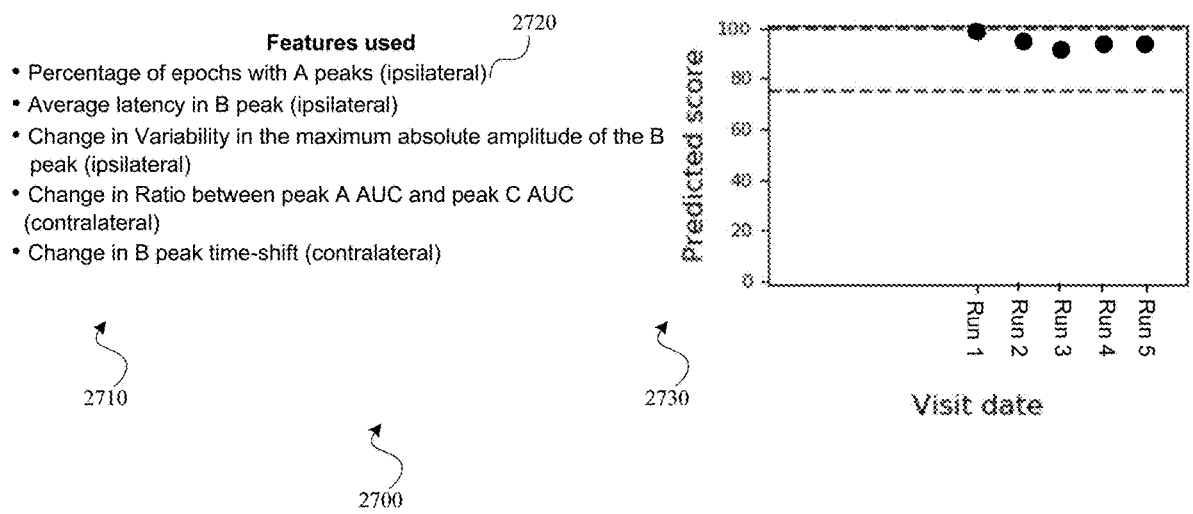
FIG. 27 illustrates a graphical user interface for presenting a cumulative score timeline, according to an embodiment.

FIG. 27 is a clinical display that takes the form of a GUI 2700, according to an embodiment. The GUI includes a first display area 2710 that lists features 2720 used in a CI model that generates a cumulative score. The GUI also includes a second display area 2730 that plots the cumulative scores at different runs. Each feature 2720 listed in the first display area 2710 may be a selectable button that allows an operator to select one of the features. Based on the selection, the GUI 2700 may switch to one of the heatmap modes shown in FIG. 18A through FIG. 26B. The points in the second display area 2730 may also be selectable buttons to turn the GUI 2700 into other modes that focuses on various heatmaps of a particular run.

In various embodiments, a clinical display may provide results in different orders. For example, in one embodiment, the clinical display may first provide a summary of the results, such as in cumulative score, key heatmaps, and a likelihood of CI that takes the form of the cumulative score or that is derived from the cumulative score. In turn, each of the following pages of the clinical display may show heatmaps and an individual feature that is used by the CI model in generating the cumulative score. The individual feature may be shown along with a range derived from NVs. The value of the individual feature for the patient over time may also be shown as a timeline, as illustrated in various examples in FIG. 18A through FIG. 26B. The display of different values over time allows the clinician to track the change of any features following significant events (e.g., start of medication). The significant events may also be displayed at the timeline.

Other variations on the GUI are envisioned, and may include any aspect of data or input discussed in this document.

In one embodiment, a graphical user interface may include a first display area configured to display a heatmap. The heatmap graphically presents a plurality of epochs representing magnetoencephalography (MEG) data of responses of a brain of a test individual to a plurality of stimulus events. At least one of the epochs includes a first peak, a second peak, and a third peak. The heatmap graphically presents a change in color to distinguish among the first peak, the second peak, and the third peak. The graphical user interface may also include a second display area configured to display a timeline of a change in values of a first feature in one or more runs of MEG scans. Each run generates a set of MEG data. The first feature may represent a measurement of the first peak, the second peak, or the third peak. The heatmap displayed in the first display area corresponds to the set of MEG data generated in one of the runs. The graphical user interface may further include a graphical element presented in the first display area and located at an area that corresponds to the measurement for the first feature in the heatmap.

In one embodiment, the graphical user interface is configured to display a score that correlates to a likelihood of the test individual being cognitively impaired.

In one embodiment, the score is determined by a model based on the first feature that is displayed in the second display area.

In one embodiment, the graphical user interface may further include a button for changing the second display area to display a second feature different from the first feature. In response to a selection of the second feature, the graphical user interface is configured to change the heatmap displayed in the first display area and the graphical element presented in the first display area to show the second feature in the heatmap.

In one embodiment, the timeline in the second display area of the graphical user interface includes a plurality of points. Each point corresponds to a value of the first feature in one of the runs. The points are selectable in the graphical user interface to change the heatmap displayed in the first display area. The heatmap displayed in the first display area corresponds to the selected one of the runs.

In one embodiment, the heatmap graphically presents a first color to represent a positive polarity of the epochs and a second color to represent a negative polarity of the epochs.

In one embodiment, the first peak, the second peak, and the third peak respectively correspond to a type-A peak, a type-B peak, and a type-C peak.

In one embodiment, the graphical user interface may further include a button for selecting a sorting of the plurality of epochs by the type-A peak, the type-B peak, or the type-C peak in displaying the heatmap.

In one embodiment, the heatmap arranges the plurality of epochs in a first axis and displays a change in values of the epochs over time in a second axis.

In one embodiment, the graphical user interface may further include a button for selecting ipsilateral data or contralateral data in displaying the heatmap.

In one embodiment, a system may include a data store configured to store magnetoencephalography (MEG) data representing a plurality of epochs measured from responses of a brain of a test individual to a plurality of stimulus events. At least one of the epochs include a first peak, a second peak, and a third peak. The system may also include a cognitive impairment detection model configured to receive one or more features to generate a cumulative score that represents a likelihood of cognitive impairment. The one or more features are extracted from the MEG data stored in the data store. At least one of the features represents a measurement of the first peak, the second peak, or the third peak. In one embodiment, the system may further include a graphical user interface that includes a first display area configured to display a heatmap that graphically presents the plurality of epochs and a second display area configured to display a timeline of a change in values of the at least one of the features in one or more runs of MEG scans.

In one embodiment, the one or more features include a measure of a percentage of the epochs with a type-A peak.

In one embodiment, wherein the one or more features include a measure of an average latency of a type-B peak in the epochs.

In one embodiment, the one or more features include a measure of a change in variability in an amplitude of a type-B peak in the epochs.

In one embodiment, the one or more features include a measure of a change in a ratio of a first area under curve of a type-A peak to a second area under curve of a type-B peak in the epochs.

In one embodiment, the one or more features include a measure of a change of a type-B peak time shift in the epochs.

In one embodiment, the stimulus events are auditory stimulus events. The one or more features include a first feature determined based on epochs captured by a first sensor located ipsilateral to the auditory stimulus events and a second feature determined based on epochs captured by a second sensor located contralateral to the auditory stimulus events.

In one embodiment, the graphical user interface may also include a button for changing the second display area to display a second feature different from the first feature. In response to a selection of the second feature, the graphical user interface is configured to change the heatmap displayed in the first display area.

In one embodiment, the heatmap graphically presents a change in color to display a change in polarity of the epochs. A first color represents a positive polarity of the epochs and a second color represents a negative polarity of the epochs.

In one embodiment, the graphical user interface may also include a button for selecting a sorting of the plurality of epochs by the first peak, the second peak, or the third peak in displaying the heatmap.

VII.Y. CI Model Feature Key

The following are a non-exhaustive list of features that may be included in a CI model, in accordance with an embodiment. Different embodiments of a CI model may use different ones of these features in combination. Features may also be referred to as parameters in this disclosure. These features may be in addition to or in place of the CI model features discussed in Sections III and IV above.

sameDayABSDiff[FEATURE]: Absolute difference between the values for FEATURE in the two scans acquired on the same day, where FEATURE is any parameter discussed in this disclosure or other similar parameters.

pctA*B*C: Percentage of epochs with peaks A, B, and C.

blueA: Area under the peak A curve (e.g., amount of "blue" in heatmaps between onset and offset of peak A).

pctA*B: Percentage of epochs with A and B peaks only.

pctA: Percentage of epochs with peaks A only.

strongAB: Number of epochs with B peaks in the epochs with strong peaks A.

blueC: Area under the C peak curve (e.g. amount of "blue" in heatmaps between onset and offset of C peak).

latencyB: average: Average latency in B peak. The average of all evoked responses (e.g. as depicted in FIG. 2B) is used to obtain the latency of each peak. That curve can also be obtained using multiple bootstraps (sampling with replacement) of the individual epochs. So, for each bootstrapped curve, one estimate of latency is obtained. the ": average" feature is the mean of that distribution, and the ": variability" feature is the standard deviation. This is applicable to the other features below with ": average" and ": variability in their name, except with that feature value rather than latency as is the case here.

onsetB: variability: Variability in the timing onset of the B peak.

durationB: average: Average duration (offset minus onset) of the B peak.

onsetB: average: Average onset for B peak (e.g. time point where signal surpasses 2 standard deviations of the average baseline signal).

latencyAsd: Standard deviation of the latency of A across all epochs.

amplitudeA: average: Average amplitude of the peak A.

latencyBsd: Standard deviation of the latency of B across all epochs.

offsetB: average: Average offset for B peak (e.g. time point where signal returns to levels below 2 standard deviations of the average baseline signal).

ApctWindowGood: Metric of peak A timing variability; the more of the onset to offset window has the peak color, the closer to 1 the value of the feature.

blueC: Area under the C peak curve (e.g., the amount of "blue" in heatmaps between onset and offset of C peak).

blueRatio: Area under the A curve divided by the area under the C curve.

BpctWindowGood: Metric of B peak timing variability; the more of the onset to offset window has the peak color, the closer to 1 the value of the feature.

nFeatureNaNs: How often the algorithm was unable to calculate a given feature. Any other feature from the CI models may be used. This feature acts as a proxy for MEG signal quality, so if this feature has a low value it is indicative of a process error in testing the patient.

VII.X. Cognitive Test Table

| Variable | Test name |
|---|---|
| mms | mini mental state-standard |
| mms7 | mini mental state-using serial sevens |
| Mmsw | mini mental state-using "world" backwards |
| Wrec | verbal learning trial one |
| wrec2 | verbal learning trial two |
| wrec3 | verbal learning trial three |
| Wrecde | verbal delayed recall |
| Targets | recognition memory hits |
| Foils | Recognition memory false alarms |
| Reyim | Visual memory immediate |
| Reyde | Visual memory delayed |
| logmema1/2ss | Paragraph recall-scaled score |
| boston1/3 | Boston naming tests |
| Fluen | Semantic fluency |
| Fluenf | Letter fluency-F |
| Fluena | Letter fluency-A |
| Fluens | Letter fluency-S |
| Spanfbasal | digit span forward |
| Spanbbasal | digit span backward |
| Trailas | Trail making A time |
| Trailbs | Trail making B time |
| Trailbe | Trail making B errors |
| Clockd | clock drawing |
| Reyco | visual figure copy |
| Blkdsn | block design |
| boston60 | 60 item Boston naming |
| bos60phone | 60 item Boston naming with cues |
| bnt60ss | 60 item Boston naming scaled score |
| Stpw | Stroop test words |
| Stpc | Stroop test colors |
| Stpcw | Stroop test interference |
| Stroopintss | Stroop test scaled score |
| Trailae | Trail making A errors |
| bos60seman | 60 item Boston naming semantic |

VIII. Example Process of Data Collection

Figure 28:
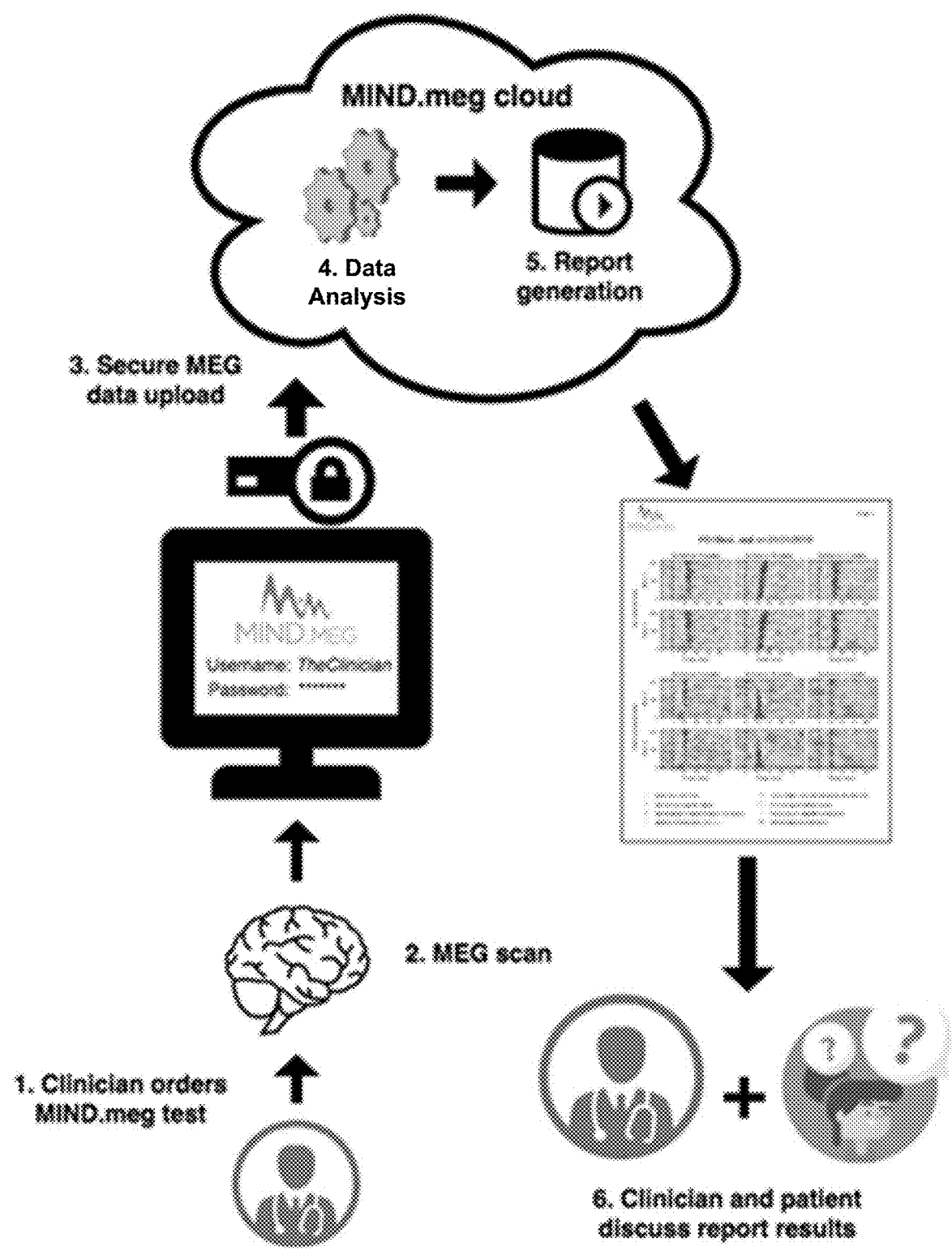
FIG. 28 is a flowchart depicting an example process of collecting MEG data, analyzing data and presenting results, according to an embodiment.

FIG. 28 is a flow diagram illustrating an example process of collection of data and presenting data, according to an embodiment. In a particular MEG run, an individual's MEG data in the form of epochs are captured in response to repeated stimuli. In one case, the individual listens to an identical sound repeatedly while having her eyes closed. The individual may be exposed to about 250 stimuli sound tones with loudness adjusted for the individual's hearing. The sound tones may occur once about every 2.5 seconds, or at other suitable rates. A run, which generates a plurality of epochs, may last for about 20 minutes. After a break, a second run may also be conducted for the same clinical visit. The MEG data are generated and transferred to a data store such as the cloud through a network such as the Internet. The MEG data is analyzed on the cloud through one of more feature extractions and analysis procedures. A cumulative score may also be generated using a CI model described herein. Analyzed data are generated and transmitted to a clinical display such as in the form of a GUI for presenting one or more reports to the individual.

IX.A. Example Process of Selection of Sensors and Features

Figure 29:
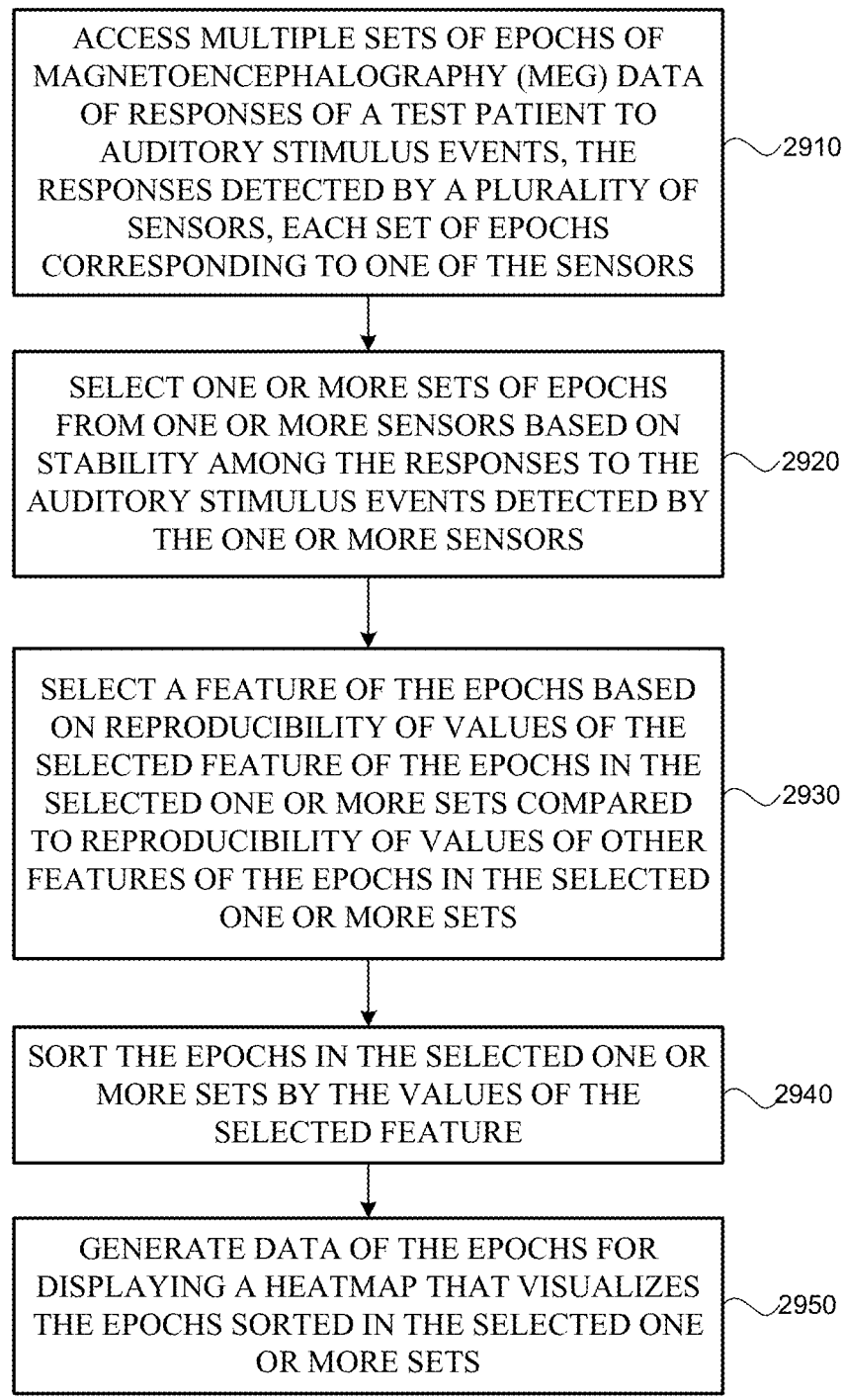
FIG. 29 is a flowchart depicting an example process of processing and analyzing MEG data, according to an embodiment.

FIG. 29 is a flow diagram illustrating an example process 2900 of collection of MEG data and processing data, according to an embodiment. The process 2900 may be a computer-implemented process. A computer may be a single operation unit in a conventional sense (e.g., a single personal computer), a virtual machine, or a set of computing devices that cooperate to execute the code instructions in a centralized or a distributed manner. For example, a computer may include a set of computing devices in a server room or computing nodes that communicate with a network in a distributed manner (e.g., cloud computing). A computer may include one or more processors and memory that store computer code including executable instructions. The instructions, when executed, cause the one or more processors to perform various processes described herein.

In one embodiment, a computer accesses 2910 multiple sets of epochs of MEG data of responses of a test patient to auditory stimulus events. The test patient may participate in one or more auditory stimulation test sessions that are performed in one or more days across one or more clinical visits. In one example, two of the auditory stimulation test sessions are performed on the same day during a first visit and an additional auditory stimulation test session is performed on another day during a second visit that are days or weeks apart from the first visit. During each auditory stimulation test sessions, the test patient may be stimulated repeatedly using one or more auditory sources under the setting described in FIG. 1A through 1D. A sensor head that carries multiple sensors distributed at different locations around the test patient's brain may be used to detect the responses of the test patient. An example distribution of sensors is illustrated in FIG. 2A. Each sensor detects the response of the test patient at a specific location and generates a set of MEG data of responses. The sensor signals are captured and may be converted to data of a suitable format such as digital data for storage. Each set of epochs of MEG data corresponds to one of the sensors. For example, a set of epochs may include data values generated by a sensor in different test sessions. Multiple sets of epochs of MEG data of responses may be transmitted to a data store. In one embodiment, the data may be uploaded to a Cloud data store that can be accessed by the computer.

The computer selects 2920 one or more sets of epochs from one or more sensors based on the stability among the responses to the auditory stimulus events detected by the selected one or more sensors. For example, the computer selects datasets from one or more stable sensors or from the most stable sensor. In some cases, the computer may focus on sensors that are located ipsilateral to the auditory stimulus events because, in some situations, ipsilateral responses to simple sound stimuli have been shown to display significant delays in different peaks of the neural response.

In selecting 2920 one or more sets of epochs that are relatively stable or a set that is the most stable, the computer may start with a pool of candidate sensors. The computer may select the sensor whose epoch data have the least variability across epochs or one or more sensors whose epoch data have low variability across epochs. The determination of variability across epochs may be evaluated based on various suitable statistical methods. For example, the selection 2920 may include a process in which the computer determines, for each of the candidate sensors, values of a metric of sensor stability among the epochs in the set corresponding to the candidate sensor. The metric of sensor stability may be defined in any suitable manner and, in some cases, may be specific to each epoch. In other words, in some cases, each epoch may include its value of the metric of sensor stability. For example, the metric may be defined as a range, the maximum value from a baseline reference epoch, a delay, or any model parameter that is disclosed above, such as in Section III.C. The metric value may be specific to each epoch or may be calculated based on an average of a number of epochs. For a set of epochs corresponding to a candidate sensor, the computer determines a variance metric that is calculated from the values of the metric of sensor stability. The variance metric may be the statistical variance, standard deviation, or another suitable statistical metric. The computer repeats the determination of the variance metric for each of the candidate sensor. The computer selects one or more candidate sensors based on the variance metric corresponding to each of the selected candidate sensors. For example, the computer may select the most stable sensor or a few more stable sensors that are associated with a low variance. The selected one or more sets of epochs are corresponding to the one or more selected candidate sensors.

Figure 30:
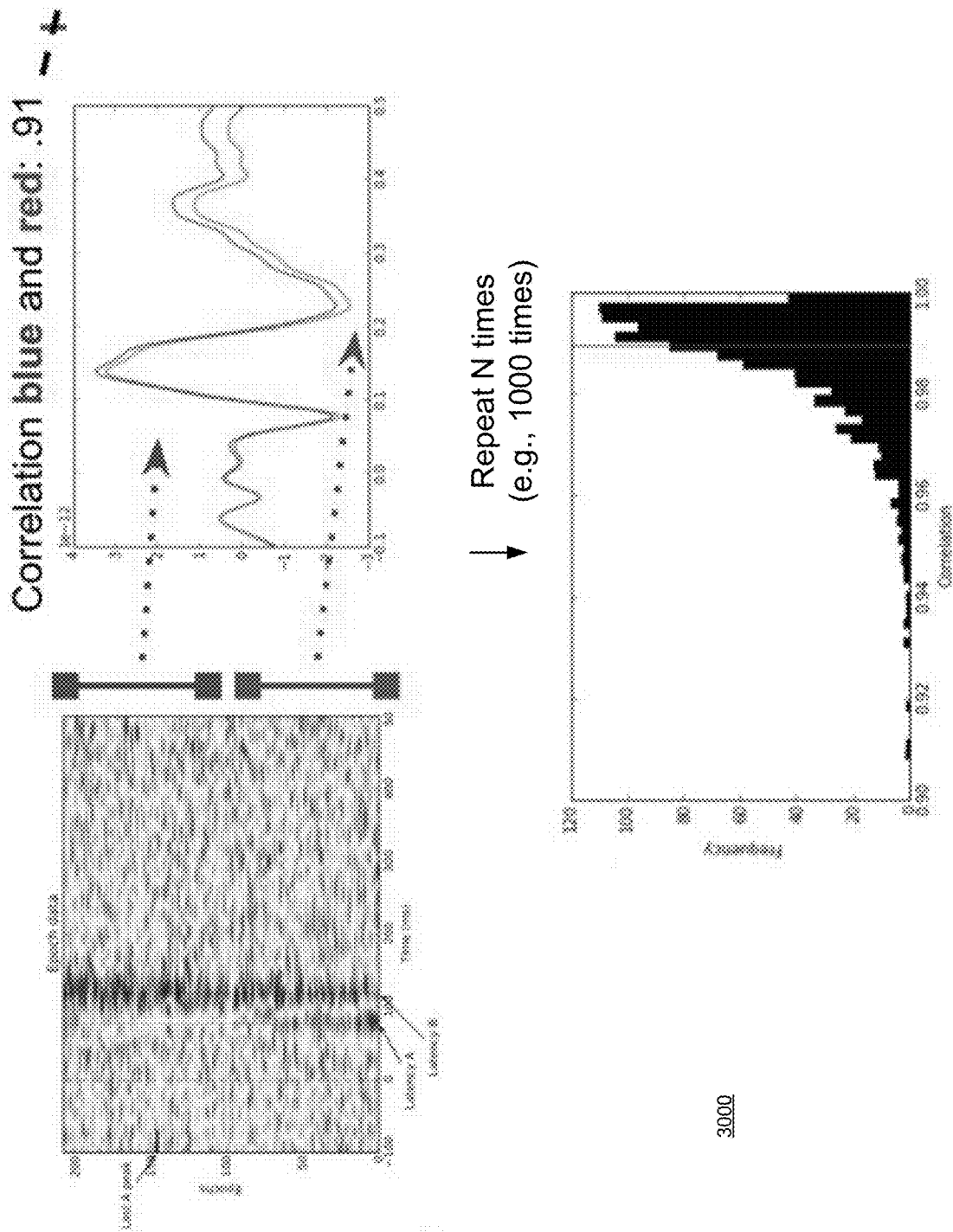
FIG. 30 is a conceptual diagram illustrating a sensor selection process, according to an embodiment.

In one example of the selection process 2920, the computer uses an iteration process 3000 to select the stable sets of epochs. This example process 3000 is graphically illustrated in FIG. 30. From a set of candidate sensors, the computer calculates two evoked responses (e.g., response averaged over epochs) after randomly splitting the epochs in a set into two subsets. The computer calculates the correlation between the two evoked responses. The computer may repeat this process many times (e.g., 1000 times) and define stability as the ones with high or the highest aggregate correlation between the two evoked responses. Sensor stability may be computed as the median over all iterations. This sensor selection process may be referred to as stimulus response variability.

In other words, for each of the candidate sensors, the computer separates the set of epochs corresponding to the candidate sensor into two or more subsets. The computer averages the epochs in each of the two or more subsets to generate two or more averaged epochs. The computer determines a metric of sensor stability corresponding to a correlation among the two or more averaged epochs. The computer repeats the above step multiple times (e.g., 1000 times) to generate a plurality of values of the metric of sensor stability. The computer determines the statistical value (e.g., medium) of the plurality of values of the metric of sensor stability. The computer selects the most stable candidate sensor or one or more stable candidate sensors based on the statistical values corresponding to each of the selected candidate sensors. The sets of epochs that are selected 2920 correspond to the stable candidate sensors.

Continuing to refer to the process 2900 shown in FIG. 29, the computer selects 2930 a feature of the epochs in the one or more sets selected in 2920. The selection 2930 may be based on stability such as reproducibility of values of the selected feature of the epochs in the selected one or more sets compared to the stability of values of other features of the epochs in the selected one or more sets. A feature may be selected from any model parameters that are discussed above in this disclosure such as in Section III.C. Reproducibility may be a special type of stability that evaluates a feature's values among epochs that are detected across different testing sessions. For example, in determining reproducibility, the computer may compare the epochs generated in different sessions of the same visit or across different visits that occurred on separate days to determine whether the epochs across different sessions show similar patterns.

The computer selects 2930 a feature that has high stability such as a high reproducibility. In one embodiment, the selection of a feature may be a two-step process that includes a first round of selection of relative stable features and a second round of selection to narrow the final result to a single feature. In various embodiments, one or more steps of the two-step process may be skipped, or additional steps may be added.

In the first round of selection 2930, the computer may narrow down a subset of features that are relatively stable or reproducible across visits. In one embodiment, feature stability may be defined as the Pearson correlation between the feature measured across days. For example, for each candidate feature, the computer constructs a first vector using a number of metrics (e.g., 20 metrics) for the candidate feature of a group of participants based on data obtained from a first visit. The metric may be any measures, such as statistical measures, of the feature, such as average, median, mode, range, variance, etc. of one or more participants in the group. The computer constructs a second vector using the same metrics for the same candidate feature of the group of participants based on data obtained from a second visit. The computer measures the correlation between two vectors that represent two different visits. The computer repeats the construction of vectors and the measurement of correlations for other candidate features. Relatively stable candidate features are selected for the second round. For example, features that have a significant correlation between the two vectors ($p<0.05$, corrected using False Discovery Rate at $q<0.05$) may be selected.

In other words, the first round of selection may include dividing the one or more sets of epochs selected in step 2920 into two or more subsets of epochs. Each subset corresponds to the responses generated in a different visit of the test patient. The computer generates, for each candidate feature, two or more metric vectors. Each metric vector includes one or more metric values of the candidate feature measured from a group of participants that includes the test patient. Each metric vector corresponds to each subset of epochs that are generated in a different visit of those participants. For each candidate feature, the computer determines a correlation between the two or more metric vectors. The computer repeats the correlation determination for different candidate features. The computer selects one or more candidate features whose correlation among the two or more metric vectors is above a threshold. The ultimately selected feature may be selected from this pool of relatively stable candidate features.

In a second round of selection 2930, a feature may be selected using one or more criteria that will each be discussed in further detail below. The criteria may include how well the ultimately selected feature distinguishes between normal volunteers and cognitively-impaired individuals through a machine learning model such as a decision-tree classifier. Another criterion may be how many cognitively-impaired individuals are outside the normal volunteer range. Yet another criterion may be how many cognitive tests with which the feature is significantly correlated.

For each of the criteria above, the computer may establish an acceptable threshold by conducting nonparametric permutation tests. The computer stores the best possible outcome when running the approach using data shuffled among participants. For example, taking into consideration of the first criterion that involves the use of a machine learning model, by using permutation tests, the computer may find that it is extremely unlikely ($p<0.05$) that one of the candidate features would perform a classification between normal volunteers and cognitively-impaired individuals with more than 70% accuracy when using shuffled data. Therefore, the computer may conclude that the candidate feature performs better than 70% in that criterion. Candidate features performed better than a threshold determined in one or more of the criteria may be kept for final selection.

To elaborate, the permutation tests include shuffling data across participants. For example, the computer may test how well a candidate feature pctA can distinguish between normal volunteers and cognitively-impaired individuals. The computer may set a threshold of accuracy at a certain level (e.g., 85%). The computer shuffles the data across all participants so that there is no relationship between a participant's number for pctA and their diagnosis. The computer tries the criteria again. The computer should get the result from shuffled data close to 50%, as there is no relationship between data and labels if the number of normal volunteers and cognitively-impaired individuals in the participant pool is close to 50-50. The computer may continue this shuffling routine many times to come up with a null distribution. The computer computes a number of how often the computer can find the true value (e.g., set at a threshold of 85%) when there is no real relationship between data and labels.

The framework of the permutation test may be expanded for candidate features being considered at the same time. For example, if there are 10 candidate features, the chances that one of them would get above the threshold level (e.g., 85%) just by accident would be higher. For even more candidate features such as 1000 features, even with shuffled data, the chance of locating one or more apparently stable features by accident would still be higher. Thus, the computer may correct for all those tests at the same time (i.e. the number of candidate features that are being considered at the same time). The computer shuffles the data for all candidate features at the same time, and observes that it was unlikely (less than 5% probability) that any of the stable features would go above 70% accuracy just by chance. Then, the threshold may be set at 70% or a similar number.

The permutation tests in the second round of selection 2930 may be repeated for one or more criteria in order to select a final feature that passes each permutation test for each criterion. The first criterion may be how well the feature distinguishes between normal volunteers and cognitively-impaired individuals through a machine learning model. The machine learning model may be a decision tree classifier, a support vector machine, a neural network, etc. Training and the execution of the machine learning model are discussed above in Section III.D.1. For a candidate feature, the computer inputs the data of the candidate feature into the machine learning model. The computer uses the machine learning model to select the feature. The machine learning model outputs a determination of whether a participant is cognitively impaired. The output of the machine learning model may be compared to the actual label of the participant (whether the participant is known to be cognitively impaired) to determine how well the feature performs. The determination using the machine learning model may be repeated for shuffled data (e.g., shuffling the participant's label on whether he/she is cognitively impaired) in a permutation test.

The second criterion may be how many cognitively-impaired individuals are outside the normal volunteer range. For each candidate feature, the computer determines a range of values of the candidate feature among normal volunteers. The detail of determining a range will be discussed with reference to FIG. 50. The computer determines, for the candidate feature, the number of cognitively-impaired individuals whose values of the candidate feature are outside the range of the values among normal volunteers. The computer selects the feature based on the number of cognitively-impaired individuals whose values of the selected feature are outside the range of values among normal volunteers. The second criterion can also be used as another round of permutation test. Based on the range of values among normal volunteers, shuffled data of the values may be compared to the range to determine a participant with the shuffled data is cognitively impaired. The determination is compared to the actual label of the participant. This can be repeated for many participants to generate a null distribution.

The third criterion may be how many cognitive tests with which the feature is significantly correlated. For each candidate feature, the computer determines a correlation of the candidate feature with a set of cognitive tests. This may include using one or more different cognitive tests (e.g., 20 cognitive tests) that are discussed above in Section VII.X. Example correlation study is discussed with reference to FIG. 10. The computer may select a feature based on the correlations of the candidate features with the set of cognitive tests. The third criterion may also be used in an additional round of permutation test by using the correlations as prediction criteria of whether participants with shuffled data are cognitively impaired.

The various sub-processes discussed above with reference to the selection process 2930 may be used together or separately to select a feature. In various embodiments, one or more sub-processes may be skipped and additional suitable sub-processes or selection criteria that are not explicitly discussed may also be added.

Continuing with the process 2900 shown in FIG. 29, the computer sorts 2940 the epochs in the one or more sets selected in step 2920 by the values of the feature selected in step 2930. For example, each epoch may include peak A, peak B, and peak C as shown in FIG. 2B. A set of epochs may be graphically represented as a heatmap as shown in, for example, FIGS. 3A and 3B. The heatmap graphically presents a first color of different scales to represent a positive polarity of the epochs and a second color of different scales to represent a negative polarity of the epochs. The heatmap arranges the epochs in a set in a first axis and displays changes in values of the epochs over time in a second axis. In the first axis, the computer sorts the epochs based on the value of the feature associated with each epoch. The epochs may be sorted by the ascending or descending order of the feature values. For example, the selected feature may be an amplitude of one of the peak A, peak B, or peak C. The epoch can be sorted by the amplitude.

The computer generates 2950 data for displaying a heatmap that visualizes the epochs sorted in the one or more sets selected in step 2920. The data may be in a format that is suitable for graphical visualization. As a result, a heatmap with sorted epochs can be presented at the display device to illustrate the cognitive condition of the test patient. The computer may repeat 2960 step 2930 through step 2950 to select additional stable features and sort the epochs based on the additionally selected features. Additional heatmaps that are sorted by different features can be generated. A feature may also be a compound feature that includes several sub-features, such as the number of B peaks in weak A peaks. The heatmaps may be displayed in a report.

Based on the report, whether the test patient is cognitively impaired is determined 2970. For example, one or more heatmaps with sorted epochs are displayed. A medical professional may rely on the heatmaps to decide whether the test patient is cognitively impaired. In one embodiment, a machine learning model may be trained. The detail of training a machine learning model is discussed above in Section III.D.1. The computer inputs the data of the epochs to a machine learning model. The machine learning model provides an output such as a label or a score that corresponds to the likelihood of the test patient being cognitively impaired.

IX.A. Example Sorted Heatmaps

Figure 31:
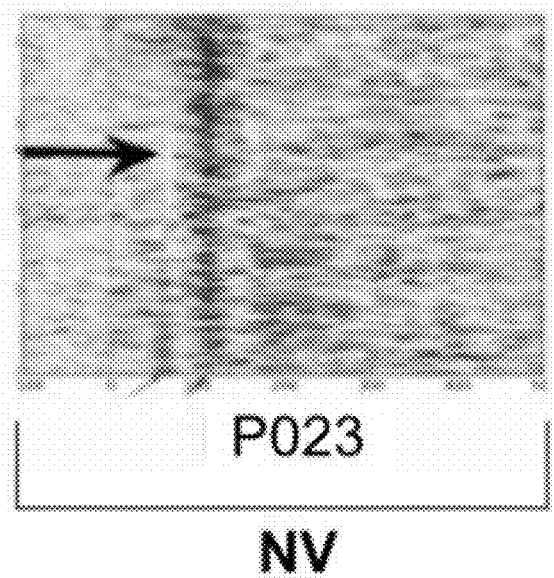
FIG. 31 shows example heatmaps of different subjects with epochs sorted by the feature of increased number of A peaks, according to an embodiment.
Figure 31:
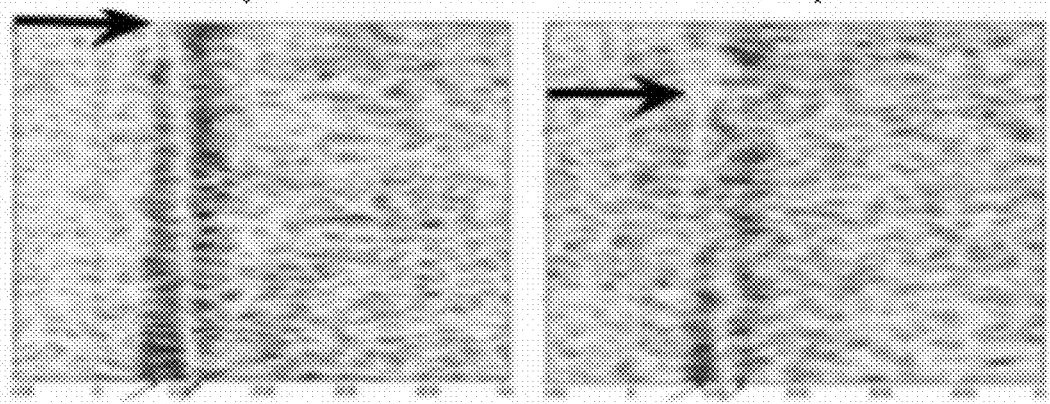

FIG. 31 shows a few examples of heatmaps of different subjects with epochs sorted by the feature of the increased number of A peaks. The feature may be selected based on process 2900. Each of the heatmaps is sorted based on signal similarity in A peak window. The standard MMS score (0 to 30) for each subject and the feature percentage of epochs with A peaks are shown in FIG. 31. The epochs starting below the arrow in each heatmap are epochs identified to have A peak. FIG. 31 shows an inverse correlation between the percentage of A peaks and the standard MMS score. The increase in the number of A peaks reflects an increased cognitive processing effort correlated with worsening cognitive function.

Figure 32:
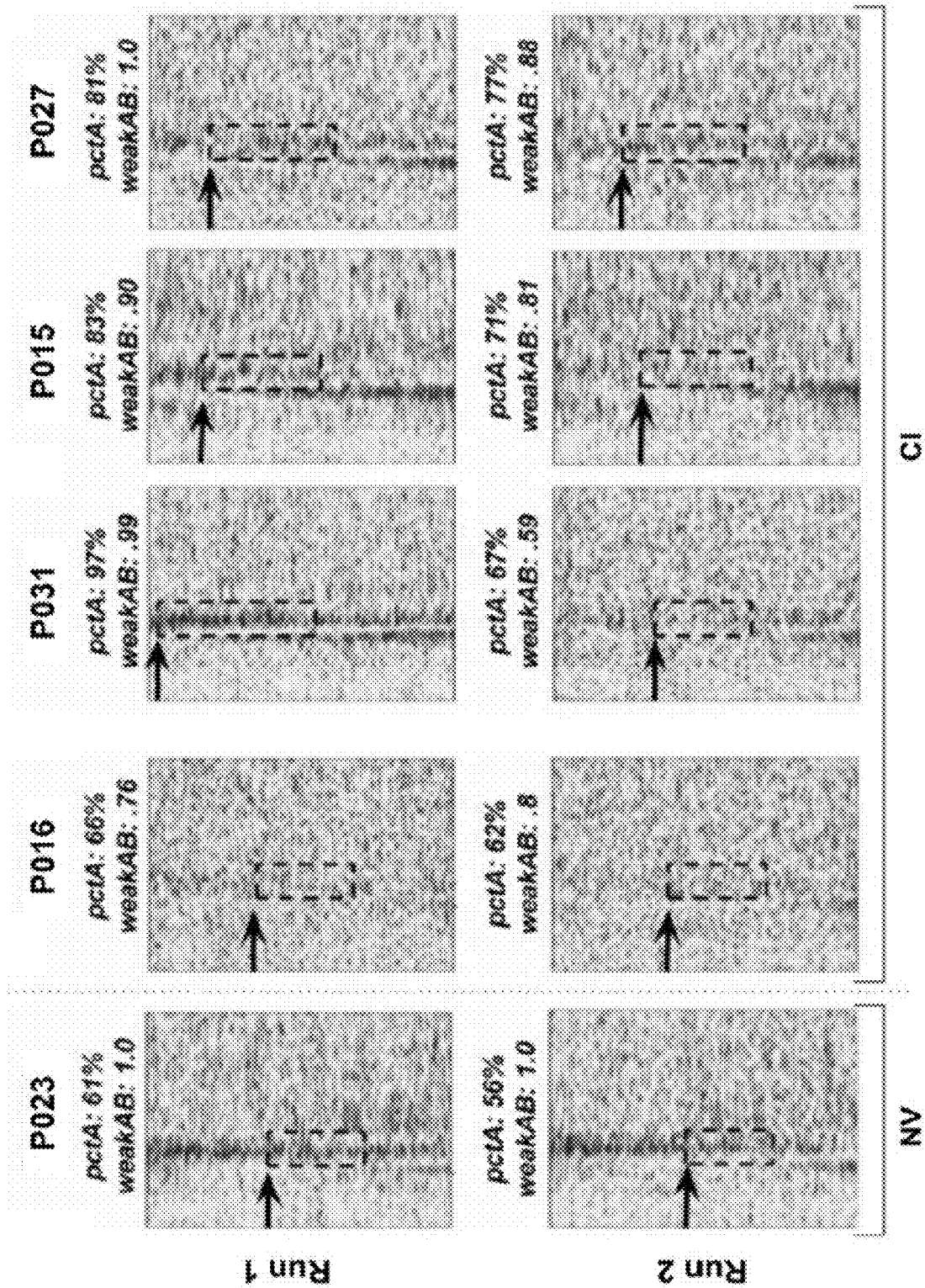
FIG. 32 shows example heatmaps of different subjects with epochs sorted by the feature of B peak attenuation, according to an embodiment.

FIG. 32 shows example heatmaps of different subjects in which the epochs are sorted by the feature of B peak attenuation. The computer may use intra-subject (same-day) variability to select the features displayed in the report. For example, subjects that have a progressively lower percentage of A peaks (pctA) perform better and generate progressively more B peaks in weaker A epochs (weakAB) in the second run of the same visit. The change reflects "fatigue" associated with the cognitive cost of increase A peak response. The enhanced attenuation of stimulus response is not seen with stimulus repetition in cognitively-impaired patients without an increased number of A peaks as well as in normal volunteers, as evident in P016 (participant #016) and P023.

In FIG. 32, heatmaps of five representative subjects are displayed. Each heatmap is sorted based on the feature signal similarity in A peak window. Run 1 and run 2 were acquired on the same visit. The three cognitively-impaired participants on the right have a high percentage of epochs with A peaks (pctA), but the fraction of epochs with B peaks in weak A epochs (weakAB) is reduced in the second run. There is little change from run 1 to run 2 in both subjects on the left. Arrows show the last epochs with A peaks and dashed squares highlight the B peak window for weak A peak epochs. FIG. 32 demonstrates how the report may be derived from multiple feature analysis, as the B peak amplitude of P016 is marked impaired, despite the lack of the "fatigue" effect.

Figure 33:
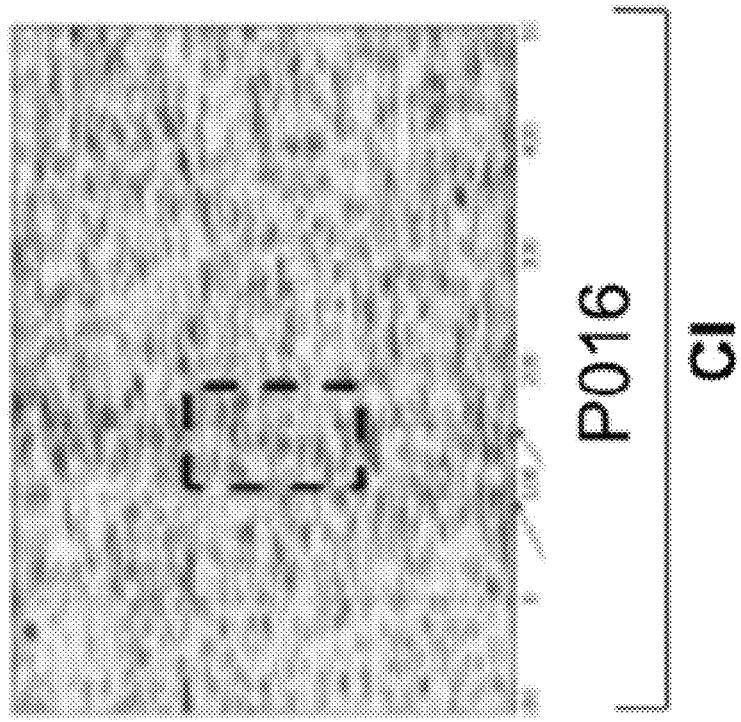
FIG. 33 shows example heatmaps of different subjects with epochs sorted based on the feature of signal similarity in A peak windows, according to an embodiment.
Figure 33:
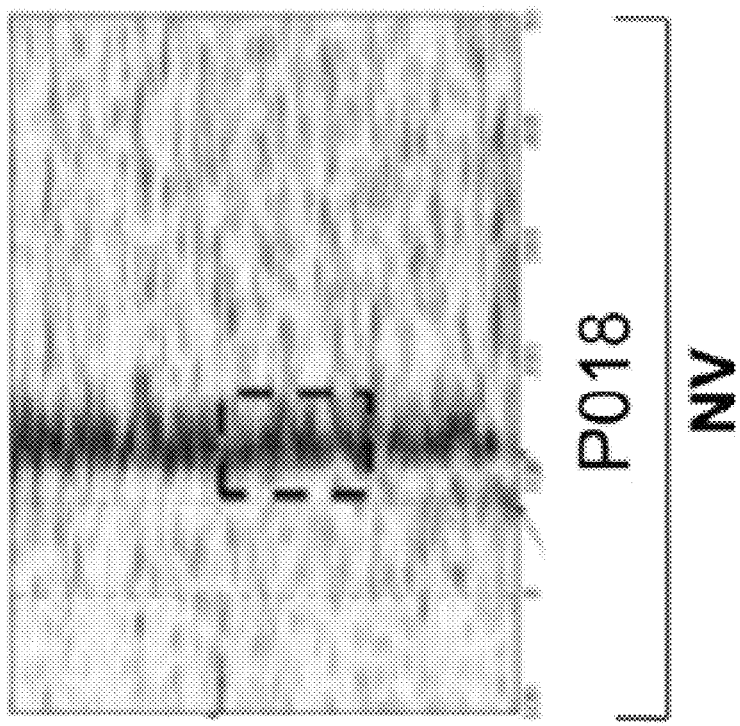

FIG. 33 are heatmaps of two representative subjects with epochs sorted based on the feature of signal similarity in A peak windows. The standard MMS score for each participant and the feature B peak amplitude in weak A epochs are also shown. A group of cognitively-impaired individuals has notably smaller B peak amplitude in weak A epochs when compared to normal volunteers. As noted above, P016 is an example of decreased amplitude in B peak amplitude in epochs with weak A peaks (top half of epochs identified to show A peaks). The amplitude of the B peak in those epochs with weak A peaks is markedly smaller in a cognitively-impaired patient when compared to normal volunteers, as shown in FIG. 33. The result shows that decreased B peaks amplitude in weak A peaks may be associated with decreased cognitive processing.

Figure 34:
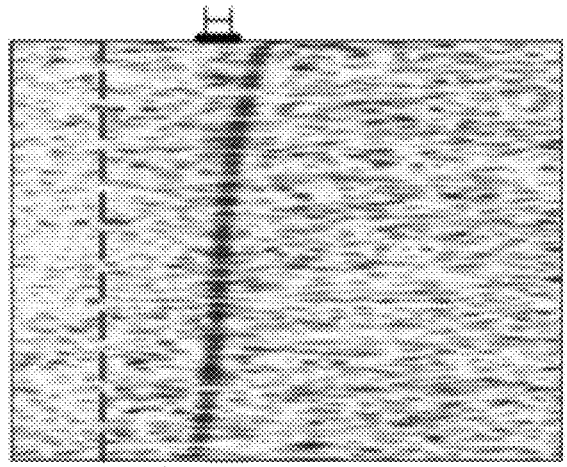
FIG. 34 shows example heatmaps of different subjects with epochs sorted based on the feature of B peak latency, according to an embodiment.
Figure 34:
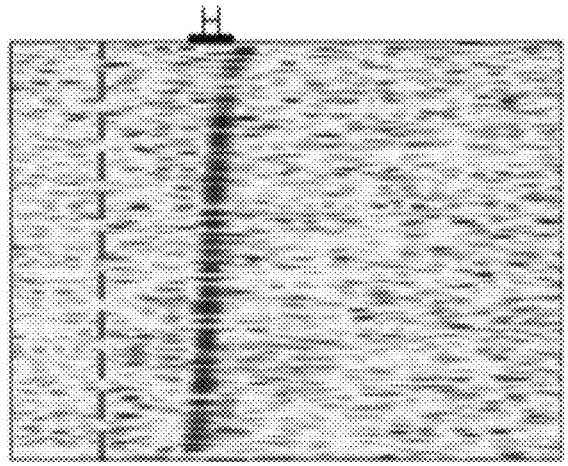
Figure 34:
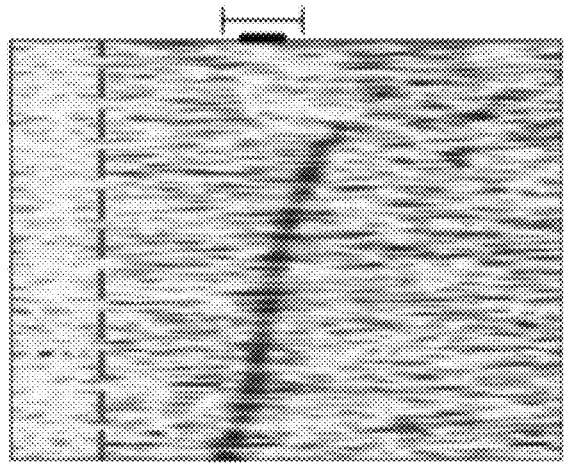
Figure 34:
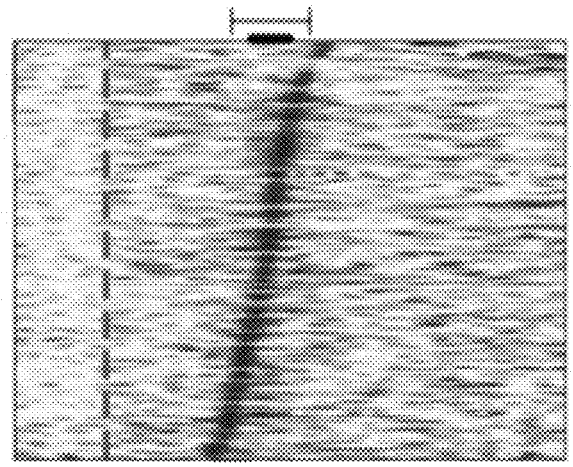

FIG. 34 are heatmaps of four representative subjects. Each heatmap is sorted based on the feature of B peak latency. The standard MMS score for each participant and the feature B peak latency variability is also shown. Black bars in the top horizontal axis indicate normal ranges of B peak latency variability. Interval markers indicate B peak latency variability for that subject. A group of cognitively-impaired individuals has notably higher B peak latency variability compared to normal volunteers. The heatmaps in FIG. 34 show that an increase in the peak latency variability across epochs is associated with an increased in signal instability.

Figure 35:
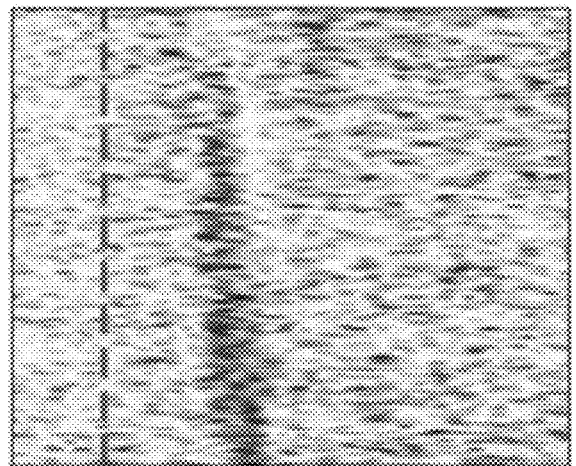
FIG. 35 shows example heatmaps of different subjects with epochs sorted based on the feature of signal similarity in B peak windows for B peak onset, according to an embodiment.
Figure 35:
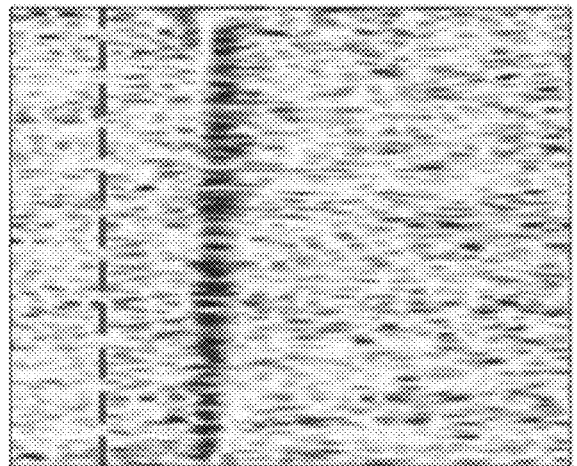
Figure 35:
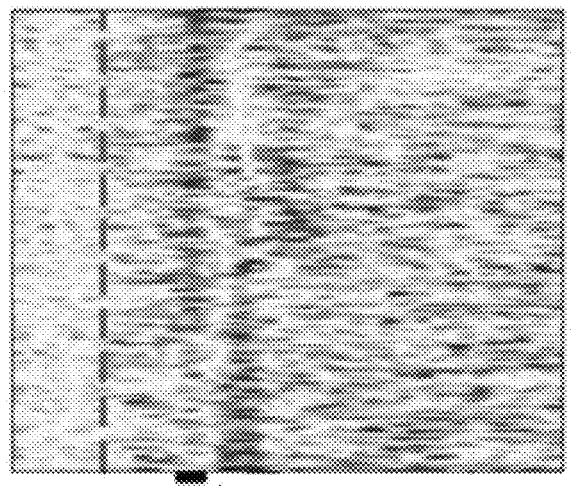
Figure 35:
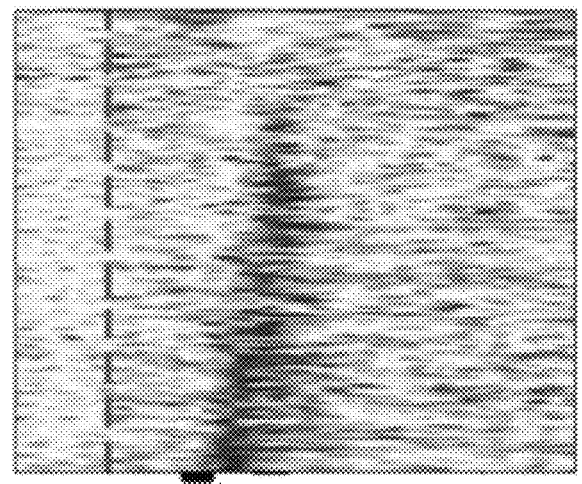

FIG. 35 are heatmaps of four representative subjects. Each heatmap is sorted based on the feature of signal similarity in B peak windows for B peak onset. The standard MMS score for each participant and the feature B peak average onset is also shown. Black bars in the bottom horizontal axis indicate normal ranges of B peak onset. Black arrows indicate the B peak onset for that subject. A group of cognitively-impaired individuals has notably delayed B peak average onset when compared to normal volunteers. Similar to what is observed for increase B peak latency variability in FIG. 34, an increase in the timing of B peak onset had no apparent effect on B peak amplitude or on signal processing, but appears to have an effect on cognition.

Figure 36:
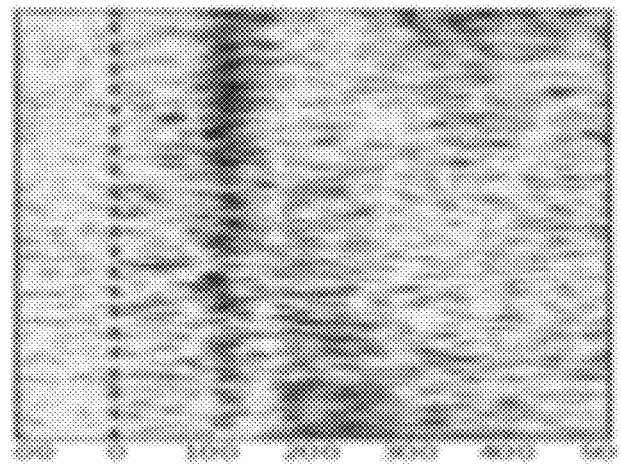
Figure 36:
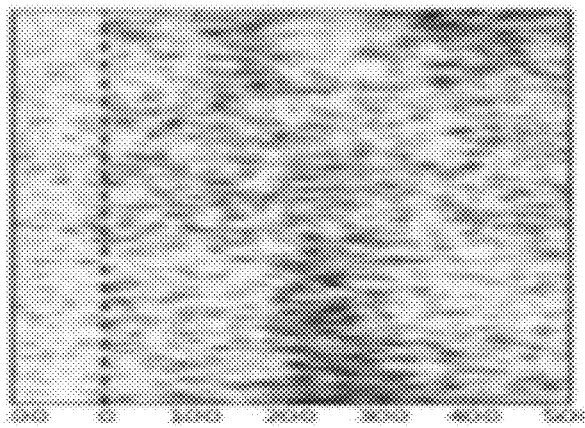
Figure 36:
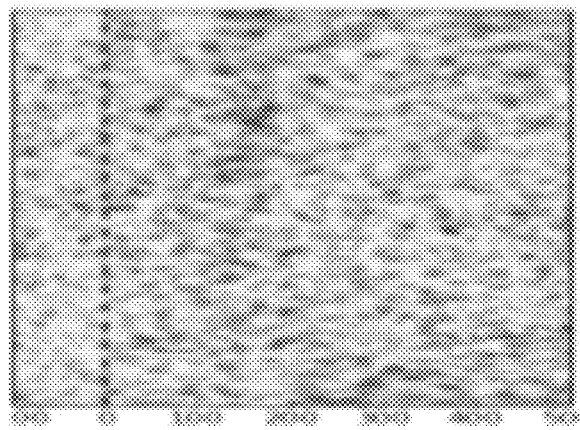

FIG. 36 are heatmaps of three representative subjects. Each heatmap is sorted based on the feature signal similarity in the C peak window. The summed MMS scores for each participant and the feature percentage of epochs with C peaks are also shown. FIG. 36 shows that the percentage of epochs with C peaks is related to improved cognition. P030 has the negative features of a lower B peak amplitude in epochs with weak A peak amplitude, as well as greater epoch to epoch stimulus response variability than P016. Yet, instead of a lower MMS score, P030 has an MMS score higher than P016's MMS score. Favorable correlation of a higher number of C peaks and MMS is evident between normal volunteers, such as P023.

IX.C. Additional Information: Feature Sorting

A process evaluates magnetoencephalography (MEG) data collected from evoked responses of a patient to a stimulus to determine the cognitive state of the patient. The system includes a clinical test based on MEG data that produces a report listing several features that are highly correlated with well-established neurocognitive tests. The system is robustly informative and highly individual-specific, producing reports designed to be easily interpretable by clinicians in the medical practice.

Conventionally diagnosis of many cognitive impairments is dependent upon pathologic evaluation of brain tissue. There is a need beyond diagnosis for a real-time test of the effects of therapeutic intervention on cognitive function. The system displays features highly correlated with well-known cognitive tests, yet different signal patterns can have similar cognitive test scores. These patterns themselves are potential markers for different, more focused interventions not accessible by current diagnostic evaluation including currently-used cognitive testing. The system provides a real-time clinical test of cognitive function, and may potentially allow for the assessment of cognitive effects of therapeutic interventions of all types. Unlike current neuropsychiatric testing, the system involves the brain response to a repeated sound stimulus and thus requires, beyond adequate hearing, only minimal subject attention and cooperation.

In exemplary embodiments, MEG data for a patient is acquired from a MEG sensor, such as, for example, under the conditions described in U.S. Patent Application Publication No. 2019/0099101, entitled "Methods and Magnetic Imaging Devices to Inventory Human Brain Cortical Function" and published Apr. 4, 2019; U.S. Patent Application Publication No. 2017/0281071, entitled "Methods and Magnetic Imaging Devices to Inventory Human Brain Cortical Function" and published Oct. 5, 2017; or U.S. Provisional Patent Application No. 62/828,687, filed Apr. 3, 2019 and entitled "Methods and Magnetic Imaging Devices to Inventory Human Brain Cortical Function".

In exemplary embodiments, MEG data is collected for multiple epochs of evoked response. Each epoch represents the response to a single stimulus. The evoked responses generally show three major brain wave peaks, termed an A peak, a B peak, and a C peak, as described further in U.S. Patent Application Publication No. 2019/0099101. In exemplary embodiments, the epochs are not averaged but instead ordered individually on a predetermined basis and evaluated collectively, but on an epoch-by-epoch, and hence stimulus-by-stimulus basis.

In exemplary embodiments, the MEG data for a set of epochs is from a single MEG sensor. In exemplary embodiments, the single MEG sensor is selected based on a comparison of MEG data from an array of MEG sensors from a single MEG device, as described in U.S. Patent Application Publication No. 2019/0099101. In exemplary embodiments, the single-channel selection is based on the stimulus response variability for the entire response signal, with the selected MEG sensor being the one giving the least variability among epochs across the entire signal. In other words, the selected MEG sensor is the one that provides the MEG data set with the greatest overall consistency of the response pattern across all epochs for a particular run.

In exemplary embodiments, the epochs of MEG data are then ordered and displayed as a two-dimensional "heatmap" with the positive and negative values being indicated by different colors and relative amplitude being indicated by color intensity. In some embodiments, a computer directs the ordering and display of the epochs of MEG data. In some embodiments, the generated heatmap is displayed on an electronic screen. In some embodiments, the electronic screen is a computer screen of a computer monitor. The epochs of MEG data may be ordered in any of a number of different protocols, depending on the desired parameters to be acquired. In exemplary embodiments, the epochs are ordered based on the timing of maximum intensity of response (latency) for each of the major brain wave response peaks, the A peak, the B peak, and the C peak.

In exemplary embodiments, a model for each desired parameter from analysis of the MEG data is developed based on values of the desired parameter from MEG data acquired from model patients with a known, independently-acquired cognitive state, as described in more detail in U.S. Patent Application Publication No. 2019/0099101. For a given test subject, the desired parameter from that test subject's MEG data is determined and compared to the model to assess the cognitive state of that test subject. In exemplary embodiments, multiple parameters are evaluated and weighed in assessing the test patient's cognitive state.

FIG. 37 through FIG. 44 show heatmaps of epochs sorted vertically, with the x-axis representing time after the stimulus, in milliseconds. In FIG. 37 through FIG. 40, the epochs are sorted based on the latency of the A peak. In FIG. 41 through FIG. 44, the epochs are sorted based on the latency of the B peak. Epochs lacking the requisite peak and hence lacking a relevant latency appear above the epochs with the requisite peak in the heatmaps in an order based on the initial sorting criterion, such as, for example, the Euclidean distance in a one-dimensional space after spectral embedding.

FIG. 37, FIG. 39, FIG. 41, and FIG. 43 show heatmaps for a single patient with normal cognitive function. FIG. 38, FIG. 40, FIG. 42, and FIG. 44 show heatmaps for a single patient with impaired cognitive function. FIG. 37, FIG. 38, FIG. 41, and FIG. 42 show heatmaps from a set of epochs from a first run of a particular day. FIG. 39, FIG. 40, FIG. 43, and FIG. 44 show heatmaps for a set of epochs from a second run of the same particular day, but later in the day than the first run after about a 45-minute break.

A comparison of the heatmaps of FIG. 37 and FIG. 38 shows clear differences between the latency of the A peak for a normal patient and for a cognitively-impaired patient in a first run. The A peak in FIG. 37 and FIG. 38 is the band extending from the bottom of the heatmap at about 40 milliseconds up and to the right and ending at about 100 milliseconds about ⅔ of the way up the heatmaps. The latency for the A peak for the normal patient (FIG. 37) has a greater slope and less of a deviation from linearity than the latency for the A peak for the cognitively-impaired patient (FIG. 38).

The heatmaps of FIG. 39 and FIG. 40, similar to FIG. 37 and FIG. 38, show the latency for the A peak for the normal patient having a greater slope than the latency for the A peak for the cognitively-impaired patient in a second run. The latency for the A peaks for the second runs has a slightly lower slope than for the respective first runs.

A comparison of the heatmaps of FIG. 41 and FIG. 42 shows clear differences between the latency of the B peak for a normal patient (FIG. 41) and for a cognitively-impaired patient (FIG. 42) in a first run. The B Peak in FIG. 41 and FIG. 42 is the band extending from the bottom of the heatmap at about 100 milliseconds up and to the right and ending at about 200 milliseconds about ⅚ of the way up the heatmap in FIG. 42 and almost all the way to the top of FIG. 41. The latency for the B peak for the normal patient (FIG. 41) has less of a deviation from linearity than the latency for the B peak for the cognitively-impaired patient (FIG. 42). If the tails at the tops and bottoms are disregarded, the latency for the B peak for the normal patient (FIG. 41) has a greater slope than the latency for the B peak for the cognitively-impaired patient (FIG. 42). Furthermore, the cognitively-impaired patient has significantly fewer B peaks than the normal patient.

The heatmaps of FIG. 43 and FIG. 44, similar to FIG. 41 and FIG. 42, show the latency for the B peak for the normal patient having a greater slope than the latency for the B peak for the cognitively-impaired patient in a second run. The latency for the B peak for the second runs has a slightly lower slope than for the respective first runs.

Additional analysis comparing MEG data from a first run with MEG data from a second run has shown that a test subject having a progressively lower percentage of epochs including an A peak perform better and generate progressively more epochs including a B peak in epochs with a weaker A peak in the second run of the same visit. This change may reflect "fatigue" associated with the cognitive cost of "excessive" A peak responses. The enhanced attenuation of stimulus response is not seen with stimulus repetition in cognitively-impaired test subjects without an increased number of epochs including an A peak as well as in test subjects with normal cognition.

In exemplary embodiments, the latency variability of the A peak, the B peak, and/or the C peak serves as a parameter to evaluate the cognitive state of a test subject. Organizing the MEG data as a heatmap with epochs ordered based on peak latency provides a visual representation of the variability of the latency, which is much more informative than a simple averaged value of latency. The potentially very complex distribution of the individual epochs sorted on the basis of peak latency captures an important parameter that is visually displayed with the heatmaps but would be lost by the use of averaging metrics and displays. In addition to the slope and linearity just discussed, other parameters that are more visually apparent from heatmaps sorted based on peak latency may include, but are not limited to, the number of epochs having the sorted peak out of the total number of epochs, the average latency of a peak, and the deviation of the latency across all epochs.

Other metrics to identify cognitively-impaired patients may include, but are not limited to, fixed timing deficits (in contrast to variable timing of the B peak latency) as well as the C peak amplitude and possibly the B peak amplitude and the A peak amplitude. Many cognitively-impaired patients may have more than one metric abnormality.

Six different patterns of cognitive decline have been identified from the epochs and heatmaps. Without wishing to be bound by theory, these patterns are believed to be associated with specific manifestations associated with cognitive decline. An increased number of A peaks is believed to be indicative of a heightened startle in cognitively-impaired subjects. A first run to second run B peak attenuation is believed to be indicative of an increased fatigue in cognitively-impaired subjects. A decreased B peak amplitude in weak A peaks is believed to be indicative of decreased cognitive processing in cognitively-impaired subjects. An increased B peak latency variability is believed to be indicative of an increased signal processing instability in cognitively-impaired subjects. An increased fixed delay in B peak onset is believed to be indicative of increased fixed processing defect in cognitively-impaired subjects. An increased C peak amplitude is believed to be indicative of increased cognitive remediation in cognitively-impaired subjects.

In some embodiments, the metrics used herein may be used in combination with metrics disclosed in U.S. Patent Application Publication No. 2019/0099101; U.S. Patent Application Publication No. 2017/0281071; or U.S. Provisional Patent Application No. 62/828,687.

The MEG data from which the heatmaps of FIG. 37 through FIG. 44 were derived was collected from a MEG device with a full helmet of 306 individual MEG sensors. Since the analysis relies on the MEG data from a single MEG sensor, a MEG device including a single MEG sensor may be used instead of a conventional MEG device, which may have 300 sensors or more. A single sensor MEG device is a fraction of the cost of a conventional MEG to manufacture and significantly simplifies data acquisition.

FIG. 45 schematically shows the layout of the MEG sensors in the helmet of the MEG device used to acquire the MEG data for further analysis. The dashed ellipsoids 4501, 4502, 4503 show the three spatially-closest MEG sensors in the candidate pool, sharing the same gradiometer orientation, with the MEG signal being similar for all three of them for two different patients, one being a cognitively-impaired patient and the other being a normal patient. These did not happen to be the same two patients whose MEG data is shown in the heatmaps of FIG. 37 through FIG. 44.

MEG data was acquired from each of the two patients in one session on a first day and in two separate sessions on a second day. Data from the indicated MEG sensors 4504, 4505, 4506 were selected for heatmap analysis. The MEG sensor 4505 within the middle dashed ellipsoid 4502 was used from the first run for the cognitively-impaired patient. The MEG sensor 4504 within the top dashed ellipsoid 4501 was used from the first run for the normal patient. The MEG sensor 4506 within the bottom dashed ellipsoid 4503 was used from the second and third runs for the cognitively-impaired patient. The MEG sensor 4505 within the middle dashed ellipsoid 4502 was used from the second and third runs for the normal patient. The spatial resolution of the MEG sensor does not significantly affect the quality of the acquired data, and a single sensor placed anywhere in that vicinity is expected to be capable of acquiring an appropriate signal for analysis. The variability in the location of the selected sensor in FIG. 45 is believed to be based on a change in patient head position with respect to the MEG sensor between runs rather than a different best data acquisition location in the brain, indicating the importance of placing the MEG sensor as close as possible to the head.

As shown in FIG. 45, the MEG sensor of maximum intensity response and least A peak latency variability for the normal patient differs from the first run to the second run. The MEG sensor from the first run lies in the row above the MEG sensor from the second run. The MEG data for the third run shows a marked global reduction in amplitude. These varying results only make sense as evidence of head movement relative to the helmet rather than there being a different brain region of maximum intensity response between runs.

Referring to FIG. 46 and FIG. 47, a MEG device 4600 includes a single MEG sensor 4601 sized to collect data from the brain region of interest of the test subject 4602. The MEG sensor 4601 is applied close to the head. In exemplary embodiments, the MEG device 4600 also includes a support apparatus 4603, preferably a very comfortable reclining chair, such as, for example, a conventional dental chair with an adjustable support back 4604, for the comfort of the test subject 4602 that also largely immobilizes the back of the head to stabilize the head position with respect to the support back 4604. In some embodiments, the support back 4604 includes a neck support 4605 that aids in immobilizing the head by immobilizing the neck of the test subject 4602. The MEG sensor 4601 is also immobilized with respect to the support back 4604 such that variability in the placement of the head of the test subject 4602 with respect to the MEG sensor 4601 is reduced or minimized. The MEG sensor 4601 is operatively connected to a computer with appropriate software for the collection of MEG data associated with the auditory stimulus.

The MEG sensor 4601 is located on a probe 4606 that preferably places the MEG sensor 4601 as close to the scalp as possible or in direct contact with the scalp and that may be contoured to a part of the contour of the head and also may help to stabilize the head position with respect to the support back 4604 and the MEG sensor 4601. The probe 4606 shown in FIG. 46 and FIG. 47 only covers a small portion of the scalp while locating the MEG sensor 4601 over the region of interest of the brain of the test subject 4602. In alternative embodiments, the probe 4606 may be a full or near-full helmet that covers all or most of the scalp. In some embodiments, the inner contour of the probe 4606 is selected or the configuration of the probe 4606 is adjustable based on a measured size and/or contour of the head of the test subject 4602. The support back 4604 may be adjustable 4607 across a range of inclinations, as shown in FIG. 46.

In some embodiments, the MEG device 4600 further includes a strap 4608 extending from the support back 4604 or the probe 4606 for placement around the head of the test subject 4602 to further stabilize the head position with respect to the support back 4604 and probe 4606 and hence with respect to the MEG sensor 4601. A second similar strap (not shown) may extend from the support back 4604 or the probe 4606 on the other side of the head as well. The straps 4608 may be flexible or rigid, may extend partially or fully around the head, and may be reversibly fastened to each other or to another structure on the opposite side of the head.

The straps 4608 may contact the face over the cheekbones to prevent lateral movement of the head.

Conventional MEG sensors 4601 are generally cylindrical with a diameter in the range of about 0.25 mm to about 1.5 mm. In some embodiments, the single sensor of a MEG device 4600 of the present disclosure is larger than a conventional MEG sensor. The increased sensor detection area based on the increased MEG sensor size increases the timing/amplitude sensitivity of the sensor at the cost of spatial localization. Spatial localization of the signal, however, is not of particular importance for methods of the present disclosure. Appropriate diameters of the single MEG sensor 4601 of a MEG device 4600 of the present disclosure are in the range of about 0.25 mm to about 2 cm, alternatively about 0.5 mm to about 2 cm, alternatively about 1 mm to about 2 cm, alternatively at least 2 mm, alternatively about 2 mm to about 2 cm, alternatively at least 5 mm, alternatively about 5 mm to about 2 cm, alternatively at least 1 cm, alternatively about 1 cm to about 2 cm, or any value, range, or sub-range therebetween.

It is expected that the metrics and methods of the present disclosure improve in power with sensitivity. Although the MEG sensor 4601 may be a conventional sensor cooled to 4 K with liquid helium, a MEG sensor 4601 that operates at a higher temperature may alternatively be used in a MEG system 4600 of the present disclosure and may be more sensitive than the conventional 4 K MEG sensor 4601.

FIG. 48 shows a system and a process for acquiring and analyzing MEG data and reporting results of the analysis for a test subject. The process includes a web application that consumes the data files generated by a neuroscan of a patient and returns to the clinician a detailed report of features reflecting the patient's cognitive function based on our proprietary algorithms.

The system may be broken down between two parts: the analysis of the data and the portal. The analysis of the data includes a script that processes data and another script that generates the visual report. The portal encompasses all the online infrastructure for user authentication, data upload, providing the report back to the user, and additional functionalities. The portal receives, organizes, and pipes the data uploaded by clinicians into the processing script and then stores and feeds the report back to the clinician.

Since the system is designed as a web application, it is deployed in a secure virtual private cloud (VPC) using a web service, such as, for example, Amazon Web Services (AWS), and is accessed through online computers in a clinic.

The subject sits in a comfortable chair while the MEG helmet covers at least the relevant portion of the subject's head. The MEG protocol includes the subject listening for an identical sound repeatedly while keeping her eyes closed. The subject merely needs to stay still and is sometimes distracted by a different sound to help maintain focus.

The MEG helmet is part of a device approved by the Food and Drug Administration (FDA) for clinical use (for example, Elekta Neuromag's System: K050035 or CTF's OMEGA System: K030737). The data acquired in the device is the input signal (i.e. files to be uploaded), which later returns the visual report to clinicians.

The subject is exposed to about 250 stimuli sound tones with loudness adjusted for the subject's hearing. The sound tones occur one every 2.5 seconds, and the series of epochs (a run) lasts about 20 minutes. After a 45 minute break, there is a repeat 20-minute run. The entire data acquisition, including the break, takes about 1.5 hours. For the data to be useful, the subject must be able to lie reasonably still and cannot be completely hearing impaired. In addition, if the subject has extensive dental hardware that cannot be removed, or other ferromagnetic metal in their bodies that interfere with the MEG signal, the data may not be useful.

The clinician then securely transfers the MEG data to the system cloud, where it is analyzed and the system report is generated within a few minutes. The clinician can then discuss those results with the patient.

All data analysis is performed on secure servers. Results are ready in less than ten minutes, and the practitioner then gets notified that a report for that patient's visit is ready for review. All servers are Health Insurance Portability and Accountability Act (HIPAA) compliant and adhere to the highest security standards in the market.

After logging in to her account, the practitioner can see all of her patients in a single list and also can edit, remove, or view visit information for each patient. Results for each assessment are stored in Visit records. In the Visit view, the practitioner can also see the visit date, analysis status, and any comments entered when creating that visit record. Finally, three familiar icons can be seen to the right of each visit entry that allows the practitioner to remove, view visit details, or view the report for a visit.

When data is successfully acquired for a visit, one file for each run should be uploaded, along with the visit date. The data are uploaded in the background, and processing commences as soon as the files are received by the servers. When the processing is complete and the report is ready, the visit status is updated on the website, and the practitioner is notified by e-mail that a report is ready for viewing.

FIG. 49 shows a portion of an exemplary report of results from the analysis of the MEG data of a test subject. The report displays a longitudinal view of feature values, across the many visits for the given patient. The images on the left side display the normal range (vertical bars) of each feature (or feature run-to-run change), and the center of each circle marks the feature value. The greater the circle diameter, the longer it has been since the measurement was taken. The current measurement result is marked with a filled dot.

In exemplary embodiments, a circle becomes red when it is outside the normal range. These plots make it natural to observe the evolution of a specific feature for a test subject over time, whether the value trends towards the abnormal range, or it becomes closer to normal values, such as, for example, as a result of an intervention. Finally, the feature values over time are also shown in the table to the right of the display. For the longitudinal display, individual features are shown in columns, and the multiple measurements over time are the rows.

The top and bottom features on the left of FIG. 49 show stable normal values. The second feature from the top shows a consistently-abnormal value, and the one below displays a significant worsening over time. As noted above, the oldest measurement is represented by the biggest circle, and all other (more recent) measurements are marked by smaller circles with radius decreasing linearly with time, i.e., a circle for a measurement acquired 2 years ago is twice the size of the circle for a measurement from 1 year ago. The current measurement is represented by a filled circle.

In one embodiment, in a graphical user interface, the plurality of epochs are ordered in the heatmap based on a latency of one of the first peak, the second peak, and the third peak. The graphical user interface is configured to display a score that correlates to a slope of the latency. The plurality of epochs are ordered in the heatmap based on a latency of one of the first peak, the second peak, and the third peak.

In one embodiment, a method may include accessing a set of epochs of magnetoencephalography (MEG) data of responses of a brain of a test patient to a plurality of sequential auditory stimulus events. The method may also include processing the set of epochs to identify a presence of at least one peak of a tri-peak subset in each epoch of the set of epochs, the tri-peak subset comprising an A peak, a B peak, and a C peak. The method may further include processing the set of epochs to identify a latency of the at least one peak of the tri-peak subset for epochs having a presence of the at least one peak. The method may further include displaying the set of epochs as a heatmap in an order based on the latency of the at least one peak.

In one embodiment, the at least one peak is the A peak. In one embodiment, the at least one peak is the B peak. In one embodiment, the at least one peak is the C peak.

In one embodiment, the method may further include acquiring at least one parameter from the heatmap and comparing a value the at least one parameter to a model for the at least one parameter to assess a cognitive state of the test patient. In one embodiment, the at least one parameter includes a slope of the latency. In one embodiment, the at least one parameter includes a deviation from linearity of the latency.

In one embodiment, a method may include acquiring at least one parameter from a heatmap of a set of epochs of magnetoencephalography (MEG) data of responses of a brain of a test patient to a plurality of sequential auditory stimulus events. A normal response includes a tri-peak subset that includes an A peak, a B peak, and a C peak. The heatmap includes the epochs displayed in an order based on the latency of one peak of the tri-peak subset. The method may also include comparing a value for the at least one parameter to a model for the at least one parameter to assess a cognitive state of the test patient.

In one embodiment, the one peak of the tri-peak subset is the A peak. In one embodiment, the one peak of the tri-peak subset is the B peak. In one embodiment, the one peak of the tri-peak subset is the C peak. In one embodiment, the at least one parameter comprises a slope of the latency. In one embodiment, the at least one parameter includes a deviation from linearity of the latency.

In one embodiment, a magnetoencephalography (MEG) device may include a MEG sensor and a support apparatus that includes a support back immobilizing a location of a head of a patient with respect to the location of the single MEG sensor. The MEG sensor is immobilized with respect to the support back. In one embodiment, a reclined angle of the support back is adjustable. In one embodiment, the MEG device includes a probe shaped to contact at least a portion of the head of the patient, the probe being mounted to the support back and the MEG sensor being mounted in the probe. In one embodiment, the MEG device further includes a strap immobilizing the head of the patient with respect to the location of the single MEG sensor. In one embodiment, the MEG device further includes a neck support extending from the back support and immobilizing a neck of a patient with respect to the back support. In one embodiment, the MEG sensor has a diameter of at least 0.25 mm. In one embodiment, the MEG sensor has a diameter in the range of 2 mm to 2 cm. In one embodiment, the support apparatus is a reclining chair.

IX.D. Example Evoked Potential Summary Plots

In some embodiments, a computer may provide a summary plot of an aggregated epoch of a test patient in the background of a normal range of evoked potential to provide a quick summary on certain features of the test patient that derivate from the normal range.

FIG. 50 is a conceptual diagram illustrating a computer-implemented process of generating a background of the normal range of evoked potential of normal volunteers, according to an embodiment. A computer may access datasets of epochs of normal volunteers. For each normal volunteer, the computer may aggregate the epochs to generate an averaged line. The plots 5010 are the aggregated plot of a normal volunteer respectively in two different runs, R1 and R2. The computer may repeat the aggregation process for other normal volunteers to generate multiple aggregated plots for the runs R1 and R2. The plots 5020 shows the aggregated plots of multiple normal volunteers. Based on the aggregated plots of multiple normal volunteers, the computer may determine a range of epochs of normal volunteers and turn the range into a grey background, as shown in the plots 5030. In the plots 5030, the middle line in each run shows an average among the normal volunteers. The data of the normal range and the average may be saved by the computer and be retrieved for future use.

For test patients, a computer may also aggregate the epochs of a test patient and put the aggregated plot onto the grey background that shows the range of normal volunteers. The plot may server as a summary plot of a test patient. The summary plot may be presented in a graphical user interface as part of the cognitive capacity report of the test patient. FIG. 51 shows two example summary plots of a test patient P11 for the first run and the second run. For the first run R1, the grey area 5110 shows the normal range. The thinner middle line 5120 shows an average plot of normal volunteers. The thicker line 5130 with dotted portions shows the aggregated plot of the test patient P11. The dotted portions indicate the part of the aggregated plot that is out of the normal range.

In one embodiment, the summary plots highlight the features that are out of the normal range so that a computer or a medical professional can make a determination on selecting a feature that can be used to sort the epochs to generate a heatmap. For example, in FIG. 51, the left plot for the first run R1 indicates that one or more features of the test patient P11 may be out of range. Region 5140 indicates that there might be a fixed timing delay for the epochs of the test patient P11. Region 5150 indicates that the feature of A peak amplitudes of the test patient P11 is out of range and the feature of B peak onset variability is also abnormal. Region 5160 shows two peaks at the B peak region, indicating that the test patient P11 might have an abnormally large value of B peak latency variability because the epochs aggregated do not form a single B peak. Likewise, in the region 5170 of the second run R2, the presence of two peaks at the B peak region indicates that the test patient P11 might have an abnormally large value of B peak latency variability. Based on the summary plots, a computer or a medical professional may select a feature for further investigation. For example, the epochs of the test patient P11 may be sorted by the selected feature to generate a heatmap for further evaluation. In one embodiment, the selection of the features and the generation of the heatmaps may be performed automatically by a computer. In another embodiment, a graphical user interface may present the summary plot and allow a user to click on various regions on the plot, such as a region with a dotted line that shows an out-of-range section of the aggregated plot. In response to the selection by the user, the graphical user interface may provide suggestions of features to investigate. Based on a selection of the user, a computer may generate a heatmap and cause the graphical user interface to display the heatmap.

FIG. 52 shows two example summary plots of a test patient P15 for the first run and the second run. The plots show that the amplitude of A peaks of the test patient P15 is abnormally high. Also, the latency value of A peaks and the latency value of B peaks are larger than normal.

FIG. 53 shows two example summary plots of a test patient P16 for the first run and the second run. The plots show that A peak latency variability may be abnormal so that the A peaks are not aggregated in the summary plots to an easily identifiable peak in each run. The plots also show that the B peak amplitude may be lower than normal and the number of epochs that have B peaks may also be lower than normal so that the aggregated plots show that the amplitude of the B peak is below the normal range. The abnormal features may be confirmed based on heatmaps that are generated by sorting the epochs by the potentially abnormal features.

FIG. 54 shows two example summary plots of a test patient P24 for the first run and the second run. For the first run, the C peak in the aggregated plot of the test patient P24 is hardly identifiable. This might be due to the variability of the latency of C peaks in various epochs. The B peaks are also delayed in both runs, indicating that the feature B peak latency might be out of range for the patient P24. The variability of the latency of A peaks may also be larger than normal in the first run R1 so that A peak in the aggregated plot is also hardly identifiable.

FIG. 55 shows two example summary plots of a test patient P24 for the first run and the second run. Based on the summary plots, the test patient P24 might have a cognitive condition that is closer to normal volunteers because the aggregated plots are mostly within the normal range. The amplitude of the A peak in the first run R1 is slight out of range.

FIG. 56 shows two example summary plots of a test patient P27 for the first run and the second run. Based on the summary plots, the test patient P27 might have a higher-than-normal number of A peaks present in the epochs and the B peak onset may also be delayed, leading to the dotted portion of the plots being out of the normal range. The amplitude of A peaks may also be larger than normal. The precise features that are abnormal may be confirmed by generating the heatmaps that are sorted by the features.

FIG. 57 shows two example summary plots of a test patient P30 for the first run and the second run. The regions 5700 and 5710 show that the B peak region does not form a clear peak. This might indicate that the B peak latency and onset variability are high so that the aggregated plots do not form a clear B peak. The high latency variability of B peak might also be shown by regions 5720 and 5730, which show large negative values in the C peak region because the negative values may indicate that the offset of a large number of B peaks are delayed.

FIG. 58 shows two example summary plots of a test patient P31 for the first run and the second run. The first run R1 may indicate that the test patient P31 has a higher-than-normal number of A peaks and the amplitude of A peak is abnormally high. FIG. 51 through FIG. 57 show that most test patients' features and abnormality are consistent across the first run R1 and second run R2. In contrast, for test patient P31, the aggregated plots in the first run R1 and the second run R2 are quite different, particularly in the amplitude of B peaks. This might indicate that the test patient P31 experienced fatigue in the second run.

FIG. 59 shows two example summary plots of a test patient P32 for the first run and the second run. Both runs show that the test patient P32 does not have clear A peak, B peak, or C peak. This might indicate that the test patient P32 have abnormally large variability in the latency and onset of A peaks, B peaks, and C peaks.

FIG. 60 shows two example summary plots of a test patient P33 for the first run and the second run. The plots show that the onset of B peak is delayed so that the rising of B peak is out of the normal range in both first run R1 and second run R2. The plots also show that the B peaks are consistently delayed so that the test patient P33 has sharp aggregated B peaks in both runs but the aggregated B peaks are delayed compared to the normal range.

A computer may identify the features that are outside the normal range and use the data to determine whether a test patient is cognitively impaired. The computer may train one or more machine learning models to determine whether a test patient is cognitively impaired. The training and execution of a similar machine learning model are discussed in further detail above in Section III.D.1. The computer may also use the summary plots to lead to further presentations of various heatmaps that are used to determine whether a test patient is cognitively impaired.

X. Additional Considerations

Similar methodologies may be developed that may be useful in monitoring for other specific medical conditions or generally monitoring human brain function. The model described herein analyzes the MEG data collected after an auditory stimulus, including the relative extent of brain activation/excitation and subsequent response to the activation. The MEG data for the model may come from only a small number of the SQUID sensors generally from as few as a single SQUID sensor up to about six, although a full set of SQUID sensors (e.g., 306 sensors) may also be used.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A computer-implemented method, comprising:
accessing multiple sets of epochs of response data of responses of a test patient to auditory stimulus events, the responses detected by a plurality of sensors, each set of epochs corresponding to one of the sensors;
selecting one or more sets of epochs from one or more sensors based on stability among the responses to the auditory stimulus events detected by the one or more sensors, wherein selecting one or more sets of epochs based on stability of the responses to the auditory stimulus events comprises:

determining, for each of one or more candidate sensors, values of a metric of sensor stability among the epochs in the set corresponding the each of one or more candidate sensors, determining, for each of the one or more candidate sensors, a variance metric calculated from the values of the metric of sensor stability, and selecting one or more candidate sensors based on the variance metric corresponding to each of the selected candidate sensors, the selected one or more sets of epochs corresponding to the one or more selected candidate sensors;

selecting a feature of the epochs based on reproducibility of values of the selected feature of the epochs in the selected one or more sets compared to reproducibility of values of other features of the epochs;

sorting the epochs in the selected one or more sets by the values of the selected feature; and generating data for displaying a heatmap that visualizes the epochs sorted in the selected one or more sets.

2. The computer-implemented method of claim 1, wherein at least a first set of epochs in the multiple sets is generated in a first visit of the test patient and at least a second set of epochs in the multiple sets is generated in a second visit of the test patient on a different day.

3. The computer-implemented method of claim 1, wherein the plurality of sensors are carried by a helmet worn by the test patients, and the plurality of sensors are distributed on different locations of the helmet.

4. The computer-implemented method of claim 1, wherein the selected one or more sets of epochs corresponds to the one or more sensors that are located ipsilateral to the auditory stimulus events.

5. The computer-implemented method of claim 1, wherein selecting one or more sets of epochs based on stability of the responses to the auditory stimulus events comprises:

for each of one or more candidate sensors:
(i) separating the set of epochs corresponding to the candidate sensor into two or more subsets,
(ii) averaging the epochs in each of the two or more subsets to generate two or more averaged epochs,
(iii) determining a metric of sensor stability corresponding to a correlation among the two or more averaged epochs,
(iv) repeating at least steps (i), (ii), (iii) multiple times to generate a plurality of values of the metric of sensor stability, and
(v) determining a statistical value of the plurality of values of the metric of sensor stability;

selecting one or more candidate sensors based on the statistical value corresponding to each of the selected one or more candidate sensors, the selected one or more sets of epochs corresponding to the one or more selected candidate sensors.

6. The computer-implemented method of claim 1, wherein selecting the feature of the epochs in the selected one or more sets based on reproducibility of the values of the selected features in the epochs of the selected one or more sets comprises:

dividing the selected one or more sets of epochs into two or more subsets of epochs, each subset corresponding to the responses generated in a different visit of the test patient;

generating, for each of a plurality of candidate features, two or more metric vectors, each metric vector comprising one or more metric values of the candidate feature, each metric vector corresponding to each of the two or more subsets of epochs;

determining, for each of the plurality of candidate features, a correlation among the two or more metric vectors; and selecting one or more candidate features whose correlation among the two or more metric vectors is above a threshold, wherein the selected feature is selected from the selected one or more candidate features.

7. The computer-implemented method of claim 6, wherein selecting the feature of the epochs in the selected one or more sets based on reproducibility of the values of the selected features in the epochs of the selected one or more sets further comprises:

inputting the selected one or more candidate features into a machine learning model, wherein the machine learning model is a decision-tree classifier, a support vector machine, or a neural network; and using the machine learning model to select the feature, wherein the machine learning model outputs a determination of whether a participant is cognitively impaired.

8. The computer-implemented method of claim 1, wherein selecting the feature of the epochs in the selected one or more sets based on reproducibility of the values of the selected features in the epochs of the selected one or more sets comprises:

determining, for each of a plurality of candidate features, a range of values of the candidate feature among normal volunteers;

determining, for each of the plurality of candidate features, a number of cognitively-impaired individuals whose values of the candidate feature are outside the range of values among normal volunteers; and selecting the feature based on the number of cognitively-impaired individuals whose values of the candidate feature are outside the range of values among normal volunteers for each of the plurality of candidate features.

9. The computer-implemented method of claim 1, wherein selecting the feature of the epochs in the selected one or more sets based on reproducibility of the values of the selected features in the epochs of the selected one or more sets comprises:

determining, for each of a plurality of candidate features, a correlation of the candidate feature with a set of cognitive tests; and selecting the feature based on the correlations of the candidate features with the set of cognitive tests.

10. The computer-implemented method of claim 1, wherein selecting the feature of the epochs in the selected one or more sets based on reproducibility of the values of the selected features in the epochs of the selected one or more sets comprises:

conducting nonparametric permutation tests for a plurality of candidate features; and selecting one or more the candidate features having results of the nonparametric permutation tests that exceed a threshold, the selected feature being one of the selected candidate features.

11. The computer-implemented method of claim 1, wherein a value of the selected feature is determined based on latency of a peak in an epoch compared to a temporal reference point.

12. The computer-implemented method of claim 1, wherein at least some of the epochs in the selected one or more sets comprises first peaks, second peaks, and third peaks, and a value of the selected feature is determined based on a number of one of the first peaks, second peaks, or third peaks that exceed a threshold amplitude.

13. The computer-implemented method of claim 1, wherein a value of the selected feature is determined based an amplitude of a type of peak in the epochs in the selected one or more sets.

14. The computer-implemented method of claim 1, wherein a value of the selected feature is determined based on a value of onset of a type of peak in the epochs in the selected one or more sets.

15. The computer-implemented method of claim 1, further comprising:
    inputting the data of the epochs to a machine learning model; and
    providing, by the machine learning model, whether the test patient is cognitively impaired.

16. The computer-implemented method of claim 1, wherein the heatmap arranges the epochs in the selected one or more sets sorted by the selected feature in a first axis and displays changes in values of the epochs over time in a second axis.

17. The computer-implemented method of claim 1, wherein the heatmap graphically presents a first color to represent a positive polarity of the epochs in the selected one or more sets and a second color to represent a negative polarity of the epochs in the selected one or more sets.

18. A system comprising a memory and a processor, the memory storing instructions, wherein the instructions, when executed by the processor, causes the processor to perform steps comprising:
    accessing multiple sets of epochs of response data of responses of a test patient to auditory stimulus events, the responses detected by a plurality of sensors, each set of epochs corresponding to one of the sensors;
    selecting one or more sets of epochs from one or more sensors based on stability among the responses to the auditory stimulus events detected by the one or more sensors, wherein selecting one or more sets of epochs based on stability of the responses to the auditory stimulus events comprises:
        determining, for each of one or more candidate sensors, values of a metric of sensor stability among the epochs in the set corresponding the each of one or more candidate sensors,
        determining, for each of the one or more candidate sensors, a variance metric calculated from the values of the metric of sensor stability, and
        selecting one or more candidate sensors based on the variance metric corresponding to each of the selected candidate sensors, the selected one or more sets of epochs corresponding to the one or more selected candidate sensors; and
    causing a graphical user interface to display the selected one or more sets of epochs, wherein the graphical user interface comprises:
        a first display area configured to display a heatmap, the heatmap graphically presenting the selected one or more sets of epochs, at least one of the epochs comprising a first peak, a second peak, and a third peak, the heatmap graphically presenting a change in color to distinguish among the first peak, the second peak, and the third peak;
        a second display area configured to display a timeline of a change in values of a first feature in one or more runs, each run generating a set of response data, the first feature representing a measurement of the first peak, the second peak, or the third peak, the heatmap displayed in the first display area corresponding to the set of response data generated in one of the runs; and
        a graphical element presented in the first display area and located at an area that corresponds to the measurement for the first feature in the heatmap.

19. A system comprising:
    a server comprising a memory and a processor, the memory storing instructions, wherein the instructions, when executed by the processor, causes the processor to perform steps comprising:
        accessing multiple sets of epochs of response data of responses of a test patient to auditory stimulus events, the responses detected by a plurality of sensors, each set of epochs corresponding to one of the sensors; and
        selecting one or more sets of epochs from one or more sensors based on stability among the responses to the auditory stimulus events detected by the one or more sensors, wherein selecting one or more sets of epochs based on stability of the responses to the auditory stimulus events comprises:
            determining, for each of one or more candidate sensors, values of a metric of sensor stability among the epochs in the set corresponding the each of one or more candidate sensors,
            determining, for each of the one or more candidate sensors, a variance metric calculated from the values of the metric of sensor stability, and
            selecting one or more candidate sensors based on the variance metric corresponding to each of the selected candidate sensors, the selected one or more sets of epochs corresponding to the one or more selected candidate sensors; and
    a graphical user interface in communication with the server, the graphical user interface configured to display the selected one or more sets of epochs, wherein the graphical user interface comprises:
        a first display area configured to display a heatmap, the heatmap graphically presenting the selected one or more sets of epochs, at least one of the epochs comprising a first peak, a second peak, and a third peak, the heatmap graphically presenting a change in color to distinguish among the first peak, the second peak, and the third peak;
        a second display area configured to display a timeline of a change in values of a first feature in one or more runs, each run generating a set of response data, the first feature representing a measurement of the first peak, the second peak, or the third peak, the heatmap displayed in the first display area corresponding to the set of response data generated in one of the runs; and
        a graphical element presented in the first display area and located at an area that corresponds to the measurement for the first feature in the heatmap.

* * * * *